US012205675B2

(12) United States Patent
Nuzhdina et al.

(10) Patent No.: US 12,205,675 B2
(45) Date of Patent: Jan. 21, 2025

(54) TECHNIQUES FOR BIAS CORRECTION IN SEQUENCE DATA

(71) Applicant: BostonGene Corporation, Waltham, MA (US)

(72) Inventors: Ekaterina Nuzhdina, Moscow (RU); Alexander Bagaev, Moscow (RU); Maksim Chelushkin, Moscow (RU); Yaroslav Lozinsky, Moscow (RU); Natalia Miheecheva, Moscow (RU); Aleksandr Zaitsev, Drozhzhino (RU)

(73) Assignee: BostonGene Corporation, Waltham, MA (US)

( * ) Notice: Subject to any disclaimer, the term of this patent is extended or adjusted under 35 U.S.C. 154(b) by 0 days.

(21) Appl. No.: 16/920,641

(22) Filed: Jul. 3, 2020

(65) Prior Publication Data

US 2021/0005284 A1 Jan. 7, 2021

Related U.S. Application Data

(60) Provisional application No. 62/991,570, filed on Mar. 18, 2020, provisional application No. 62/870,622, filed on Jul. 3, 2019.

(51) Int. Cl.
| | |
|---|---|
| *G16B 30/10* | (2019.01) |
| *C12Q 1/6806* | (2018.01) |
| *C12Q 1/6869* | (2018.01) |
| *G16B 20/00* | (2019.01) |
| *G16B 20/20* | (2019.01) |
| *G16B 25/10* | (2019.01) |
| *G16B 35/10* | (2019.01) |
| *G16H 50/30* | (2018.01) |

(52) U.S. Cl.
CPC .......... *G16B 30/10* (2019.02); *C12Q 1/6806* (2013.01); *C12Q 1/6869* (2013.01); *G16B 20/00* (2019.02); *G16B 20/20* (2019.02); *G16B 25/10* (2019.02); *G16B 35/10* (2019.02); *G16H 50/30* (2018.01)

(58) Field of Classification Search
None
See application file for complete search history.

(56) References Cited

U.S. PATENT DOCUMENTS

| | | |
|---|---|---|
| 4,777,127 A | 10/1988 | Suni et al. |
| 5,219,740 A | 6/1993 | Miller et al. |
| 5,422,120 A | 6/1995 | Kim |
| 5,580,859 A | 12/1996 | Felgner et al. |
| 5,814,482 A | 9/1998 | Dubensky, Jr. et al. |
| 5,981,568 A | 11/1999 | Kunz et al. |
| 2013/0184999 A1 | 7/2013 | Ding |
| 2018/0357372 A1 | 12/2018 | Bagaev et al. |
| 2020/0098448 A1 | 3/2020 | Shah et al. |
| 2021/0005283 A1 | 1/2021 | Nuzhdina et al. |
| 2022/0119881 A1 | 4/2022 | Nuzhdina et al. |

FOREIGN PATENT DOCUMENTS

| | | |
|---|---|---|
| CN | 105349617 A | 2/2016 |
| EP | 0345242 A2 | 12/1989 |
| EP | 0524968 A1 | 2/1993 |
| GB | 2200651 A | 8/1988 |
| JP | 2005-505267 A | 2/2005 |
| JP | 2019-528697 A | 10/2019 |
| WO | WO 90/07936 A1 | 7/1990 |
| WO | WO 90/11092 A1 | 10/1990 |
| WO | WO 91/02805 A2 | 3/1991 |
| WO | WO 91/14445 A1 | 10/1991 |
| WO | WO 93/03769 A1 | 3/1993 |
| WO | WO 93/10218 A1 | 5/1993 |
| WO | WO 93/11230 A1 | 6/1993 |
| WO | WO 93/19191 A1 | 9/1993 |
| WO | WO 93/25234 A1 | 12/1993 |
| WO | WO 93/25698 A1 | 12/1993 |
| WO | WO 94/03622 A1 | 2/1994 |
| WO | WO 94/12649 A2 | 6/1994 |
| WO | WO 94/23697 A1 | 10/1994 |
| WO | WO 94/28938 A1 | 12/1994 |
| WO | WO 95/00655 A1 | 1/1995 |
| WO | WO 95/07994 A2 | 3/1995 |
| WO | WO 95/11984 A2 | 5/1995 |
| WO | WO 95/13796 A1 | 5/1995 |
| WO | WO 95/30763 A2 | 11/1995 |
| WO | WO 96/17072 A2 | 6/1996 |
| WO | WO 97/42338 A1 | 11/1997 |
| WO | WO 00/53211 A2 | 9/2000 |
| WO | WO 2018/231762 A1 | 12/2018 |
| WO | WO 2018/231771 A1 | 12/2018 |

OTHER PUBLICATIONS

Trowsdale et al. (Annual Reviews in Genomics and Human Genetics (2013) vol. 14:301-323).*
U.S. Appl. No. 16/920,636, filed Jul. 3, 2020, Nuzhdina et al.
PCT/US2020/040834, Oct. 21, 2020, Invitation to Pay Additional Fees.
PCT/US2020/040834, Dec. 15, 2020, International Search Report and Written Opinion.
International Search Report and Written Opinion for International Application No. PCT/US2020/040834 mailed Dec. 15, 2020.

(Continued)

*Primary Examiner* — Lori A. Clow
(74) *Attorney, Agent, or Firm* — Wolf, Greenfield & Sacks, P.C.

(57) ABSTRACT

Described herein are various methods of collecting and processing of tumor and/or healthy tissue samples to extract nucleic acid and perform nucleic acid sequencing. Also described herein are various methods of processing nucleic acid sequencing data to remove bias from the nucleic acid sequencing data. Also described herein are various methods of evaluating the quality of nucleic acid sequence information. The identity and/or integrity of nucleic acid sequence data is evaluated prior to using the sequence information for subsequent analysis (for example for diagnostic, prognostic, or clinical purposes). The methods enable a subject, doctor, or user to characterize or classify various types of cancer precisely, and thereby determine a therapy or combination of therapies that may be effective to treat a cancer in a subject based on the precise characterization.

1 Claim, 70 Drawing Sheets

(56) References Cited

OTHER PUBLICATIONS

Invitation to Pay Additional Fees for International Application No. PCT/US2020/040834 mailed Oct. 21, 2020.

[No Author Listed], How to Prepare a Single-Cell Suspension from Primary Tissue Samples (e.g. Mouse Spleen). YouTube, STEMCELL Technologies. Sep. 24, 2012:13 pages. https://www.youtube.com/watch?v=N0jftyYqM38 [last accessed Jan. 19, 2021].

[No Author Listed], 10x Red Blood Cell (RBC) Lysis Buffer (ab204733). Abcam plc. 2021:3 pages. https://www.abcam.com/10x-red-blood-cell-rbc-lysis-buffer-ab204733.html [last accessed Jan. 19, 2021].

[No Author Listed], About the European Nucleotide Archive. European Nucleotide Archive. 2020:3 pages. https://www.ebi.ac.uk/ena/browser/about [last accessed Dec. 14, 2020].

[No Author Listed], BBMap Guide. DOE Joint Genome Institute (JGI). 2021:9 pages. https://jgi.doe.gov/data-and-tools/bbtools/bb-tools-user-guide/bbmap-guide/ [last accessed Feb. 2, 2021].

[No Author Listed], BioFiles for Life Science Research. Sigma-Aldrich. 2006;2:28 pages. https://www.sigmaaldrich.com/content/dam/sigma-aldrich/docs/Sigma/General_Information/2/biofiles_issue2.pdf [last accessed Dec. 14, 2020].

[No Author Listed], CaptureSeq. Illumina, Inc. 2021:1 page. https://sapac.illumina.com/science/sequencing-method-explorer/kits-and-arrays/captureseq.html [last accessed Jan. 19, 2021].

[No Author Listed], Cell Dissociation Buffer, enzyme-free, Hanks' Balanced Salt Solution, Thermo Fisher Catalog No. 13150016. Thermo Fisher Scientific. 2021:3 pages. https://www.thermofisher.com/order/catalog/product/13150016#/13150016 [last accessed Jan. 21, 2021].

[No Author Listed], Cell Dissociation Buffer, enzyme-free, PBS, Thermo Fisher Catalog No. 13151014. Thermo Fisher Scientific. 2021:4 pages. https://www.thermofisher.com/order/catalog/product/13151014?us&en#/13151014?us&en [last accessed Jan. 21, 2021].

[No Author Listed], ContEst. Broad Institute Cancer Genome Analysis. 2013:1 page. http://software.broadinstitute.org/cancer/cga/contest [last accessed Dec. 22, 2020].

[No Author Listed], EMBL-EBI, the home for big data in biology. EMBL-EBI. 2020:4 pages. https://www.ebi.ac.uk/ [last accessed Dec. 14, 2020].

[No Author Listed], Enzyme Free Cell Dissociation Solution PBS Based (1X), liquid, 500ml, Millipore Sigma Aldrich catalog No. S-014-B. Millipore Sigma. 2020:3 pages. https://www.emdmillipore.com/US/en/product/Enzyme-Free-Cell-Dissociation-Solution-PBS-Based-1X-liquid-500ml,MM_NF-S-014-B [last accessed Jan. 21, 2021].

[No Author Listed], For all you seq . . . Illumina, Inc. 2015:2 pages. https://www.illumina.com/content/dam/illumina-marketing/documents/applications/ngs-library-prep/ForAllYouSeqMethods.pdf [last accessed Feb. 2, 2021].

[No Author Listed], GenBank Overview. National Center for Biotechnology Information. Oct. 20, 2020:2 pages. https://www.ncbi.nlm.nih.gov/genbank/ [last accessed Dec. 14, 2020].

[No Author Listed], GenCode. EMBL-EBI. 2020:2 pages. https://www.gencodegenes.org/ [last accessed Dec. 14, 2020].

[No Author Listed], Genome Analysis Toolkit. GATK. 2021:3 pages. https://gatk.broadinstitute.org/hc/en-us [last accessed Feb. 2, 2021].

[No Author Listed], LifeScience. Roche Molecular Systems, Inc. Sep. 16, 2020:7 pages. https://www.lifescience.roche.com/en_us.html [last accessed Jan. 15, 2021].

[No Author Listed], PacBio. Pacific Biosciences of California, Inc. 2021:6 pages. https://www.pacb.com/ [last accessed Jan. 28, 2021].

[No Author Listed], QIAsymphony SP/AS instruments. Qiagen. 2020:8 pages. https://www.qiagen.com/us/products/instruments-and-automation/pcr-setup-liquid-handling/qiasymphony-spas-instruments/#orderinginformation [last accessed Feb. 2, 2021].

[No Author Listed], RefSeq: NCBI Reference Sequence Database. National Center for Biotechnology Information. Jan. 8, 2021:1 page. https://www.ncbi.nlm.nih.gov/refseq/ [last accessed Jan. 19, 2021].

[No Author Listed], Release 23. EMBL-EBI. 2020:8 pages. https://www.gencodegenes.org/human/release_23.html [last accessed Dec. 14, 2020].

[No Author Listed], SeQuiLa User Guide. biodatageeks.org. May 22, 2019:3 pages. https://web.archive.org/web/20191229100046/biodatageeks.org/sequila/ [last accessed Dec. 21, 2020].

[No Author Listed], SureSelect Clinical Research Exome V2. Agilent Technologies, Inc. 2021:4 pages. https://www.agilent.com/en/product/next-generation-sequencing/hybridization-based-next-generation-sequencing-ngs/exome-probes/sureselect-clinical-research-exome-v2-232867 [last accessed Feb. 2, 2021].

[No Author Listed], SureSelect Human All Exon V6. Agilent Technologies. May 14, 2015:2 pages. https://www.agilent.com/cs/library/datasheets/public/SureSelect%20V6%20DataSheet%205991-5572EN.pdf [last accessed Dec. 14, 2020].

[No Author Listed], TapeStation Systems. Agilent Technologies, Inc. 2021:1 page. https://www.agilent.com/en/product/automated-electrophoresis/tapestation-systems?gclid=CjwKCAiAo5qABhBdEiwAOtGmbg30JCRqBJgosCgVVTy1885MhWpMVIVeXvm8ss6AgM10So5uYxJriBoCeiAQAvD_BwE&gclsrc=aw.ds [last accessed Jan. 19, 2021].

[No Author Listed], Thermo Fisher Scientific. Thermo Fisher Scientific. 2021:2 pages. https://www.thermofisher.com/us/en/home.html [last accessed Jan. 19, 2021].

[No Author Listed], VerifyBamID. Center for Statistical Genetics. Sep. 9, 2017:8 pages. https://genome.sph.umich.edu/wiki/VerifyBamID [last accessed Jan. 19, 2021].

[No Author Listed], Whole Exome Sequencing Guide. Genohub, Inc. 2019:6 pages. https://genohub.com/exome-sequencing-library-preparation/ [last accessed Dec. 22, 2020].

[No Author Listed], XGBoost Documentation. Xgboost developers. 2020:2 pages. https://xgboost.readthedocs.io/en/latest/ [last accessed Dec. 22, 2020].

Andrews, FastQC. Babraham Institute. Jan. 8, 2019:6 pages. http://www.bioinformatics.babraham.ac.uk/projects/fastqc/ [last accessed Dec. 22, 2020].

Bagnoli et al., Studying cancer heterogeneity by single-cell RNA sequencing. Methods in Molecular Biology. 2019:305-319.

Behbehani, Applications of mass cytometry in clinical medicine: the promise and perils of clinical CyTOF. Clinics in Laboratory Medicine. Dec. 1, 2017;37(4):945-64.

Bray et al., Near-optimal probabilistic RNA-seq quantification. Nature biotechnology. May 2016;34(5):525-7.

Brodin, The biology of the cell-insights from mass cytometry. The FEBS journal. Apr. 2019;286(8):1514-22.

Clark et al., Subtractive Hybridization. Elsevier B.V .. 2020:18 pages. https://www.sciencedirect.com/topics/immunology-and-microbiology/subtractive-hybridization [last accessed Dec. 22, 2020].

Connelly et al., In vivo gene delivery and expression of physiological levels of functional human factor VIII in mice. Human gene therapy. Feb. 1, 1995;6(2):185-93.

Curiel et al., High-efficiency gene transfer mediated by adenovirus coupled to DNA-polylysine complexes. Human gene therapy. Apr. 1, 1992;3(2):147-54.

De Wildt et al., Characterization of human variable domain antibody fragments against the U1 RNA?associated A protein, selected from a synthetic and a patient?derived combinatorial V gene library. European journal of immunology. Apr. 1996;26(3):629-39.

Enblad et al., CAR T-cell therapy: the role of physical barriers and immunosuppression in lymphoma. Human gene therapy. Aug. 1, 2015;26(8):498-505.

Ewing et al., Base-calling of automated sequencer traces using phred. II. Error probabilities. Genome research. Mar. 1, 1998;8(3):186-94.

Ewing et al., Base-calling of automated sequencer traces usingPhred. I. Accuracy assessment. Genome research. Mar. 1, 1998;8(3):175-85.

Findeis et al., Targeted delivery of DNA for gene therapy via receptors. Trends in biotechnology. May 1, 1993;11(5):202-5.

(56) References Cited

OTHER PUBLICATIONS

Galli et al., The end of omics? High dimensional single cell analysis in precision medicine. European journal of immunology. Feb. 2019;49(2):212-20.
Gan et al., Identification of cancer subtypes from single-cell RNA-seq data using a consensus clustering method. BMC medical genomics. Dec. 1, 2018;11(6):117.
Gomez-Acata et al., Methods for extracting'omes from microbialites. Journal of microbiological methods. May 1, 2019;160:1-10.
Gondhalekar et al., Alternatives to current flow cytometry data analysis for clinical and research studies. Methods. Feb. 1, 2018;134:113-29.
Heng et al., Comparison of enzymatic and non-enzymatic means of dissociating adherent monolayers of mesenchymal stem cells. Biological procedures online. Dec. 2009;11(1):161-9.
Huang et al., High throughput single cell RNA sequencing, bioinformatics analysis and applications. Advances in Experimental Medicine and Biology. 2018;1068:33-43.
Jazayeri et al., RNA-SEQ: a glance at technologies and methodologies. Acta Biológica Colombiana. May 2015;20(2):23-35.
Kaplitt et al., Long-term gene expression and phenotypic correction using adeno-associated virus vectors in the mammalian brain. Nature genetics. Oct. 1994;8(2):148-54.
Kashima et al., An Informative Approach to Single-Cell Sequencing Analysis. Advances in Experimental Medicine and Biology. 2019;1129:81-96.
Kimura et al., Retroviral delivery of DNA into the livers of transgenic mice bearing premalignant and malignant hepatocellular carcinomas. Human gene therapy. Jul. 1, 1994;5(7):845-52.
Kiselev et al., hemberg-lab/scRNA.seq.course. GitHub. Oct. 15, 2020:5 pages. https://github.com/hemberg-lab/scRNA.seq.course [last accessed Jan. 19, 2021].
Kulkarni et al., Beyond bulk: a review of single cell transcriptomics methodologies and applications. Current opinion in biotechnology. Aug. 1, 2019;58:129-36.
Macaulay et al., Single-cell multiomics: multiple measurements from single cells. Trends in Genetics. Feb. 1, 2017;33(2):155-68.
Melsted et al., kallisto. GitHub. Feb. 12, 2020:3 pages. https://github.com/pachterlab/kallisto [last accessed Dec. 14, 2020].
Millis et al., Strand-specific RNA-seq provides greater resolution of transcriptome profiling. Current genomics. May 1, 2013;14(3):173-81.
Moore et al., Isolation and Purification of DNA. In: Molecular Biology. Current Protocols in Immunology. Chapter 10:2001:10 pages.
Olsen et al., The anatomy of single cell mass cytometry data. Cytometry Part A. Feb. 2019;95(2):156-72.
Pedersen et al., mosdepth. Github. Sep. 29, 2020:13 pages. https://github.com/brentp/mosdepth [last accessed Dec. 14, 2020].
Pereira et al., RNA-seq: From reads to counts. Github. Jul. 27, 2015:1-4. http://bioinformatics-core-shared-training.github.io/cruk-bioinf-sschool/Day2/rnaSeq_align.pdf [last accessed Feb. 2, 2021].
Petrova et al., Comparative evaluation of rRNA depletion procedures for the improved analysis of bacterial biofilm and mixed pathogen culture transcriptomes. Scientific reports. Jan. 24, 2017;7(1):1-15.
Pfeifer, From next-generation resequencing reads to a high-quality variant data set. Heredity. Feb. 2017;118(2):111-24.
Philip et al., Efficient and sustained gene expression in primary T lymphocytes and primary and cultured tumor cells mediated by adeno-associated virus plasmid DNA complexed to cationic liposomes. Molecular and Cellular Biology. Apr. 1, 1994;14(4):2411-8.
Quatromoni et al., An optimized disaggregation method for human lung tumors that preserves the phenotype and function of the immune cells. Journal of leukocyte biology. Jan. 2015;97(1):201-9.
Rani, Major Histocompatibility Complex (MHC), Applications. In: Dubitzky et al., Eds. Encyclopedia of systems biology. Springer Publishing Company, Incorporated. Jan. 1, 2013:10 pages.
Scheimer, Illumina TruSeq DNA Adapters De-Mystified. Tufts University Core Facility. 2011:1-5. http://tucf-genomics.tufts.edu/documents/protocols/TUCF_Understanding_Illumina_TruSeq_Adapters.pdf [last accessed Dec. 22, 2020].
Seki et al., Single-cell DNA-seq and RNA-seq in cancer using the C1 system. Advances in Experimental Medicine and Biology. 2019;1129:27-50.
Shelton et al., nygenome/Conpair. GitHub. Jun. 24, 2018:6 pages. https://github.com/nygenome/Conpair [last accessed Dec. 14, 2020].
Soares et al., Go with the flow: advances and trends in magnetic flow cytometry. Analytical and bioanalytical chemistry. Mar. 16, 2019;411(9):1839-62.
Sun et al., Single-cell RNA sequencing reveals gene expression signatures of breast cancer-associated endothelial cells. Oncotarget. Feb. 16, 2018;9(13):10945-61.
Vaught et al., Biological sample collection, processing, storage and information management. IARC Sci Publ. 2011;163:23-42.
Vaught et al., Biospecimens and biorepositories: from afterthought to science. Cancer Epidemiol Biomarkers Prev. Feb. 2012;21(2):253-5.
Wagner et al., Measurement of mRNA abundance using RNA-seq data: RPKM measure is inconsistent among samples. Theory in biosciences. Dec. 1, 2012;131(4):281-5.
Wang, RSeQC: An RNA-seq Quality Control Package. Liguo Wang. Aug. 21, 2020:41 pages. http://rseqc.sourceforge.net/ [last accessed Jan. 19, 2021].
Wingett et al., Introduction. Babraham Institute. 2019:9 pages. http://www.bioinformatics.babraham.ac.uk/projects/fastq_screen/_build/html/index.html [last accessed Dec. 22, 2020].
Wingett, FastQ Screen. Babraham Institute. Jun. 17, 2019:5 pages. https://www.bioinformatics.babraham.ac.uk/projects/fastq_screen/ [last accessed Dec. 14, 2020].
Woffendin et al., Nonviral and viral delivery of a human immunodeficiency virus protective gene into primary human T cells. Proceedings of the National Academy of Sciences. Nov. 22, 1994;91(24):11581-5.
Wu et al., Incorporation of adenovirus into a ligand-based DNA carrier system results in retention of original receptor specificity and enhances targeted gene expression. Journal of Biological Chemistry. Apr. 15, 1994;269(15):11542-6.
Wu et al., Receptor-mediated gene delivery and expression in vivo. Journal of Biological Chemistry. Oct. 15, 1988;263(29):14621-4.
Wu et al., Receptor-mediated gene delivery in vivo. Partial correction of genetic analbuminemia in Nagase rats. Journal of Biological Chemistry. Aug. 5, 1991;266(22):14338-42.
Wu et al., Targeting genes: delivery and persistent expression of a foreign gene driven by mammalian regulatory elements in vivo. Journal of Biological Chemistry. Oct. 15, 1989;264(29):16985-7.
Zenke et al., Receptor-mediated endocytosis of transferrin-polycation conjugates: an efficient way to introduce DNA into hematopoietic cells. Proceedings of the National Academy of Sciences. May 1, 1990;87(10):3655-9.
Zilionis et al., Single-cell transcriptomics of human and mouse lung cancers reveals conserved myeloid populations across individuals and species. Immunity. May 21, 2019;50(5):1317-34.
PCT/IB2020/000928, Feb. 9, 2021, Invitation to Pay Additional Fees.
PCT/IB2020/000928, Mar. 30, 2021, International Search Report and Written Opinion.
International Search Report and Written Opinion for International Application No. PCT/IB2020/000928 mailed Mar. 30, 2021.
Invitation to Pay Additional Fees for International Application No. PCT/IB2020/000928 mailed Feb. 9, 2021.
[No Author Listed], SOLiD® Total RNA-Seq Kit. Life Technologies. Jul. 2011:1-106. 106 pages. http://tools.thermofisher.com/content/sfs/manuals/cms_078610.pdf [last accessed Dec. 22, 2020].
Conesa et al., A survey of best practices for RNA-seq data analysis. Genome biology. Jan. 26, 2016;17(1):13. 19 pages.
Fisher et al., A scalable, fully automated process for construction of sequence-ready human exome targeted capture libraries. Genome biology. Jan. 4, 2011;12(1):R1. 15 pages.
Imbeaud et al., Towards standardization of RNA quality assessment using user-independent classifiers of microcapillary electrophoresis traces. Nucleic acids research. Mar. 30, 2005;33(6):e56. 12 pages.

(56) References Cited

OTHER PUBLICATIONS

Larjo et al., Accuracy of programs for the determination of human leukocyte antigen alleles from next-generation sequencing data. Frontiers in Immunology. Dec. 13, 2017;8:1815. 9 pages.
Luecken et al., Current best practices in single?cell RNA?seq analysis: a tutorial. Molecular systems biology. Jun. 2019;15(6):e8746. 23 pages.
Macosko et al., Highly parallel genome-wide expression profiling of individual cells using nanoliter droplets. Cell. May 21, 2015;161(5):1202-14. 107 pages.
Mestan et al., Genomic sequencing in clinical trials. Journal of translational medicine. Dec. 30, 2011;9(1):222. 10 pages.
Pennartz et al., Generation of single-cell suspensions from mouse neural tissue. JoVE (Journal of Visualized Experiments). Jul. 7, 2009;(29):e1267. 4 pages.
See et al., A single-cell sequencing guide for immunologists. Frontiers in immunology. Oct. 23, 2018;9:2425. 13 pages.
Vento-Tormo et al., Single-cell reconstruction of the early maternal-fetal interface in humans. Nature. Nov. 2018;563(7731):347-53. 26 pages.
Woo et al., Genomic data analysis workflows for tumors from patient-derived xenografts (PDXs): challenges and guidelines. BMC medical genomics. Jul. 1, 2019;12(1):92. 53 pages.
[No Author Listed], Vault RNA. Wikipedia. Nov. 29, 2021. https://en.wikipedia.org/wiki/Vault_RNA#:~:text=The%20vault%20complex%20comprises%20the,transcribed%20by%20RNA%20polymerase%20III [Last accessed Jan. 12, 2022].
[No Author Listed], Automatic annotation of non-coding genes. US East Ensembl. Dec. 2021. http://useast.ensembl.org/info/genome/genebuild/ncrna.html [Last accessed Jan. 12, 2022].
[No Author Listed], Gene/Transcript Biotypes in GENCODE & Ensembl. Gencode. 2020. https://www.gencodegenes.org/pages/biotypes.html [Last accessed Jan. 12, 2022].
Albini et al., Metastasis signatures: genes regulating tumor-microenvironment interactions predict metastatic behavior. Cancer and Metastasis Reviews. Mar. 2008;27(1):75-83.
Byron et al., Translating RNA sequencing into clinical diagnostics: opportunities and challenges. Nature Reviews Genetics. May 2016;17(5):257-71.
Chen et al., New horizons in tumor microenvironment biology: challenges and opportunities. BMC medicine. Dec. 2015;13(1):1-4.
Chen et al., Turning foes to friends: targeting cancer-associated fibroblasts. Nature reviews Drug discovery. Feb. 2019;18(2):99-115.
Jia et al., Mining TCGA database for genes of prognostic value in glioblastoma microenvironment. Aging (Albany NY). Apr. 2018;10(4):592.
Ma et al., On the classification of long non-coding RNAs. RNA biology. Jun. 1, 2013;10(6):924-33.
Moncada et al., Building a tumor atlas: integrating single-cell RNA-Seq data with spatial transcriptomics in pancreatic ductal adenocarcinoma. bioRxiv. Jan. 1, 2018:254375.
Ostrander, Pseudogene. National Human Genome Research Institute. 2021. https://www.genome.gov/genetics-glossary/Pseudogene [Last accessed Jan. 12, 2022].
Singh et al., Increasing the complexity of chromatin: functionally distinct roles for replication-dependent histone H2A isoforms in cell proliferation and carcinogenesis. Nucleic acids research. Nov. 1, 2013;41(20):9284-95.
Vogt, Cancer genes. Western journal of medicine. Mar. 1993;158(3):273.
Klein et al., Droplet barcoding for single-cell transcriptomics applied to embryonic stem cells. Cell. May 21, 2015;161(5):1187-201.
PCT/IB2020/000928, Jan. 13, 2022, International Preliminary Report on Patentability.
EP 20829631.9, Jun. 25, 2024, Communication pursuant to Article 94(3) EPC.
International Preliminary Report on Patentability for International Application No. PCT/IB2020/000928 mailed Jan. 13, 2022.
Communication pursuant to Article 94(3) EPC for European Application No. 20829631.9 dated Jun. 25, 2024. 6 pages.
Moncada et al., Integrating single-cell RNA-Seq with spatial transcriptomics in pancreatic ductal adenocarcinoma using multimodal intersection analysis. bioRxiv 254375; Mar. 13, 2019. 41 pages. doi: https://doi.org/10.1101/254375.
Nathanson et al., Somatic mutations and neoepitope homology in melanomas treated with CTLA-4 blockade. Cancer immunology research. Jan. 1, 2017;5(1):84-91. Published online Dec. 12, 2016.
Ren et al., RNA-seq analysis of prostate cancer in the Chinese population identifies recurrent gene fusions, cancer-associated long noncoding RNAs and aberrant alternative splicings. Cell research. May 2012;22(5):806-21.
Tarazona et al., Data quality aware analysis of differential expression in RNA-seq with NOISeq R/Bioc package. Nucleic acids research. Dec. 2, 2015;43(21):e140-. 15 pages.
Van Allen et al., Genomic correlates of response to CTLA-4 blockade in metastatic melanoma. Science. Author Manuscript; available in PMC Oct. 7, 2016. Published in final edited form as: Oct. 9, 2015;350(6257):207-11.

* cited by examiner

Histone length (Hela)
Gene     Median length, nt
HIST1H4C    20,0
HIST1H1C    25,5
HIST1H2BK   71,0
HIST1H2AE   14,0
HIST1H3B    15,0
HIST3H2A    17,0

TECHNIQUES FOR BIAS CORRECTION IN SEQUENCE DATA

CROSS REFERENCE TO RELATED APPLICATIONS

This application claims the benefit under 35 U.S.C. § 119(e) of U.S. Provisional Application No. 62/870,622, filed Jul. 3, 2019, entitled "Compositions and Methods for Sample Preparation and Characterization of Cancer Therefrom" and U.S. Provisional Application No. 62/991,570, filed Mar. 18, 2020, entitled "Nucleic Acid Data Quality Control," the entire disclosure of each is hereby incorporated by reference.

FIELD

Some aspects of the technology described herein relate to collecting and processing of tumor and/or healthy tissue samples to extract nucleic acid and perform nucleic acid sequencing. Some aspects of the technology described herein relate to processing nucleic acid sequencing data to remove bias from the nucleic acid sequencing data. Also described herein are various methods of evaluating the quality of nucleic acid sequence information obtained by sequencing.

BACKGROUND

Correctly characterizing the type or types of cancer a patient or subject has and, potentially, selecting one or more effective therapies for the patient based on the characterization can be crucial for the survival and overall wellbeing of that patient. The manner in which biological samples from a subject are processed to obtain sequence data (e.g., RNA expression data) to characterize the type or types of cancer, and the manner in which the data is processed may have detrimental effects on the characterization of the cancer or cancers. For example, high throughput nucleic acid sequencing platforms (e.g., next generation sequencing platforms) can generate large amounts of DNA and RNA sequence data from patient samples. Advances in sample preparation, data processing, and evaluation of sequence information from different NGS platforms by custom software for characterizing cancers, predicting prognoses, identifying effective therapies, and otherwise aiding in personalized care of patients with cancer are needed.

SUMMARY

Some embodiments provide for a system comprising: at least one computer hardware processor; and at least one non-transitory computer-readable storage medium storing processor executable instructions that, when executed by the at least one computer hardware processor, cause the at least one computer hardware processor to perform a method, the method comprising: obtaining nucleic acid data comprising: sequence data indicating a nucleotide sequence for at least 5 kilobases (kb) of DNA and/or RNA from a previously obtained biological sample of a subject having, suspected of having, or at risk of having a disease; and asserted information indicating an asserted source and/or an asserted integrity of the sequence data; and validating the nucleic acid data by: processing the sequence data to obtain determined information indicating a determined source and/or a determined integrity of the sequence data; and determining whether the determined information matches the asserted information.

Some embodiments provide at least one non-transitory computer-readable storage medium storing processor executable instructions that, when executed by at least one computer hardware processor, cause the at least one computer hardware processor to perform a method.

The method comprising: obtaining nucleic acid data comprising: sequence data indicating a nucleotide sequence for at least 5 kilobases (kb) of DNA and/or RNA from a previously obtained biological sample of a subject having, suspected of having, or at risk of having a disease; and asserted information indicating an asserted source and/or an asserted integrity of the sequence data; and validating the nucleic acid data by: processing the sequence data to obtain determined information indicating a determined source and/or a determined integrity of the sequence data; and determining whether the determined information matches the asserted information.

Some embodiments using at least one computer hardware processor to perform: obtaining nucleic acid data comprising: sequence data indicating a nucleotide sequence for at least 5 kilobases (kb) of DNA and/or RNA from a previously obtained biological sample of a subject having, suspected of having, or at risk of having a disease; and asserted information indicating an asserted source and/or an asserted integrity of the sequence data; and validating the nucleic acid data by: processing the sequence data to obtain determined information indicating a determined source and/or a determined integrity of the sequence data; and determining whether the determined information matches the asserted information.

In some embodiments, the sequence data may include raw DNA or RNA sequence data, DNA exome sequence data (e.g., from whole exome sequencing (WES), DNA genome sequence data (e.g., from whole genome sequencing (WGS)), RNA expression data, gene expression data, bias-corrected gene expression data or any other suitable type of sequence data comprising data obtained from a sequencing platform and/or comprising data derived from data obtained from a sequencing platform.

In some embodiments, the method further comprises processing the sequence data to determine whether the sequence data is indicative of one or more disease features when it is determined that the asserted information matches the determined information.

In some embodiments, the method further comprises determining that the determined information matches the asserted information; and processing the sequence data to determine whether it is indicative of one or more disease features.

In some embodiments, the method further comprises generating an indication: that the determined information does not match the asserted information, to not process the sequence data in a subsequent analysis, and/or to obtain additional sequence data and/or other information about the biological sample and/or the subject, when it is determined that the asserted information does not match the determined information.

In some embodiments, the method further comprises: determining that the asserted information does not match the determined information; and generating an indication: that the determined information does not match the asserted information, to not process the sequence data in a subsequent analysis, and/or to obtain additional sequence data and/or other information about the biological sample and/or the subject.

In some embodiments, the asserted information indicates the asserted source of the sequence data, the method further comprising processing the sequence data to obtain determined information indicative of a determined source for the sequence data; and determining whether the determined source matches the asserted source for the sequence data.

In some embodiments, the determined information indicative of the determined source for the sequence data is indicative of an MHC genotype of the subject; whether the nucleic acid data is RNA data or DNA data; a tissue type of the biological sample; a tumor type of the biological sample; a sequencing platform used to generate the sequence data; SNP concordance, and/or a whether an RNA sample is polyA enriched.

In some embodiments, the determined information indicative of the determined source for the sequence data is indicative of at least two of an MHC genotype of the subject; whether the nucleic acid data is RNA data or DNA data; a tissue type of the biological sample; a tumor type of the biological sample; a sequencing platform used to generate the sequence data; SNP concordance, and a whether an RNA sample is polyA enriched.

In some embodiments, the determined information indicative of the determined source for the sequence data is indicative of at least three of an MHC genotype of the subject; whether the nucleic acid data is RNA data or DNA data; a tissue type of the biological sample; a tumor type of the biological sample; a sequencing platform used to generate the sequence data; SNP concordance, and a whether an RNA sample is polyA enriched.

In some embodiments, the asserted information indicates the asserted integrity of the sequence data, the method further comprising: processing the sequence data to obtain determined information indicative of a determined integrity of the sequence data; and determining whether the determined integrity matches the asserted integrity for the sequence data.

In some embodiments, the determined information indicative of the determined integrity is indicative of total sequence coverage; exon coverage; chromosomal coverage; a ratio of nucleic acids encoding two or more subunits of a multimeric protein; species contamination; single nucleotide polymorphisms (SNPs); complexity; and/or guanine (G) and cytosine (C) percentage (%) of the sequence data.

In some embodiments, the determined information indicative of the determined integrity is indicative of at least two of total sequence coverage; exon coverage; chromosomal coverage; a ratio of nucleic acids encoding two or more subunits of a multimeric protein; species contamination; single nucleotide polymorphisms (SNPs); complexity; and guanine (G) and cytosine (C) percentage (%) of the sequence data.

In some embodiments, the determined information indicative of the determined integrity is indicative of at least three of total sequence coverage; exon coverage; chromosomal coverage; a ratio of nucleic acids encoding two or more subunits of a multimeric protein; species contamination; single nucleotide polymorphisms (SNPs); complexity; and guanine (G) and cytosine (C) percentage (%) of the sequence data.

In some embodiments, the asserted information for the sequence data comprises MHC allele information for the subject.

In some embodiments, the method further comprises determining one or more MHC allele sequences from the sequence data and determining whether the one or more MHC alleles sequences match the asserted MHC allele information for the subject.

In some embodiments, determining the one or more MHC allele sequences comprises determining MHC allele sequences for six MHC loci from the sequence data.

In some embodiments, wherein the sequence data indicates the nucleotide sequence for RNA, the asserted information indicates whether the RNA is polyA enriched.

In some embodiments, determining, using the sequence data, a therapy for the subject when it is determined that the asserted information matches the determined information.

In some embodiments, determining the therapy comprises: determining a plurality of gene group expression levels, the plurality of gene group expression levels comprising a gene group expression level for each gene group in a set of gene groups, wherein the set of gene groups comprises at least one gene group associated with cancer malignancy, and at least one gene group associated with cancer microenvironment; and identifying the therapy using the determined gene group expression levels.

In some embodiments, the method further comprises administering the therapy to the subject.

In some embodiments, wherein it is determined that the determined information matches the asserted information, the sequence data is processed to determine a therapy for the subject, and the therapy is administered to the subject.

In some embodiments, wherein the disease is cancer, and the therapy is a cancer treatment. In some embodiments, the subject is human.

In some embodiments, processing the sequence data to obtain the determined source comprises determining one or more single nucleotide polymorphisms (SNPs) in the sequence data, and determining whether the one or more SNPs in the sequence data match one or more SNPs in a reference sequence.

In some embodiments, the reference sequence is a sequence of a nucleic acid in a second biological sample of the subject.

In some embodiments, processing the sequence data to obtain a determined integrity comprises: determining a first level of a first nucleic acid encoding a first subunit of a multimeric protein, determining a second level of a second nucleic acid encoding a second subunit of a multimeric protein, and determining whether a ratio between the first level and the second level matches an expected ratio. In some embodiments, the multimeric protein is a dimer. In some embodiments, the first subunit and the second subunits are first and second CD3 subunits, first and second CD8 subunits, or first and second CD79 subunits.

Some embodiments provide for a system for identifying a cancer treatment for a subject having, suspected having, or at risk of having cancer, the system comprising: at least one sequencing platform configured to generate gene expression data from enriched RNA obtained from a first biological sample previously obtained from the subject, wherein the enriched RNA was obtained by: (i) extracting RNA from the first biological sample of the first tumor to obtain extracted RNA; and (ii) enriching the extracted RNA for coding RNA to obtain enriched RNA, wherein the RNA expression data comprises at least 5 kilobases (kb); at least one computer hardware processor; and at least one non-transitory computer-readable storage medium storing processor-executable instructions that, when executed by the at least one computer hardware processor, cause the at least one computer hardware processor to perform: obtaining the RNA expression data using the at least one sequencing platform; converting the RNA expression data to gene expression data; determining bias-corrected gene expression data from the gene expression data at least in part by removing, from the gene expression data, expression data for at least one gene that introduces bias in the gene expression data; and identifying a cancer treatment for the subject using the bias-corrected gene expression data.

Some embodiments provide for a system for identifying a cancer treatment for a subject having, suspected having, or at risk of having cancer, the system comprising: at least one computer hardware processor; and at least one non-transitory computer-readable storage medium storing processor-executable instructions that, when executed by the at least one computer hardware processor, cause the at least one computer hardware processor to perform: obtaining RNA expression data from at least one sequencing platform, the RNA expression data comprising at least 5 kilobases (5kb), wherein the RNA expression data was obtained, from a first biological sample of a first tumor previously obtained from the subject, at least in part by: (i) extracting RNA from the first biological sample of the first tumor to obtain extracted RNA; and (ii) enriching the extracted RNA for coding RNA to obtain enriched RNA; converting the RNA expression data to gene expression data; determining bias-corrected gene expression data from the gene expression data at least in part by removing, from the gene expression data, expression data for at least one gene that introduces bias in the gene expression data; and identifying a cancer treatment for the subject using the bias-corrected gene expression data. The system may further comprise the at least one sequencing platform in some embodiments.

Some embodiments provide for at least one non-transitory computer-readable storage medium storing processor-executable instructions that, when executed by at least one computer hardware processor, cause the at least one computer hardware processor to perform: obtaining RNA expression data from at least one sequencing platform, the RNA expression data comprising at least 5 kilobases (5kb), wherein the RNA expression data was obtained, from a first biological sample of a first tumor previously obtained from a subject having, suspected of having or at risk of having cancer, at least in part by: (i) extracting RNA from the first biological sample of the first tumor to obtain extracted RNA; and (ii) enriching the extracted RNA for coding RNA to obtain enriched RNA; converting the RNA expression data to gene expression data; determining bias-corrected gene expression data from the gene expression data at least in part by removing, from the gene expression data, expression data for at least one gene that introduces bias in the gene expression data; and identifying a cancer treatment for the subject using the bias-corrected gene expression data.

Some embodiments provide for a method comprising: obtaining a first biological sample of a first tumor, the first biological sample previously obtained from a subject having, suspected of having or at risk of having cancer; extracting RNA from the first biological sample of the first tumor to obtain extracted RNA; enriching the extracted RNA for coding RNA to obtain enriched RNA; sequencing, using at least one sequencing platform, the enriched RNA to obtain RNA expression data comprising at least 5 kilobases (kb); using at least one computer hardware processor to perform: obtaining the RNA expression data using the at least one sequencing platform; converting the RNA expression data to gene expression data; determining bias-corrected gene expression data from the gene expression data at least in part by removing, from the gene expression data, expression data for at least one gene that introduces bias in the gene expression data; and identifying a cancer treatment for the subject using the bias-corrected gene expression data.

In some embodiments, the method further comprises administering the identified cancer treatment to the subject.

In some embodiments, enriching the RNA for coding RNA comprises performing polyA enrichment.

In some embodiments, the at least one gene that introduces bias in the gene expression data comprises: a gene having an average transcript length that is higher or lower than an average length of transcripts in the gene expression data; a gene having at least a threshold variation in average transcript expression level based on transcript expression levels in reference samples; and/or a gene that has a polyA tail that is at least a threshold amount smaller in length compared to an average length of polyA tails of genes from: the first biological sample from which the RNA expression data was obtained and/or a reference sample.

In some embodiments, the at least one gene that introduces bias in the gene expression data belongs to a family of genes selected from the group consisting of: histone-encoding genes, mitochondrial genes, interleukin-encoding genes, collagen-encoding genes, B-cell receptor-encoding genes, and T cell receptor-encoding genes.

In some embodiments, the at least one gene comprises at least one histone-encoding gene selected from the group consisting of: HIST1H1A, HIST1H1B, HIST1H1C, HIST1H1D, HIST1H1E, HIST1H1T, HIST1H2AA, HIST1H2AB, HIST1H2AC, HIST1H2AD, HIST1H2AE, HIST1H2AG, HIST1H2AH, HIST1H2AI, HIST1H2AJ, HIST1H2AK, HIST1H2AL, HIST1H2AM, HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2BO, HIST1H3A, HIST1H3B, HIST1H3C, HIST1H3D, HIST1H3E, HIST1H3F, HIST1H3G, HIST1H3H, HIST1H3I, HIST1H3J, HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L, HIST2H2AA3, HIST2H2AA4, HIST2H2AB, HIST2H2AC, HIST2H2BE, HIST2H2BF, HIST2H3A, HIST2H3C, HIST2H3D, HIST2H3PS2, HIST2H4A, HIST2H4B, HIST3H2A, HIST3H2BB, HIST3H3, and HIST4H4.

In some embodiments, the at least one gene comprises at least one mitochondrial gene selected from the group consisting of: MT-ATP6, MT-ATP8, MT-CO1, MT-CO2, MT-CO3, MT-CYB, MT-ND1, MT-ND2, MT-ND3, MT-ND4, MT-ND4L, MT-ND5, MT-ND6, MT-RNR1, MT-RNR2, MT-TA, MT-TC, MT-TD, MT-TE, MT-TF, MT-TG, MT-TH, MT-TI, MT-TK, MT-TL1, MT-TL2, MT-TM, MT-TN, MT-TP, MT-TQ, MT-TR, MT-TS1, MT-TS2, MT-TT, MT-TV, MT-TW, MT-TY, MTRNR2L1, MTRNR2L10, MTRNR2L11, MTRNR2L12, MTRNR2L13, MTRNR2L3, MTRNR2L4, MTRNR2L5, MTRNR2L6, MTRNR2L7, and MTRNR2L8.

In some embodiments, determining the bias-corrected gene expression data further comprises: after removing the expression data for the at least one gene that introduces bias in the gene expression data, renormalizing the gene expression data.

In some embodiments, converting the RNA expression data to gene expression data comprises: removing non-coding transcripts from the RNA expression data to obtain filtered RNA expression data; and after removing the noncoding transcripts, normalizing the filtered RNA expression data to obtain gene expression data in transcripts per million (TPM) and/or any other suitable format.

In some embodiments, removing the non-coding transcripts from the RNA expression data comprises removing non-coding transcripts that belong to groups selected from the list consisting of: pseudogenes, polymorphic pseudogenes, processed pseudogenes, transcribed processed pseudogenes, unitary pseudogenes, unprocessed pseudogenes, transcribed unitary pseudogenes, constant chain immunoglobulin (IG C) pseudogenes, joining chain immunoglobulin (IG J) pseudogenes, variable chain immunoglobulin (IG V) pseudogenes, transcribed unprocessed pseudogenes, translated unprocessed pseudogenes, joining chain T cell receptor (TR J) pseudogenes, variable chain T cell receptor (TR V) pseudogenes, small nuclear RNAs (snRNA), small nucleolar RNAs (snoRNA), microRNAs (miRNA), ribozymes, ribosomal RNA (rRNA), mitochondrial tRNAs (Mt tRNA), mitochondrial rRNAs (Mt rRNA), small Cajal body-specific RNAs (scaRNA), retained introns, sense intronic RNA, sense overlapping RNA, nonsense-mediated decay RNA, non-stop decay RNA, antisense RNA, long intervening noncoding RNAs (lincRNA), macro long non-coding RNA (macro lncRNA), processed transcripts, 3prime overlapping non-coding RNA (3prime overlapping ncrna), small RNAs (sRNA), miscellaneous RNA (misc RNA), vault RNA (vaultRNA), and TEC RNA.

In some embodiments, information (e.g., sequence information) for one or more transcripts for one of more of these types of transcripts can be obtained in a nucleic acid database (e.g., a Gencode database, for example Gencode V23, Genbank database, EMBL database, or other database).

In some embodiments, the method further comprises, prior to performing the removal of the non-coding transcripts, aligning the RNA expression data to a reference; and annotating the RNA expression data.

In some embodiments, the RNA expression data comprises at least 25 million paired-end reads. In some embodiments, the RNA expression data comprises at least 50 million paired-end reads, with an average read length of at least 100 bp.

In some embodiments, identifying the cancer treatment for the subject using the bias-corrected gene expression data comprises: determining, using the bias-corrected gene expression data, a plurality of gene group expression levels, the plurality of gene group expression levels comprising a gene group expression level for each gene group in a set of gene groups, wherein the set of gene groups comprises at least one gene group associated with cancer malignancy, and at least one gene group associated with cancer microenvironment; and identifying the cancer treatment using the determined gene group expression levels.

In some embodiments, the cancer treatment is selected from the group consisting of a radiation therapy, a surgical therapy, a chemotherapy, and an immunotherapy.

In some embodiments, the method further comprises obtaining a second biological sample of a second tumor, the second biological sample previously obtained from the subject.

In some embodiments, the method further comprises combining the first biological sample and the second biological sample to form a combined tumor sample, and extracting the RNA comprises extracting the RNA from the combined tumor sample.

In some embodiments, the method further comprises extracting RNA from the second biological sample; and combining the RNA extracted from the second biological sample with the RNA extracted from the first biological sample to form combined extracted RNA, and enriching the RNA for coding RNA comprises enriching the combined extracted RNA for coding RNA.

In some embodiments, the extracted RNA comprises at least 1 µg of RNA upon RNA extraction.

In some embodiments, the extracted RNA is at least 1000-6000 ng in total mass, and has a purity corresponding to a ratio of absorbance at 260 nm to absorbance at 280 nm of at least 2.0.

In some embodiments, the method further comprises performing quality control assessment on the RNA expression data at least in part by: obtaining asserted information indicating an asserted source and/or an asserted integrity of the RNA expression data; processing the RNA expression data to obtain determined information indicating a determined source and/or a determined integrity of the RNA expression data; and determining whether the determined information matches the asserted information.

In some embodiments, processing the RNA expression data comprises processing the RNA expression RNA to determine: a tissue type of the first biological sample; a tumor type of the first biological sample; and/or guanine (G) and/or cytosine (C) percentage (%).

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. The drawings are not necessarily drawn to scale.

FIG. 1A provides an example of a process pipeline that includes one or more quality control assessments during biopsy sample collection, DNA/RNA extraction and library construction, and/or nucleic acid bioinformatic analysis. FIG. 1B provides an example of a process for obtaining a biopsy sample of a subject, extracting nucleic acid from the sample, sequencing the nucleic acid, and processing the nucleic acid sequence to identify one or more cancer therapies appropriate for the subject.

FIG. 2A provides a graphical representation of distribution of RNA after RNA enrichment by either depletion of ribosomal RNA (r-RNA) or by poly A enrichment. FIG. 2B provides a graphical representation of levels of RNA measured after RNA sequencing of either stranded or non-stranded RNA for IL24, ICAM4, and GAPDH.

Figure 20:
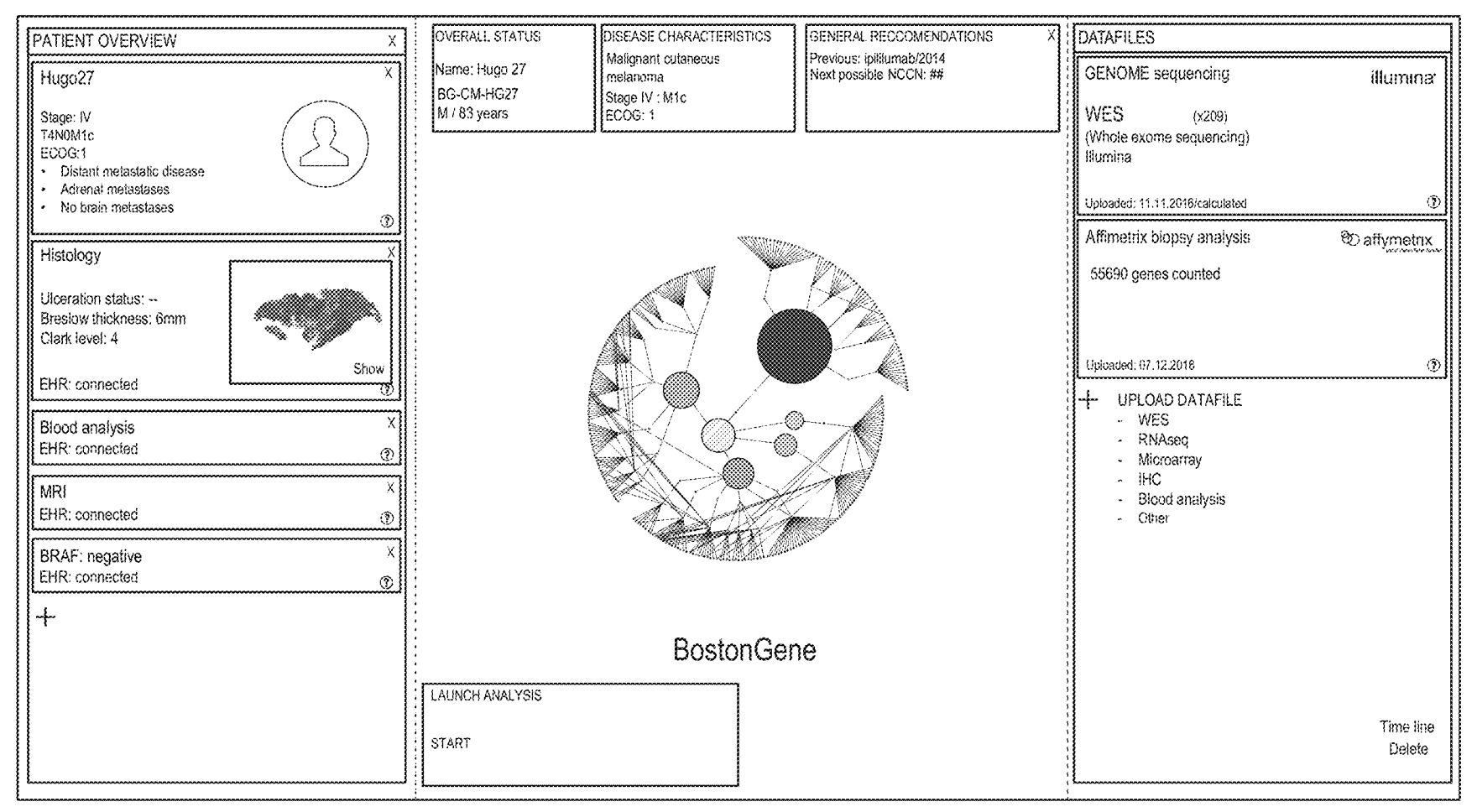

FIG. 20 is a screenshot presenting the selected patient's information provided to the user in response to the user selecting the patient.

Figure 25:
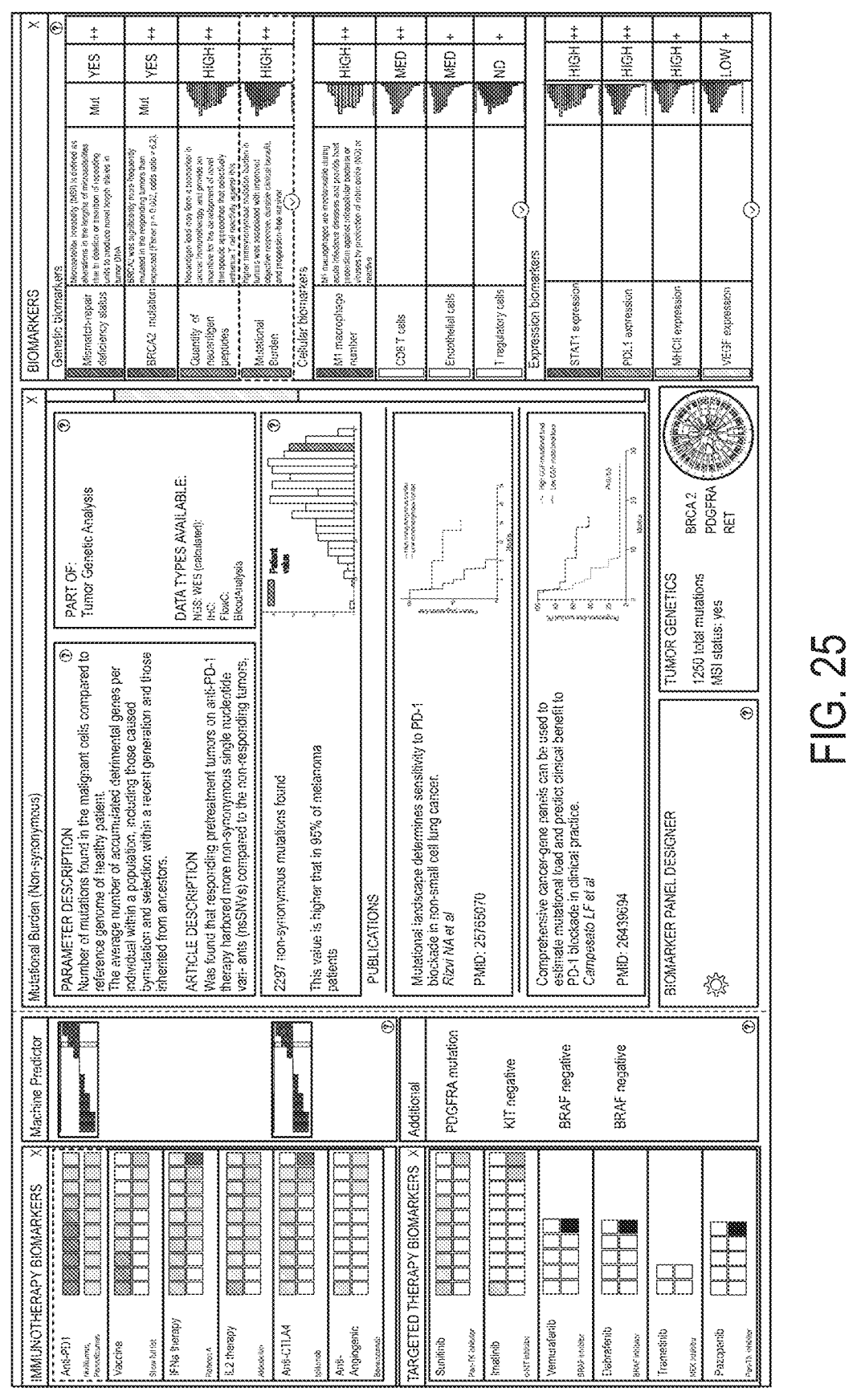

FIG. 25 is a screenshot presenting information relating to the mutational burden biomarker (as shown in the middle panel) provided in response to the user selecting the mutational burden biomarker.

provided in response to the user selecting anti-PD1 immunotherapy (as shown in the left panel).

Figure 31:
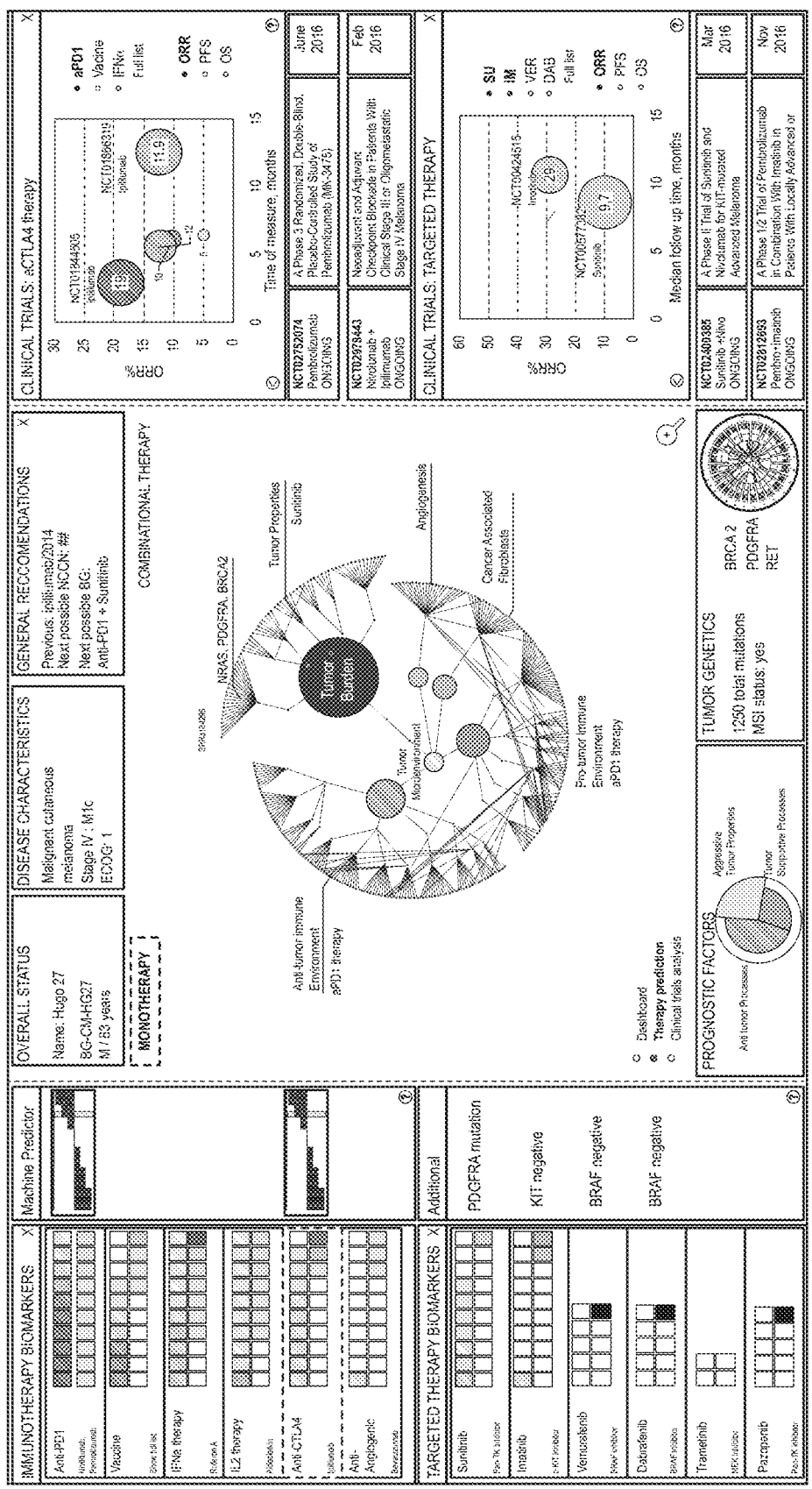

FIG. 31 is a screenshot presenting clinical trial data relating to anti-CTLA4 therapy effectivity in patients having stage IV metastatic melanoma (as shown in the right panel) provided in response to the user selecting anti-CTLA4 immunotherapy (as shown in the left panel).

Figure 32:
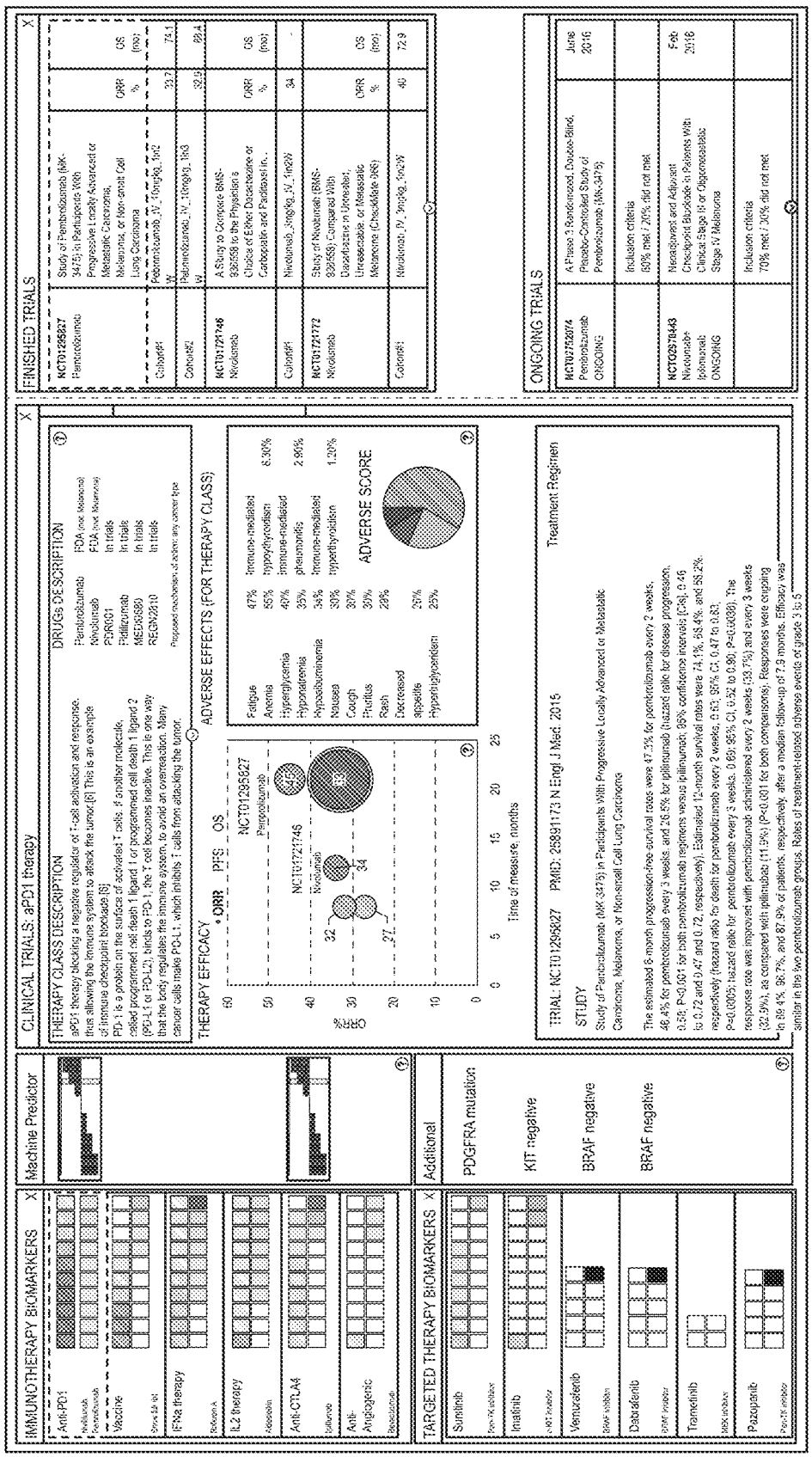

FIG. 32 is a screenshot presenting clinical trial data relating to the NCT01295827 clinical trial of anti-PD1 treatment (as shown in the middle panel) provided in response to the user selecting the NCT01295827 clinical trial (as shown in the right panel).

Figure 33:
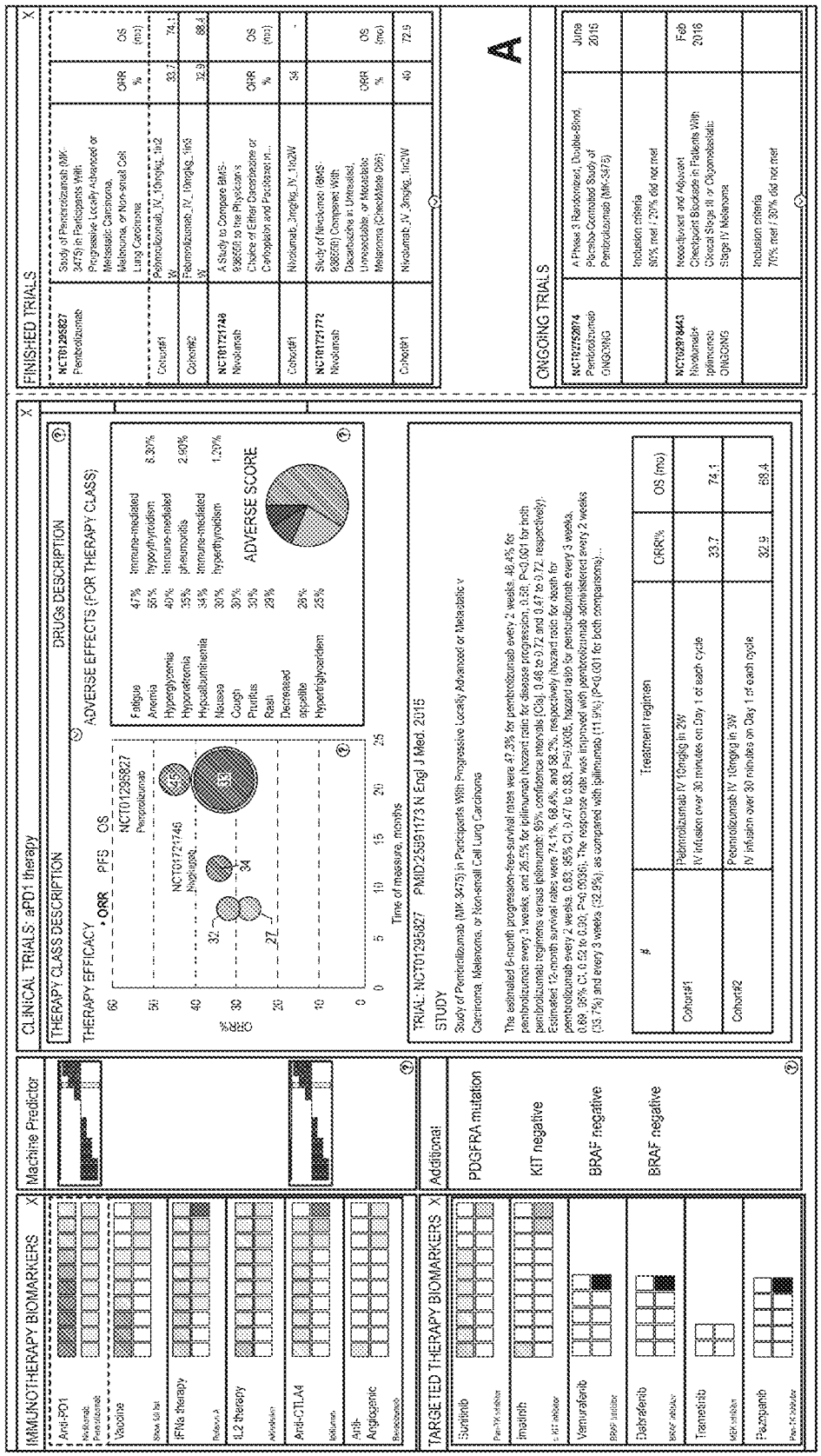

FIG. 33 is a screenshot presenting the treatment regimen of the selected clinical data provided in response to the user minimizing the therapy class description and drug description portions. The screen may also present information relating to ongoing clinical trials (marked by the letter A).

Figure 34:
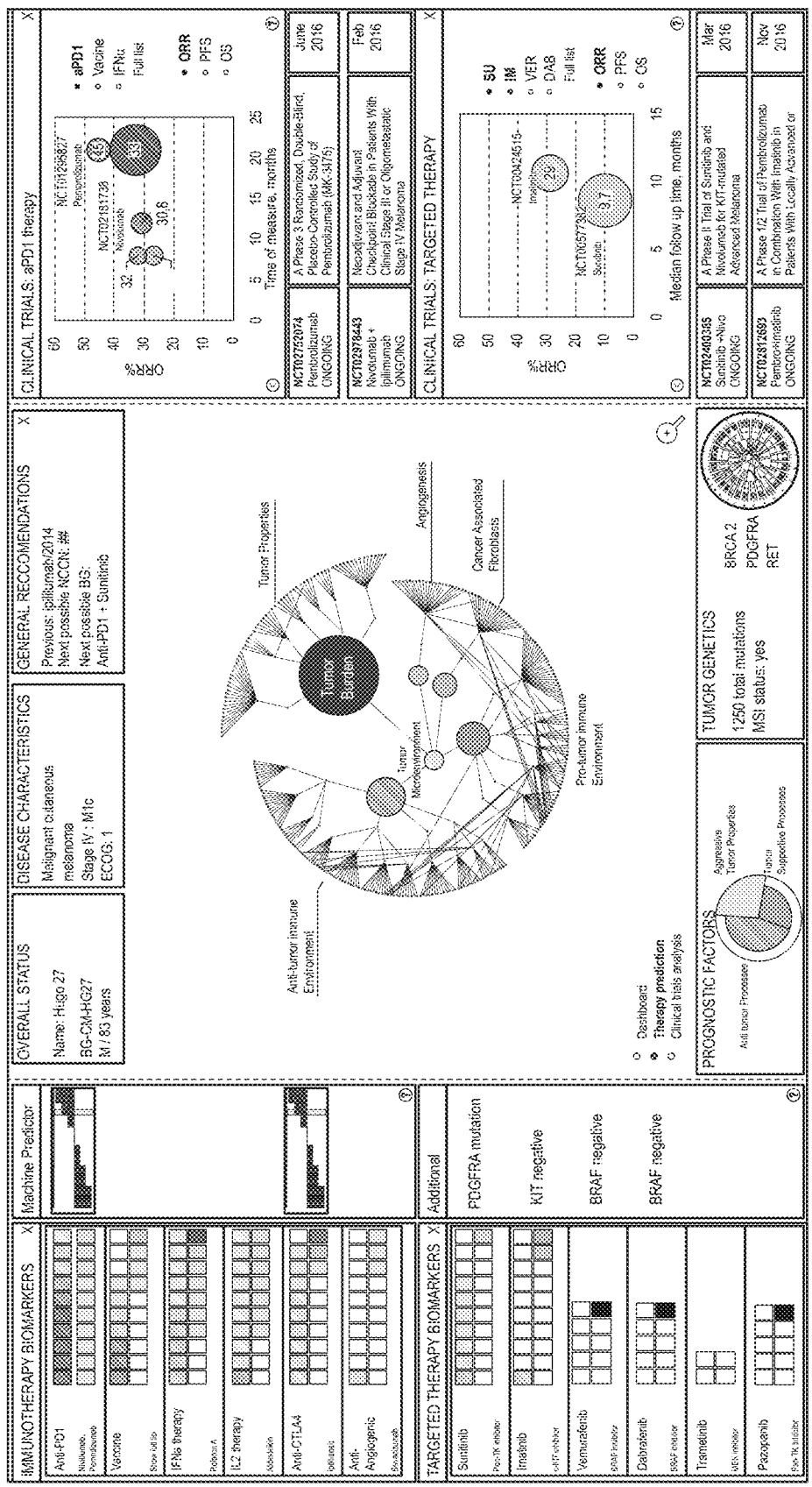

FIG. 34 is a screenshot presenting a patient's MF profile (as shown in the middle panel).

Figure 35:
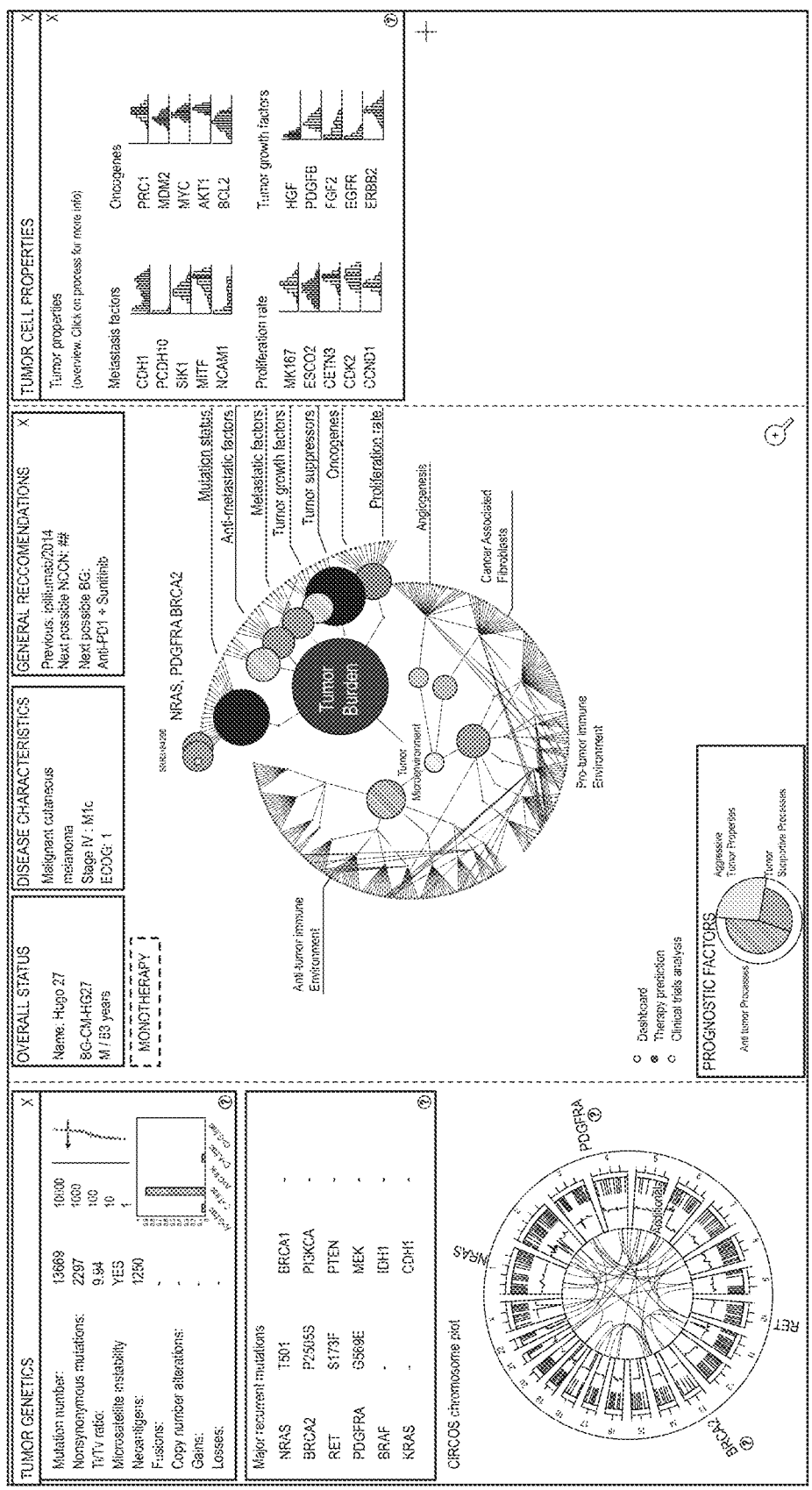

FIG. 35 is a screenshot presenting additional gene groups associated with the tumor properties gene group provided to the user in response to selecting the tumor properties gene group.

Figure 36:
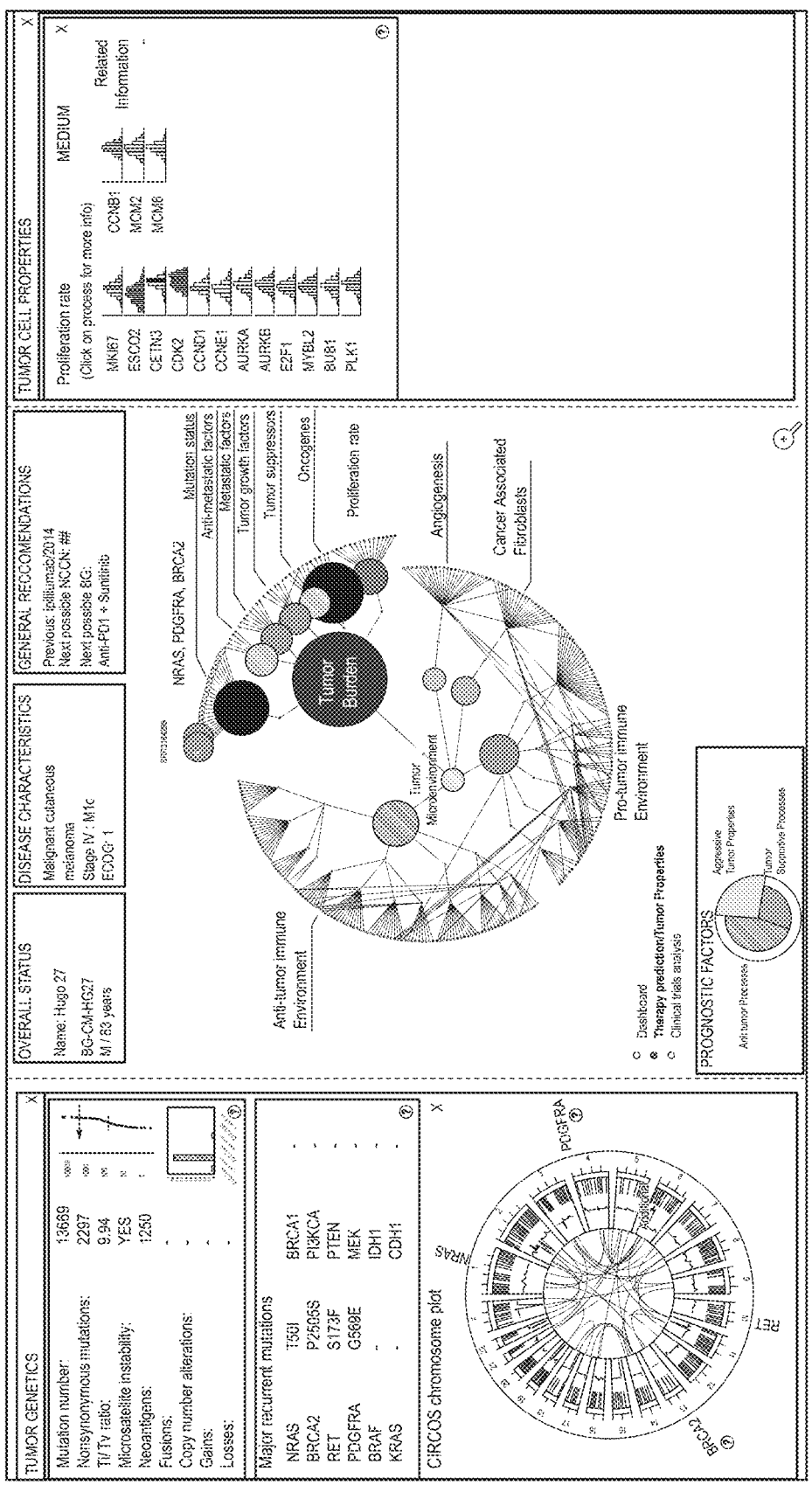

FIG. 36 is a screenshot presenting information relating to the tumor proliferation rate (as shown in the right panel) provided in response to the user selecting the tumor proliferation rate gene group (as shown in highlighting) in the MF profile.

Figure 37:
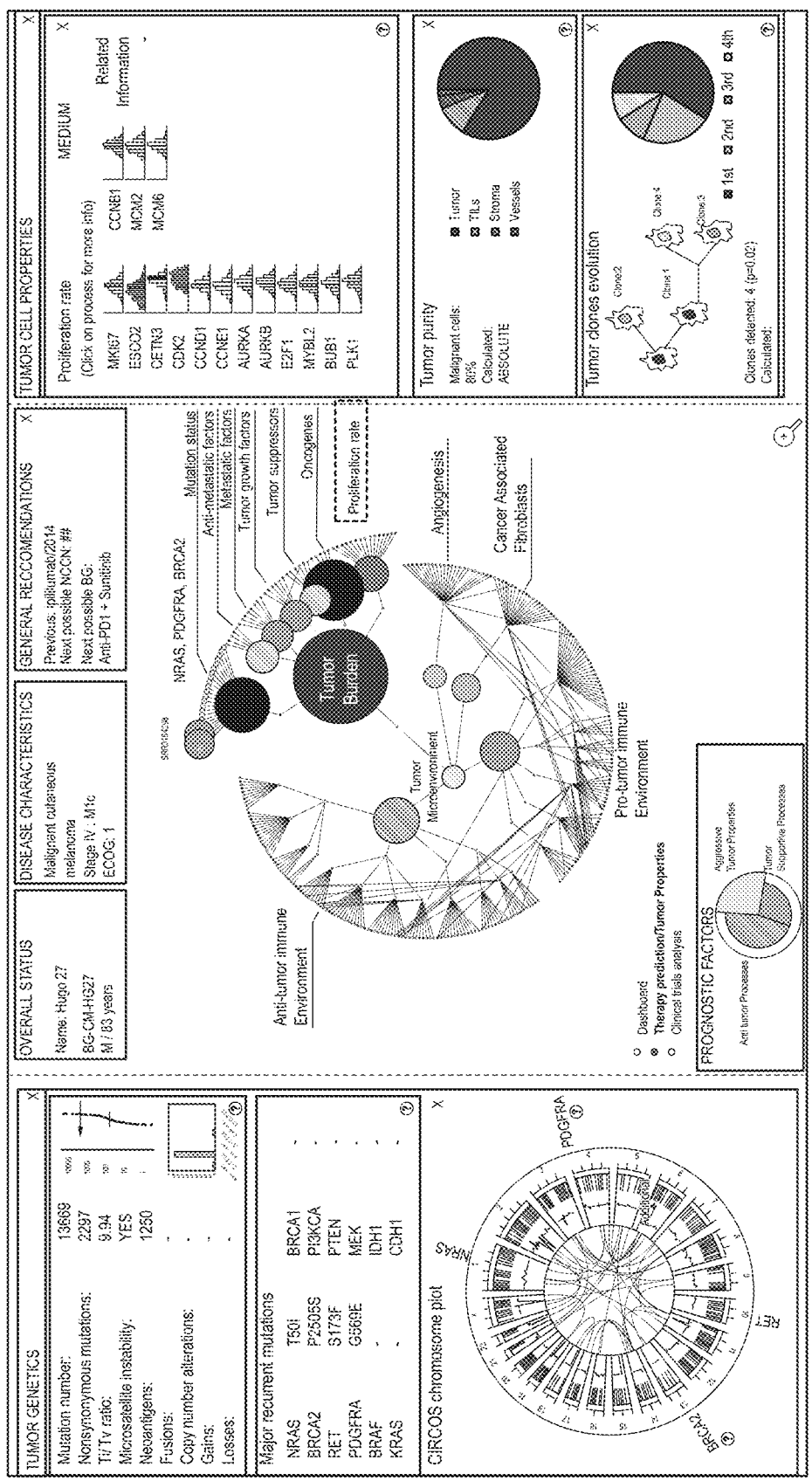

FIG. 37 is a screenshot presenting information relating to the purity of the patient's tumor in the tumor purity portion (as shown in the lower right panel) and information relating to the clonal evolution of the patient's tumor in the tumor clones evolution portion (as shown in the lower right panel).

Figure 38:
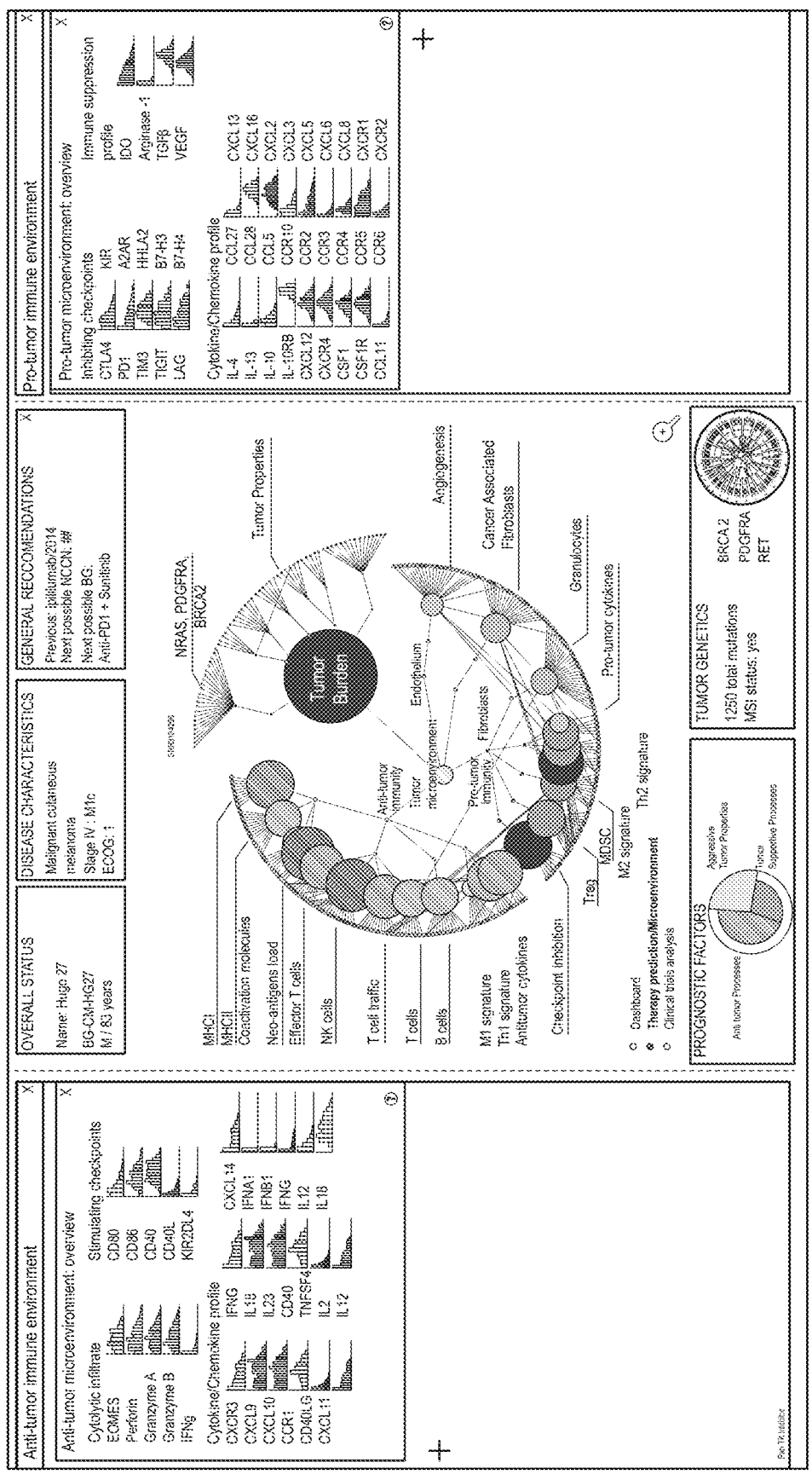

FIG. 38 is a screenshot presenting information relating to the anti-tumor immune environment (as shown in the left panel) provided in response to the user selecting the anti-tumor immune environment gene group and information relating to the pro-tumor immune environment (as shown in the right panel) in response to the user selecting the pro-tumor immune environment gene group.

Figure 39:
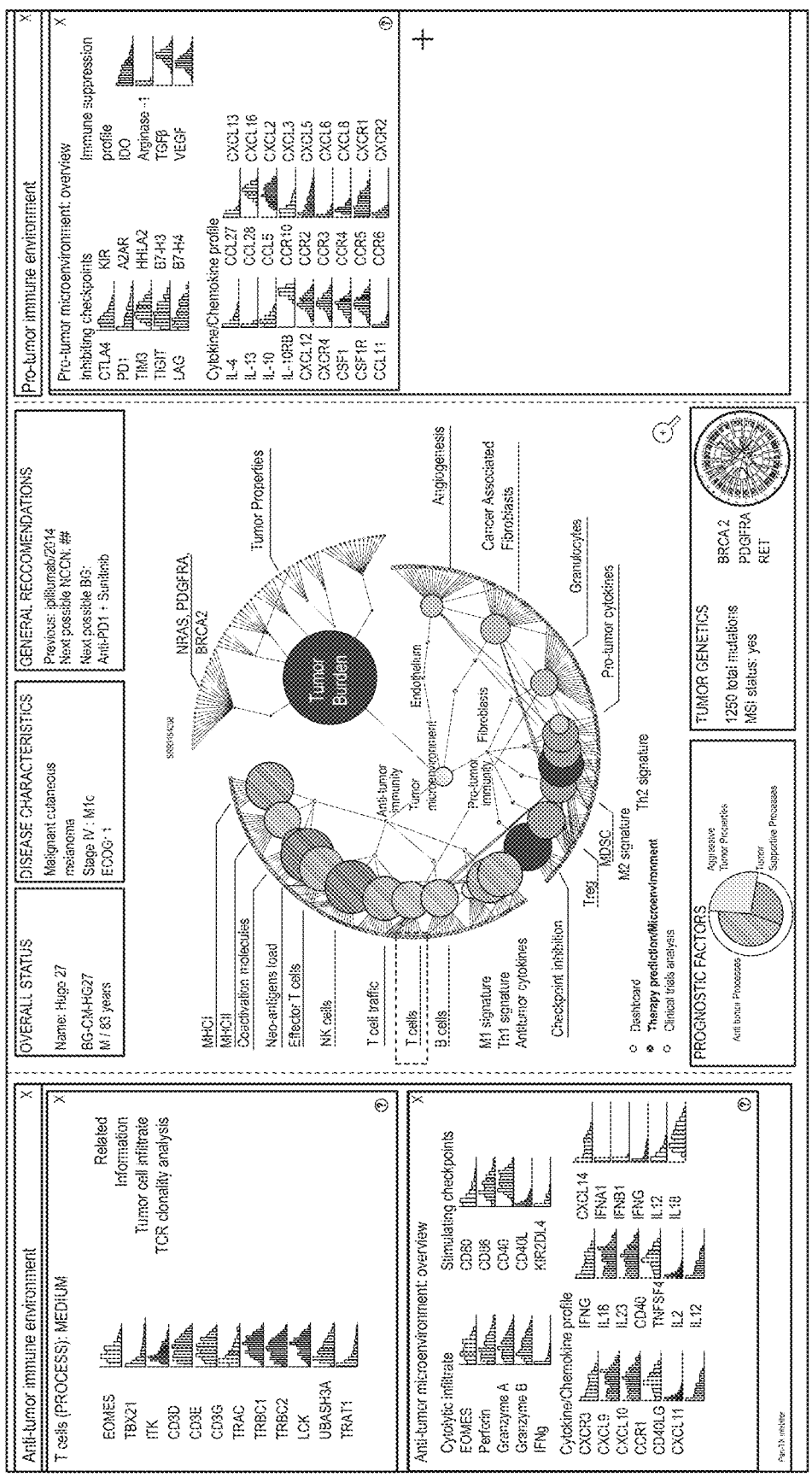

FIG. 39 is a screenshot presenting information relating to expression of genes that determine T cell activity within the tumor in the anti-tumor microenvironment portion (as shown in the lower left panel) provided in response to the user selecting the T cell gene group in the MF profile (as shown by highlighting).

Figure 40:
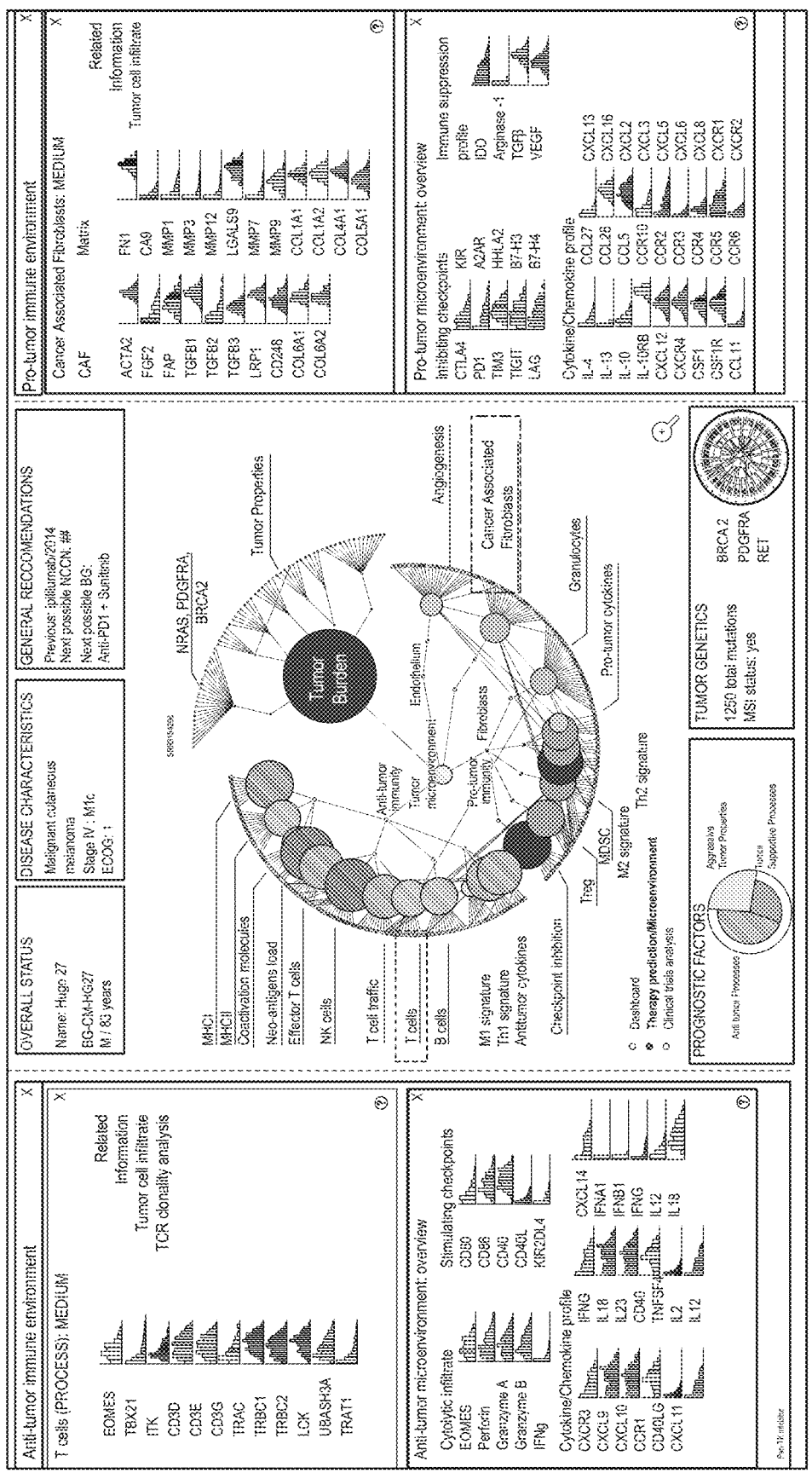

FIG. 40 is a screenshot presenting information relating to expression of genes that determine cancer associated fibroblast activity within the tumor in the pro-tumor microenvironment portion (as shown in the lower right panel) provided in response to the user selecting the cancer associated fibroblast gene group in the MF profile (as shown by highlighting).

Figure 41:
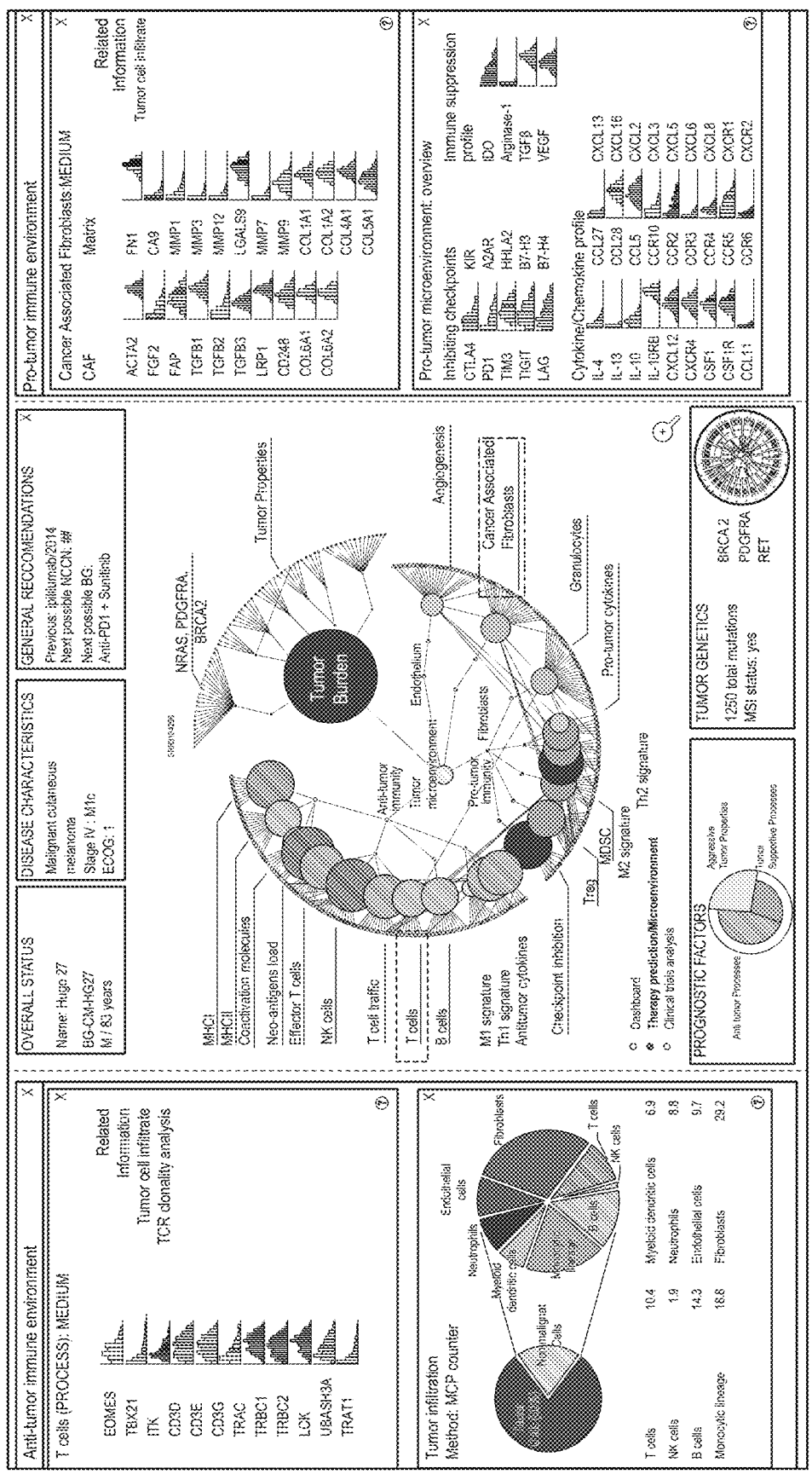

FIG. 41 is a screenshot presenting information relating to the number of non-malignant cells in the patient's tumor (as shown in the lower left panel) provided in response to the user selecting tumor infiltrate in the anti-tumor immune environment portion (as shown in the upper left panel).

Figure 42:
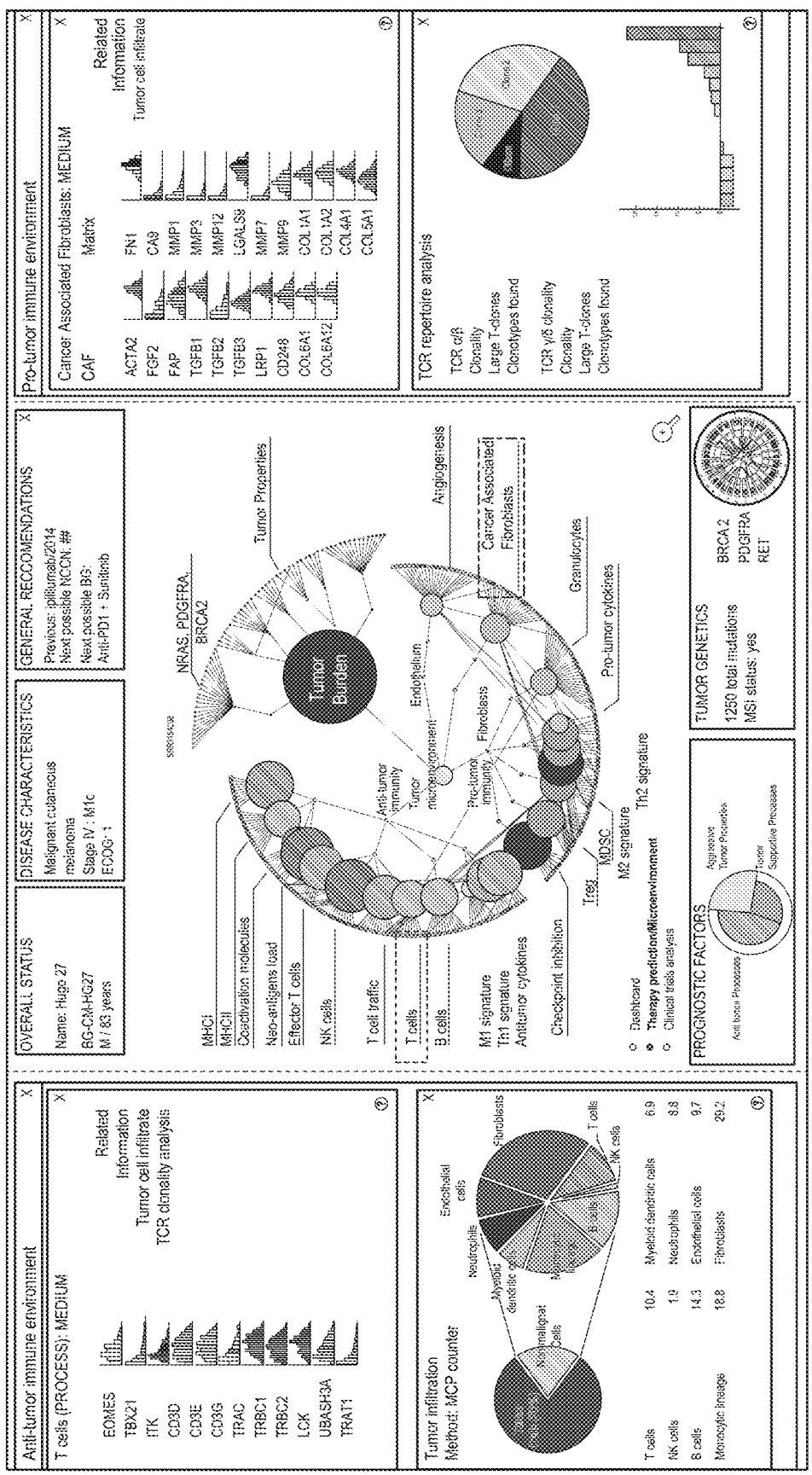

FIG. 42 is a screenshot presenting information relating to the TCR repertoire in the patient's tumor (as shown in the lower right panel) provided in response to the user selecting tumor infiltrate in the pro-tumor immune environment portion (as shown in the upper right panel).

Figure 43:
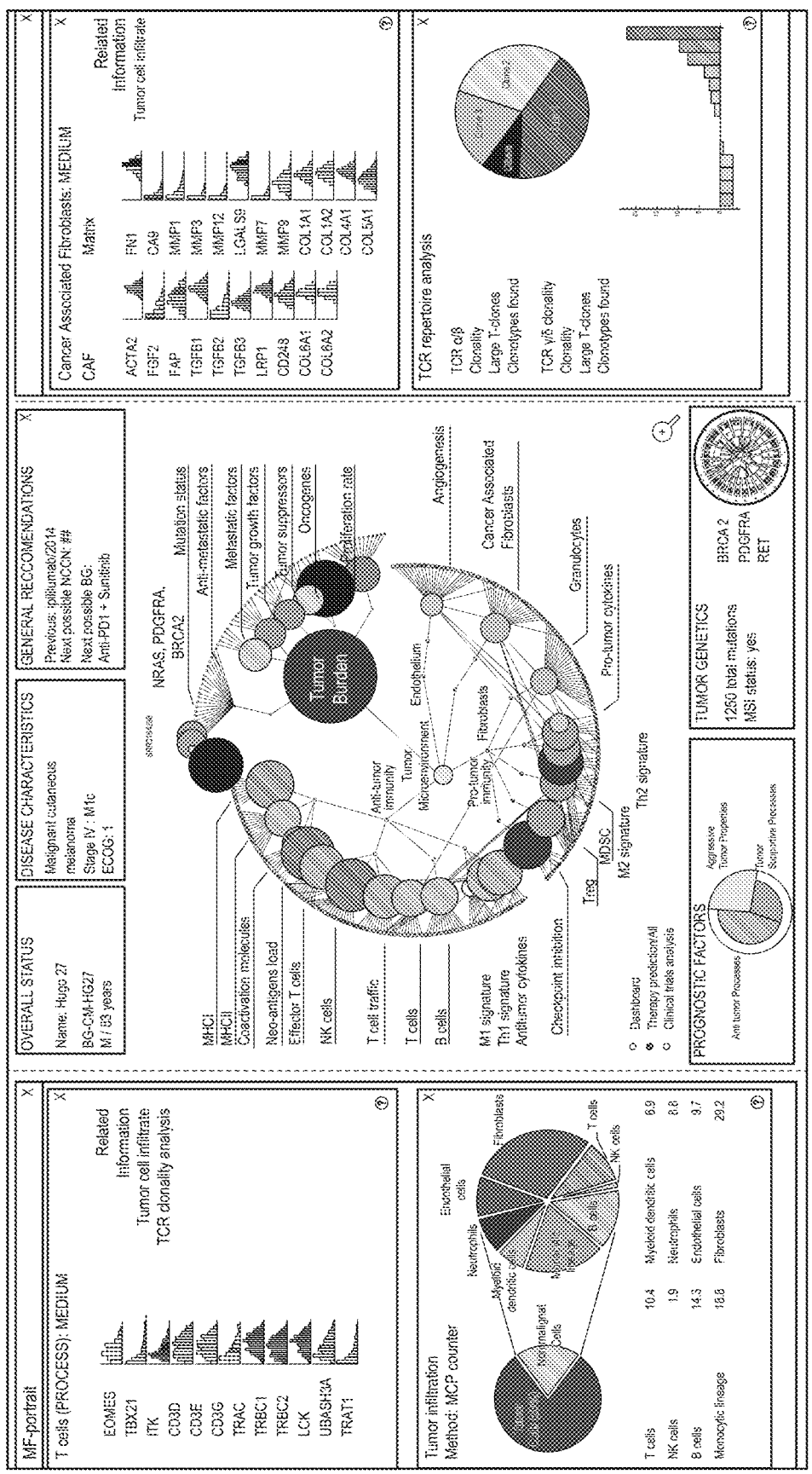

FIG. 43 is a screenshot showing a MF profile presenting twenty-eight gene groups is shown in (as shown in the middle panel).

Figure 44:
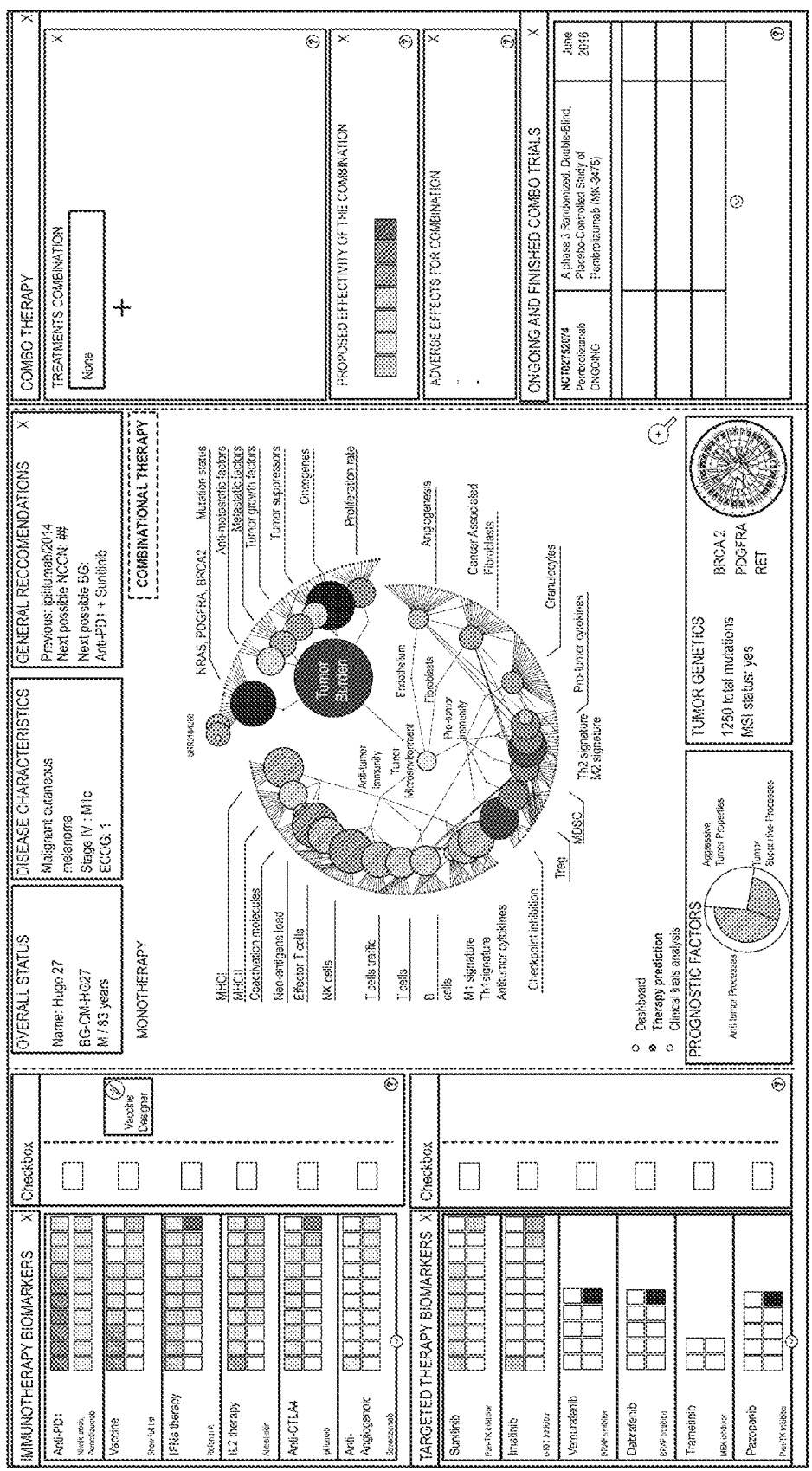

FIG. 44 is a screenshot presenting the combo therapy portion (as shown in the right panel) provided to the user in response to selecting the combinational therapy portion (as shown in the middle panel).

Figure 45:
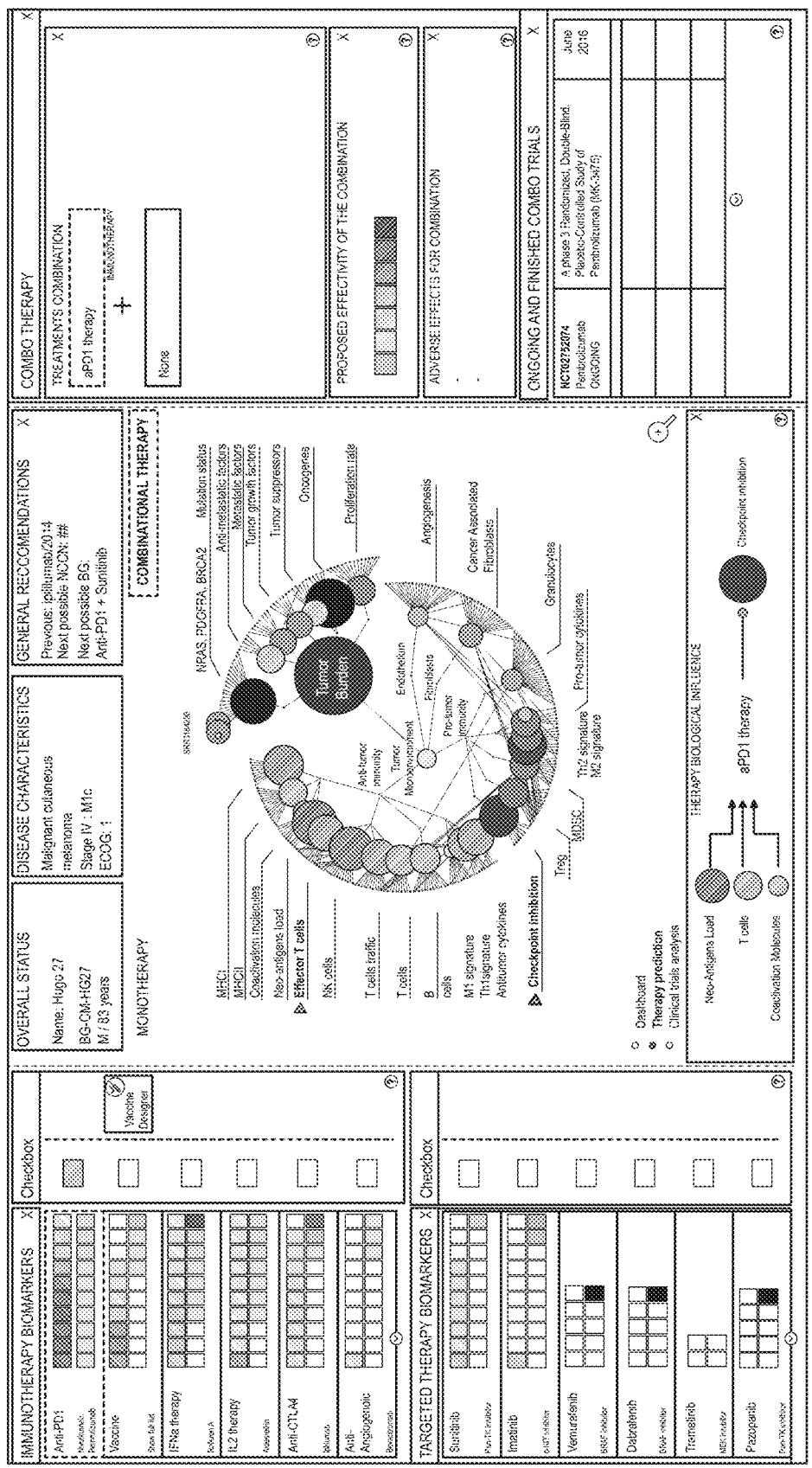

FIG. 45 is a screenshot presenting anti-PD1 therapy incorporated into the combo therapy portion (as shown in the upper right panel).

Figure 46:
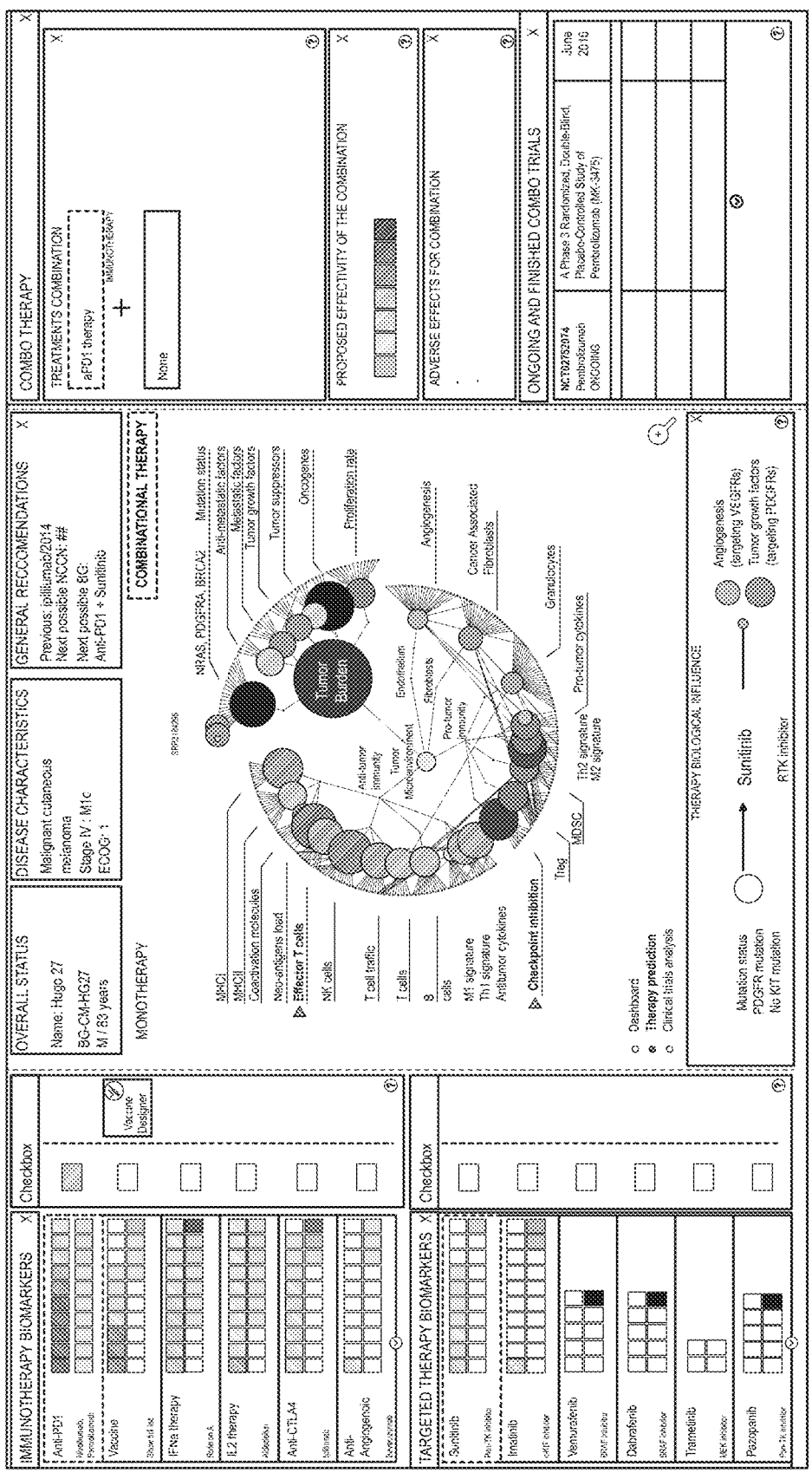

FIG. 46 is a screenshot presenting information related to sunitinib treatment in the therapy biological influence portion (as shown in the lower middle panel) in response to the user selecting sunitinib in the targeted therapy biomarkers portion (as shown by highlighting).

Figure 47:
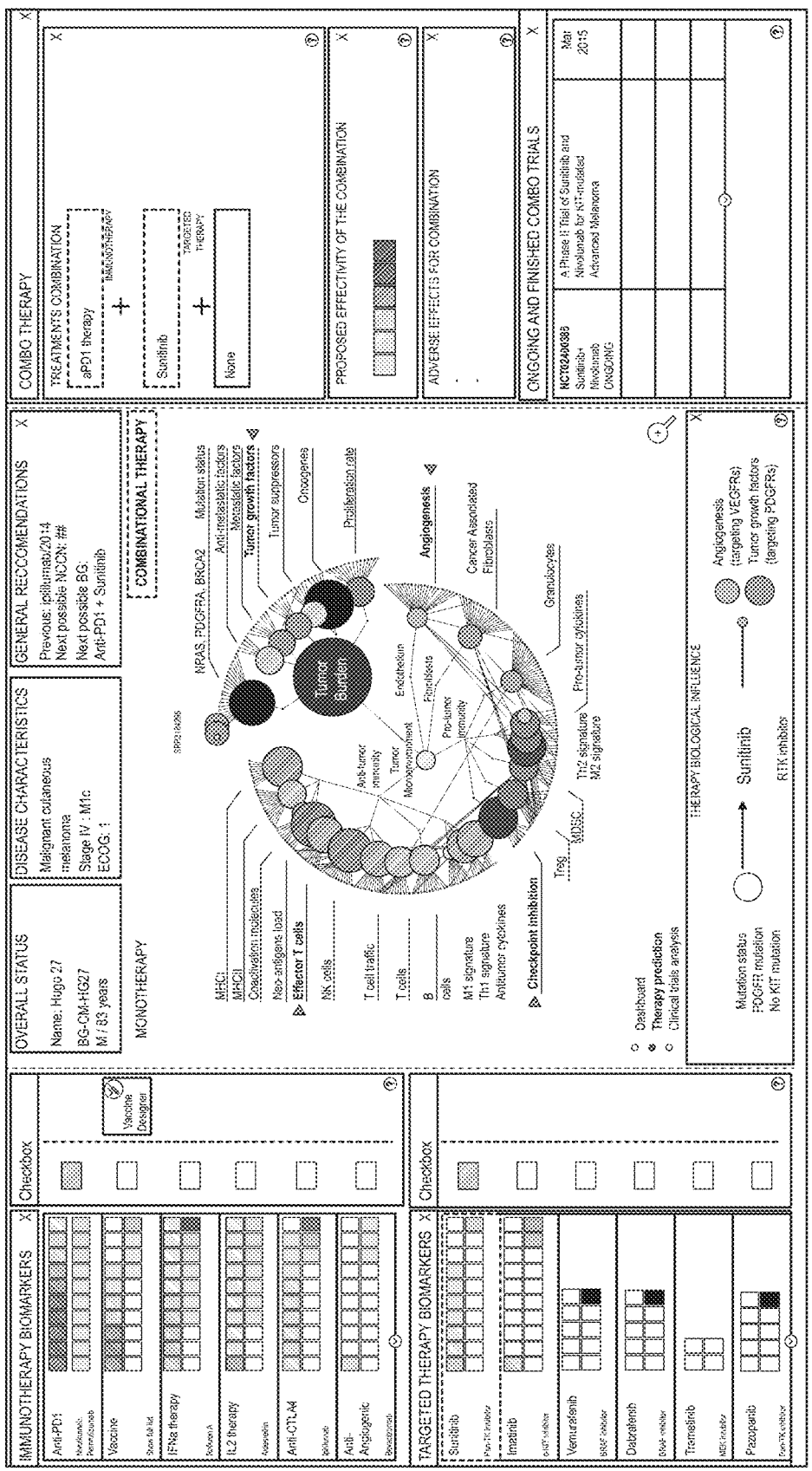

FIG. 47 is a screenshot presenting sunitinib incorporation in the combo therapy portion in response to the user selecting sunitinib.

Figure 48:
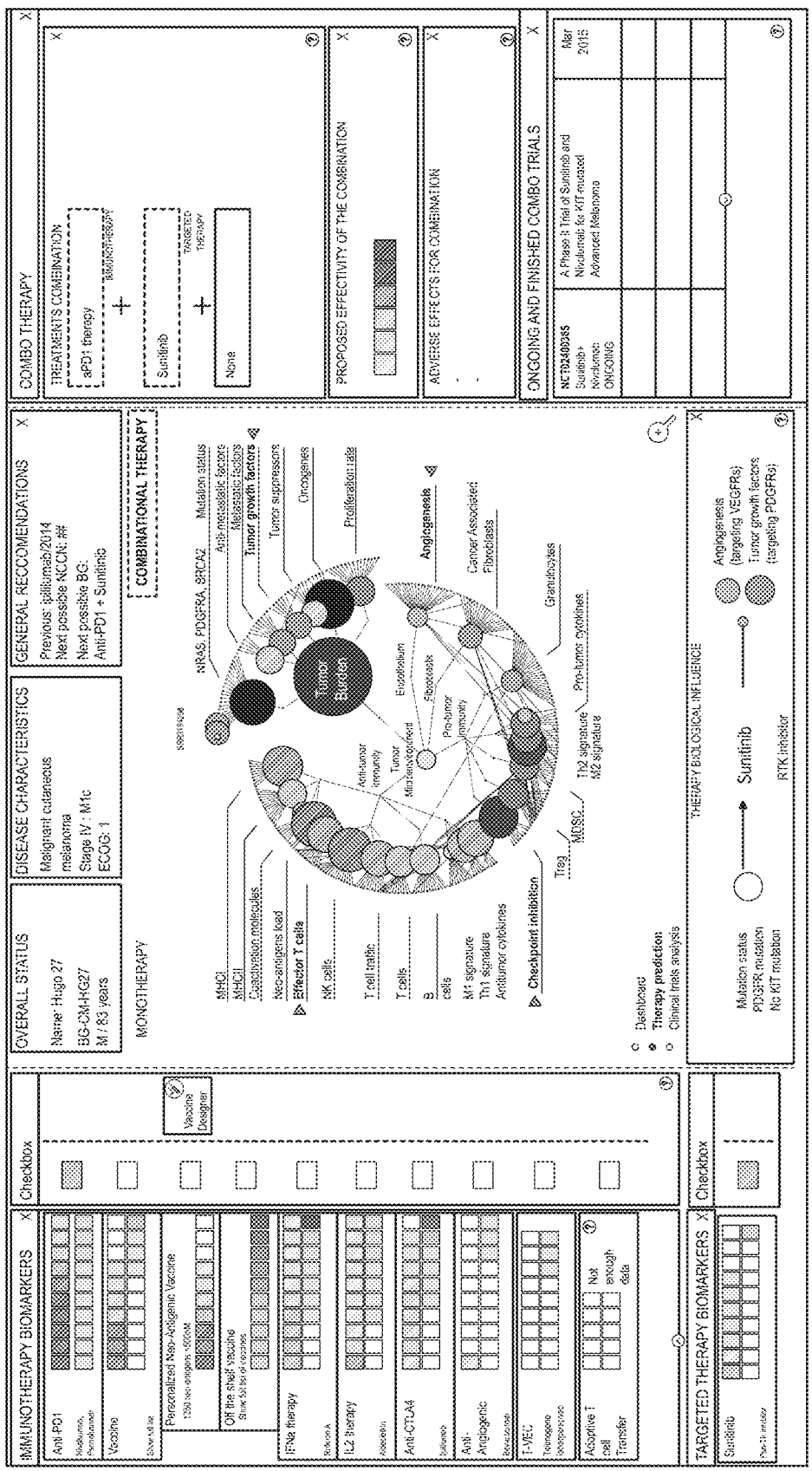

FIG. 48 is a screenshot presenting potential vaccine therapies such as a personalized neo-antigenic vaccine and an off the shelf vaccine provided to the user in response to selecting vaccine in the immunotherapy biomarkers portion (as shown in the left panel).

Figure 49:
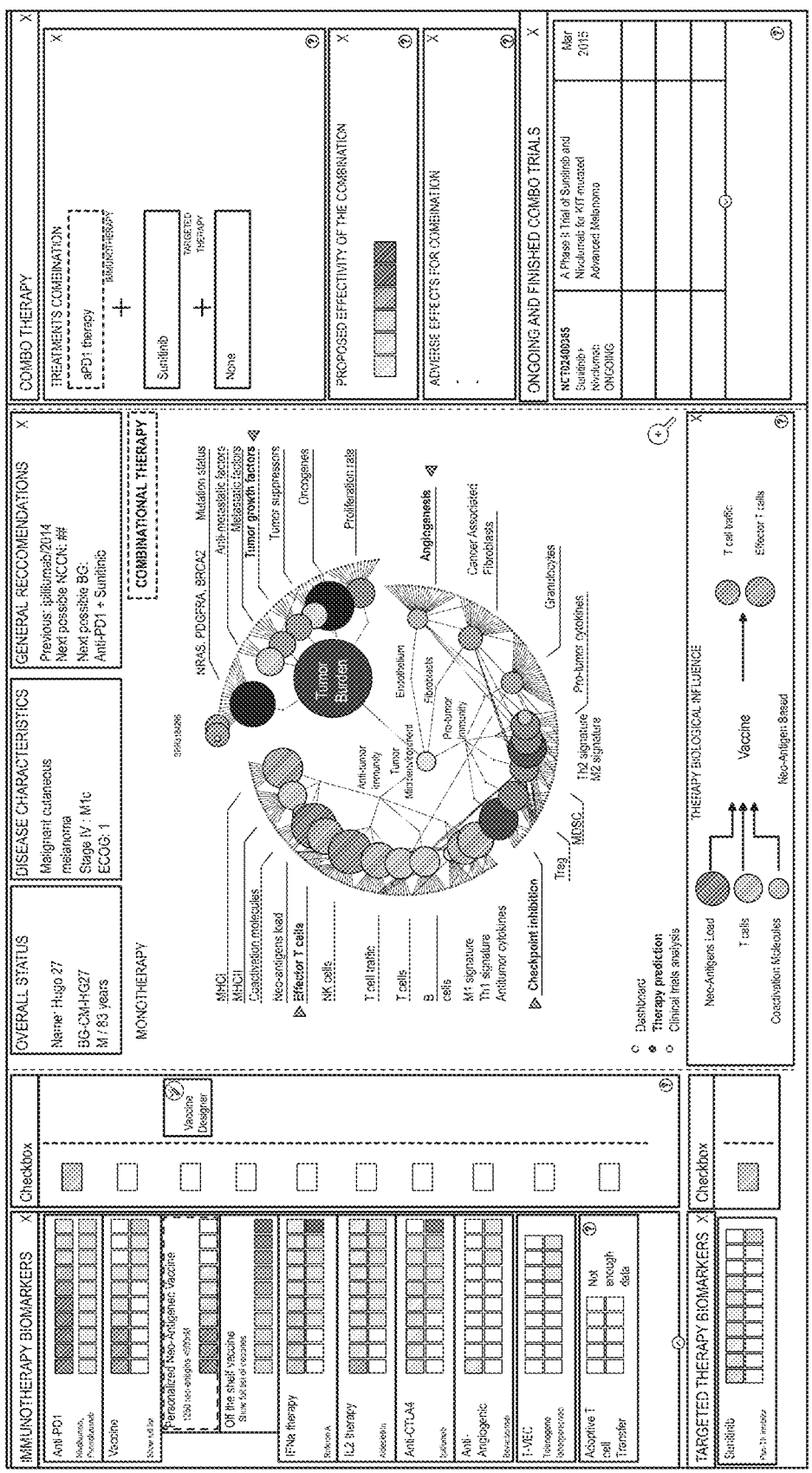

FIG. 49 is a screenshot presenting information relating to treatment with a personalized neo-antigenic vaccine (as shown in the lower middle panel) provided to the user in response to selecting a personalized neo-antigenic vaccine (as shown by highlighting).

Figure 50:
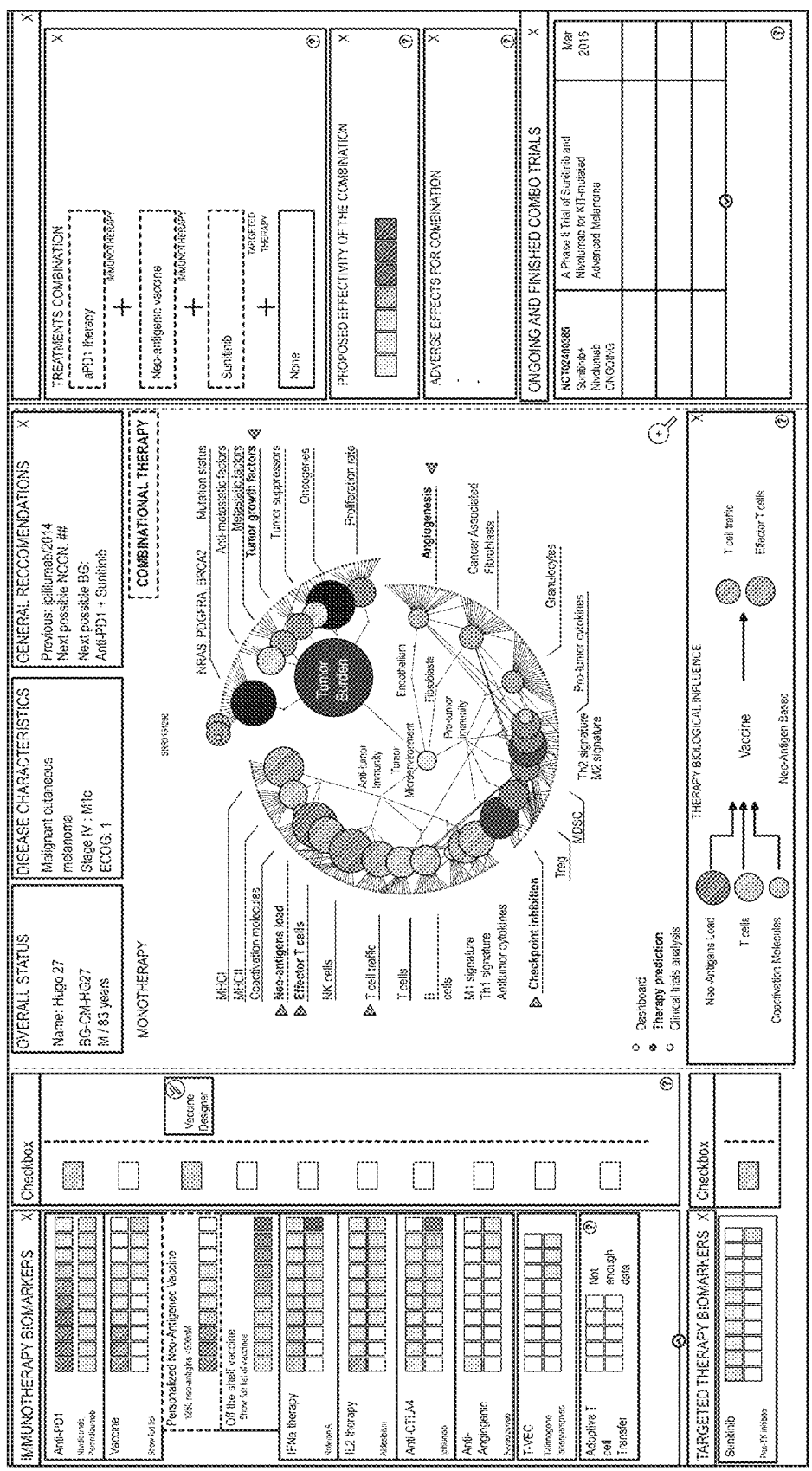

FIG. 50 is a screenshot presenting incorporation of a personalized neo-antigenic vaccine in the combo therapy portion provided to the user in response to the user selecting the personalized neo-antigenic vaccine.

Figure 51:
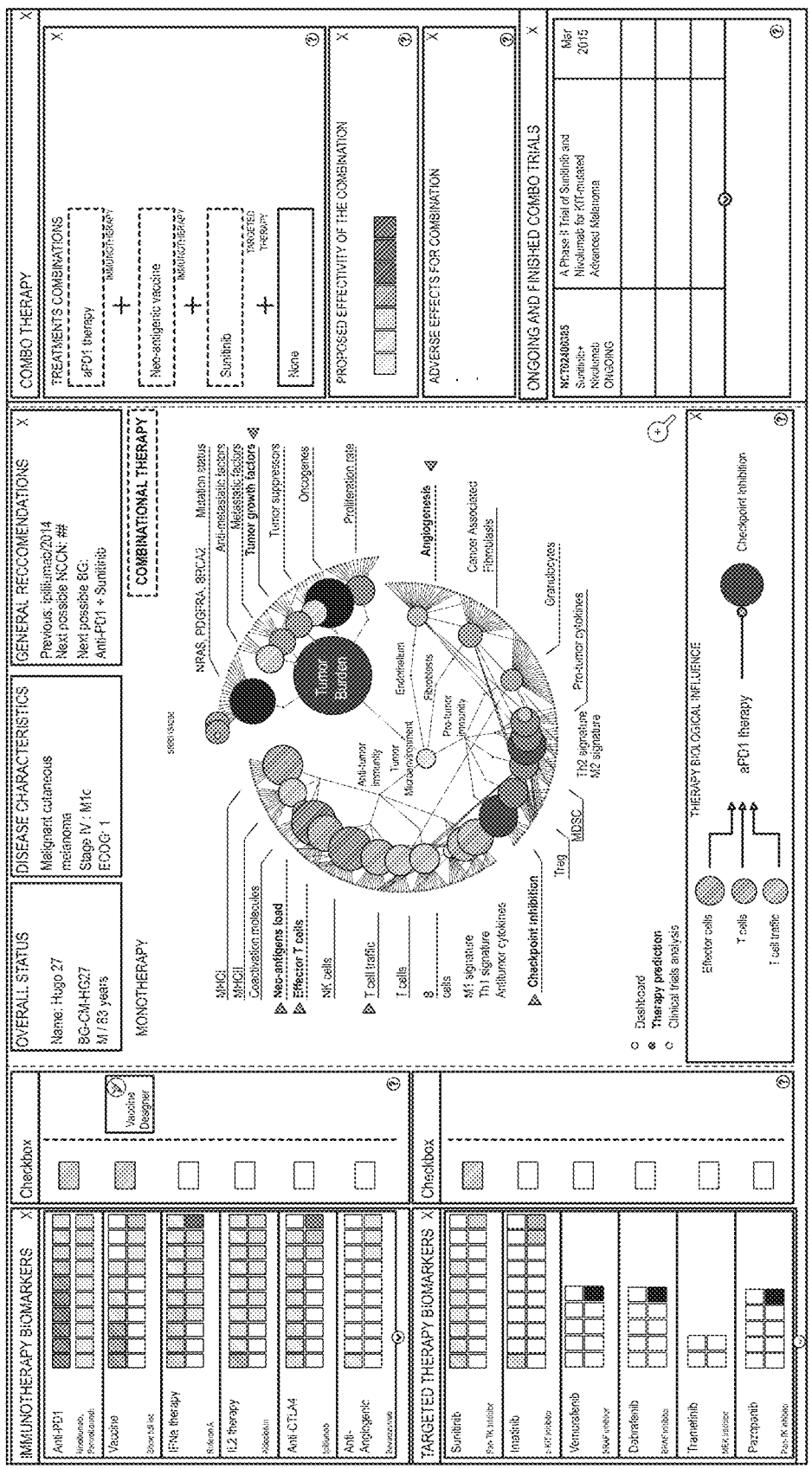

FIG. 51 is a screenshot presenting the personalized neo-antigenic vaccine therapy, anti-PD1 therapy, and sunitinib therapy in the combo therapy portion provided to the user in response to the user incorporating each of these therapies into the combo therapy portion.

Figure 52:
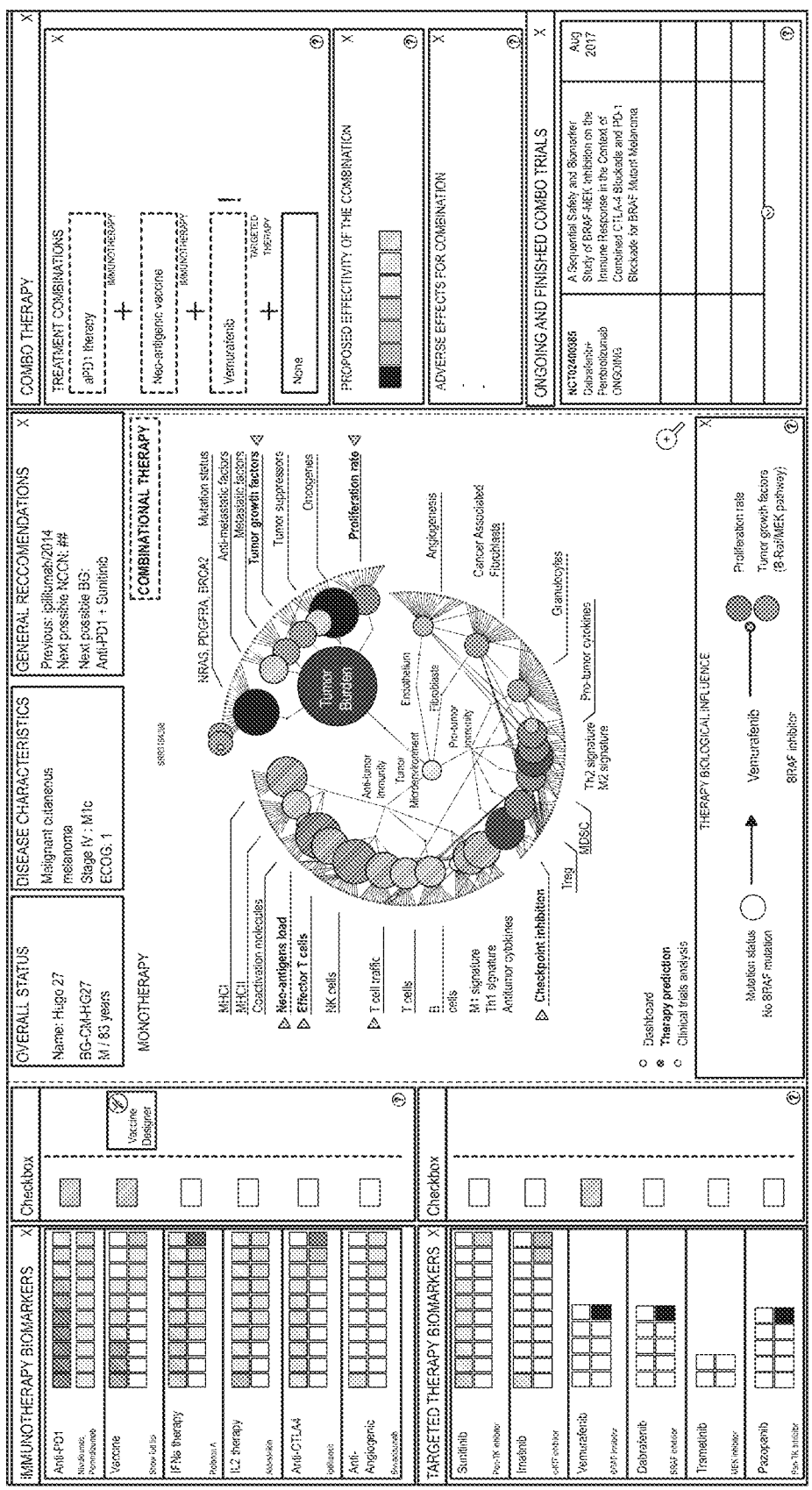

FIG. 52 is a screenshot presenting an alert that substitution of sunitinib therapy with vemurafenib therapy is recognized by the software as an inappropriate combination for the patient.

Figure 53:
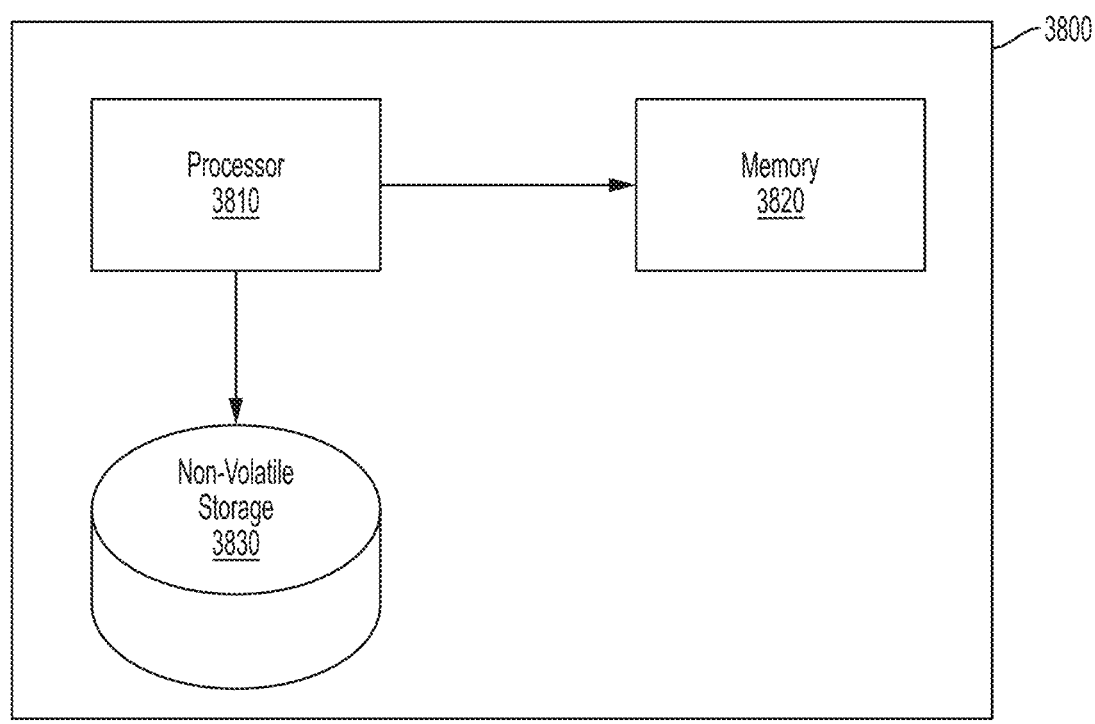

FIG. 53 is a block diagram of an illustrative computer system that may be used in implementing some embodiments of the technology described herein.

Figure 54A:
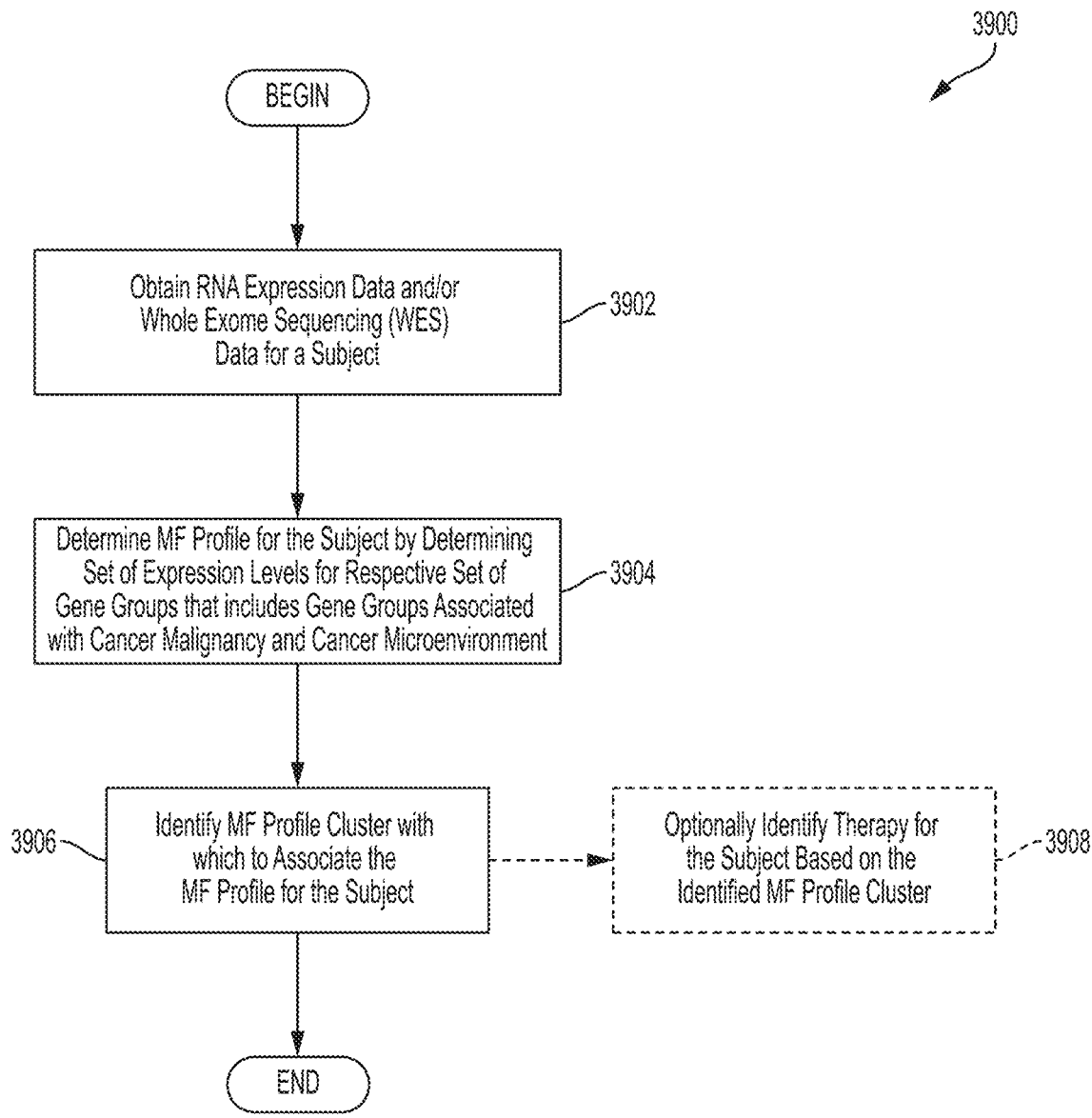

FIG. 54A is a flowchart of an illustrative process 3900 for identifying an MF profile cluster with which to associate an MF profile for a subject, in accordance with some embodiments of the technology described herein.

Figure 54B:
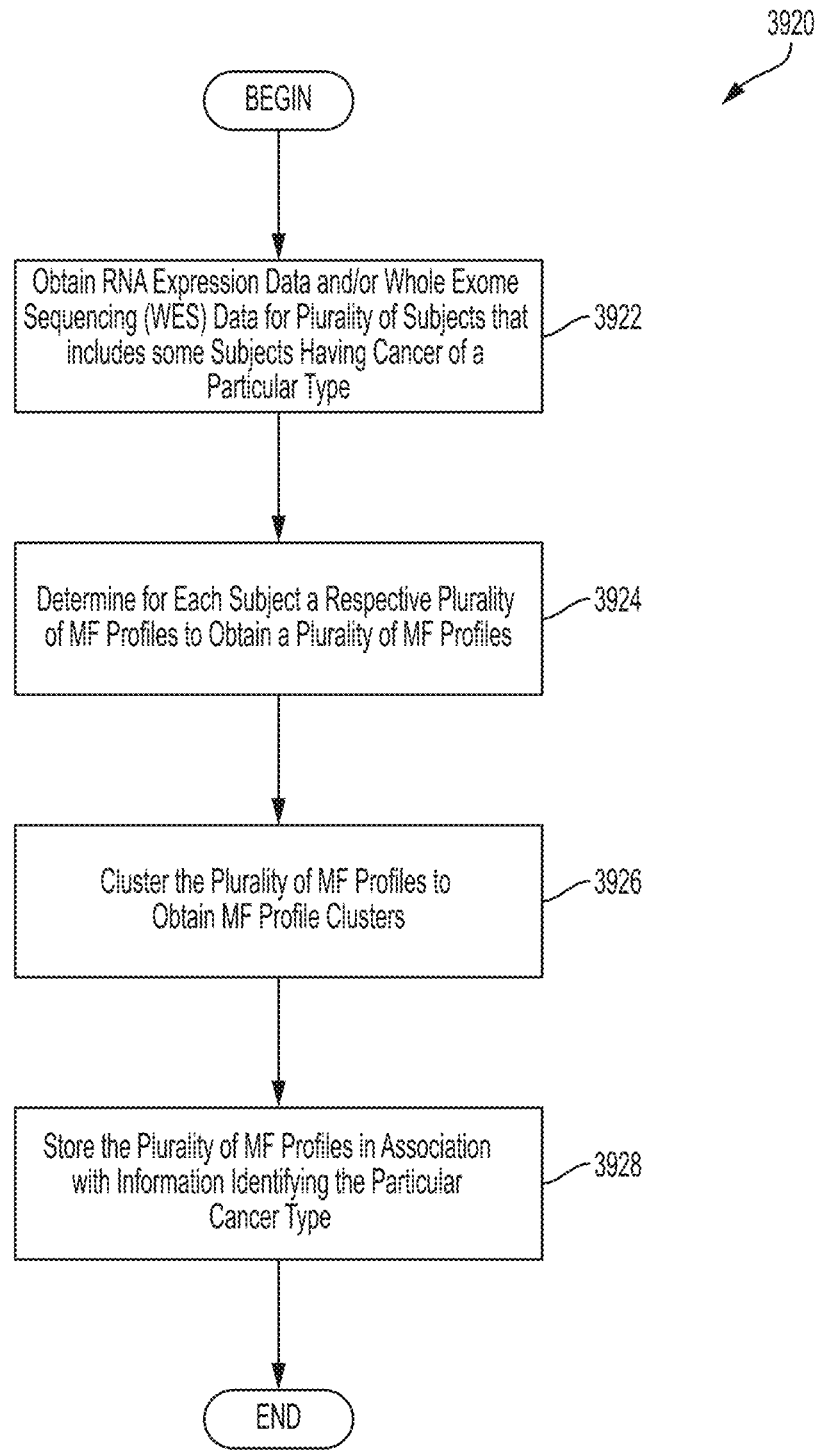

FIG. 54B is a flowchart of an illustrative process 3920 for generating MF profile clusters using RNA expression data obtained from subjects having a particular type of cancer, in accordance with some embodiments of the technology described herein.

Figure 54C:
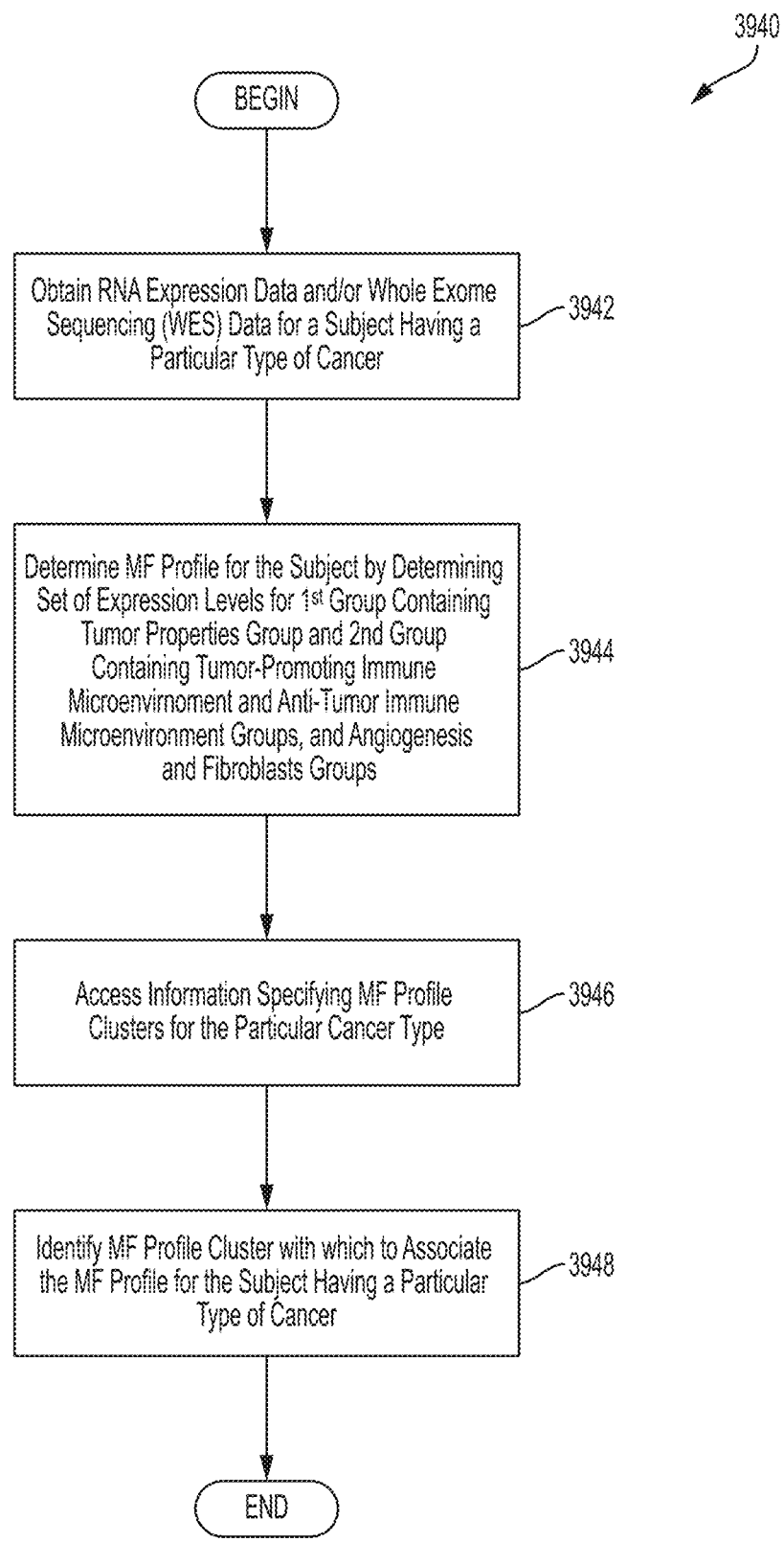

FIG. 54C is a flowchart of an illustrative process 3940 for identifying an MF profile cluster with which to associate an MF profile determined for a subject at least in part by determining the subject's expression levels for multiple gene groups, in accordance with some embodiments of the technology described herein.

Figure 54D:
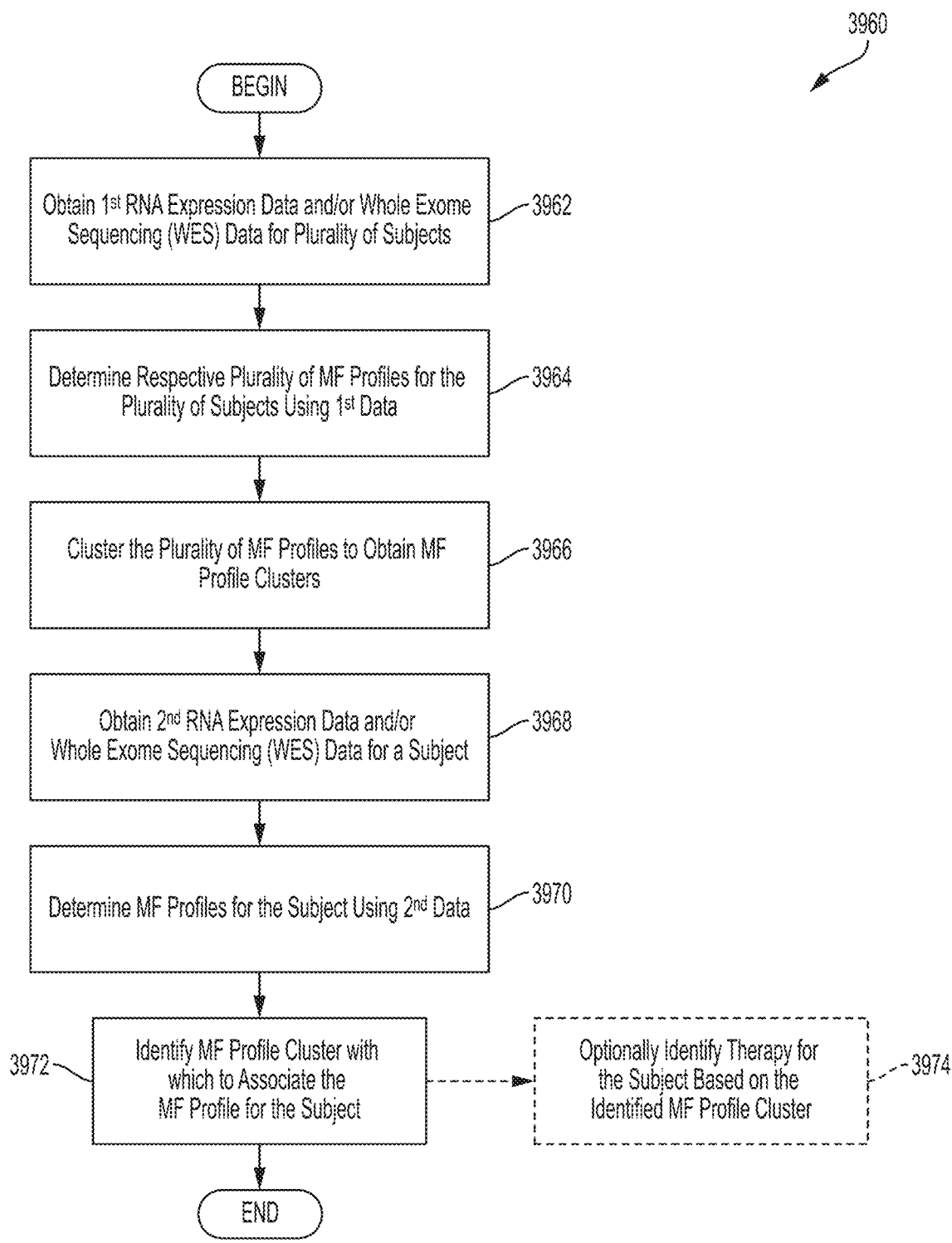

FIG. 54D is a flowchart of an illustrative process 3960 for generating MF profile clusters using RNA expression data obtained from subjects having a particular type of cancer, and associating a subject with one of the generated MF clusters based on the subject's MF profile, in accordance with some embodiments of the technology described herein.

Figure 55A:
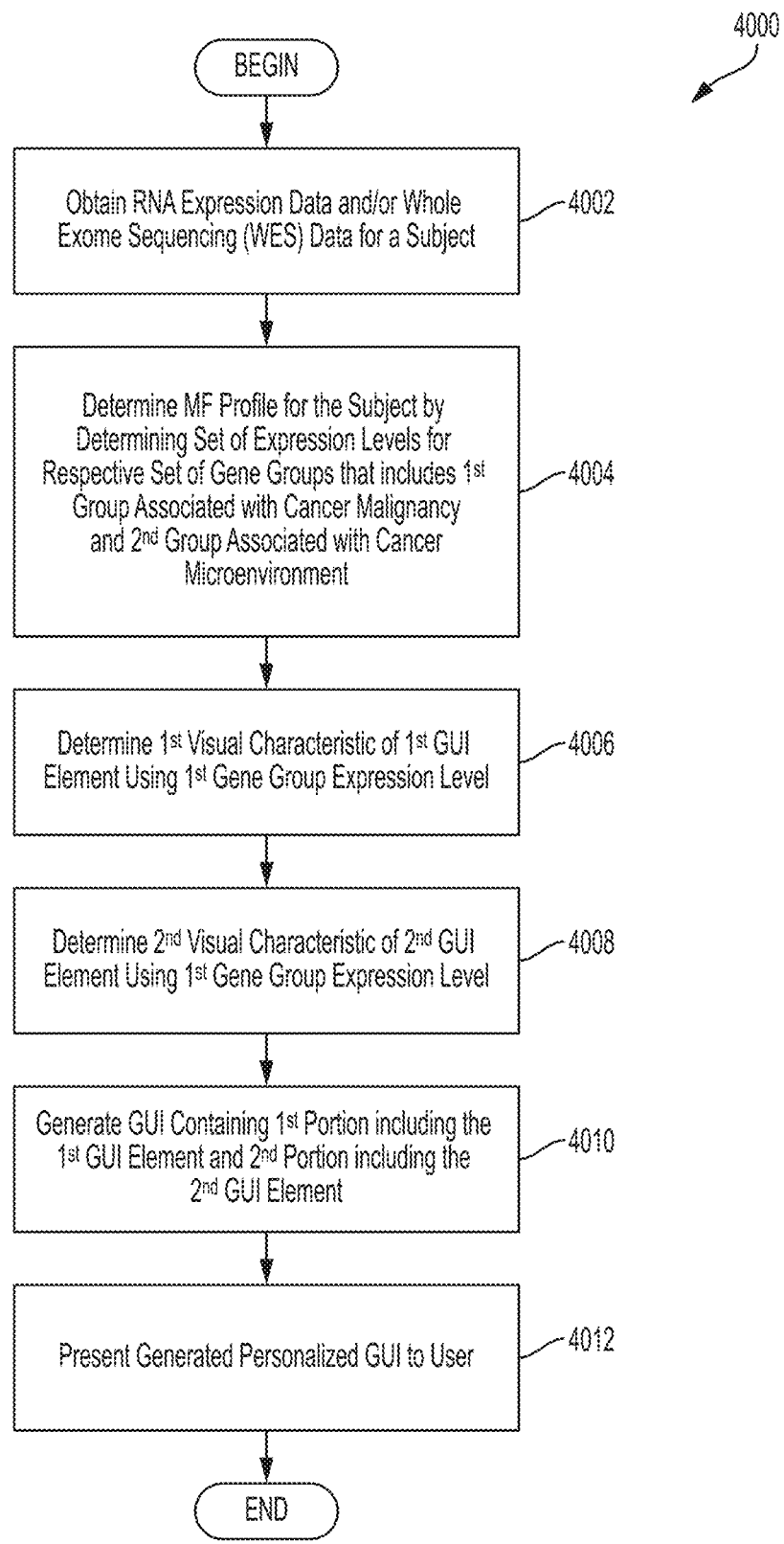

FIG. 55A is a flowchart of an illustrative process 4000 for generating an MF profile and generating an MF portrait for visualizing the MF profile in a graphical user interface (GUI), in accordance with some embodiments of the technology described herein.

Figure 55B:
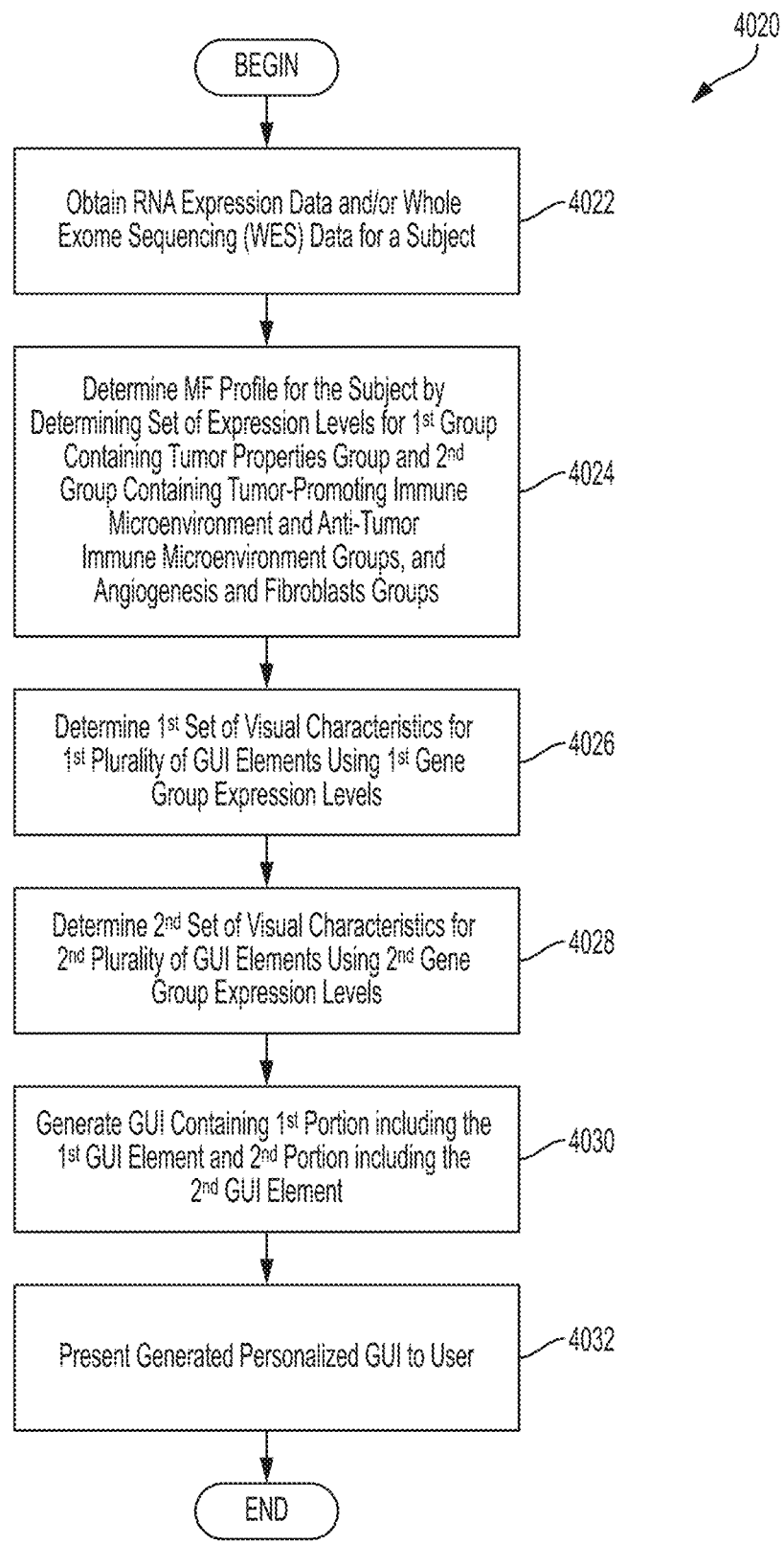

FIG. 55B is a flowchart of an illustrative process 4020 for generating an MF profile by determining expression levels for multiple gene groups and generating an MF portrait for visualizing the MF profile in a graphical user interface (GUI), in accordance with some embodiments of the technology described herein.

DETAILED DESCRIPTION

Recent advances in personalized genomic sequencing and cancer genomic sequencing technologies have made it possible to obtain patient-specific information about cancer cells (e.g., tumor cells) and cancer microenvironments from one or more biological samples obtained from individual patients. The inventors have appreciated that this information may be used to characterize the type(s) of cancer a patient has and, potentially, select one or more effective therapies for the patient. This information may also be used to determine how a patient is responding over time to a treatment and, if necessary, to select a new therapy or therapies for the patient as necessary. This information may also be used to determine whether a patient should be included or excluded from participating in a clinical trial.

The inventors have recognized that the workflow used to obtain sequence data for a patient strongly influences the inferences that can be drawn about the patient's cancer. Such inferences include, but are not limited to, determining whether the patient will respond to a particular therapy or therapies, whether the patient will have an adverse reaction to a particular therapy or therapies, whether the patient is a candidate for enrollment in a clinical trial, whether the patient has one or more particular biomarkers (e.g., biomarkers indicative of potential response to a therapy, biomarkers indicative of survival, etc.), whether the patient's disease has progressed (e.g., from an earlier stage cancer to a later stage cancer, relapsed from remission, etc.), whether a different therapy or therapies should be selected for the patient, and/or any other suitable prognostic, diagnostic, and/or clinical inferences.

When the workflow used to obtain sequence data contains errors, sub-optimal processing, sources of bias in the data, and the like, it is often not possible to make inferences about the subject's cancer with the desired or necessary confidence, or even make any such inferences at all. Even worse, errors in the workflow for producing sequence data may result in incorrect inferences about the patient, potentially leading to incorrect treatment or missed opportunities for better treatment. Moreover, workflow errors lead to wasted resources in the laboratory (e.g., having to reprocess samples) and wasted computing resources (e.g., performing expensive computational processing on megabytes and gigabytes of sequence data, taking up processor and networking resources, only to discard the results at a later time and/or have to repeat the processing).

A conventional workflow used to obtain sequence data for a patient includes multiple steps including: obtaining a biological sample from the patient (e.g., by performing a biopsy, obtaining a blood sample, a salivary sample or any other suitable biological sample from the patient), preparing the biological sample for sequencing using a sequencing platform (e.g., a next generation sequencing (NGS) platform), and obtaining raw data output by the sequencing platform. Various conventional bio-informatics processing pipelines and other algorithms may then use the raw data output by the sequencing platform in an attempt to make one or more of the above-described inferences.

However, such conventional workflows for obtaining sequencing data are prone to errors at all stages. For example, errors may be made in a laboratory when handling samples for multiple patients. Indeed, it is not uncommon for a laboratory to receive a biological sample asserted to be from one patient, when that sample is from another patient. As another example, a biological sample may not be processed properly by the laboratory and may not have the concentration and/or quality of nucleic acid needed for subsequent analysis. As yet another example, errors may be introduced by the sequencing platform itself and/or subsequent post processing steps (e.g., alignment and variant calling). As yet another example, raw sequencing data produced by a sequencing platform may contain artefacts and undesired sequences and/or transcripts. Other examples of various errors are described herein.

In some embodiments, sequence data or sequencing data may include raw DNA or RNA sequence data, DNA exome sequence data (e.g., from whole exome sequencing (WES), DNA genome sequence data (e.g., from whole genome sequencing (WGS)), RNA expression data, gene expression data, bias-corrected gene expression data or any other suitable type of sequence data comprising data obtained from a sequencing platform and/or comprising data derived from data obtained from a sequencing platform.

To address shortcomings of conventional workflows for obtaining sequencing data for patients, the inventors have developed techniques that address various sources of error that may be present in sequencing data. These techniques developed by the inventors include: (1) novel sample preparation techniques to prepare biological samples for sequencing using one or multiple sequencing platforms; (2) novel techniques for post processing raw data output by the sequencing platform(s) to filter out irrelevant data and sources of bias (e.g., transcripts for non-coding regions and expression data associated with genes that introduce bias in the sequence data); and (3) novel quality control techniques that facilitate the detection and remediation of errors in the sequence data. In some embodiments, techniques from each of these three categories may be utilized in a workflow to obtain sequence data for a patient, though it should be appreciated that this is not a limitation of the techniques described herein, and that, in some embodiments, any one or more of the techniques (but not necessarily all of them) may be used in a workflow.

As one example, in some embodiments, novel sample preparation techniques and post-processing techniques include obtaining sequencing data and removing sources of bias from the sequencing data by: (1) obtaining a first biological sample of a first tumor, the first biological sample previously obtained from a subject having, suspected of having or at risk of having cancer; (2) extracting RNA from the first biological sample of the first tumor to obtain extracted RNA; (3) enriching the extracted RNA for coding RNA to obtain enriched RNA; (4) sequencing, using at least one sequencing platform, the enriched RNA to obtain RNA expression data comprising at least 5 kilobases (kb); and (5) using at least one computer hardware processor to perform: (a) obtaining the RNA expression data using the at least one sequencing platform; (b) converting the RNA expression data to gene expression data; (c) determining bias-corrected gene expression data from the gene expression data at least in part by removing, from the gene expression data, expression data for at least one gene that introduces bias in the gene expression data; and (d) identifying a cancer treatment for the subject using the bias-corrected gene expression data.

Removing bias from the gene expression data in this way provides an improvement to sequencing technology for numerous reasons. First, it removes artefacts and sources of bias from sequencing data, resulting in fewer errors in any downstream processing and a higher fidelity output. Second, the inventors have recognized that removing sources of bias in this way allows for more accurately and faithfully representing a patient's molecular functional characteristics (e.g., via molecular functional expression signatures described herein). The inventors have recognized that the bias-corrected gene expression data may be used to identify more effective therapies for a patient, improve ability to determine whether one or more cancer therapies will be effective if administered to the patient, improve the ability to identify clinical trials in which the subject may participate, and/or improvements to numerous other prognostic, diagnostic, and clinical applications.

As another example, in some embodiments, novel quality control techniques include using at least one computer hardware processor to perform: (a) obtaining nucleic acid data comprising: (i) sequence data indicating a nucleotide sequence for at least 5 kilobases (kb) of DNA and/or RNA from a previously obtained biological sample of a subject having, suspected of having, or at risk of having a disease; and (ii) asserted information indicating an asserted source and/or an asserted integrity of the sequence data; and (b) validating the nucleic acid data by: (i) processing the sequence data to obtain determined information indicating a determined source and/or a determined integrity of the sequence data; and (ii) determining whether the determined information matches the asserted information. Examples of various such validation techniques are described herein, and they are important examples of quality control techniques developed by the inventors and described herein.

Employing such quality control techniques also provides an improvement to sequencing technology and computer technology. First, sequencing data that do not pass one or more quality control checks are not used for some or all of downstream processing reducing or eliminating errors in downstream applications (e.g., identifying biomarkers, tumor microenvironment types, possible therapies for a patient, etc.). Often such downstream processing requires performing expensive (frequently cloud-based) computational processing of large data sets (e.g., sequencing data may contain tens of millions of reads, which have to be aligned, annotated and processed in other numerous ways). Using quality control to prevent computationally expensive processes from executing will reduce or eliminate wasteful use of computing resources, saving processing power, memory, and networking resources (which is an improvement to computing technology in addition to being an improvement to sequencing technology). Identifying errors will also reduce waste of resources at a laboratory that processes multiple samples, by freeing up equipment for processing biological samples that have passed initial quality control checks. In addition, using sequence data for downstream processing that has passed various quality control checks may be used to identify more effective therapies for a patient, improve ability to determine whether one or more cancer therapies will be effective if administered to the patient, improve the ability to identify clinical trials in which the subject may participate, and/or improvements to numerous other prognostic, diagnostic, and clinical applications.

Figure 1A:
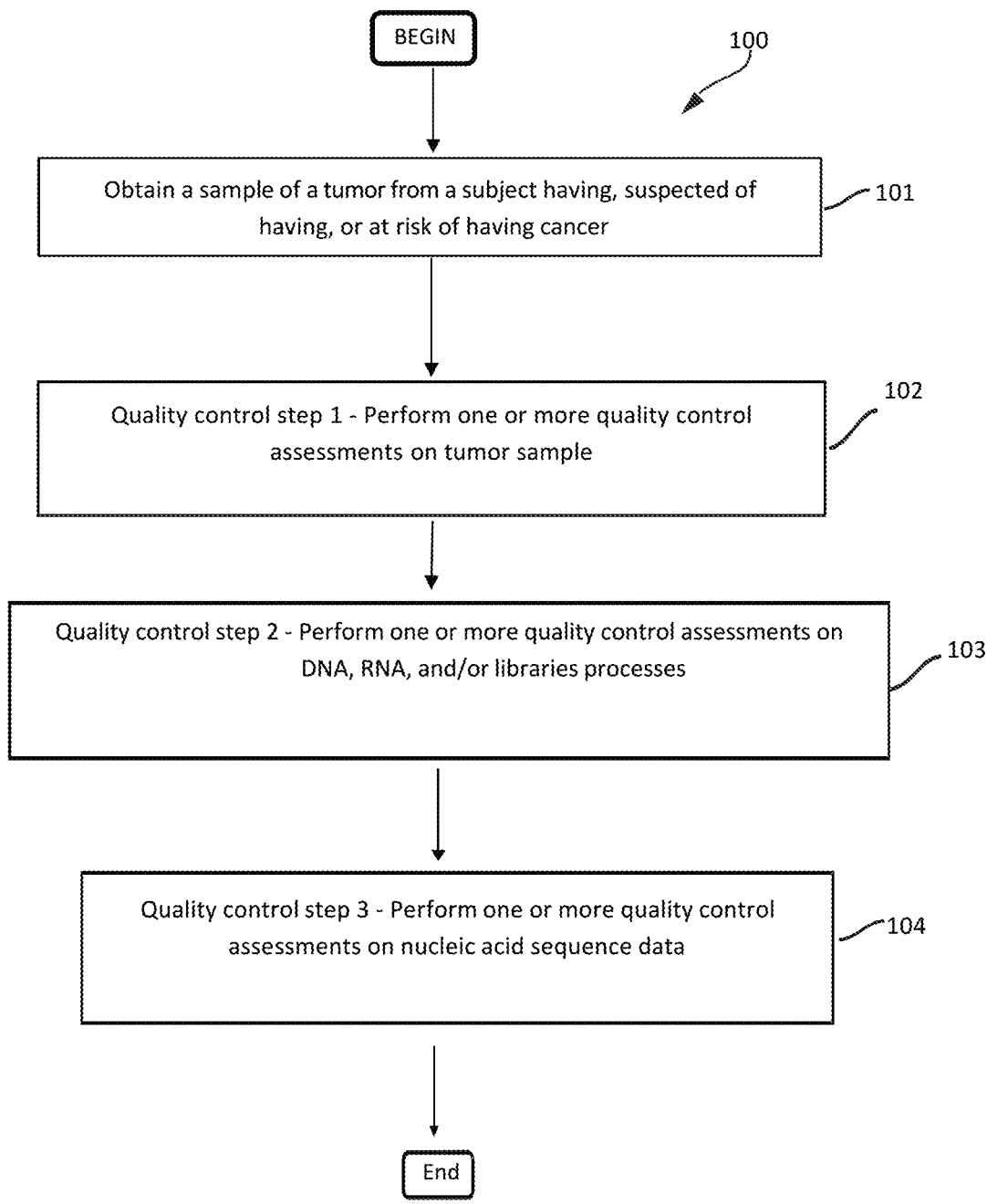
FIG. 1A and FIG. 1B provide exemplary flow charts that illustrate processes of sample preparation and quality control.
Figure 1B:
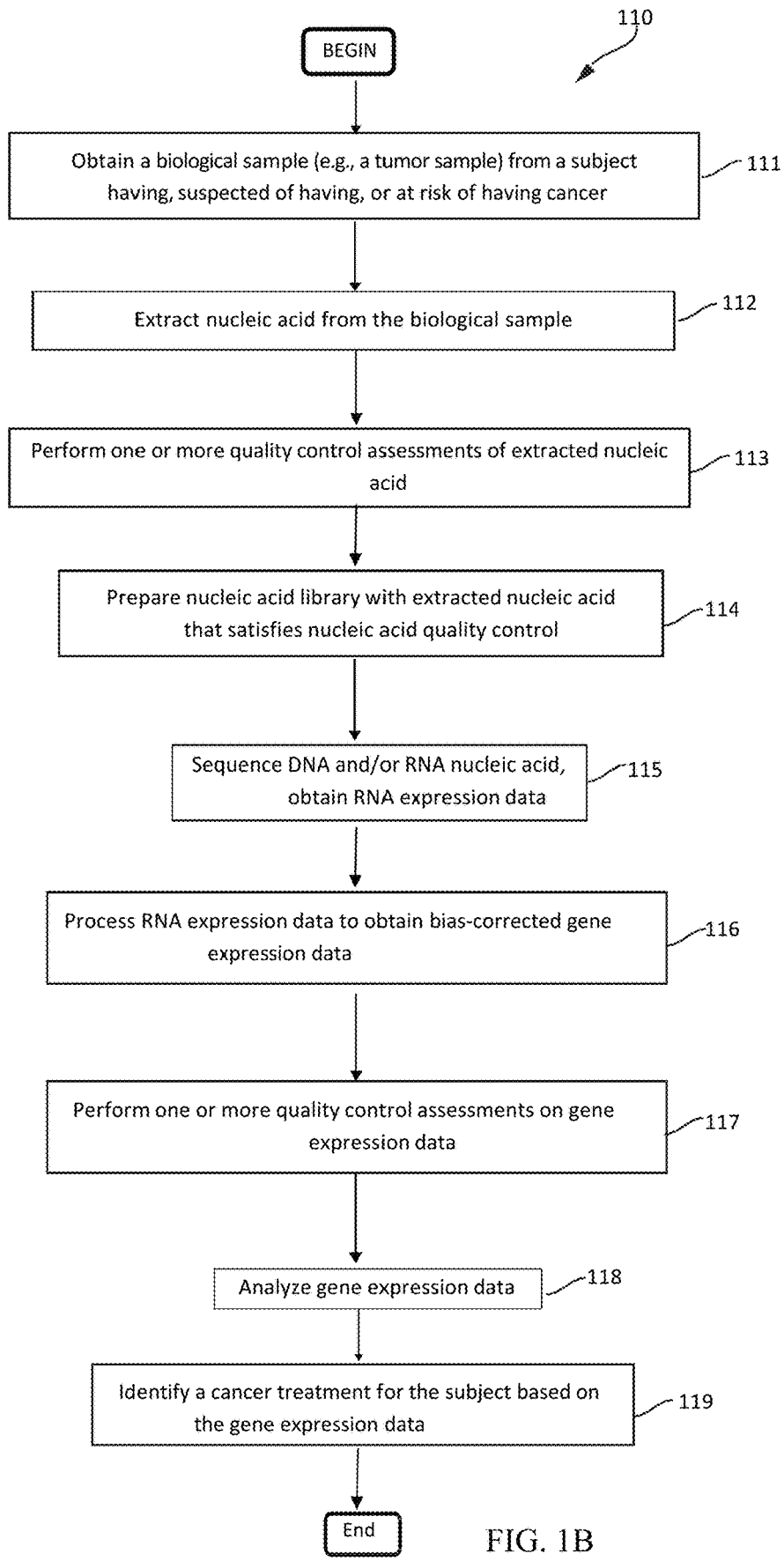

FIGS. 1A and 1B illustrate examples of process pipelines for sample preparation and quality control as described herein. The process pipeline in FIG. 1 illustrate embodiments of methods and systems provided in the present disclosure and are not to be construed in any way as limiting their scope. The present disclosure provides that a process pipeline does not need to include all of the process steps or the order of process steps illustrated in FIG. 1. One or more processes can be omitted, repeated, or performed in a different order depending on the application.

FIG. 1A illustrates a non-limiting process pipeline 100 that includes one or more quality control assessments. A biological sample (e.g., a tumor biopsy) is obtained for a subject (e.g., a subject having, suspected of having, or at risk of having cancer) in act 101. In some embodiments, the sample is obtained from a physician, hospital, clinic, or other healthcare provider. One or more sample quality control assessments at quality control act 102 can be performed on the biological sample. In some embodiments, a quality control assessment on the biological sample (e.g., biopsy material) comprises determining whether the sample is in an appropriate form (e.g., fresh frozen or FFPE) and/or is accompanied by sufficient information to identify the nature and source of the sample. Subsequently, nucleic acid (e.g., DNA and/or RNA) can be extracted from a biological sample that satisfies sample quality control act 102. One or more nucleic acid quality control assessments at act 103 then can be performed, for example to evaluate one or more physical attributes of the extracted nucleic acid, of a nucleic acid library prepared from the extracted nucleic acid, and/or of pooled nucleic acids or libraries. Subsequently, nucleic acid (e.g., DNA and/or RNA) that satisfies nucleic acid quality control act 103 can be processed (e.g., to enrich for polyA RNA) and/or sequenced to obtain raw DNA and/or RNA sequence data (e.g., RNA expression data). In some embodiments, RNA expression data can be processed to obtain gene expression data and optionally to remove data for one or more types of genes that could interfere with (e.g., bias) subsequent analysis of the gene expression data. In some embodiments, gene expression data is normalized (e.g., after removal of the data for the one or more interfering genes). In some embodiments, one or more sequence quality control assessments are performed on DNA and/or RNA sequence data (e.g., on processed, for example normalized, gene expression data) for bioinformatic quality control act 104. In some embodiments, one or more bioinformatic quality control assessments are performed to determine whether sequence data is from an expected source (e.g., patient, tissue, tumor, etc.) and/or whether it has sufficient integrity for further analysis. In some embodiments, sequence data that satisfies bioinformatic quality control act 104 is further processed, for example, to determine a diagnosis, prognosis, and/or therapy for a subject, to evaluate and/or monitor a subject, and/or for one or more clinical applications (e.g., to evaluate a therapy).

In some embodiments, the sequence data may include raw DNA or RNA sequence data, DNA exome sequence data (e.g., from whole exome sequencing (WES), DNA genome sequence data (e.g., from whole genome sequencing (WGS)), RNA expression data, gene expression data, bias-corrected gene expression data or any other suitable type of sequence data comprising data obtained from a sequencing platform and/or comprising data derived from data obtained from a sequencing platform including, but not limited to, examples of such data described herein.

FIG. 1B illustrates a non-limiting process pipeline 110 for preparing nucleic acid from a biological sample (e.g., a tumor biopsy) and obtaining and processing nucleic acid sequence data for subsequent analysis (e.g., for diagnostic, prognostic, therapeutic, and/or other clinical applications). Process pipeline 110 is performed by obtaining a biological sample (e.g., a tumor sample) from a subject having, suspected of having, or at risk of having cancer at act 111. Nucleic acid (e.g., DNA and/or RNA) is obtained (e.g., extracted) from the sample at act 112. One or more quality control assessments of the nucleic acid is performed in act 113. One or more nucleic acid libraries is prepared in act 114, for example using nucleic acid that satisfies at least one quality control assessment of act 113. The nucleic acid libraries are sequenced using at least one sequencing platform in sequencing act 115 (e.g., to obtain RNA expression data for RNA). In some embodiments, RNA expression data is converted to gene expression data in act 116, and the gene expression data is optionally bias-corrected, at least in part, by removing expression data for at least one gene that introduces bias in the gene expression data. One or more bioinformatic quality control assessments are performed on the DNA sequence data or RNA sequence data from act 115 and/or RNA sequence data (e.g., the bias-corrected gene expression data from act 116) in bioinformatics quality control act 117. In some embodiments, nucleic acid data (e.g., that satisfies at least one bioinformatic quality control assessments of act 117), is further processed in act 118 (e.g., to determine one or more indicia of disease from the gene expression data), to perform a diagnostic, prognostic, therapeutic, and/or other clinical assessment of the subject (e.g., to identify a treatment, for example a cancer treatment, for the subject) in act 119. In some embodiments, a treatment (e.g., a cancer treatment) is administered to the subject.

In some embodiments, act 111 comprises obtaining bulk biopsy tissues of a subject or a patient. In some embodiments, act 111 comprises obtaining a blood sample of a subject or a patient. In some embodiments, act 111 comprises obtaining a single cell suspension. In some embodiments, act 111 comprises obtaining any types of sample that are suitable for preparing nucleic acids for subsequent sequencing analysis. In some embodiments, act 111 comprises obtaining more than one type of samples.

In some embodiments, when the bulk biopsy tissues are obtained, the tissues are processed (e.g., homogenized in the presence of TriZol) to extract nucleic acids such as DNA or RNA at act112. In some embodiments, when a single cell suspension is obtained, the suspension is processed to extract nucleic acids such as DNA or RNA at act 112. In some embodiments, nucleic acids can be extracted that are suitable for germline whole exome sequencing (WES) at act 112. In some embodiments, nucleic acids can be extracted that are suitable for tumor whole exome sequencing (WES) at act 112. In some embodiments, nucleic acids can be extracted that are suitable for tumor RNA sequencing at act 112. In some embodiments, nucleic acids can be extracted that are suitable for CYTOF (mass cytometry) at act 112. In some embodiments, nucleic acids can be extracted that are suitable for any type of sequencing known in the art at act 112.

At act 113, one or more quality control assessments can be performed. Acceptable and/or target thresholds can be determined and used as references. In some embodiments, the total amount of extracted DNA or RNA can be used for quality control assessment. In some embodiments, a spectrophotometer, for example a small volume full-spectrum, UV-visible spectrophotometer (e.g., NanoDrop spectrophotometer available from ThermoFisher Scientific, thermofisher.com) can be used for quality control assessment of DNA or RNA. In some embodiments, a fluorometer, for example for quantification of DNA or RNA (e.g., a Qubit fluorometer available from ThermoFisher Scientific, thermofisher.com) can be used for quality control assessment of DNA or RNA.

In some embodiments, an automated electrophoresis system (e.g., TAPESTATION) can be used for quality control assessment of DNA or RNA. In some embodiments, a real-time PCR system (e.g., LIGHTCYCLER®) can be used for quality control assessment of DNA or RNA.

In some embodiments, act 114 comprises preparing libraries for the extracted nucleic acids that have satisfied at least one quality control threshold at act 113. In some embodiments, act 114 comprises one or more methods described in Example 2.

In some embodiments, act 115 comprises sequencing nucleic acid (e.g., the DNA, RNA, or related libraries of act 114) to obtain DNA sequence data and/or RNA sequence data (e.g., RNA expression data) using at least one nucleic acid sequencing platform (e.g., a next generation nucleic acid sequencing platform). Sequence data obtained at act 115 can be stored in any suitable format (e.g., in the form of one or more FASTQ files).

In some embodiments, RNA expression data is converted to gene expression data at act 116. In some embodiments, RNA expression data is aligned to known genes in a database, for example to a known assembled genome (e.g., a human genome) or to a transcriptome in the database. In some embodiments, a program for quantifying transcripts, for example from bulk and single-cell RNA-Seq data, using high-throughput sequencing reads (e.g., Kallisto (hg38) available from Github, github.com, for example as described in Nicolas L Bray, Harold Pimentel, Pill Melsted and Lior Pachter, Near-optimal probabilistic RNA-seq quantification, Nature Biotechnology 34, 525-527 (2016), doi:10.1038/nbt.3519), and/or Gencode (e.g., Gencode V23) is used for sequence alignment, and/or annotation. In some embodiments, act 116 comprises gene aggregation. In some embodiments, act 116 comprises removing expression data for one or more non-coding transcripts from the gene expression data. In some embodiments, act 116 comprises removing expression data for one or more genes that can bias the gene expression data. In some embodiments, act 116 comprises removing expression data for histone encoding genes and/or mitochondrial-encoding genes. In some embodiments, act 116 comprises normalization (e.g., TPM normalization) after removal of expression data for non-coding and/or bias-associated genes from the gene expression data. This normalization may be termed "renormalization" herein.

At act 117, one or more bioinformatic quality control assessments is performed on nucleic acid sequence data, for example DNA sequence data and/or RNA sequence data (e.g., bias corrected, and/or normalized, gene expression data). In some embodiments, one or more bioinformatic quality control assessments can be performed to evaluate the source and/or integrity of the nucleic acid sequence data. In some embodiments, one or more bioinformatic quality control assessments described in this application are performed.

In some embodiments, a method comprises all processes illustrated in FIG. 1. However, in some embodiments, a subset of the processes is performed and any one or more of the processes may be omitted, duplicated, and/or performed in a different order than illustrated in FIG. 1. In some embodiments, a method comprises a process, optionally including one or more quality control steps, for preparing a nucleic acid from a biological sample, wherein the nucleic acid is sequenced on at least one sequencing platform. In some embodiments, a method comprises processing nucleic acid information obtained (e.g., received) from a sequencing platform to generate DNA or RNA sequence data for subsequent analysis (e.g., to generate bias-corrected, optionally normalized gene expression data for subsequent analysis). In some embodiments, one or more processes of FIG. 1 are implemented on a computer. In some embodiments, a method comprises identifying a treatment (e.g., a cancer treatment) for a subject (e.g., a subject having, suspected of having, or at risk of having cancer). In some embodiments, a method comprises administering the treatment to the subject.

Biological samples

Any of the methods, systems, or other claimed elements may use or be used to analyze a biological sample from a subject. In some embodiments, a biological sample is obtained from a subject having or suspected of having cancer. One or more biological samples from a subject may be analyzed as described herein to obtain information about the subject's cancer. The biological sample may be any type of biological sample including, for example, a biological sample of a bodily fluid (e.g., blood, urine or cerebrospinal fluid), one or more cells (e.g., from a scraping or brushing such as a cheek swab or tracheal brushing), a piece of tissue (cheek tissue, muscle tissue, lung tissue, heart tissue, brain tissue, or skin tissue), or some or all of an organ (e.g., brain, lung, liver, bladder, kidney, pancreas, intestines, or muscle), or other types of biological samples (e.g., feces or hair).

In some embodiments, the biological sample is a sample of a tumor from a subject. In some embodiments, the biological sample is a sample of blood from a subject. In some embodiments, the biological sample is a sample of tissue from a subject.

A sample of a tumor, in some embodiments, refers to a sample comprising cells from a tumor. In some embodiments, the sample of the tumor comprises cells from a benign tumor, e.g., non-cancerous cells. In some embodiments, the sample of the tumor comprises cells from a premalignant tumor, e.g., precancerous cells. In some embodiments, the sample of the tumor comprises cells from a malignant tumor, e.g., cancerous cells.

Examples of tumors include, but are not limited to, adenomas, fibromas, hemangiomas, lipomas, cervical dysplasia, metaplasia of the lung, leukoplakia, carcinoma, sarcoma, germ cell tumors, and blastoma.

A sample of blood, in some embodiments, refers to a sample comprising cells, e.g., cells from a blood sample. In some embodiments, the sample of blood comprises non-cancerous cells. In some embodiments, the sample of blood comprises precancerous cells. In some embodiments, the sample of blood comprises cancerous cells. In some embodiments, the sample of blood comprises blood cells. In some embodiments, the sample of blood comprises red blood cells. In some embodiments, the sample of blood comprises white blood cells. In some embodiments, the sample of blood comprises platelets. Examples of cancerous blood cells include, but are not limited to, leukemia, lymphoma, and myeloma. In some embodiments, a sample of blood is collected to obtain the cell-free nucleic acid (e.g., cell-free DNA) in the blood.

A sample of blood may be a sample of whole blood or a sample of fractionated blood. In some embodiments, the sample of blood comprises whole blood. In some embodiments, the sample of blood comprises fractionated blood. In some embodiments, the sample of blood comprises buffy coat. In some embodiments, the sample of blood comprises serum. In some embodiments, the sample of blood comprises plasma. In some embodiments, the sample of blood comprises a blood clot.

A sample of a tissue, in some embodiments, refers to a sample comprising cells from a tissue. In some embodiments, the sample of the tumor comprises non-cancerous cells from a tissue. In some embodiments, the sample of the tumor comprises precancerous cells from a tissue. In some embodiments, the sample of the tumor comprises precancerous cells from a tissue.

Methods of the present disclosure encompass a variety of tissue including organ tissue or non-organ tissue, including but not limited to, muscle tissue, brain tissue, lung tissue, liver tissue, epithelial tissue, connective tissue, and nervous tissue. In some embodiments, the tissue may be normal tissue or it may be diseased tissue or it may be tissue suspected of being diseased. In some embodiments, the tissue may be sectioned tissue or whole intact tissue. In some embodiments, the tissue may be animal tissue or human tissue. Animal tissue includes, but is not limited to, tissues obtained from rodents (e.g., rats or mice), primates (e.g., monkeys), dogs, cats, and farm animals.

The biological sample may be from any source in the subject's body including, but not limited to, any fluid [such as blood (e.g., whole blood, blood serum, or blood plasma), saliva, tears, synovial fluid, cerebrospinal fluid, pleural fluid, pericardial fluid, ascitic fluid, and/or urine], hair, skin (including portions of the epidermis, dermis, and/or hypodermis), oropharynx, laryngopharynx, esophagus, stomach, bronchus, salivary gland, tongue, oral cavity, nasal cavity, vaginal cavity, anal cavity, bone, bone marrow, brain, thymus, spleen, small intestine, appendix, colon, rectum, anus, liver, biliary tract, pancreas, kidney, ureter, bladder, urethra, uterus, vagina, vulva, ovary, cervix, scrotum, penis, prostate, testicle, seminal vesicles, and/or any type of tissue (e.g., muscle tissue, epithelial tissue, connective tissue, or nervous tissue).

Any of the biological samples described herein may be obtained from the subject using any known technique. See, for example, the following publications on collecting, processing, and storing biological samples, each of which are incorporated herein in its entirety: Biospecimens and biorepositories: from afterthought to science by Vaught et al. (Cancer Epidemiol Biomarkers Prev. 2012 February;21(2): 253-5), and Biological sample collection, processing, storage and information management by Vaught and Henderson (IARC Sci Publ. 2011;(163):23-42).

In some embodiments, the biological sample may be obtained from a surgical procedure (e.g., laparoscopic surgery, microscopically controlled surgery, or endoscopy), bone marrow biopsy, punch biopsy, endoscopic biopsy, or needle biopsy (e.g., a fine-needle aspiration, core needle biopsy, vacuum-assisted biopsy, or image-guided biopsy). In some embodiments, the biological sample may be obtained from an autopsy.

In some embodiments, one or more than one cell (i.e., a cell biological sample) may be obtained from a subject using a scrape or brush method. The cell biological sample may be obtained from any area in or from the body of a subject including, for example, from one or more of the following areas: the cervix, esophagus, stomach, bronchus, or oral cavity. In some embodiments, one or more than one piece of tissue (e.g., a tissue biopsy) from a subject may be used. In certain embodiments, the tissue biopsy may comprise one or more than one (e.g., 2, 3, 4, 5, 6, 7, 8, 9, 10, or more than 10) biological samples from one or more tumors or tissues known or suspected of having cancerous cells.

Any of the biological samples from a subject described herein may be stored using any method that preserves stability of the biological sample. In some embodiments, preserving the stability of the biological sample means inhibiting components (e.g., DNA, RNA, protein, or tissue structure or morphology) of the biological sample from degrading until they are measured so that when measured, the measurements represents the state of the sample at the time of obtaining it from the subject. In some embodiments, a biological sample is stored in a composition that is able to penetrate the same and protect components (e.g., DNA, RNA, protein, or tissue structure or morphology) of the biological sample from degrading. As used herein, degradation is the transformation of a component from one from to another such that the first form is no longer detected at the same level as before degradation.

In some embodiments, the biological sample is stored using cryopreservation. Non-limiting examples of cryopreservation include, but are not limited to, step-down freezing, blast freezing, direct plunge freezing, snap freezing, slow freezing using a programmable freezer, and vitrification. In some embodiments, the biological sample is stored using lyophilisation. In some embodiments, a biological sample is placed into a container that already contains a preservant (e.g., RNALater to preserve RNA) and then frozen (e.g., by snap-freezing), after the collection of the biological sample from the subject. In some embodiments, such storage in frozen state is done immediately after collection of the biological sample. In some embodiments, a biological sample may be kept at either room temperature or 4° C. for some time (e.g., up to an hour, up to 8 h, or up to 1 day, or a few days) in a preservant or in a buffer without a preservant, before being frozen.

Non-limiting examples of preservants include formalin solutions, formaldehyde solutions, RNALater or other equivalent solutions, TriZol or other equivalent solutions, DNA/RNA Shield or equivalent solutions, EDTA (e.g., Buffer AE (10 mM Tris-Cl; 0.5 mM EDTA, pH 9.0)) and other coagulants, and Acids Citrate Dextronse (e.g., for blood specimens).

In some embodiments, special containers may be used for collecting and/or storing a biological sample. For example, a vacutainer may be used to store blood. In some embodiments, a vacutainer may comprise a preservant (e.g., a coagulant, or an anticoagulant). In some embodiments, a container in which a biological sample is preserved may be contained in a secondary container, for the purpose of better preservation, or for the purpose of avoid contamination.

Any of the biological samples from a subject described herein may be stored under any condition that preserves stability of the biological sample. In some embodiments, the biological sample is stored at a temperature that preserves stability of the biological sample. In some 10 embodiments, the sample is stored at room temperature (e.g., 25° C.). In some embodiments, the sample is stored under refrigeration (e.g., 4° C.). In some embodiments, the sample is stored under freezing conditions (e.g., −20° C.). In some embodiments, the sample is stored under ultralow temperature conditions (e.g., −50° C. to −800° C.). In some embodiments, the sample is stored under liquid nitrogen (e.g., −1700° C.). In some embodiments, a biological sample is stored at −60° C. to −8-° C. (e.g., −70° C.) for up to 5 years (e.g., up to 1 month, up to 2 months, up to 3 months, up to 4 months, up to 5 months, up to 6 months, up to 7 months, up to 8 months, up to 9 months, up to 10 months, up to 11 months, up to 1 year, up to 2 years, up to 3 years, up to 4 years, or up to 5 years). In some embodiments, a biological sample is stored as described by any of the methods described herein for up to 20 years (e.g., up to 5 years, up to 10 years, up to 15 years, or up to 20 years).

Methods of the present disclosure encompass obtaining one or more biological samples from a subject for analysis. In some embodiments, one biological sample is collected from a subject for analysis. In some embodiments, more than one (e.g., 2, 3, 4, 5, 6, 7, 8, 9, 10, 11, 12, 13, 14, 15, 16, 17, 18, 19, 20, or more) biological samples are collected from a subject for analysis. In some embodiments, one biological sample from a subject will be analyzed. In some embodiments, more than one (e.g., 2, 3, 4, 5, 6, 7, 8, 9, 10, 11, 12, 13, 14, 15, 16, 17, 18, 19, 20, or more) biological samples may be analyzed. If more than one biological sample from a subject is analyzed, the biological samples may be procured at the same time (e.g., more than one biological sample may be taken in the same procedure), or the biological samples may be taken at different times (e.g., during a different procedure including a procedure 1, 2, 3, 4, 5, 6, 7, 8, 9, 10 days; 1, 2, 3, 4, 5, 6, 7, 8, 9, 10 weeks; 1, 2, 3, 4, 5, 6, 7, 8, 9, 10 months, 1, 2, 3, 4, 5, 6, 7, 8, 9, 10 years, or 1, 2, 3, 4, 5, 6, 7, 8, 9, 10 decades after a first procedure).

A second or subsequent biological sample may be taken or obtained from the same region (e.g., from the same tumor or area of tissue) or a different region (including, e.g., a different tumor). A second or subsequent biological sample may be taken or obtained from the subject after one or more treatments and may be taken from the same region or a different region. As a non-limiting example, the second or subsequent biological sample may be useful in determining whether the cancer in each biological sample has different characteristics (e.g., in the case of biological samples taken from two physically separate tumors in a patient) or whether the cancer has responded to one or more treatments (e.g., in the case of two or more biological samples from the same tumor or different tumors prior to and subsequent to a treatment). In some embodiments, each of the at least one biological sample is a bodily fluid sample, a cell sample, or a tissue biopsy sample.

In some embodiments, one or more biological specimens are combined (e.g., placed in the same container for preservation) before further processing. For example, a first sample of a first tumor obtained from a subject may be combined with a second sample of a second tumor from the subject, wherein the first and second tumors may or may not be the same tumor. In some embodiments, a first tumor and a second tumor are similar but not the same (e.g., two tumors in the brain of a subject). In some embodiments, a first biological sample and a second biological sample from a subject are sample of different types of tumors (e.g., a tumor in muscle tissue and brain tissue).

In some embodiments, a sample from which RNA and/or DNA is extracted (e.g., a sample of tumor, or a blood sample) is sufficiently large such that at least 2 µg (e.g., at least 2 µg, at least 2.5 µg, at least 3 µg, at least 3.5 µg or more) of RNA can be extracted from it. In some embodiments, the sample from which RNA and/or DNA is extracted can be peripheral blood mononuclear cells (PBMCs). In some embodiments, the sample from which RNA and/or DNA is extracted can be any type of cell suspension. In some embodiments, a sample from which RNA and/or DNA is extracted (e.g., a sample of tumor, or a blood sample) is sufficiently large such that at least 1.8 µg RNA can be extracted from it. In some embodiments, at least 50 mg (e.g., at least 1 mg, at least 2 mg, at least 3 mg, at least 4 mg, at least 5 mg, at least 10 mg, at least 12 mg, at least 15 mg, at least 18 mg, at least 20 mg, at least 22 mg, at least 25 mg, at least 30 mg, at least 35 mg, at least 40 mg, at least 45 mg, or at least 50 mg) of tissue sample is collected from which RNA and/or DNA is extracted. In some embodiments, at least 20 mg of tissue sample is collected from which RNA and/or DNA is extracted. In some embodiments, at least 30 mg of tissue sample is collected. In some embodiments, at least 10-50 mg (e.g., 10-50 mg, 10-15 mg, 10-30 mg, 10-40 mg, 20-30 mg, 20-40 mg, 20-50 mg, or 30-50 mg) of tissue sample is collected from which RNA and/or DNA is extracted. In some embodiments, at least 30 mg of tissue sample is collected. In some embodiments, at least 20-30 mg of tissue sample is collected from which RNA and/or DNA is extracted. In some embodiments, a sample from which RNA and/or DNA is extracted (e.g., a sample of tumor, or a blood sample) is sufficiently large such that at least 0.2 µg (e.g., at least 200 ng, at least 300 ng, at least 400 ng, at least 500 ng, at least 600 ng, at least 700 ng, at least 800 ng, at least 900 ng, at least 1 µg, at least 1.1 µg, at least 1.2 µg, at least 1.3 µg, at least 1.4 µg, at least 1.5 µg, at least 1.6 µg, at least 1.7 µg, at least 1.8 µg, at least 1.9 µg, or at least 2 µg) of RNA can be extracted from it. In some embodiments, a sample from which RNA and/or DNA is extracted (e.g., a sample of tumor, or a blood sample) is sufficiently large such that at least 0.1 µg (e.g., at least 100 ng, at least 200 ng, at least 300 ng, at least 400 ng, at least 500 ng, at least 600 ng, at least 700 ng, at least 800 ng, at least 900 ng, at least 1 µg, at least 1.1 µg, at least 1.2 µg, at least 1.3 µg, at least 1.4 µg, at least 1.5 µg, at least 1.6 µg, at least 1.7 µg, at least 1.8 µg, at least 1.9 µg, or at least 2 µg) of RNA can be extracted from it.

Subjects Aspects of this disclosure relate to a biological sample that has been obtained from a subject. In some embodiments, a subject is a mammal (e.g., a human, a mouse, a cat, a dog, a horse, a hamster, a cow, a pig, or other domesticated animal). In some embodiments, a subject is a human. In some embodiments, a subject is an adult human (e.g., of 18 years of age or older).

In some embodiments, a subject is a child (e.g., less than 18 years of age). In some embodiments, a human subject is one who has or has been diagnosed with at least one form of cancer. In some embodiments, a cancer from which a subject suffers is a carcinoma, a sarcoma, a myeloma, a leukemia, a lymphoma, or a mixed type of cancer that comprises more than one of a carcinoma, a sarcoma, a myeloma, a leukemia, and a lymphoma. Carcinoma refers to a malignant neoplasm of epithelial origin or cancer of the internal or external lining of the body. Sarcoma refers to cancer that originates in supportive and connective tissues such as bones, tendons, cartilage, muscle, and fat. Myeloma is cancer that originates in the plasma cells of bone marrow. Leukemias ("liquid cancers" or "blood cancers") are cancers of the bone marrow (the site of blood cell production). Lymphomas develop in the glands or nodes of the lymphatic system, a network of vessels, nodes, and organs (specifically the spleen, tonsils, and thymus) that purify bodily fluids and produce infection-fighting white blood cells, or lymphocytes. Non-limiting examples of a mixed type of cancer include adenosquamous carcinoma, mixed mesodermal tumor, carcinosarcoma, and teratocarcinoma. In some embodiments, a subject has a tumor. A tumor may be benign or malignant. In some embodiments, a cancer is any one of the following: skin cancer, lung cancer, breast cancer, prostate cancer, colon cancer, rectal cancer, cervical cancer, and cancer of the uterus. In some embodiments, a subject is at risk for developing cancer, e.g., because the subject has one or more genetic risk factors, or has been exposed to or is being exposed to one or more carcinogens (e.g., cigarette smoke, or chewing tobacco).

Single cell suspensions

In some embodiments, methods (e.g., RNA sequencing, DNA sequencing, or multiplexed flow cytometry) to characterize a cancer that a subject has or is suspected of having is performed at a single-cell level to capture the heterogeneity of a single tumor or cancerous tissue, or multiple tumors or cancerous tissues. That is, measurements and assessment of single cells in a tumor sample provides information that is not confounded by genotypic or phenotypic heterogeneity of bulk samples. In some embodiments, a single cell-suspension is prepared from one or more biological samples obtained from a subject for use in methods such as single-cell RNA or DNA sequencing, or mass cytometry.

Accordingly, some embodiments of any one of the methods described herein comprise forming a single-cell suspension of cells from a sample of tumor (e.g., a first sample of tumor). In some embodiments, forming a single-cell suspension of cells comprises from a sample of tumor comprises dissecting a tumor sample to obtain tumor sample fragments. A curved scissor may be used to dissect a tumor tissue sample. In some embodiments, a tumor sample fragment is 0.5-3 mm$^3$ (e.g., 1-2 mm$^3$). In some embodiments, a tumor tissue sample or fragment thereof is kept moist while dissecting.

A method of preparing a single-cell suspension from a tumor sample may comprise any one or more of the following steps in any order: fine mincing, enzymatic and/or non-enzymatic digestion, vigorous pipetting, passage through a cell-strainer, washing, and counting. In some embodiments, one or more of these steps are repeated (e.g., 1 time, 2 times, 3 times, 4 times, or 5 or more times).

In some embodiments, a tumor sample or tumor sample fragment/s is incubated in an enzyme cocktail. Any number and combination of enzymes can be used, see e.g., BioFiles: For Life Science Research, Issue 2, 2006 sigmaaldrich.com/content/dam/sigma-aldrich/docs/Sigma/General_Information/2/biofiles_issue2.pdf, which is incorporated herein by reference in its entirety, and especially to incorporate herein any of enzyme or other component (e.g., media) listed therein.

Quatromoni et al. (An optimized disaggregation method for human lung tumors that preserves the phenotype and function of the immune cells; J Leukoc Biol. 2015 January; 97(1): 201-209) provides a comparison of different enzymatic cocktails and is incorporated herein by reference in its entirety. In some embodiments, an enzyme cocktail comprises any one or more of the following components: media (e.g., L-15 media), anti-bacterials (e.g., penicillin and/or streptomycin), anti-fungals (e.g., amphoterecin), collagenase (e.g., collagenase I, collagenase II, collagenase IV), DNAse (e.g., DNAse I), elastase, hyaluronidase, and proteases (e.g., protease XIV, trypsin, papain, or termolysin). Coll I has the original balance of collagenase, caseinase, clostripain, and tryptic activities; Coll II contains higher relative levels of protease activity, particularly clostripain; and Coll IV is designed to be especially low in tryptic activity (Quatromoni et al., J Leukoc Biol. 2015 January; 97(1): 201-209). In some embodiments, only collagenase I, collagenase II, or collagenase IV is used. In some embodiments, a mixture of two collegenases is used (e.g., collagenase I and collagenase II, collagenase I and collagenase IV, or collagenase II and collagenase IV). In some embodiments, more than 2 collegenases are used (e.g., collagenase I, collagenase II, and collagenase IV).

In some embodiments, an enzyme cocktail comprises one or more of the following components: media (e.g., complete media), penicillin, streptomycin, collagenase (e.g., collagenase I or collagenase IV). Concentrations of enzymes in a cocktail can be adjusted. A non-limiting example of an enzyme cocktail is as follows: collagenase I (0.2 mg/ml), collagenase IV (1 mg/ml), complete medium, penicillin (0.001%), and DNAse.

In some embodiments, at least 25 ml (e.g., at least 25 ml, at least 26 ml, at least 27 ml, at least 28 ml, at least 29 ml, or at least 30 ml) of enzyme cocktail is added per 0.5 μm of tumor tissue. In some embodiments, a sample of tumor or fragments thereof is incubated in enzyme cocktail while the sample is being shaken or agitated (e.g., tumbled at 85 RPM, and/or vigorous pipetting). In some embodiments, sample of tumor or fragments thereof is incubated in enzyme cocktail at a temperature between 20-50° C. (e.g., 20-50° C., 20-25° C., 25-30° C., 25-35° C., 30-40° C., 35-45° C., 40-50° C., or 30-50° C.). In some embodiments, a method of preparing a single-cell suspension comprises filtering the enzyme cocktail, e.g., through a cell strainer (e.g., 50 μm, 70 μm, or 100 μm). In some embodiments, too fine of a filter may result in a cell composition having a high concentration of fibroblast cells. In some embodiments, too coarse a filter may result in clumps of cells. In some embodiments, clumps of cells are disaggregated using mechanical force (e.g., vigorous pipetting, or applying pressure using a syringe).

In some embodiments, filtered cells are lysed using RBC lysis buffer to lyse red blood cells. RBC lysis buffers are available commercially (see e.g., abcam.com/red-blood-cell-rbc-lysis-buffer-ab204733.html).

In some embodiments, a method of preparing a single-cell suspension comprises enzymatic and mechanical dissociation. Examples of methods of dissociating cells from tissue can be found in the following publications: Quatromoni et al., An optimized disaggregation method for human lung tumors that preserves the phenotype and function of the immune cells; J Leukoc Biol. 2015 January; 97(1): 201-209, Pennartz et al., Generation of Single-Cell Suspensions from Mouse Neural Tissue; JOVE Issue 29; doi: 10.3791/1267; Published: 7/07/2009, and youtube.com/watch?v=N0jftyYqM38.

In some embodiments, cell-dissociation buffers that do not contain enzymes are used. See e.g., ThermoFisher Scientific catalog numbers 13151014 and 13150016, or Millipore Sigma Aldrich catalog number S-014-B. Heng et al. (Biol Proced Online. 2009; 11: 161-169) provides a comparison of enzymatic and non-enzymatic means of dissociating cells and is incorporated herein by reference in its entirety.

In some embodiments, the number of cells in a single-cell suspension is counted and their viability tested. The Examples below provide an example of an overall process of forming a single-cell suspension from a sample of tumor tissue.

In some embodiments, a method comprises forming a single-cell suspension of cells from a sample of tumor and partitioning in into at least a first and second part. A first and second part of a single-cells suspension may be of equal size or of different sizes (e.g., comprising a different number of cells). In some embodiments all the parts of a single-cell suspension (e.g., a first part, a second part, and so on) are stored in separate containers and stored under the same or similar conditions (e.g., in liquid nitrogen, or −80° C.). In some embodiments, the different parts of a single-cell suspension are stored under different conditions, either before or after any further processing (e.g., labeling with antibodies for protein expression studies). In some embodiments, cells isolated from a biological sample are cultured and expanded and then stored. In some embodiments, cells isolated from a biological sample are cultured and expanded after storage.

In some embodiments, any one of the methods described herein further comprises forming a lysate from at least a part (e.g., a first or second part) of the single-cell suspension. In some embodiments, different parts of a single-cell suspension comprise different types of cells. In some embodiments, a part of the single-cell suspension from which a lysate is formed comprises at least $1 \times 10^6$ cells (e.g., at least $1 \times 10^6$ cells, at least $2 \times 10^6$ cells, at least $3 \times 10^6$ cells, at least $4 \times 10^6$ cells, or at least $5 \times 10^6$ cells). In some embodiments, a part of the single-cell suspension from which a lysate is formed comprises at least $2 \times 10^6$ cells. Lysate may be stored in storage mediums that will prevent the degradation of DNA and/or RNA (e.g., RNALater). In some embodiments, a method comprises extracting RNA from the lysate from a single-cell suspension or each part of a single-cell suspension and performing RNA sequencing on the extracted RNA to obtain RNA expression data. These RNA expression data can be used to determine the heterogeneity of a tumor.

Figure 2A:
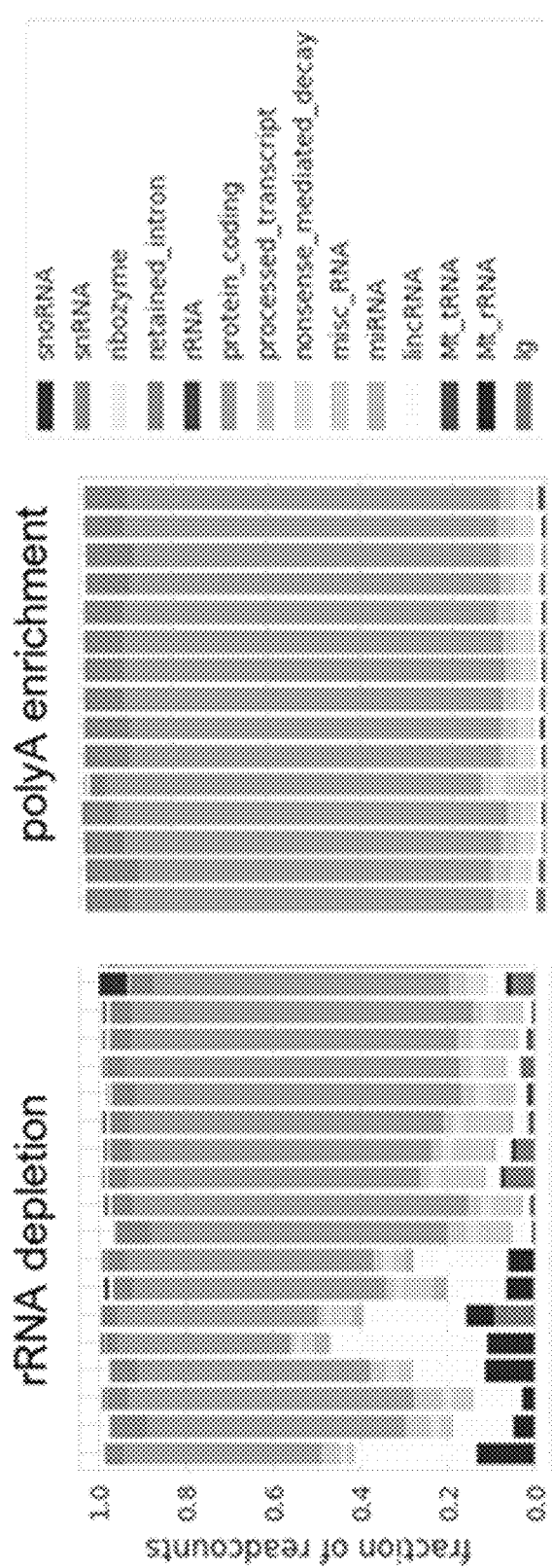
FIGS. 2A and 2B provide graphical representations of the levels and distribution of RNA transcripts depending on the type of RNA enrichment methods used and whether stranded or non-stranded RNA was used for sequencing.

An overview of single-cell RNA sequencing can be found at hemberg-lab.github.io/scRNA.seq.course/introduction-to-single-cell-rna-seq.html, FIG. 2.1 of which is incorporated by reference herein. In some embodiments, a method of performing RNA sequencing a single-cell suspension comprises single-cell RNA isolation, reverse transcription cDNA pre-amplification, cDNA library preparation (e.g., using Fluidigm C1 Protocol), and sequencing of sequenced using platforms such as Illumina HiSeq 2500.

Methods of performing single-cell RNA sequencing are described by the following references, each of which is incorporated herein by reference in its entirety: Bagnoli et al. (Studying Cancer Heterogeneity by Single-Cell RNA Sequencing; Methods Mol Biol. 2019; 1956:305-319); Sun et al. (Single-cell RNA sequencing reveals gene expression signatures of breast cancer-associated endothelial cells; Oncotarget. 2018 Feb. 16; 9(13): 10945-10961); Kulkarni et al. (Beyond bulk: a review of single cell transcriptomics methodologies and applications; Curr Opin Biotechnol. 2019 Apr. 9; 58:129-136); Huang et al (High Throughput Single Cell RNA Sequencing, Bioinformatics Analysis and Applications; Adv Exp Med Biol. 2018; 1068:33-43); Zilionis et al. (Single-Cell Transcriptomics of Human and Mouse Lung Cancers Reveals Conserved Myeloid Populations across Individuals and Species; Immunity. 2019 Apr 5. pii: S1074-7613(19)30126-8); and Kashima et al. (An Informative Approach to Single-Cell Sequencing Analysis; Adv Exp Med Biol. 2019; 1129:81-96. doi: 10.1007/978-981-13-6037-4_6); Seki et al. (Single-Cell DNA-Seq and RNA-Seq in Cancer Using the C1 System; Adv Exp Med Biol. 2019; 1129:27-50. doi: 10.1007/978-981-13-6037-4_3); and See et al. (A Single-Cell Sequencing Guide for Immunologists; Front Immunol. 2018; 9: 2425).

Gan et al. (Identification of cancer subtypes from single-cell RNA-seq data using a consensus clustering method; BMC Med Genomics. 2018; 11(Suppl 6): 117) describes a clustering method for single-cell RNA sequencing data, which is incorporated herein in its entirety by reference.

In some embodiments, any one of the following single-cell RNA sequencing methods is used: Fluidigm C1 system (SMART-seq), Fluidigm C1 system (mRNA Seq HT), SMART-seq2, 10X Genomics Chromium system, and MARS-seq. See et al. (Front Immunol. 2018; 9: 2425) provides a comparison of these methods and is incorporated herein in its entirety by reference.

In some embodiments, any one of the methods described herein further comprises performing measurement of a single-cell suspension. In some embodiments, different measurements are made in parallel on the same cells. Macaulay et al. (Trends Genet. 2017 February; 33(2): 155-168) describes methods of making multiple measurements from single cells and is incorporated herein by reference in its entirety.

In some embodiments, any one of the methods described herein further comprises performing mass cytometry on at least a first part of the single-cell suspension. Mass cytometry is a mass spectrometry technique based on inductively coupled plasma mass spectrometry and time of flight mass spectrometry used for the determination of the properties of cells. In some embodiments, mass cytometry comprises conjugating antibodies with isotopically pure elements, and then using them to label cellular molecules (e.g., proteins). In some embodiments, cells are nebulized and sent through an argon plasma, which ionizes the metal-conjugated antibodies. The metal signals are then analyzed by a time-of-flight mass spectrometer to identify and quantify the cellular molecules in the cells. In some embodiments, a single-cell suspension or part thereof on which mass cytometry is performed comprises at least $1\times10^6$ cells (e.g., at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, or at least $10\times10^6$ cells). In some embodiments, a single-cell suspension or part thereof on which mass cytometry is performed comprises at least $5\times10^6$ cells.

Methods of performing mass cytometry are described by the following references, each of which is incorporated herein by reference in its entirety: Galli et al. (The end of omics? High dimensional single cell analysis in precision medicine; Eur J Immunol. 2019 February;49(2):212-220); Brodin (The biology of the cell—insights from mass cytometry; FEBS J. 2018 Nov 3. doi: 10.1111/febs.14693); Olsen et al. (The anatomy of single cell mass cytometry data; Cytometry A. 2019 February;95(2):156-172); Behbehani (Applications of Mass Cytometry in Clinical Medicine: The Promise and Perils of Clinical CyTOF; Clin Lab Med. 2017 December; 37(4):945-964); Gondhalekar et al. (Alternatives to current flow cytometry data analysis for clinical and research studies; Methods. 2018 Feb. 1; 134-135:113-129); and Soares et al. (Go with the flow: advances and trends in magnetic flow cytometry; Anal Bioanal Chem. 2019 March; 411(9):1839-1862. doi: 10.1007/s00216-019-01593-9. Epub 2019 Feb 19).

Other Assays

Any of the biological samples described herein can be used for obtaining expression data using conventional assays or those described herein. Expression data, in some embodiments, includes gene expression levels. Gene expression levels may be detected by detecting a product of gene expression such as mRNA and/or protein.

In some embodiments, gene expression levels are determined by detecting a level of a protein in a sample and/or by detecting a level of activity of a protein in a sample. As used herein, the terms "determining" or "detecting" may include assessing the presence, absence, quantity and/or amount (which can be an effective amount) of a substance within a sample, including the derivation of qualitative or quantitative concentration levels of such substances, or otherwise evaluating the values and/or categorization of such substances in a sample from a subject.

The level of a protein may be measured using an immunoassay. Examples of immunoassays include any known assay (without limitation), and may include any of the following: immunoblotting assay (e.g., Western blot), immunohistochemical analysis, flow cytometry assay, immunofluorescence assay (IF), enzyme linked immunosorbent assays (ELISAs) (e.g., sandwich ELISAs), radioimmunoassays, electrochemiluminescence-based detection assays, magnetic immunoassays, lateral flow assays, and related techniques. Additional suitable immunoassays for detecting a level of a protein provided herein will be apparent to those of skill in the art.

Such immunoassays may involve the use of an agent (e.g., an antibody) specific to the target protein. An agent such as an antibody that "specifically binds" to a target protein is a term well understood in the art, and methods to determine such specific binding are also well known in the art. An antibody is said to exhibit "specific binding" if it reacts or associates more frequently, more rapidly, with greater duration and/or with greater affinity with a particular target protein than it does with alternative proteins. It is also understood by reading this definition that, for example, an antibody that specifically binds to a first target peptide may or may not specifically or preferentially bind to a second target peptide. As such, "specific binding" or "preferential binding" does not necessarily require (although it can include) exclusive binding. Generally, but not necessarily, reference to binding means preferential binding. In some examples, an antibody that "specifically binds" to a target peptide or an epitope thereof may not bind to other peptides or other epitopes in the same antigen. In some embodiments, a sample may be contacted, simultaneously or sequentially, with more than one binding agent that binds different proteins (e.g., multiplexed analysis).

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')2, Fd fragments, Fv fragments, scFv, and domain antibodies (dAb) fragments (de Wildt et al., Eur J Immunol. 1996; 26(3):629-39.)) as well as complete antibodies. An antibody can have the structural features of IgA, IgG, IgE, IgD, IgM (as well as subtypes thereof). Antibodies may be from any source including, but not limited to, primate (human and non-human primate) and primatized (such as humanized) antibodies.

In some embodiments, the antibodies as described herein can be conjugated to a detectable label and the binding of the detection reagent to the peptide of interest can be determined based on the intensity of the signal released from the detectable label. Alternatively, a secondary antibody specific to the detection reagent can be used. One or more antibodies may be coupled to a detectable label. Any suitable label known in the art can be used in the assay methods described herein. In some embodiments, a detectable label comprises a fluorophore. As used herein, the term "fluorophore" (also referred to as "fluorescent label" or "fluorescent dye") refers to moieties that absorb light energy at a defined excitation wavelength and emit light energy at a different wavelength. In some embodiments, a detection moiety is or comprises an enzyme. In some embodiments, an enzyme is one (e.g., β-galactosidase) that produces a colored product from a colorless substrate.

It will be apparent to those of skill in the art that this disclosure is not limited to immunoassays. Detection assays that are not based on an antibody, such as mass spectrometry, are also useful for the detection and/or quantification of a protein and/or a level of protein as provided herein. Assays that rely on a chromogenic substrate can also be useful for the detection and/or quantification of a protein and/or a level of protein as provided herein.

Alternatively, the level of nucleic acids encoding a gene in a sample can be measured via a conventional method. In some embodiments, measuring the expression level of nucleic acid encoding the gene comprises measuring mRNA. In some embodiments, the expression level of mRNA encoding a gene can be measured using real-time reverse transcriptase (RT) Q-PCR or a nucleic acid microarray. Methods to detect nucleic acid sequences include, but are not limited to, polymerase chain reaction (PCR), reverse transcriptase-PCR (RT-PCR), in situ PCR, quantitative PCR (Q-PCR), real-time quantitative PCR (RT Q-PCR), in situ hybridization, Southern blot, Northern blot, sequence analysis, microarray analysis, detection of a reporter gene, or other DNA/RNA hybridization platforms.

In some embodiments, the level of nucleic acids encoding a gene in a sample can be measured via a hybridization assay. In some embodiments, the hybridization assay comprises at least one binding partner. In some embodiments, the hybridization assay comprises at least one oligonucleotide binding partner. In some embodiments, the hybridization assay comprises at least one labeled oligonucleotide binding partner. In some embodiments, the hybridization assay comprises at least one pair of oligonucleotide binding partners. In some embodiments, the hybridization assay comprises at least one pair of labeled oligonucleotide binding partners.

Any binding agent that specifically binds to a desired nucleic acid or protein may be used in the methods and kits described herein to measure an expression level in a sample. In some embodiments, the binding agent is an antibody or an aptamer that specifically binds to a desired protein. In other embodiments, the binding agent may be one or more oligonucleotides complementary to a nucleic acid or a portion thereof. In some embodiments, a sample may be contacted, simultaneously or sequentially, with more than one binding agent that binds different proteins or different nucleic acids (e.g., multiplexed analysis).

To measure an expression level of a protein or nucleic acid, a sample can be in contact with a binding agent under suitable conditions. In general, the term "contact" refers to an exposure of the binding agent with the sample or cells collected therefrom for suitable period sufficient for the formation of complexes between the binding agent and the target protein or target nucleic acid in the sample, if any. In some embodiments, the contacting is performed by capillary action in which a sample is moved across a surface of the support membrane.

In some embodiments, an assay may be performed in a low-throughput platform, including single assay format. In some embodiments, an assay may be performed in a high-throughput platform. Such high-throughput assays may comprise using a binding agent immobilized to a solid support (e.g., one or more chips). Methods for immobilizing a binding agent will depend on factors such as the nature of the binding agent and the material of the solid support and may require particular buffers. Such methods will be evident to one of ordinary skill in the art.

Extraction of DNA and/or RNA

In some embodiments of any one of the methods described herein, RNA is extracted from a biological sample to prevent it from being degraded and/or to prevent the inhibition of enzymes in downstream processing, e.g., the preparation of DNA (i.e., a cDNA library from RNA). In some embodiments of any one of the methods described herein, DNA is extracted from a biological sample to prevent it from being degraded and/or to prevent the inhibition of enzymes in downstream processing, e.g., the preparation of DNA. In some embodiments, the term "extraction" in the context of obtaining DNA or RNA from a biological sample is used interchangeably with the term "isolation."

Methods described herein involve extraction of RNA and/or DNA from a biological sample (e.g., a tumor sample or sample of blood). As described above, a biological sample may be comprised of more than one sample from one or more than one tissues (e.g., one or more than one different tumors). In some embodiments, RNA and/or DNA are extracted from a combined sample. In some embodiments, RNA and or DNA is extracted from multiple biological samples from a subject, and then then combined before further processing (e.g., storage, or DNA library preparation). In some embodiments, more than one sample of extracted RNA and/or DNA are combined with each other after retrieval from storage. In some embodiments, at least tumor DNA is extracted from one or more tumor tissues. In some embodiments, at least tumor RNA is extracted from one or more tumor tissues. In some embodiments, at least normal DNA is extracted from one or more normal tissues to serve as a control. In some embodiments, at least normal RNA is extracted from one of more normal tissues to serve as a control. Protocols of DNA/RNA extraction can be found at least in Example 2.

Methods for extracting DNA and/or RNA from biological samples are known in the art, and reagents and kits for doing so are commercially available. Gómez-Acata et al. (Methods for extracting 'omes from microbialites, J Microbiol Methods. 2019 Mar. 12; 160:1-10) describes methods for extracting applied for DNA and RNA extraction from microbialites and describes their advantages and disadvantages and is incorporated herein by reference in its entirety. The methods described in Gómez-Acata et al. are generally applicable for RNA and/or DNA extracted from tissue. Moore (Curr Protoc Immunol. 2001 May; Chapter 10:Unit 10.1) describes purification and concentration of DNA from aqueous solutions and is also incorporated by reference herein in its entirety.

In some embodiments, extracting DNA and/or RNA comprises lysing cells of a biological sample and isolating DNA and/or RNA from other cellular components. Examples of methods for lysing cells include, but are not limited to, mechanical lysis, liquid homogenization, sonication, freeze-thaw, chemical lysis, alkaline lysis, and manual grinding.

Methods for extracting DNA and/or RNA include, but are not limited to, solution phase extraction methods and solid-phase extraction methods. In some embodiments, a solution phase extraction method comprises an organic extraction method, e.g., a phenol chloroform extraction method. In some embodiments, a solution phase extraction method comprises a high salt concentration extraction method, e.g., guanidinium thiocyantate (GuTC) or guanidinium chloride (GuCl) extraction method. In some embodiments, a solution phase extraction method comprises an ethanol precipitation method. In some embodiments, a solution phase extraction method comprises an isopropanol precipitation method. In some embodiments, a solution phase extraction method comprises an ethidium bromide (EtBr)-Cesium Chloride (CsCl) gradient centrifugation method. In some embodiments, extracting DNA and/or RNA comprises a nonionic detergent extraction method, e.g., a cetyltrimethylammonium bromide (CTAB) extraction method.

In some embodiments, extracting DNA and/or RNA comprises a solid phase extraction method. Any solid phase that binds to DNA and/or RNA may be used for extracting DNA and/or RNA in methods and systems described herein. Examples of solid phases that bind DNA and/or RNA include, but are not limited to, silica matrices, ion exchange matrices, glass particles, magnetizable cellulose beads, polyamide matrices, and nitrocellulose membranes.

In some embodiments, a solid phase extraction method comprises a spin-column based extraction method. In some embodiments, a solid phase extraction method comprises a bead-based extraction method. In some embodiments, a solid phase extraction method comprises a cation exchange resin, e.g., a styrene divinylbenzene copolymer resin.

Systems and methods described herein encompass extracting DNA and/or RNA from a single biological sample or a plurality of biological samples. In some embodiments, extracting DNA comprises extracting DNA from a single sample. In some embodiments, extracting DNA comprises extracting DNA from a plurality of samples. In some embodiments, extracting DNA comprises extracting DNA from a first sample and a second sample. In some embodiments, extracting DNA comprises extracting DNA from one or more, two or more, three or more, four or more, five or more, six or more, seven or more, eight or more, nine or more, or ten or more samples.

In some embodiments, extracting RNA comprises extracting RNA from a single sample. In some embodiments, extracting RNA comprises extracting RNA from a plurality of samples. In some embodiments, extracting RNA comprises extracting RNA from a first sample and a second sample. In some embodiments, extracting RNA comprises extracting RNA from one or more, two or more, three or more, four or more, five or more, six or more, seven or more, eight or more, nine or more, or ten or more samples.

Extracted DNA and/or RNA from a biological sample may be combined with extracted DNA and/or RNA from another biological sample. This may be accomplished by combining one or more biological samples and extracting nucleic acids or by combining nucleic acids extracted from one or more biological samples. In some embodiments, a first biological sample is combined with a second biological sample to form a combined sample and extracting DNA and/or RNA from the combined sample. In some embodiments, extracted DNA and/or RNA from a first biological sample may be combined with extracted DNA and/or RNA from a second biological sample.

Systems and methods described herein encompass extracting any type of DNA and/or RNA from a biological sample. In some embodiments, extracting DNA comprises extracting genomic DNA (gDNA). In some embodiments, extracting DNA comprises extracting mitochondrial DNA. In some embodiments, extracting RNA comprises extracting messenger RNA (mRNA). In some embodiments, extracting RNA comprises extracting precursor mRNA (pre-mRNA). In some embodiments, extracting RNA comprises extracting ribosomal RNA (rRNA). In some embodiments, extracting RNA comprises extracting transfer RNA (tRNA).

In some embodiments, a single kit is used to purity DNA and RNA from the same sample. A non-limiting example of kit for doing so is the Qiagen AllPrep DNA/RNA kit. In some embodiments, robotics is employed to carry out DNA and/or RNA extraction.

In some embodiments, if a sample of extracted RNA is not of sufficient yield and/or quality, anyone of the following outcome may occur. First, there may be an overrepresentation of common transcripts in RNA sequencing data, and underrepresentation of low abundance transcripts. Second, poor quality RNA can lead to insufficient read lengths (i.e., reads are shorter) and/or inadequate read quality leading to potential misidentification of RNA.

For whole exome sequencing, poor quantity and quality of DNA can lead to misidentification of base pairs leading to false variant discovery (e.g., a false positive) or incidences where variants are not identified (e.g., a false negative). Another problem that can arise resulting from low DNA quantity and/or quality is inadequate coverage of the exome (e.g., missing sequences).

In some embodiments, before extracted RNA and/or DNA is processed further for RNA sequencing or whole exome sequencing (WES), the quality and/or quantity of RNA or DNA is checked. In some embodiments, a sample of extracted RNA is at least 1000-6000 ng in total mass. In some embodiments, a sample of extracted RNA is at least 100-60000 ng (e.g., 100-60000 ng, 500-30000 ng, 800-20000 ng, 1000-15000 ng, 1000-10000 ng, 1000-8000 ng, 1000-6000 ng, 10000-20000 ng, 20000-60000 ng) in total mass. In some embodiments, the acceptable total RNA amount for further sequencing is at least 100-1,000 ng (e.g., 100-1,000 ng, 500-1,000 ng, or 300-900 ng). In some embodiments, the target total RNA amount for further sequencing is more than 200-1,000 ng (e.g., 200-1,000 ng, 500-1,000 ng, or 300-1,000 ng). In some embodiments, the purity of a sample of extracted RNA is such that it corresponds to a ratio of absorbance at 260 nm to absorbance at 280 nm of at least 1 (e.g., at least 1, at least 1.2, at least 1.4, at least 1.6, at least 1.8, or at least 2). In some embodiments, the purity of a sample of extracted RNA is such that it corresponds to a ratio of absorbance at 260 nm to absorbance at 280 nm of at least 2. The ratio of absorbance at 260 nm and 280 nm is used to assess the purity of DNA and RNA. A ratio of ~1.8 is generally accepted as "pure" for DNA; a ratio of ~2.0 is generally accepted as "pure" for RNA. If the ratio is appreciably lower in either case, it may indicate the presence of protein, phenol or other contaminants that absorb strongly at or near 280 nm. Absorbances can be measured using a spectrophotometer.

In some embodiments, the purity or integrity of extracted RNA or DNA (e.g., a DNA fragment library) by any one of the methods described herein is such that it corresponds to a RNA integrity number (RIN) of at least 4 (e.g., at least 4, at least 5, at least 6, at least 7, at least 8, or at least 9). In some embodiments, the purity of extracted nucleic acid (e.g., RNA or DNA) by any one of the methods described herein is such that it corresponds to a RNA integrity number (RIN) of at least 7. RIN has been demonstrated to be robust and reproducible in studies comparing it to other RNA integrity calculation algorithms, cementing its position as a preferred method of determining the quality of RNA to be analyzed (Imbeaud et al., Towards standardization of RNA quality assessment using user-independent classifiers of microcapillary electrophoresis traces; Nucleic Acids Research. 33 (6): e56).

In some embodiments, a sample of extracted DNA is at least 100-20000 ng (e.g., 100-20000 ng, 500-15000 ng, 800-10000 ng, 1000-15000 ng, 1000-10000 ng, 1000-8000 ng, 1000-6000 ng, or 1000-2000 ng) in total mass. In some embodiments, a sample of extracted DNA is at least 1000-2000 ng in total mass. In some embodiments, the acceptable total DNA amount for further sequencing is at least 20-200 ng (e.g., 20-200 ng, 30-200 ng, or 50-150 ng). In some embodiments, the target total DNA amount for further sequencing is more than 30-200 ng (e.g., 30-200 ng, 50-200 ng, or 100-200 ng). In some embodiments, the target purity of a sample of extracted DNA is such that it corresponds to a range of a ratio of absorbance at 260 nm to absorbance at 280 nm of at least 1.8-2 (e.g., at least 1.8-2, at least 1.8-1.9). In some embodiments, the purity of a sample of extracted DNA is such that it corresponds to a ratio of absorbance at 260 nm to absorbance at 280 nm of at least 1 (e.g., at least 1, at least 1.2, at least 1.4, at least 1.6, at least 1.8, or at least 2). In some embodiments, the acceptable purity of a sample of extracted DNA is such that it corresponds to a ratio of absorbance at 260 nm to absorbance at 280 nm of at least 1.5 (e.g., at least 1.5, at least 1.7, at least 2). In some embodiments, the target purity of a sample of extracted DNA is such that it corresponds to a range of a ratio of absorbance at 260 nm to absorbance at 230 nm of at least 2-2.2 (e.g., at least 2-2.2, at least 2-2.1). In some embodiments, the acceptable purity of a sample of extracted DNA is such that it corresponds to a ratio of absorbance at 260 nm to absorbance at 230 nm of at least 1.5 (e.g., at least 1.5, at least 1.7, at least 2). In some embodiments, the purity of a sample of extracted DNA as described herein is analyzed by a spectrophotometer, for example a small volume full-spectrum, UV-visible spectrophotometer (e.g., Nanodrop spectrophotometer available from ThermoFisher Scientific, thermofisher.com).

In some embodiments, a sample of extracted DNA has a target concentration of at least 4.5 ng/µl (e.g., 4.5 ng/µl, 5.5 ng/µl, 6.5 ng/µl). In some embodiments, a sample of extracted DNA has an acceptable concentration of at least 3 ng/µl (e.g., 3 ng/µl, 5 ng/µl, 10 ng/µl). In some embodiments, the concentration of the extracted DNA is performed by a fluorometer, for example for quantification of DNA or RNA (e.g., a Qubit fluorometer available from ThermoFisher Scientific, thermofisher.com).

In some embodiments, a sample of extracted DNA has a target concentration of at least 4 ng/µl (e.g., 4 ng/µl, 6 ng/µl, 8 ng/µl). In some embodiments, a sample of extracted DNA has an acceptable concentration of at least 2.5 ng/µl (e.g., 2.5 ng/µl, 4.5 ng/µl, 5.5 ng/µl). In some embodiments, the concentration of the extracted DNA is performed by Tapestation.

In some embodiments, a sample of extracted RNA has a target concentration of at least 2 ng/µl (e.g., 2 ng/µl, 4 ng/µl, 6 ng/µl). In some embodiments, a sample of extracted RNA has an acceptable concentration of at least 4 ng/µl (e.g., 4 ng/µl, 6 ng/µl, 10 ng/µl). In some embodiments, the concentration of the extracted DNA is performed by a fluorometer, for example for quantification of DNA or RNA (e.g., a Qubit fluorometer available from ThermoFisher Scientific, thermofisher.com).

In some embodiments, a sample of extracted RNA has a target concentration of at least 4 ng/µl (e.g., 4 ng/µl, 6 ng/µl, 8 ng/µl). In some embodiments, a sample of extracted RNA has an acceptable concentration of at least 1.5 ng/µl (e.g., 1.5 ng/µl, 3.5 ng/µl, 5.5 ng/µl). In some embodiments, the concentration of the extracted RNA is performed by Tapestation. In some embodiments, the acceptable RNA integrity number (RIN) is at least 5 (e.g., 5, 6, 7). In some embodiments, the target RNA integrity number (RIN) is at least 8 (e.g., 8, 9, 10). In some embodiments, the RIN is performed by Tapestation.

In some embodiments, the target purity of a sample of extracted RNA is such that it corresponds to a range of a ratio of absorbance at 260 nm to absorbance at 280 nm of at least 1.8-2 (e.g., at least 1.8-2, at least 1.8-1.9). In some embodiments, the purity of a sample of extracted RNA is such that it corresponds to a ratio of absorbance at 260 nm to absorbance at 280 nm of at least 1.8. In some embodiments, the acceptable purity of a sample of extracted RNA is such that it corresponds to a ratio of absorbance at 260 nm to absorbance at 280 nm of at least 1.5 (e.g., at least 1.5, at least 1.7, at least 2). In some embodiments, the target purity of a sample of extracted RNA is such that it corresponds to a range of a ratio of absorbance at 260 nm to absorbance at 230 nm of at least 2-2.2 (e.g., at least 2-2.2, at least 2-2.1). In some embodiments, the acceptable purity of a sample of extracted RNA is such that it corresponds to a ratio of absorbance at 260 nm to absorbance at 230 nm of at least 1.5 (e.g., at least 1.5, at least 1.7, at least 2). In some embodiments, the purity of a sample of extracted RNA as described herein is analyzed by a spectrophotometer, for example a small volume full-spectrum, UV-visible spectrophotometer (e.g., Nanodrop spectrophotometer available from ThermoFisher Scientific, thermofisher.com). In some embodiments, the concentration of extracted DNA is at least 10-2000 ng/µl (e.g., 10-2000 ng/µl, 10-1000 ng/µl, 10-200 ng/µl, 1-200 ng/µl, 0.5-400 ng/µl, 0.5-200 ng/µl, 100-200 ng/µl, 100-400 ng/µl, 100-500 ng/µl, 50-500 ng/µl, or 50-250 ng/µl).

Protocols for quality control of a sample of extracted RNA or DNA can be found at least in Example 6. In some embodiments, the purity of a sample of extracted DNA and/or RNA as described herein can be analyzed by any other suitable technologies or tools. In some embodiments, a sample of extracted RNA or DNA is not processed further if it does not meet a particular quantity or purity standard as described above. In some embodiments, if a sample of extracted RNA or DNA does not meet a particular quantity or purity standard, it is combined with another sample.

Library preparation for RNA sequencing Methods of preparing cDNA libraries from a sample of RNA are known in the art. For example, illumina.com/content/dam/illumina-marketing/documents/applications/ngs-library-prep/for-all-you-seq-rna.pdf provides illustrations of different methods for preparing cDNA libraries for RNA sequencing. Non-limiting examples of cDNA library preparation include ClickSeq, 3Seq, and cP-RNA-Seq. In some embodiments, preparing a cDNA library from RNA comprises purifying mRNA from the sample of RNA (RNA enrichment). In some embodiments, enriched RNA is fragmented. In some embodiments, after selection of the appropriate RNA fraction is completed, the molecules are fragmented into smaller pieces, to a size between 50-1000 bp (e.g., 50-100 bp, 100-800 bp, 100-500 bp, or 200-500 bp) depending on the sequencing platform being used. This fragmentation can be achieved either by fragmenting double-stranded (ds) cDNA or by fragmenting RNA. Both methods result in the same end product of a double stranded cDNA library in which each fragment has an adapter attached.

In some embodiments, a library preparation method comprises one or more amplification steps to add function elements (e.g., sample indices, molecular barcodes or flow cell oligo binding sites), enrich for sequencing-competent DNA fragments, and/or generate a sufficient amount of library DNA for downstream processing. In some embodiments, enriched RNA (e.g., fragmented enriched RNA) is amplified using random primers (e.g., random hexamers). In some embodiments, enriched RNA (e.g., fragmented enriched RNA) is amplified using oligodTs. In some embodiments, RNA is then removed from the formed cDNA. In some embodiments, cDNA is amplified to include sequencing adapters and indices (i.e., a plurality of indexes). An adapter is a DNA sequence of 10-100 bp (e.g., 10-20, 10-100, 20-80, 30-70, 40-60, 20-100, 40-100, 40-80, 30-60, or 45-65 bp) that can bind to a flow cell for sequencing. Adapters also allow for PCR enrichment of adapter-ligated DNA fragments. Adapters also can allow for indexing or barcoding of samples so that multiple cDNA libraries can be mixed together into one sequencing sample (or lane); i.e., it allows for multiplexing. In some embodiments, an index or a barcode is 4-20 bp long (e.g., 4, 5, 6, 7, 8, 9, 10, 11, 12, 13, 14, 15, 16, 17, 18, 19, 4-20, 5-15, 6-12, or 4-12 bp long). tucf-genomics.tufts.edu/documents/protocols/ TUCF_Understanding_Illumina_TruSeq_Adapters.pdf provides example protocols for preparing cDNA libraries using adapters and indexing and is incorporated herein by reference in its entirety. Protocols for constructing a DNA or RNA library can at least be found in Example 3 and Example 5.

RNA enrichment

Methods for RNA enrichment to enrich for mRNA (herein also described as "RNA enrichment") during cDNA library preparation are known in the art. RNA enrichment can be targeted or non-targeting. Targeted methods of RNA enrichment include use of sequence-specific capture probes. A non-limiting example of targeted mRNA enrichment includes CaptureSeq (sapac.illumina.com/science/sequencing-method-explorer/kits-and-arrays/captureseq.html), which makes use of capture probes specific to sequences of interest. Other platforms or tools suitable for targeted mRNA enrichment can also be used.

Examples of non-targeted mRNA enrichment methods include polyA capture using oligodT (e.g., those on conjugated to beads), and rRNA depletion. Petrova et al. (Scientific Reports volume 7, Article number: 41114 (2017) provides a comparison of various rRNA depletion methods and is incorporated by reference herein in its entirety. In some embodiments, rRNA depletion can be performed using enzymatic approaches (e.g., using an exonuclease that does not process mRNA). In some embodiments, rRNA depletion method comprises subtractive hybridization, whereby rRNA is captured using sequence specific probes (see e.g., sciencedirect.com/topics/immunology-and-microbiology/subtractive-hybridization)

In some embodiments, polyA capture comprises capturing of mRNA bearing a polyA tail by using polyA-specific capture probes (oligodT). In some embodiments, capture probes are immobilized for ease of purification. In some embodiments, capture probes are immobilized on beads (e.g., magnetic beads). In some embodiments, a commercial kit is used to prepare a DNA library from an RNA sample. In some embodiments, an Illumina TruSeq RNA Library Prep kit is used.

The choice of mRNA enrichment can have a huge impact on the selection of transcripts that are sequenced. For example, in some embodiments, compared to rRNA depletion methods, cDNA libraries prepared using polyA enrichment result in libraries comprising a higher fraction of protein-coding transcripts (e.g., greater than 80%, greater than 90%, greater than 95%, greater than 96%, greater than 97%, greater than 98%, greater than 99%, or greater than 99.9%) compared to non-coding transcripts (e.g., rRNA, miRNA, and lncRNA).

In some embodiments, prepared cDNA libraries are tested for quality. In some embodiments, quantification of libraries for use in sequencing is generally performed before the libraries are pooled for target enrichment or amplification to ensure equal representation of indexed libraries in multiplexed applications. In some embodiments, quantification is also used to confirm that individual libraries or library pools are diluted optimally prior to sequencing. Accurate and reproducible quantification of adapter-ligated library molecules contributes to obtaining consistent and reproducible results, and for maximizing sequencing yields. Loading more than the recommended amount of DNA could lead to saturation of the flowcell or increased cluster density while loading too little DNA can lead to decreased cluster density and reduced coverage and depth.

Methods of quantifying DNA libraries include electrophoresis, fluorometry, spectrophotometry, digital PCR, droplet-digital PCR and qPCR. Various instruments for measuring the quantity and/or quality of DNA libraries exist, e.g., the Agilent High Sensitivity D1000 ScreenTape System.

Aspects of the present disclosure provide quality control of nucleic acids for the sequencing analysis. Aspects of the present disclosure provide quality control of DNA for the sequencing analysis. Aspects of the present disclosure provide quality control of RNA for the sequencing analysis. In some embodiments, the nucleic acids can include any suitable types of DNA or RNA. In some embodiments, the quality control of nucleic acid comprises the confirmation of biopsy condition and documents. In some embodiments, the confirmation of biopsy condition and documents can include, but are not limited to the inventory and registration of the nucleic acid materials. In some embodiments, the confirmation of biopsy condition and documents include nucleic acid material acceptance. By way of example, patient samples received from a healthcare provider are confirmed whether the patient tissues are in the condition of fresh frozen or formalin-fixed paraffin-embedded. The laboratory personnel verify the compliance of the biopsy of the registered entity. The laboratory personnel verify the proper storage of the biopsy sample during transportation. The laboratory personnel verify the physical condition of the biopsy samples. In the event that the laboratory personnel identify any errors regarding the biopsy samples, the source of the biopsy samples (e.g., a healthcare provider) may be notified. In some embodiments, if the received biopsy samples are patient tissue cell lines, the samples are prepared for extraction. In some embodiments, if the received biopsy samples are extracted DNA or RNA, the samples are stored at −80° C. for further sequencing. In some embodiments, the extracted DNA can be a reference gDNA. In some embodiments, the extracted RNA can be a reference RNA.

Figure 7:
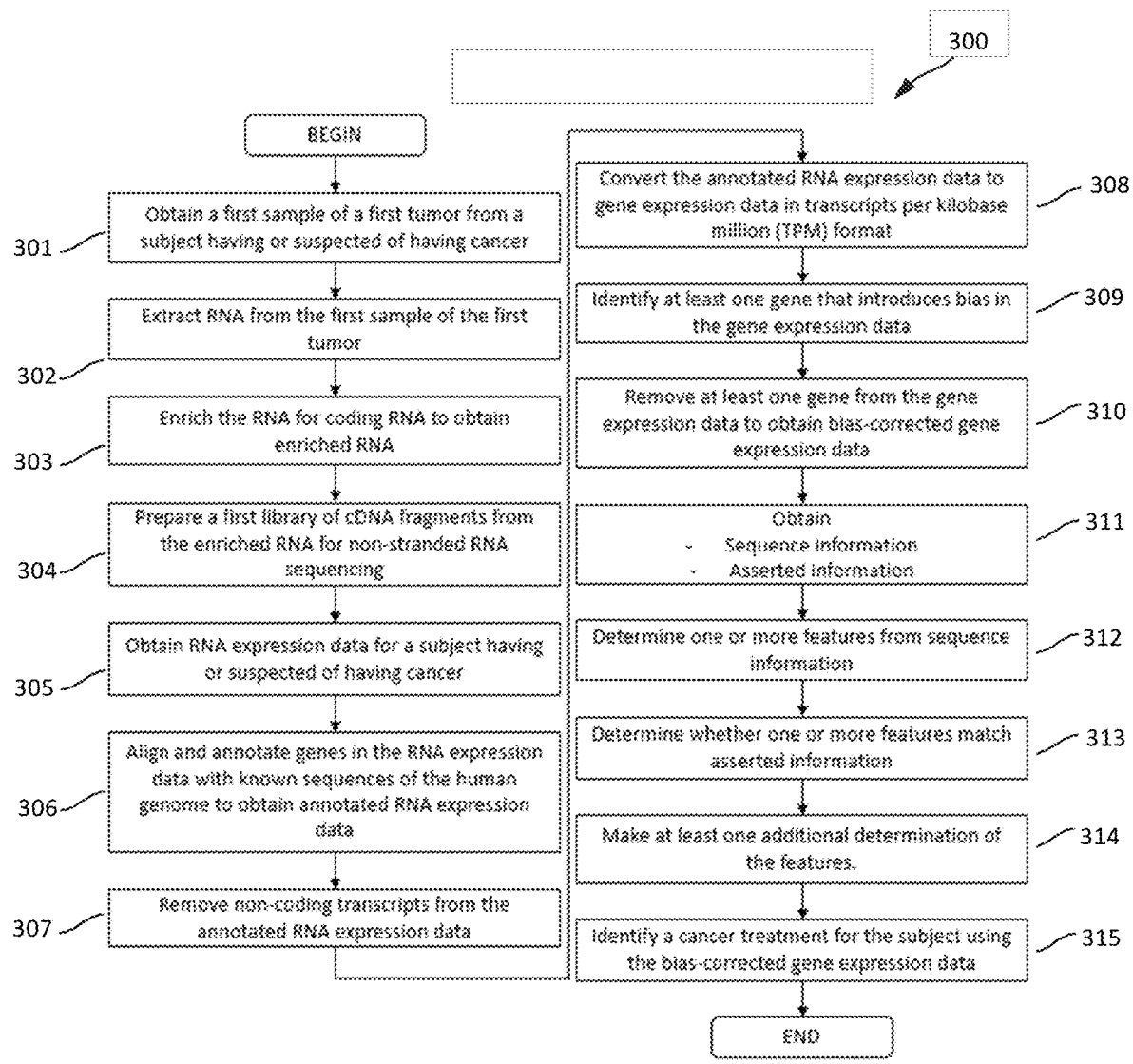
FIG. 7 is flowchart of an illustrative process pipeline 300 comprising bioinformatic quality control processes for assessing nucleic acid sequence data obtained from a tumor sample and using the nucleic acid sequence data to identify a cancer treatment for a subject having, suspected of having, or at risk of having cancer.

In some embodiments, the quality control procedures provide a target range. The target range may represent the most ideal quality of a given step (e.g., extraction). In some embodiments, the quality control procedures provide an acceptable range. The acceptable range may represent ideal or acceptable quality of a given step. In some embodiments, the quality control of nucleic acid comprises ensuring the quality in the process of constructing a DNA library. In some embodiments, the quality control of nucleic acid comprises ensuring the quality in the process of constructing an RNA library. As shown in FIG. 7 and Example 6, the preparation of the DNA or RNA libraries comprises the extraction of the DNA or RNA from the patient tissue samples. In some embodiments, a spectrophotometer, fo example a small volume full-spectrum, UV-visible spectrophotometer (e.g., Nanodrop spectrophotometer available from ThermoFisher Scientific, thermofisher.com) can be used for determining the quality of the DNA or RNA extraction. By way of example, the extracted DNA at >100 ng/µl shows that the extracted DNA passes the quality control test. The extracted RNA at >500 ng/µl shows that the extracted RNA passes the quality control test. In another example, the ratio of absorbance at 260 nm and 280 nm (260/280) of the extracted DNA at 1.8-2.0 shows that the extracted DNA passes the quality control test. The ratio of absorbance at 260 nm and 280 nm (260/280) of the extracted RNA at 2.0 shows that the extracted RNA passes the quality control test. In another example, the ratio of absorbance at 260 nm and 230 nm (260/230) of the extracted DNA at 2.0-2.2 shows that the extracted DNA passes the quality control test. The ratio of absorbance at 260 nm and 230 nm (260/230) of the extracted RNA at 2.0-2.2 shows that the extracted RNA passes the quality control test. In some embodiments, a fluorometer, for example for quantification of DNA or RNA (e.g., a Qubit fluorometer available from ThermoFisher Scientific, thermofisher.com) can be used for determining the quality of the DNA or RNA extraction. In some embodiments, an electrophoresis device, for example an automated electrophoresis device (e.g., a TapeStation System available from Agilent, agilent.com) can be used for determining the quality of the DNA or RNA extraction. In some embodiments, any suitable technology or tool can be used for determining the quality of the DNA or RNA extraction.

In some embodiments, the acceptable total DNA amount for further DNA library construction is at least 200-1,000 ng (e.g., 200-1,000 ng, 300-1,000 ng, or 300-1,000 ng). In some embodiments, the target total DNA amount for further sequencing is more than 500-1,000 ng (e.g., 500-1,000 ng, 600-1,000 ng, or 800-1,000 ng). In some embodiments, the acceptable total RNA amount for further RNA library construction is at least 0.5-4 nmol/l (e.g., 200-1,000 ng, 300-1,000 ng, or 300-1,000 ng). In some embodiments, the target total RNA amount for further RNA library construction is at least 0.5-4 nmol/l (e.g., 500-1,000 ng, 600-1,000 ng, or 800-1,000 ng).

In some embodiments, the acceptable DNA concentration for further DNA library construction is at least 17 ng/μl (e.g., 17 ng/μl, 25 ng/μl, 35 ng/μl). In some embodiments, the target DNA concentration for further DNA library construction is at least 42 ng/μl (e.g., 42 ng/μl, 50 ng/μl, 80 ng/μl). In some embodiments, the acceptable RNA concentration for further RNA library construction is at least 0.1 ng/μl (e.g., 0.1 ng/μl, 1 ng/μl, 3 ng/μl). In some embodiments, the target RNA concentration for further RNA library construction is at least 0.1 ng/μl (e.g., 0.1 ng/μl, 1 ng/μl, 3 ng/μl). In some embodiments, the DNA and RNA concentration is detected by a fluorometer, for example for quantification of DNA or RNA (e.g., a Qubit fluorometer available from ThermoFisher Scientific, thermofisher.com).

In some embodiments, the acceptable DNA concentration for further DNA library construction is at least 15 ng/μl (e.g., 15 ng/μl, 25 ng/μl, 35 ng/μl). In some embodiments, the target DNA concentration for further DNA library construction is at least 402 ng/μl (e.g., 40 ng/μl, 50 ng/μl, 80 ng/μl). In some embodiments, the acceptable RNA concentration for further RNA library construction is at least 0.1 ng/μl (e.g., 0.1 ng/μl, 1 ng/μl, 3 ng/μl). In some embodiments, the target RNA concentration for further RNA library construction is at least 0.1 ng/μl (e.g., 0.1 ng/μl, 1 ng/μl, 3 ng/μl). In some embodiments, the acceptable RNA concentration for further RNA library construction is at least 0.5 nmol/l (e.g., 0.5 nmol/l, 1 nmol/l, 5 nmol/l). In some embodiments, the target RNA concentration for further RNA library construction is at least 0.5 nmol/l (e.g., 0.5 nmol/l, 1 nmol/l, 5 nmol/l). In some embodiments, the DNA and RNA concentrations are detected by Tapestation.

In some embodiments, the acceptable RNA concentration for further RNA library construction is at least 0.5 nmol/l (e.g., 0.5 nmol/l, 1 nmol/l, 5 nmol/l). In some embodiments, the target RNA concentration for further RNA library construction is at least 0.5 nmol/l (e.g., 0.5 nmol/l, 1 nmol/l, 5 nmol/l). In some embodiments, the DNA and RNA concentration is detected by a nucleic acid amplification device (e.g., a PCR system), for example a real-time PCR system (e.g., a LightCycler Instrument available from Roche, life-science.roche.com). In some embodiments, the DNA and RNA concentration can be detected by any suitable technologies or tools.

In some embodiments, if RNA is extracted, reverse transcription can be performed. In some embodiments, an RNA library can be constructed after the reverse transcription is performed. In some embodiments, a fluorometer, for example for quantification of DNA or RNA (e.g., a Qubit fluorometer available from ThermoFisher Scientific, thermofisher.com) can be used for determining the quality of the DNA or RNA libraries. In some embodiments, any suitable method can be used for determining the quality of the DNA or RNA libraries. In some embodiments, an electrophoresis device, for example an automated electrophoresis device (e.g., a TapeStation System available from Agilent, agilent.com) can be used for determining the quality of the DNA or RNA libraries. In some embodiments, a fluorometer, for example for quantification of DNA or RNA (e.g., a Qubit fluorometer available from ThermoFisher Scientific, thermofisher.com) can be used for determining the quality of the DNA or RNA extraction. In some embodiments, a nucleic acid amplification device (e.g., a PCR system), for example a real-time PCR system (e.g., a LightCycler Instrument available from Roche, lifescience.roche.com) can be used for determining the quality of the RNA library. In some embodiments, one or more RNA libraries can be pooled. In some embodiments, if DNA is extracted, the extracted DNA can be used for a DNA library construction. In some embodiments, the DNA fragments in the constructed DNA library can be hybridized and/or captured. In some embodiments, a fluorometer, for example for quantification of DNA or RNA (e.g., a Qubit fluorometer available from ThermoFisher Scientific, thermofisher.com) can be used for determining the quality of the DNA hybridization and capture step. In some embodiments, an electrophoresis device, for example an automated electrophoresis device (e.g., a TapeStation System available from Agilent, agilent.com) can be used for determining the quality of the DNA hybridization and capture step. In some embodiments, a nucleic acid amplification device (e.g., a PCR system), for example a real-time PCR system (e.g., a LightCycler Instrument available from Roche, lifescience.roche.com) can be used for determining the quality of the DNA hybridization and capture step. In some embodiments, any suitable method can be used for determining the quality of the DNA hybridization and capture step. In some embodiments, one or more DNA libraries can be pooled. In some embodiments, an electrophoresis device, for example an automated electrophoresis device (e.g., a TapeStation System available from Agilent, agilent.com) can be used for determining the quality of the DNA or RNA library pooling. In some embodiments, any suitable methods can be used for determining the quality of the DNA or RNA library pooling.

In some embodiments, the acceptable and/or target final DNA concentration range for 15 pooling is at least 0.5-4 nmol/l (e.g., 0.5-4 nmol/l, 0.5-3 nmol/l, 2-4 nmol/l). In some embodiments, the acceptable DNA concentration for pooling is at least 0.1 ng/μl (e.g., 0.1 ng/μl, 0.8 ng/μl, 4 ng/μl) when a fluorometer, for example for quantification of DNA or RNA (e.g., a Qubit fluorometer available from ThermoFisher Scientific, thermofisher.com) is used. In some embodiments, the target DNA concentration for pooling is at least 0.1 ng/μl (e.g., 0.1 ng/μl, 0.8 ng/μl, 4 ng/μl) when a fluorometer, for example for quantification of DNA or RNA (e.g., a Qubit fluorometer available from ThermoFisher Scientific, thermofisher.com) is used.

In some embodiments, the acceptable DNA concentration for pooling is at least 0.1 ng/μl (e.g., 0.1 ng/μl, 0.8 ng/μl, 4 ng/μl) when an electrophoresis device, for example an automated electrophoresis device (e.g., a TapeStation System available from Agilent, agilent.com) is used. In some embodiments, the target DNA concentration for pooling is at least 0.1 ng/μl (e.g., 0.1 ng/μl, 0.8 ng/μl, 4 ng/μl) when an electrophoresis device, for example an automated electrophoresis device (e.g., a TapeStation System available from Agilent, agilent.com) is used. In some embodiments, the acceptable DNA concentration for pooling is at least 0.5 nmol/l (e.g., 0.5 nmol/l, 0.8 nmol/l, 3 nmol/l) when an electrophoresis device, for example an automated electrophoresis device (e.g., a TapeStation System available from Agilent, agilent.com) is used. In some embodiments, the target DNA concentration for pooling is at least 0.5 nmol/l (e.g., 0.5 nmol/l, 0.8 nmol/l, 3 nmol/l) when an electrophoresis device, for example an automated electrophoresis device (e.g., a TapeStation System available from Agilent, agilent.com) is used. In some embodiments, the acceptable and/or concentration of DNA is in the range of 380-440 ng (e.g., 380-440 ng, 400-440 ng, 420-440 ng) when an electrophoresis device, for example an automated electrophoresis device (e.g., a TapeStation System available from Agilent, agilent.com) is used. In some embodiments, the acceptable DNA concentration for pooling is at least 0.5 nmol/l (e.g., 0.5 nmol/l, 0.8 nmol/l, 3 nmol/l) when a nucleic acid amplification device (e.g., a PCR system), for example a real-time PCR system (e.g., a LightCycler Instrument available from Roche, lifescience.roche.com) is used. In some embodiments, the target DNA concentration for pooling is at least 0.5 nmol/l (e.g., 0.5 nmol/l, 0.8 nmol/l, 3 nmol/l) when LightCycler is used.

In some embodiments, the quality control of nucleic acid comprises ensuring the quality after DNA or RNA library construction such as during the sequencing process. In some embodiments, cluster density can be a parameter for quality control of the sample run (Example 6). Cluster density is an important factor in optimizing data quality and yield of the sequencing. Without wishing to be bound by any theory, an optimal cluster density at least shows the DNA or RNA libraries are balanced. In some embodiments, quality score and signal/noise ratio can be parameters for quality control of the sample run.

In some embodiments, the quality control of nucleic acid comprises ensuring the quality of sequencing. In some embodiments, the quality control of sequencing comprises bioinformatics quality control. In some embodiments, the sequencing can be a DNA sequencing. In some embodiments, the sequencing can be RNA sequencing. In some embodiments, the sequencing can be any type of sequencing technologies known in the art for determining the DNA or RNA expression profiles of a given biological sample. By way of example, the sequencing can be a whole-exome sequencing. The sequencing can be a transcriptome sequencing. The sequencing can be a Sanger sequencing.

In some embodiments, up to 1 ng (e.g., up to 0.1, up to 0.2, up to 0.3, up to 0.4, up to 0.5, up to 0.6, up to 0.7, up to 0.8, up to 0.9, or up to 1 ng) of library in up to 2 μl (e.g., up to 0.1 μl, up to 0.5 μl, up to 0.8 μl, up to 0.9 μl, up to 1 μl, up to 1.2 μl, up to 1.4 μl, up to 1.5 μl, up to 1.8 μl, or up to 2 μl) of solution is used for quality control testing. In some embodiments, the parameters that are tested include sizes and size distribution of DNA molecules, and purity.

In some embodiments, a standard method of preparing a library of cDNA fragments from RNA fails to preserve the information pertaining to which DNA strand was the original template during transcription and subsequent synthesis of the mRNA transcript. Since antisense transcripts are likely to have regulatory roles that are distinctly different from their protein coding complement, this loss of strand information results in an incomplete understanding of the transcriptome. Strand-specific RNA-Seq can be performed to preserve this strandedness. Methods of preserving strandedness and preparing cDNA fragment libraries for it are known in the art (see e.g., Mills et al. Strand-Specific RNA-Seq Provides Greater Resolution of Transcriptome Profiling; Curr Genomics. 2013 May; 14(3): 173-181). In some embodiments, library preparation for stranded RNA-seq makes use of known orientation strand-specific adapters. In some embodiments, strands are chemically modified to preserve knowledge of their origin.

In some embodiments, methods making use of adapters include strand-specific 3'-end RNA-Seq. In some embodiments, strand-specific 3'-end RNA-Seq comprises anchored oligo(dT) primers are first used to select for mRNA, which results in production of double-stranded cDNA molecules. Adapters for paired-end sequencing are then ligated to each end of the cDNA molecule. Subsequently, the fragments are sequenced generating pair-end reads that are aligned to a reference genome. Any aligned read that contains a stretch of adenines at the end of the transcript must be a transcript that originated from the DNA antisense strand, while any reads that align with a stretch of thymines at the front must be a transcript from the DNA sense strand.

In some embodiments, methods making use of adapters makes use of single-stranded (ss) cDNA and Illumina adapters and 4 DNA ligase that allows for linking of 3' and 5' adapters to ssDNA. As the second strand is never synthesized and does not proceed to sequencing, strand information is retained.

In some embodiments, any suitable technologies or tools can be used for preserving strandedness. For example, Flowcell reverse transcription sequencing (FRT-Seq) can be used to preserve strandedness. In some embodiments, FRT-Seq or the equivalent technologies comprises ligation of adapters to either end of fragmented and purified polyadenylated mRNA. In some embodiments, each adapter comprises two regions; a region to which the sequencing primers anneal and a region that is complementary to the oligonucleotides present on the flowcell. The complementary region allows the mRNA fragment to hybridize to the flowcell. The mRNA fragments are then reverse transcribed on the flowcell surface.

Other non-limiting adapter-based methods of preserving strandedness include direct strand-specific sequencing (DSSS) and SOLiD® Total RNA-Seq Kit (tools.thermofisher.com/content/sfs/manuals/cms_078610.pdf) that preserves strand specificity through the addition of adapters in a directional manner.

In some embodiments, chemical modification of strands to preserve knowledge of their origin comprises marking the original RNA template through the use of bisulfite treatment. In some embodiments, dUTPs are incorporated into reverse transcription reaction, resulting in ds cDNA where the original strand has deoxythymidine residues while the complementary strand contains deoxyuridine residues. Uracil-DNA-Glycosylase (UDG) treatment can then be used to degrade complementary strands.

Library preparation of WES

An "exome" is the sum of all regions in the genome comprised of exons. Exons are DNA regions that are transcribed into messenger RNA, as opposed to introns which are removed by splicing proteins. Exome sequencing is a capture-based method developed to identify variants in the coding region of genes that affect protein function. As the coding portion of the genome encompasses only 1-2% of the entire genome, this approach represents a cost-effective strategy to detect DNA alterations that may alter protein function, compared to whole genome sequencing. In some embodiments, whole exome sequencing (WES) comprises preparation of a library of DNA fragments for sequencing from a sample of DNA. In some embodiments, DNA is first fragmented to the appropriate size (depending on the sequencing platform used) and then sequencing platform-specific adapters are added. In some embodiments, libraries are amplified before the next step in the process (target enrichment or sequencing).

Kits are commercially available for the preparation of libraries, non-limiting examples of which include KAPA HyperPrep Kits, Agilent HaloPlex, Agilent SureSelect QXT, IDT xGEN Exome, Illumina Nextera Rapid Capture Exome, Roche Nimblegen SeqCap, and MYcroarray MYbaits. In some embodiments, any kit that can prepare a DNA library for WES can be used. For example, an Agilent Human All Exon V6 Capture Kit (agilent.com/cs/library/datasheets/public/SureSelect %20V6%20DataSheet %205991-5572EN.pdf) is used to prepare a DNA library for WES. In some embodiments, a Clinical Research Exome kit (agilent.com/en/promotions/clinical-research-exome-v2) is used. Quantities of DNA needed depend on the specific reagents used to prepare the library. For example, 100 ng of genomic DNA is sufficient for Agilent SureSelect XT2 V6 Exome, but 500 ng of genomic DNA is required for IDT xGEN Exome Panel. A comparison of various capture kits are provided in genohub.com/exome-sequencing-library-preparation/.

In some embodiments, a library preparation method comprises one or more amplification steps to add function elements (e.g., sample indices, molecular barcodes or flow cell oligo binding sites), enrich for sequencing-competent DNA fragments, and/or generate a sufficient amount of library DNA for downstream processing. By way of example, a library preparation method is shown in Example 3 and Example 5.

In some embodiments, prepared DNA libraries are tested for quality. In some embodiments, quantification of libraries for use in sequencing is generally performed before the libraries are pooled for target enrichment or amplification to ensure equal representation of indexed libraries in multiplexed applications. In some embodiments, quantification is also used to confirm that individual libraries or library pools are diluted optimally prior to sequencing. Accurate and reproducible quantification of adapter-ligated library molecules contributes to obtaining consistent and reproducible results, and for maximizing sequencing yields. Loading more than the recommended amount of DNA could lead to saturation of the flowcell or increased cluster density while loading too little DNA can lead to decreased cluster density and reduced coverage and depth.

Methods of quantifying DNA libraries include electrophoresis, fluorometry, spectrophotometry, digital PCR, droplet-digital PCR and qPCR. Various instruments for measuring the quantity and/or quality of DNA libraries exist, e.g., the Agilent High Sensitivity D1000 ScreenTape System.

In some embodiments, prepared DNA libraries are tested for quality. In some embodiments up to 1 ng (e.g., up to 0.1, up to 0.2, up to 0.3, up to 0.4, up to 0.5, up to 0.6, up to 0.7, up to 0.8, up to 0.9, or up to 1 ng) of library in up to 2 µl (e.g., up to 0.1 µl, up to 0.5 µl, up to 0.8 µl, up to 0.9 µl, up to 1 µl, up to 1.2 µl, up to 1.4 µl, up to 1.5 µl, up to 1.8 µl, or up to 2 µl) of solution is used for quality control testing. In some embodiments, the parameters that are tested include sizes and size distribution of DNA molecules, and purity.

RNA sequencing

RNA sequencing is a tool to measure the transcriptome. The transcriptome is comprised of different populations of RNA molecules, including mRNA, rRNA, tRNA, and other non-coding RNA (such as microRNA, lncRNA). In some embodiments, RNA sequencing is used to profile the transcriptome (e.g., the coding and/or non-coding regions). In some embodiments, it is used to identify genes that are differentially expressed in different biological samples (e.g., cells, tissue, or bodily fluid). In some embodiments, RNA sequencing is used to determine the genetic effects of splicing events, identify novel transcripts, detect structural variations (e.g., gene fusions and isoforms), and/or to detect single nucleotide variants.

In some embodiments, the term "RNA sequencing" can be used interchangeably with "RNA seq," "RNA-seq," or the variations thereof as known in the art referring to any technologies, tools, or platforms that interrogate the transcriptome. It is noted that when "RNA sequencing," "RNA seq," "RNA-seq," or the variations thereof is referred in the present disclosure, it does not refer to a specific technology or tool that is associated with a particular platform or company, unless indicated otherwise by way of non-limiting examples for demonstrating the processes or systems as described herein. In some embodiments, RNA sequencing can be conducted by using any suitable sequencing platforms and/or sequencing methods. Non-limiting examples of high-throughput sequencing platforms include mRNA-seq, total RNA-seq, targeted RNA-seq, single-cell RNA-Seq, RNA exome capture platform, or small RNA-seq (e.g., Illumina, illumina.com), SMRT (single molecule, real-time) sequencing (e.g., Pacific Biosciences, pacb.com), and RNA sequencing (e.g., ThermoFisher, thermofisher.com).

As described above, RNA sequencing can be targeted or untargeted. Targeted approaches include using sequence-specific probes or oligonucleotides to sequence one or more specific regions of the transcriptome. In some embodiments, targeted RNA sequencing includes methods such as mRNA enrichment (e.g., by polyA enrichment or rRNA depletion).

In some embodiments, RNA sequencing is whole transcriptome sequencing. Whole transcriptome sequencing comprises measurement of the complete complement of transcripts in a sample. In some embodiments, whole transcriptome sequencing is used to determine global expression levels of each transcript (e.g., both coding and non-coding), identify exons, introns and/or their junctions.

In some embodiments, RNA is sequenced directly without preparing cDNA from a sample of RNA. In some embodiments, direct RNA sequencing comprises single molecule RNA sequencing (DRS™).

In some embodiments, RNA sequencing is mRNA sequencing. In some embodiments, mRNA sequencing is the sequencing of only coding transcripts with the goal to exclude non-coding regions. In some embodiments, mRNA sequencing is independent of polyA enrichment. In some embodiments, mRNA sequencing depends on polyA enrichment.

In some embodiments, RNA is extracted from a biological sample, mRNA is enriched from the extracted RNA, cDNA libraries are constructed from the enriched mRNA. In some embodiments, single pieces of cDNA from a cDNA library are attached to a solid matrix. In some embodiments, single pieces of cDNA from a cDNA library are attached to a solid matrix by limited dilution. In some embodiments, cDNA pieces attached to a matrix are then sequenced (e.g., using Pacbio or Pacifbio technology). In some embodiments, cDNA pieces that are attached to a matrix are amplified and sequenced (e.g., using a specialized emulsion PCR (emPCR) in SOLiD, 454 Pyrosequencing, Ion Torrent, or a connector based on the bridging reaction (Illumina) platforms).

In some embodiments, cDNA transcripts can be sequenced in parallel, either by measuring the incorporation of fluorescent nucleotides (for example, Illumina), fluorescent short linkers (for example, SOLiD), by the release of the by-products derived from the incorporation of normal nucleotides (454), by measuring fluorescence emissions, or by measuring pH change (for example, Ion Torrent). In some embodiments, cDNA transcripts can be sequenced using any known sequencing platform. Jazayeri et al. (RNA-seq: a glance at technologies and methodologies; Acta biol. Colomb. vol. 20 no.2 Bogotia May/Aug. 2015) provides a comparison of different RNA-seq platforms, and is incorporated herein by reference in its entirety, including Table 3 and Table 4. Mestan et al. (Genomic sequencing in clinical trials; Journal of Translational Medicine 2011, 9:222) provides a similar analysis for sequencing in clinical trials.

In some embodiments, RNA sequencing is stranded or strand-specific. cDNA synthesis from RNA results in loss of strandedness. In some embodiments, strandedness is preserved by chemically labeling either or both the RNA strand and the cDNA strand that is formed by reverse transcription or antisense transcription, or by using adapter-based techniques to distinguish the original RNA strand from the complementary DNA strand, as described above.

In some embodiments, nonstranded RNA sequencing is performed. In some embodiments, stranded RNA-seq should be avoided for clinical samples. In some embodiments, nonstranded RNA-seq is used to compare data obtained from a biological sample to RNA sequencing data in established data sets (e.g., The Cancer Genome Atlas (TCGA) and International Cancer Genome Consortium (ICGC)).

In some embodiments, RNA sequencing yields paired-end reads. Paired-end reads are reads of the same nucleic acid fragment and are reads that start from either end of the fragment. In some embodiments, RNA sequencing is performed with paired-end reads of at least 2×25 (2×25, 2×50, 2×75, 2×100, 2×125, 2×150, 2×175, 2×200, 2×225, 2×250, 2×275, 2×300, 2×325, or 2×350) paired-end reads. In some embodiments, RNA sequencing is performed with paired-end reads of at least 2×75 paired-end reads. RNA sequencing with 2×75 paired-end reads means that on average each read, which is paired-end, reads 75 base pairs. In some embodiments, RNA sequencing is performed with a total of at least 20 million (e.g., at least 20 million, at least 30 million, at least 40 million, at least 50 million, at least 60 million, at least 70 million at least 80 million, at least 90 million, at least 100 million, at least 120 million, at least 140 million, at least 150 million, at least 160 million, at least 180 million, at least 200 million, at least 250 million, at least 300 million, at least 350 million, or at least 400 million) paired-end reads. In some embodiments, RNA sequencing is performed with a total of at least 50 million paired-end reads. In some embodiments, RNA sequencing is performed with a total of at least 100 million paired-end reads.

In some embodiments, quality control is performed for RNA sequencing. In some embodiments, cluster density or cluster PF % is a parameter for determining the quality of the sample run. In some embodiments, the target range of cluster density or cluster PF % is at least 170-220 (e.g., 170-220, 190-220, 210-220). In some embodiments, the acceptable range of cluster density or cluster PF % is at least 280 (e.g., 280, 300, 450).

In some embodiments, % ≥Q30 is a parameter for determining the quality of the sample run. In some embodiments, the target % ≥Q30 is at least 85% (e.g., 85%, 90%, 95%). In some embodiments, the acceptable % ≥Q30 is at least 75% (e.g., 75%, 85%, 95%).

In some embodiments, error rate % is a parameter for determining the quality of the sample run. In some embodiments, the target error rate % is less than 0.7% (e.g., 0.6%, 0.5%, 0.4%). In some embodiments, the acceptable error rate % is less than 1% (e.g., 0.9%, 0.8%, 0.7%).

Whole Exome Sequencing (WES)

Whole exome sequencing (WES) is a genomic technique for sequencing all of the protein-coding region of genes in a genome. In some embodiments, WES is performed to identify genetic variants that alter protein sequences. In some embodiments, WES is performed to identify genetic variants that alter protein sequences at a cost that is lower than the cost of whole genome sequencing.

In some embodiments, whole exome sequencing (WES) is performed on a sample of DNA that has been extracted from a biological sample. In some embodiments, a library of DNA fragments is prepared from the sample of extracted DNA. In some embodiments, any one of the methods described herein comprises performing whole exome sequencing (WES) on a library of DNA fragments. Preparation of DNA libraries from a sample of DNA for WES is described above.

In some embodiments, libraries of DNA are quantified before sequencing (e.g., using next-generation sequencing (NGS)). In some embodiments, DNA libraries are pooled before sequencing. In some embodiments, DNA libraries are amplified before sequencing. In some embodiments, DNA libraries are indexed before sequencing to keep track of the origin of a DNA fragment.

In some embodiments, WES comprises target-enrichment allowing the selective capture of genomic regions of interest prior to sequencing. In some embodiments, array-based capture is used (e.g., using microarrays). In some embodiments, in-solution capture is used.

Any high-throughput DNA sequencing platform and/or method can be used in any one of the methods described herein. In some embodiments, DNA sequencing can be conducted by using any suitable platforms and/or methods. Non-limiting examples of high-throughput sequencing methods include Single-molecule real-time sequencing, Ion semiconductor (Ion Torrent sequencing), Pyrosequencing (i.e., 454), Sequencing by synthesis (Illumina), Illumina (Solexa) sequencing, Combinatorial probe anchor synthesis (cPAS- BGI/MGI), Sequencing by ligation (SOLiD sequencing), Nanopore Sequencing (e.g., using an instrument from Oxford Nanopore Technologies, Chain termination (Sanger sequencing), massively parallel signature sequencing (MPSS) pology sequencing, Heliscope single molecule sequencing, and Single molecule real time (SMRT) sequencing (e.g., using an instrument from Pacific Biosciences).

Other non-limiting examples of high-throughput sequencing techniques include Tunnelling currents DNA sequencing, sequencing by hybridization, Sequencing with mass spectrometry, Microfluidic Sanger sequencing, and RNAP sequencing.

In some embodiments, DNA sequencing yields paired-end reads. Paired-end reads are reads of the same nucleic acid fragment and are reads that start from either end of the fragment. In some embodiments, DNA sequencing is performed with paired-end reads of at least 2×25 (2×25, 2×50, 2×75, 2×100, 2×125, 2×150, 2×175, 2×200, 2×225, 2×250, 2×275, 2×300, 2×325, or 10 2×350) paired-end reads. In some embodiments, DNA sequencing is performed with paired-end reads of at least 2×75 paired-end reads. DNA sequencing with 2×75 paired-end reads means that on average each read, which is paired-end, reads 75 base pairs. In some embodiments, DNA sequencing is performed with a total of at least 20 million (e.g., at least 20 million, at least 30 million, at least 40 million, at least 50 million, at least 60 million, at least 70 million at least 80 million, at least 90 million, at least 100 million, at least 120 million, at least 140 million, at least 150 million, at least 160 million, at least 180 million, at least 200 million, at least 250 million, at least 300 million, at least 350 million, or at least 400 million) paired-end reads. In some embodiments, DNA sequencing is performed with a total of at least 50 million paired-end reads. In some embodiments, DNA sequencing is performed with a total of at least 100 million paired-end reads. In some embodiments, DNA sequencing is performed so that at least a 20× (e.g., at least a 20×, at least a 30×, at least a 40×, at least a 50×, at least a 60×, at least a 70×, at least a 80×, at least a 90×, at least a 100×, at least a 120×, at least a 125×, at least a 150×, at least a 175×, at least a 200×, at least a 250×, at least a 300×, or at least a 400×) coverage is yielded. Coverage, which also is referred to as depth, is the number of times, on average, a single base pair in a sample of nucleic acid is read or sequenced. In some embodiments, the portion of the genome that is targeted for capture and sequencing is at least 10 Mb (e.g., at least 10 Mb, at least 20 Mb, at least 30 Mb, at least 40 Mb, at least 50 Mb, at least 60 Mb, at least 70 Mb, at least 80 Mb, at least 90 Mb, at least 100 Mb, at least 120 Mb, at least 150 Mb, at least 200 Mb, at least 250 Mb, at least 300 Mb, or at least 350 Mb). In some embodiments, the portion of the genome that is targeted for capture and sequencing is at least 48 Mb (e.g., after using the Agilent Human All Exon V6 Capture system). In some embodiments, the portion of the genome that is targeted for capture and sequencing is at least 54 Mb (e.g., after using the Clinical Research Exome capture system (Agilent)).

In some embodiments, quality control is performed for whole-exome sequencing. In some embodiments, cluster density or cluster PF % is a parameter for determining the quality of the sample run. In some embodiments, the target range of cluster density or cluster PF % is at least 170-220 (e.g., 170-220, 190-220, 210-220). In some embodiments, the acceptable range of cluster density or cluster PF % is at least 280 (e.g., 280, 300, 450).

In some embodiments, actual yield is a parameter for determining the quality of the sample run. In some embodiments, the target actual yield is at least 15 Gbp (e.g., 15 Gbp, 20 Gbp, 30, Gbp).

In some embodiments, % ≥Q30 is a parameter for determining the quality of the sample run. In some embodiments, the target % ≥Q30 is at least 85% (e.g., 85%, 90%, 95%). In some embodiments, the acceptable % ≥Q30 is at least 75% (e.g., 75%, 85%, 95%).

In some embodiments, error rate % is a parameter for determining the quality of the sample run. In some embodiments, the target error rate % is less than 0.7% (e.g., 0.6%, 0.5%, 0.4%). In some embodiments, the acceptable error rate % is less than 1% (e.g., 0.9%, 0.8%, 0.7%).

Reagents and kits

Contemplated herein are reagents and kits comprising reagents for performing any one of the methods described herein. In some embodiments, a kit as provided herein comprises reagents (e.g., buffers, preservatives, inhibitors, or enzymes) and/or labware (e.g., pipettes, filters, tubes, storage containers such as vacutainers, or dissection tools) for storing biological samples obtained from a subject.

In some embodiments, a kit as provided herein comprises reagents (e.g., buffers, preservatives, inhibitors or enzymes) and/or labware (e.g., pipettes, filters, or tubes) for extracting RNA and/or DNA from a biological sample or a sample derived from a biological sample (e.g., a single-cells solution). In some embodiments, a kit as provided herein comprises reagents (e.g., buffers, preservatives, inhibitors, enzymes or dyes) and/or labware (e.g., pipettes, filters, tubes, storage containers, or electrophoresis paper) for measuring the quality and quantity of RNA and/or DNA extracted from a biological sample. In some embodiments, a kit as provided herein comprises reagents (e.g., buffers, preservatives, inhibitors, enzymes or dyes) and/or labware (e.g., pipettes, filters, tubes, storage containers, or electrophoresis paper) for measuring the quality and quantity of DNA libraries for sequencing (e.g., RNA-seq or WES).

In some embodiments, a kit as provided herein comprises reagents (e.g., buffers, preservatives, inhibitors or enzymes) and/or labware (e.g., pipettes, filters, tubes, storage containers such as vacutainers, or dissection tools) for preparing a single-cell solution from a biological sample.

In some embodiments, a kit as provided herein comprises reagents (e.g., buffers, inhibitors, or enzymes such as reverse transcriptase enzyme) and/or labware (e.g., pipettes, filters, tubes, storage containers) for preparing DNA libraries for sequencing.

In some embodiments, a kit as provided herein comprises reagents (e.g., buffers, preservatives, inhibitors or enzymes) and/or labware (e.g., pipettes, filters, tubes, storage containers such as vacutainers, or dissection tools) for any combination of two or more of the following: storing biological samples, extracting RNA and/or DNA from a biological sample, testing the quality and quantity of extracted RNA and/or DNA samples and/or DNA libraries prepared therefrom, preparing single-cell solutions from a biological sample, and preparing DNA libraries from extracted RNA and/or DNA.

In some embodiments, any one of the kits described herein comprises components for making a cell-dissociation cocktail. A cell-dissociation cocktail may be enzymatic or non-enzymatic. In some embodiments, a kit comprises one or more enzyme cocktails. In some embodiments, a kit comprises any one or more of the following components: media (e.g., L-15 media), antibacterials (e.g., penicillin and/or streptomycin), anti-fungals (e.g., amphoterecin), collagenase (e.g., collagenase I, collagenase II, collagenase IV), DNAse (e.g., DNAse I), elastase, hyaluronidase, and proteases (e.g., protease XIV, trypsin, papain, or termolysin). In some embodiments, any one of the kits described herein comprises one or more of the following enzymes: collagenase I and Collagenase IV. In some embodiments, these enzymes are comprised in separate containers. In some embodiments, these enzymes are comprised in a single container.

In some embodiments, a kit comprises a smaller equipment such as a spectrophotometer. In some embodiments, a kit comprises instructions for performing any one of, or a combination of any two or more of the following: storing biological samples, extracting RNA and/or DNA from a biological sample, testing the quality and quantity of extracted RNA and/or DNA samples and/or DNA libraries prepared therefrom, preparing single-cell solutions from a biological sample, and preparing DNA libraries from extracted RNA and/or DNA. In some embodiments, a kit comprises instructions for performing any one of the methods described herein. In some embodiments, a kit is fashioned or tailored for specific tissue types, e.g., biopsies of a solid tumor, a liquid biopsy, a blood sample, or urine.

Data processing

Aspects of this disclosure relate to processing data obtained from RNA sequencing. In some embodiments, a method to process RNA expression data (e.g., data obtained from RNA sequencing (also referred to herein as RNA-seq data)) comprises aligning and annotating genes in RNA expression data with known sequences of the human genome to obtain annotated RNA expression data; removing non-coding transcripts from the annotated RNA expression data; converting the annotated RNA expression data to gene expression data in transcripts per kilobase million (TPM) format; identifying at least one gene that introduces bias in the gene expression data; and removing the at least one gene from the gene expression data to obtain bias-corrected gene expression data. In some embodiments, a method to process RNA expression data comprises obtaining RNA expression data for a subject having or suspected of having cancer.

In some embodiments, non-coding transcripts may comprise genes that belong to groups selected from the list consisting of: pseudogenes, polymorphic pseudogenes, processed pseudogenes, transcribed processed pseudogenes, unitary pseudogenes, unprocessed pseudogenes, transcribed unitary pseudogenes, constant chain immunoglobulin (IG C) pseudogenes, joining chain immunoglobulin (IG J) pseudogenes, variable chain immunoglobulin (IG V) pseudogenes, transcribed unprocessed pseudogenes, translated unprocessed pseudogenes, joining chain T cell receptor (TR J) pseudogenes, variable chain T cell receptor (TR V) pseudogenes, small nuclear RNAs (snRNA), small nucleolar RNAs (snoRNA), microRNAs (miRNA), ribozymes, ribosomal RNA (rRNA), mitochondrial tRNAs (Mt tRNA), mitochondrial rRNAs (Mt rRNA), small Cajal body-specific RNAs (scaRNA), retained introns, sense intronic RNA, sense overlapping RNA, nonsense-mediated decay RNA, non-stop decay RNA, antisense RNA, long intervening noncoding RNAs (lincRNA), macro long non-coding RNA (macro lncRNA), processed transcripts, 3prime overlapping non-coding RNA (3prime overlapping nerna), small RNAs (sRNA), miscellaneous RNA (misc RNA), vault RNA (vault RNA), and TEC RNA.

In some embodiments, information (e.g., sequence information) for one or more transcripts for one of more of these types of transcripts can be obtained in a nucleic acid database (e.g., a Gencode database, for example Gencode V23, Genbank database, EMBL database, or other database).

In some embodiments, a method to process RNA expression data (e.g., data obtained from RNA sequencing (also referred to herein as RNA-seq data)) comprises identifying a cancer treatment (also referred to herein as an anti-cancer therapy) for the subject using the bias-corrected gene expression data. In some embodiments, any one of the methods of processing RNA expression data is further combined with administering to a subject one or more anti-cancer therapy or cancer treatment. In some embodiments, any one of the methods of processing RNA expression data is further combined with directing or recommending the administering to a subject one or more anti-cancer therapy or cancer treatment.

Obtaining RNA Expression Data

In embodiments, a method to process RNA expression data (e.g., data obtained from RNA sequencing (also referred to herein as RNA-seq data)) comprises obtaining RNA expression data for a subject (e.g., a subject who has or has been diagnosed with a cancer). In some embodiments, obtaining RNA expression data comprises obtaining a biological sample and processing it to perform RNA sequencing using any one of the RNA sequencing methods described herein. In some embodiments, RNA expression data is obtained from a lab or center that has performed experiments to obtain RNA expression data (e.g., a lab or center that has performed RNA-seq). In some embodiments, a lab or center is a medical lab or center.

In some embodiments, RNA expression data is obtained by obtaining a computer storage medium (e.g., a data storage drive) on which the data exists. In some embodiments, RNA expression data is obtained via a secured server (e.g., a SFTP server, or Illumina BaseSpace). In some embodiments, data is obtained in the form of a text-based filed (e.g., a FASTQ file). In some embodiments, a file in which sequencing data is stored also contains quality scores of the sequencing data). In some embodiments, a file in which sequencing data is stored also contains sequence identifier information.

Alignment and Annotation

In some embodiments, a method to process RNA expression data (e.g., data obtained from RNA sequencing (also referred to herein as RNA-seq data)) comprises aligning and annotating genes in the RNA expression data with known sequences of the human genome to obtain annotated RNA expression data.

In some embodiments, alignment of RNA expression data comprises aligning the data to a known assembled genome for a particular species of subject (e.g., the genome of a human) or to a transcriptome database. Various sequence alignment software are available and can be used to align data to an assembled genome or a transcriptome database. Non-limiting examples of alignment software includes short (unspliced) aligners (e.g., BLAT; BFAST, Bowtie, Burrows-Wheeler Aligner, Short Oligonucleotide Analysis package, or Mosaik), spliced aligners, aligners based on known splice junctions (e.g., Errange, IsoformEx, or Splice Seq), or de novo splice aligner (e.g., ABMapper, BBMap, CRAC, or HiSAT). In some embodiments, any suitable tool can be used for aligning and annotating data. For example, Kallisto (github.com/pachterlab/kallisto) is used to align and annotate data. In some embodiments, a known genome is referred to as a reference genome. A reference genome (also known as a reference assembly) is a digital nucleic acid sequence database, assembled as a representative example of a species'set of genes. In some embodiments, human and mouse reference genomes used in any one of the methods described herein are maintained and improved by the Genome Reference Consortium (GRC). Non-limiting examples of human reference releases are GRCh38, GRCh37, NCBI Build 36.1, NCBI Build 35, and NCBI Build 34. A non-limiting example of transcriptome databased include Transcriptome Shotgun Assembly (TSA).

In some embodiments, annotating RNA expression data comprises identifying the locations of genes and/or coding regions in the data to be processed by comparing it to assembled genomes or transcriptome databases. Non-limiting examples of data sources for annotation include GENCODE (gencodegenes.org), RefSeq (see e.g., ncbi.nlm.nih.gov/refseq/), and Ensembl. In some embodiments, annotating genes in RNA expression data is based on a GENCODE database (e.g., GENCODE V23 annotation; gencodegenes.org).

Consea et al. (A survey of best practices for RNA-seq data analysis; Genome Biology201617:13) provides best practices for analyzing RNA-seq data, which are applicable to any one of the methods described herein and is incorporated herein by reference in its entirety. Pereira and Rueda (bio-informatics-core-shared-training.github.io/cruk-bioinf-sschool/Day2/rnaSeq_align.pdf) also describe methods for analyzing RNA sequencing data, which are applicable to any one of the methods described herein, and is incorporated herein by reference in its entirety.

Removing non-coding transcripts

In some embodiments, a method to process RNA expression data (e.g., data obtained from RNA sequencing (also referred to herein as RNA-seq data)) comprises removing non-coding transcripts from annotated RNA expression data. Aligning and annotating RNA expression data allows identification of coding and non-coding reads. In some embodiments, non-coding reads for transcripts are removed so as to concentrate analysis effort on expression of proteins (e.g., those that may be involved in pathology of cancer). In some embodiments, removing reads for non-coding transcripts from the data reduces the variance in the data, e.g., in replicates of the same or similar sample (e.g., nucleic acid from the same cells or cell-type). In some embodiments, non-limiting examples of expression data that is removed include one or more non-coding transcripts (e.g., 10-50, 50-100, 100-1,000, 1,000-2,500, 2,500-5,000 or more non-coding transcripts) that belong to one or more gene groups selected from the list consisting of: pseudogenes, polymorphic pseudogenes, processed pseudogenes, transcribed processed pseudogenes, unitary pseudogenes, unprocessed pseudogenes, transcribed unitary pseudogenes, constant chain immunoglobulin (IG C) pseudogenes, joining chain immunoglobulin (IG J) pseudogenes, variable chain immunoglobulin (IG V) pseudogenes, transcribed unprocessed pseudogenes, translated unprocessed pseudogenes, joining chain T cell receptor (TR J) pseudogenes, variable chain T cell receptor (TR V) pseudogenes, small nuclear RNAs (snRNA), small nucleolar RNAs (snoRNA), microRNAs (miRNA), ribozymes, ribosomal RNA (rRNA), mitochondrial tRNAs (Mt tRNA), mitochondrial rRNAs (Mt rRNA), small Cajal body-specific RNAs (scaRNA), retained introns, sense intronic RNA, sense overlapping RNA, nonsense-mediated decay RNA, non-stop decay RNA, antisense RNA, long intervening noncoding RNAs (lincRNA), macro long non-coding RNA (macro lncRNA), processed transcripts, 3prime overlapping non-coding RNA (3prime overlapping ncrna), small RNAs (sRNA), miscellaneous RNA (misc RNA), vault RNA (vaultRNA), and TEC RNA.

In some embodiments, information (e.g., sequence information) for one or more transcripts for one of more of these types of transcripts can be obtained in a nucleic acid database (e.g., a Gencode database, for example Gencode V23, Genbank database, EMBL database, or other database). In some embodiments, a fraction (e.g., 10%, 20% 30%, 40%, 50%, 60%, 70%, 80%, 90%, 95%, 98%, 99%, or 99.5% or more) of the non-coding transcripts, histone-encoding gene, mitochondrial genes, interleukin-encoding genes, collagen-encoding genes, and/or T cell receptor-encoding genes as described herein are removed from aligned and annotated RNA expression data.

Conversion to TPM and gene aggregation

In some embodiments, a method to process RNA expression data (e.g., data obtained from RNA sequencing (also referred to herein as RNA-seq data)) comprises normalizing RNA expression data per length of transcript (e.g., to transcripts per kilobase million (TPM) format) that is read. In some embodiments, RNA expression data that is normalized per length of transcript is first aligned and annotated. Conversion of data to TPM allows presentation of expression in the form of concentration, rather than counts, which in turn allows comparison of samples with different total read counts and/or length of reads.

In some embodiments, RNA expression data that is normalized per length of transcript read is then analyzed to obtain gene expression data (expression data per gene). This is also referred to as gene aggregation. Gene aggregation comprises combining expression data in reads for transcripts for all isoforms of a gene to obtain expression data for that gene. In some embodiments, gene aggregation to obtain gene expression data is performed after TPM normalization but before identifying genes that introduce bias. In some embodiments, gene aggregation is performed before conversion of the data to TPM.

Wagner et al (Theory Biosci. (2012) 131:281-285) provides an explanation of how TPM can be calculated and is incorporated herein by reference in its entirety. In some embodiments, the following formula is used to calculate TPM:

$$A \cdot \frac{1}{\sum (A)} \cdot 10^6$$

$$\text{Where } A = \frac{\text{total reads mapped to gene} \cdot 10^3}{\text{gene length in } bp}$$

Removing bias

Since conversion of RNA expression data to obtain expression in TPM format requires dividing the number of reads for a given transcript by the length of a transcript read, biases may be introduced in the data for various reasons (as described below). Accordingly, some embodiments of any one of the methods described herein comprise identifying at least one gene that introduces bias in the gene expression data. Some embodiments of any one of the methods described herein comprise identifying at least one gene that introduces bias in the gene expression data, and removing expression data for the at least one gene from the gene expression data to obtain bias-corrected gene expression data.

In some embodiments, removing data from a dataset may involve deleting the data from the dataset, marking the data so that it is not used in some or all subsequent processing of the dataset, and/or doing any other suitable processing so that the data is not used in some or all subsequent processing of the dataset. For example, removing particular expression data (e.g., expression data for at least one gene introducing bias) from gene expression data may involve deleting the particular expression data from the gene expression data, marking the particular expression data and/or doing any other suitable processing so that the particular expression data is not used in some or all subsequent processing of the gene expression data. As another example, removing non-coding transcripts from the RNA expression data (as described above) may involve deleting the non-coding transcripts, marking the non-coding transcripts, and/or doing any other suitable subsequent processing so that the non-coding transcripts are not used in some or all subsequent processing of the RNA expression data. As yet another example, removing sequence data, determined to not pass one or more quality control checks during performance of quality control techniques described herein, may involve deleting the sequence data, marking the sequence data and/or doing any other suitable processing so that the sequence data failing the quality control check(s) is not used in some or all subsequent processing.

In some embodiments, biases in expression data converted to TPM format are attributed to transcripts of an average length that is at least a threshold amount higher or lower than an average length of transcript as read in the entire expression data set. For example, a gene for which one or more transcript of one or more isoforms has a length that is a threshold (e.g., at least 1 standard deviations, 2 standard deviations, 3 standard deviations, 4 standard deviations, 5 standard deviations, 6 standard deviations, 7 standard deviations, 8 standard deviations, 9 standard deviations, 10 standard deviations, 11 standard deviations, 12 standard deviations, 13 standard deviations 13 standard deviations, or 15 standard deviations or more) lower from the mean or median transcript length in the entire expression data set, the expression of the gene in TPM format will artificially appear to be high. Conversely, if a gene for which one or more reads of one or more isoforms is of a length that is a threshold (e.g., at least 1 standard deviations, 2 standard deviations, 3 standard deviations, 4 standard deviations, 5 standard deviations, 6 standard deviations, 7 standard deviations, 8 standard deviations, 9 standard deviations, 10 standard deviations, 11 standard deviations, 12 standard deviations, 13 standard deviations 13 standard deviations, or 15 standard deviations or more) higher than the mean or median read length in the entire expression data set, the expression of the gene in TPM format will artificially appear to be low. In some embodiments, a threshold value is set in terms of standard deviations (e.g., at least 1 standard deviations, 2 standard deviations, 3 standard deviations, 4 standard deviations, 5 standard deviations, 6 standard deviations, 7 standard deviations, 8 standard deviations, 9 standard deviations, 10 standard deviations, 11 standard deviations, 12 standard deviations, 13 standard deviations 13 standard deviations, or 15 standard deviations or more). In some embodiments, a threshold value is set based on a length of transcript and/or length of read, e.g., below 5 bp, below 10 bp, below 15 bp, below 20 bp, below 25 bp, below 50 bp, below 75 bp, below 100 bp, or below 150 bp or more.

In some embodiments, biases are attributed to the lengths of polyA tail on a transcript. In some embodiments, RNA transcripts having a polyA tail that is on average smaller or higher than the average length of polyA tail for RNA transcripts in a sample are enriched more or less than the average enrichment of all RNA transcripts in a sample. Accordingly, a gene may be associated with a polyA tail that is at least a threshold amount smaller in length compared to an average length of polyA tails of genes from a sample from which the RNA expression data was obtained. In some embodiments, such expression data for such genes is also removed from the gene expression data to obtain bias-corrected gene expression data. Removing expression data associated with one or more genes from a data set to reduce bias may be considered as a type of filtering of the data. In some embodiments, "filtration" may refer to any one or more of removing expression data for genes that appear artificially high or low (e.g., because of the lengths of transcripts, or the length of the polyA tails associated with transcripts), and removing expression data of non-coding RNA from data.

In some embodiments, identifying at least one gene that introduces bias in the gene expression data comprises analyzing the length of transcripts within the data set that is being analyzed. In some embodiments, removing, from the gene expression data, expression data for at least one gene that introduces bias decreases variability and improves the overall accuracy of subsequent gene expression-based analysis.

In some embodiments, identifying at least one gene that introduces bias in the gene expression data comprises use of knowledge gained from analyzing data outside of the expression data set in questions, e.g., using reference data sets. The inventors recognized that removing (expression data for) genes having polyA tail length that is outside the average range of polyA tails in a RNA expression data set effectively removes bias and/or outliers in the gene expression data. For example, knowledge that a certain family of genes introduces biases can be had a priori (from previously performed experiments or previously performed processing of data) to processing RNA expression data and can be used to filter out data for that family of genes.

In some embodiments, a gene that introduces bias to an expression data set may belongs to a family of genes having a polyA tail that is on average smaller or higher compared to an average length of polyA tails of genes from a sample from which the RNA expression data was obtained (or another reference sample). In some embodiments, "smaller or higher" may refer to a numerical value that is smaller or higher relative to a known, average threshold value of one or more genes.

In some embodiments, a gene that introduces bias to an expression data set belongs to a family of genes selected from the group consisting of: histone-encoding genes, mitochondrial genes, interleukin-encoding genes, collagen-encoding genes, B cell receptor encoding genes, and T cell receptor-encoding genes. In some embodiments, a gene that introduces bias to an expression data set can be any other gene that has a polyA tail that is on average smaller or higher compared to an average length of polyA tails of genes from a sample from which the RNA expression data was obtained (or another reference sample).

In some embodiments, the histone-encoding genes, mitochondrial genes, interleukin-encoding genes, collagen-encoding genes, B cell receptor encoding genes, and/or T cell receptor-encoding genes are genes in the human sample that comprise a polyA tail that is on average smaller or higher compared to an average length of polyA tails of genes from a sample from which the RNA expression data was obtained. For example, histone-encoding genes comprise a polyA tail that is on average smaller to an average length of polyA tails of genes from a sample from which the RNA expression data was obtained. In some embodiments, histone-encoding genes do not comprise a polyA tail. In some embodiments, a polyA tail is minimally or not detected in histone-encoding genes.

In some embodiments, one or more gene or protein abbreviations or acronyms are used in this application to refer to the genes (or genes encoding the proteins) using their recognized scientific nomenclature. Additional information about the genes and/or encoded proteins can be found in one or more genetic sequence databases, for example the NIH genetic sequence database (GenBank, ncbi.nlm.nih.gov), the EMBL database (the European Molecular Biology Laboratory nucleotide sequence database, ebi.ac.uk/embl/index.html), the EMBL European Bioinformatics Institute database (EMBL-EBI European Nucleotide Archive, ebi.ac.uk/ena), the GENCODE database (gencodegenes.org), or other suitable database, the contents of which are incorporated by reference herein for the different types of genes and names of genes referred to herein. In some embodiments, the gene or protein abbreiations or acronyms are referring to the human genes (or human genes encoding the proteins).

In some embodiments, a histone-encoding gene is HIST1H1A, HIST1H1B, HIST1H1C, HIST1H1D, HIST1H1E, HIST1H1T, HIST1H2AA, HIST1H2AB, HIST1H2AC, HIST1H2AD, HIST1H2AE, HIST1H2AG, HIST1H2AH, HIST1H2A1, HIST1H2AJ, HIST1H2AK, HIST1H2AL, HIST1H2AM, HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2BO, HIST1H3A, HIST1H3B, HIST1H3C, HIST1H3D, HIST1H3E, HIST1H3F, HIST1H3G, HIST1H3H, HIST1H3I, HIST1H3J, HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L, HIST2H2AA3, HIST2H2AA4, HIST2H2AB, HIST2H2AC, HIST2H2BE, HIST2H2BF, HIST2H3A, HIST2H3C, HIST2H3D, HIST2H3PS2, HIST2H4A, HIST2H4B, HIST3H2A, HIST3H2BB, HIST3H3, or HIST4H4. In some embodiments, a mitochondrial gene is MT-ATP6, MT-ATP8, MT-CO1, MT-CO2, MT-CO3Segment 3, MT-CYB, MT-ND1, MT-ND2, MT-ND3, MT-ND4, MT-ND4L, MT-ND5, MT-ND6, MT-RNR1, MT-RNR2, MT-TA, MT-TC, MT-TD, MT-TE, MT-TF, MT-TG, MT-TH, MT-TI, MT-TK, MT-TL1, MT-TL2, MT-TM, MT-TN, MT-TP, MT-TQ, MT-TR, MT-TS1, MT-TS2, MT-TT, MT-TV, MT-TW, MT-TY, MTRNR2L1, MTRNR2L10, MTRNR2L11, MTRNR2L12, MTRNR2L13, MTRNR2L3, MTRNR2L4, MTRNR2L5, MTRNR2L6, MTRNR2L7, or MTRNR2L8.

In some embodiments, removing expression data for at least one gene that introduces bias in the gene expression data comprises removing expression data for one or multiple (e.g., at least 2, at least 5, at least 10, at least 15, at least 20, at least 30, at least 40, at least 50, at least 60, at least 70, at least 80, at least 90, at least 100, at least 150, at least 200, at least 250, at least 300, at least 350, at least 400, at least 450, at least 500, between 2 and 1000, or any suitable number of genes in these ranges) genes in each of one or multiple (2, 3, 4, 5, or all) gene families including histone-encoding genes, mitochondrial genes, interleukin-encoding genes, collagen-encoding genes, B cell receptor-encoding genes, and T cell receptor-encoding genes). In some embodiments, removing expression data for at least one gene that introduces bias in the gene expression data comprises removing expression date for any of one or more genes that have a polyA tail that is on average smaller or higher compared to an average length of polyA tails of genes from a sample from which the RNA expression data was obtained (or a reference sample).

In some embodiments, after expression data for at least one gene that introduces bias is removed from the gene expression data, the remaining gene expression data may be normalized again ("renormalized") (e.g., to TPM or any other suitable unit such as reads per kilobase million (RPKM) or fragments per kilobase million (FPKM)) so that the normalized expression values are not biased by the expression data of the biasing gene(s), which was removed. In some embodiments, the remaining gene expression data may have expression data for at least 1,000 genes, at least 5,000 genes, at least 10,000 genes, between 500 and 5000 genes, between 1000 and 10,000 genes, between 5,000 and 15,000 genes or any suitable number of genes within these ranges.

Post-Sequencing Nucleic Acid Data Quality Control

As provided in the present disclosure, quality control is regularly performed during sample preparation processes. For example, the purity of the extracted nucleic acids or the size distribution of the DNA libraries) are detected. When one or more of the quality control issues occurs and is not able to be remedied in the laboratory, the provider (e.g., healthcare provider) of the biological sample is notified before proceeding to the subsequence steps. After the issues in connection to the quality are solved, the processes of sample preparation are completed and bioinformatics analysis (e.g., post-sequencing) is performed.

Aspects of methods and systems described herein provide for quality control to be performed on gene expression data to improve the accuracy and reliability of subsequent expression analysis (e.g., to determine a diagnosis, prognosis, and/or treatment for the patient or subject) and any resulting recommendation.

In some embodiments, bioinformatic quality control of sequence data can be conducted as a standalone process (e.g., based on nucleic acid data that is received from a healthcare provider) or in connection with a prior sample preparation process (e.g., if a patient sample is provided by the healthcare provider as opposed to nucleic acid sequence data). As illustrated in FIG. 7, act 301 to act 310 illustrate non-limiting sample preparation processes as described in the present disclosure, whereas act 311 to act 315 illustrate non-limiting quality control processes as described in the present disclosure. In some embodiments, one or more of act 301 to act 310 can be performed independently (e.g., without one or more of act 311 to act 315). In some instances, one or more of act 301 to act 310 can be skipped or delayed. Act 311 to act 315 can be performed independently (e.g., without act 301 to act 310). In some instances, one or more of act 311 to act 315 can be skipped or delayed. In some instances, one or more sample preparation (act 301 to act 310) and quality control (act 311 to act 315) processes can both be performed. In some instances, one or more of the sample preparation processes and one or more of the quality control processes can be performed.

In some embodiments, a process pipeline 300 is performed by obtaining a first tumor sample from a subject having, suspected of having, or at risk of having cancer at act 301, extracting RNA from the first sample of the first tumor at act 302, enriching the extracted RNA for coding RNA to obtain enriched RNA at act 303, preparing a first library of cDNA fragments from the enriched RNA for non-stranded RNA sequencing at act 304, obtaining RNA expression data for a subject having, suspected of having, or at risk of having cancer at act 305, aligning and annotating genes in the RNA expression data with known sequences of the human genome to obtain annotated RNA expression data at act 306, removing non-coding transcripts from the annotated RNA expression data at act 307, converting the annotated RNA expression data to gene expression data in transcripts per kilobase million (TPM) at act 308, identifying at least one gene that introduces bias in the gene expression data at act 309, removing at least one gene from the gene expression data to obtain bias-corrected gene expression data at act 310, obtaining sequence information and asserted information at act 311, determining one or more features from sequence information at act 312, determining whether one or more features match asserted information at act 313, making at least one additional determination of the features at act 314, identifying a cancer treatment for the subject using the bias-corrected gene expression data at act 315.

In some embodiments, act 305 may comprise obtaining the RNA expression data by using a sequencing platform or by receiving from a healthcare provider or laboratory. In some embodiments, act 306 may comprise converting the RNA expression data to gene expression data. As described herein, the "known sequence of the human genome" may refer to a reference. In some embodiments, act 307 may comprise converting the RNA expression data to gene expression data. In some embodiments, act 307 may comprise obtain filtered RNA expression data. In some embodiments, act 308 may comprise normalizing the filtered RNA expression data to obtain gene expression data in transcripts per kilobase million (TPM). In some embodiments, the asserted information act 311 may indicate an asserted source and/or an asserted integrity of the sequence data. In some embodiments, act 312 may comprise determining one or more disease features. In some embodiments, act 312 may comprise processing the sequence information or data to obtain determined information indicating a determined source and/or a determined integrity of the sequence information or data. In some embodiments, act 313 may comprise determining whether the determined information matches the asserted information. In some embodiments, the at least one additional determination of the feature at process 314 may comprise determining disease features or features that are not directly related to diseases.

Aspects of methods and systems described herein provide an approach for validating nucleic acid sequence data by obtaining both the sequence data and asserted information related to one or more features of the sequence data (e.g., source, type of nucleic acid, expected integrity, etc.), determining one or more features from the sequence data, and verifying that the one or more features determined from the sequence data match the asserted information about those features. In some embodiments, the asserted information can be information about the patient, tissue type, tumor type, nucleic acid type (RNA, DNA, WES, polyA, etc.), sequencing protocol that was used, etc., or a combination thereof. In some embodiments, the asserted information can be an expected and/or acceptable (e.g., acceptable for a subsequent analysis of the sequence data) integrity threshold for the sequence information, including for example, an expected and/or acceptable level of GC content, contamination, coverage (e.g., genome, exome, exon, protein encoding, or other coverage) or other measure of integrity.

Nucleic acid sequencing, next generation sequencing (NGS) in particular, allows for the generation of large amounts of information for a given nucleic acid (DNA, RNA, genome, exome, transcriptome, etc.). However, because of the many different sequencing platforms that are available, the variety of sample preparation and sequencing protocols and techniques that are used, and the variability and inconsistency between platforms and protocols, there is substantial variability in the content and coverage of the resulting nucleic acid sequence information. Moreover, when evaluating sequence information from several sequencing runs, or large sets of sequence information from a plurality of sequencing runs (e.g., including, for example, historical data from different medical visits for one or more patients) or from different studies (e.g., from studies to create prognostic or diagnostic evaluations, or from studies to evaluate the effect of a drug or treatment on the progression of a disease, etc.) it can be can be challenging to combine sequence information from different sources. In addition, in can be challenging to detect incorrectly identified sequence data when large amounts of information are being combined from different sources.

Currently, no robust methods exist to validate (e.g., raise the confidence, reduce the uncertainty, correct for or omit low quality sequence information, provide a signal to verify or retest questionable sequence information or outliers, etc.) source and/or integrity (e.g., also as may be referred to herein as quality) of sequence information which may be the subject of further use (e.g., being used for analysis beyond the initial sequencing step), for example for diagnostic, prognostic, and/or clinical applications.

The disclosure recognizes the prevalence of next generation sequencing techniques and platforms employed across a variety of disciplines within the scientific community. The disclosure also recognizes the variety of protocols and methodologies associated with the different techniques and platforms employed. The variation in the platforms, and protocols to use the various platforms, creates variability within the data and sequence information realized from the use thereof, which presents a significant hurdle in using the sequence information for substantive analysis, especially if such sequence information is to be used for analysis beyond the initial data run by the original user of the sample (e.g., by a secondary user, beyond the user who procured and performed the initial sequencing, third parties to the sequencing, etc.).

Accordingly, the disclosure presents a variety of methods and processes to assess the quality of sequence information (e.g., for correct identification of the sequence information, sample identification, subject identification, etc.), as well as to assess the integrity of the sequence information (e.g., create checkpoints to screen for various integrity issues, for example, contamination or degradation). For example, in some embodiments, described herein are methods for evaluating sequence information by obtaining sequence information from a nucleic acid of a sample of a subject, obtaining asserted information, determining a feature (e.g., source, identity, status, characteristic) of the sequence information, and comparing the asserted information with the determined information. The sequence information may be obtained (e.g., acquired) from any source, or through any means known in the art. Accordingly, the sequence information may be generated using any suitable sequencing technology. Alternatively, the sequence information may be obtained electronically from a third party that generated the sequence information. In some embodiments, sequence information (e.g., reference sequence information) is obtained from an existing databank of sequences. In some embodiments, sequence information is obtained from a company, a non-profit organization, an academic institution, or a healthcare organization.

In some embodiments, a sample may be any specimen, biopsy, or biological component obtained (e.g., procured, taken, received) from a subject. For example, in some embodiments, the sample may be a blood sample, hair sample, tissue sample, bodily fluid sample, cell sample, blood component sample, or any other cell or tissue sample from which a nucleic acid may be obtained for sequencing.

In some embodiments, the subject may be any organism in need of treatment or diagnosis using methods or systems of the disclosure. For example, without limitation, subjects may include mammals and non-mammals. As used herein, a "mammal," refers to any animal constituting the class Mammalia (e.g., a human, mouse, rat, cat, dog, sheep, rabbit, horse, cow, goat, pig, guinea pig, hamster, chicken, turkey, or a non-human primate (e.g., Marmoset, Macaque)). In some embodiments, the mammal is a human. In some embodiments, the subject is a mammal. In some embodiments, the subject is a human.

In some embodiments, a sample may be a biological sample obtained from a subject, e.g., from a patient. In some embodiments, a sample may be blood, serum, sputum, urine, or a tissue biopsy (e.g., from any tissue, including but not limited to heart, liver, pancreas, CNS, gastro-intestinal tract, mouth, colon, kidney, and skin). In some embodiments, a sample may be suspected to be a disease sample (e.g., a cancer sample). In some embodiments, a sample may be a healthy sample (e.g., to be used as a reference).

In some embodiments, sequence information is obtained from a next generation sequencing platform (e.g., Illumina™, Roche™, Ion Torrent™, etc.), or any high-throughput or massively parallel sequencing platform. In some embodiments, these methods may be automated, in some embodiments, there may be manual intervention. In some embodiments, the sequence information may be the result of non-next generation sequencing (e.g., Sanger sequencing). In some embodiments, the sample preparation may be according to manufacturer's protocols. In some embodiments, the sample preparation may be custom made protocols, or other protocols which are for research, diagnostic, prognostic, and/or clinical purposes. In some embodiments, the protocols may be experimental. In some embodiments, the origin or preparation method of the sequence information may be unknown.

In some embodiments, the size of the obtained RNA and/or DNA sequence data comprises at least 5 kilobases (kb). In some embodiments, the size of the obtained RNA and/or DNA sequence data is at least 10 kb. In some embodiments, the size of the obtained RNA and/or DNA sequence data is at least 100 kb. In some embodiments, the size of the obtained RNA and/or DNA sequence data is at least 500 kb. In some embodiments, the size of the obtained RNA and/or DNA sequence data is at least 1 megabase (Mb). In some embodiments, the size of the obtained RNA and/or DNA sequence data is at least 10 Mb. In some embodiments, the size of the obtained RNA and/or DNA sequence data is at least 100 Mb. In some embodiments, the size of the obtained RNA and/or DNA sequence data is at least 500 Mb. In some embodiments, the size of the obtained RNA and/or DNA sequence data is at least 1 gigabase (Gb). In some embodiments, the size of the obtained RNA and/or DNA sequence data is at least 10 Gb. In some embodiments, the size of the obtained RNA and/or DNA sequence data is at least 100 Gb. In some embodiments, the size of the obtained RNA and/or DNA sequence data is at least 500 Gb.

In some embodiments, the sequence information may be generated using a nucleic acid from a sample from a subject. In some embodiments, the sequence information may be a sequence data indicating a nucleotide sequence of DNA and/or RNA from a previously obtained biological sample of a subject having, suspected of having, or at risk of having a disease. In some embodiments, the nucleic acid is deoxyribonucleic acid (DNA). In some embodiments, the nucleic acid is prepared such that the whole genome is present in the nucleic acid. In some embodiments, the nucleic acid is processed such that only the protein coding regions of the genome remain (e.g., exomes). When nucleic acids are prepared such that only the exomes are sequenced, it is referred to as whole exome sequencing (WES). A variety of methods or known in the art to isolate the exomes for sequencing, for example, solution based isolation wherein tagged probes are used to hybridize the targeted regions (e.g., exomes) which can then be further separated from the other regions (e.g., unbound oligonucleotides). These tagged fragments can then be prepared and sequenced.

In some embodiments, the nucleic acid is ribonucleic acid (RNA). In some embodiments, sequenced RNA comprises both coding and non-coding transcribed RNA found in a sample. When such RNA is used for sequencing the sequencing is said to be generated from "total RNA" and also can be referred to as whole transcriptome sequencing. Alternatively, the nucleic acids can be prepared such that the coding RNA (e.g., mRNA) is isolated and used for sequencing. This can be done through any means known in the art, for example by isolating or screening the RNA for polyadenylated sequences. This is sometimes referred to as mRNA-Seq. Sequence information can include the sequence data generated by the nucleic acid sequencing protocol (e.g., the series of nucleotides in a nucleic acid molecule identified by next-generation sequencing, sanger sequencing, etc.) as well as information contained therein (e.g., information indicative of source, tissue type, etc.) which may also be considered information that can be inferred or determined from the sequence data. For example, in some embodiments RNA sequence information may be analyzed to determine whether the nucleic acid was primarily polyadenylated or not.

Asserted information can refer to information about the sequence data, and by extension, the nucleic acid, the sample, and/or the subject from which the sequence data was obtained. In some embodiments, asserted information is provided along with the sequence data and can be verified by analyzing the sequence data as described herein. The asserted information may relate to a feature of the nucleic acid, the sample, or the subject, and can be used to evaluate the quality of the nucleic acid (e.g., the source or integrity of the nucleic acid). Asserted information can refer to an asserted source and/or an asserted integrity of the sequence data or information.

In some embodiments, a third party may provide sequence data as well as the related asserted information. In some embodiments, the asserted information is obtained from the same entity that the sequence data is obtained from. In some embodiments, the asserted information and sequence data are obtained from different parties. In some embodiments, the asserted information is obtained from a database. In some embodiments, the asserted information is a reference value or property. In some embodiments, the asserted information may allege an identity of the sequence information, an identity of the nucleic acid of the sequence information, an identity of the sample from which the sequence information was generated, an identity of the subject from which the sample was obtained. In some embodiments, the asserted information may identify the sequence data as obtained from polyadenylated RNA, as originating from whole transcriptome sequencing, or as being from WES. In some embodiments, the asserted information may identify a cell or tissue type for the sample from which the nucleic acid was obtained. In some embodiments, the asserted information may allege a tumor type for the sample from which the nucleic acid was obtained. In some embodiments, the asserted information may identify an MHC profile (e.g., sequences for alleles of the MHCs of the subject from which the nucleic acid was obtained) for the subject from which the sample was obtained. In some embodiments, the asserted information may identify an expected protein subunit ratio for the sample. In some embodiments, the asserted information may provide an expected complexity value for the sequence information. In some embodiments, the asserted information may provide an expected contamination value for the sequence information. In some embodiments, the asserted information may provide an expected coverage value for the sequence information. In some embodiments, the asserted information may provide an expected exon coverage value for the sequence information. In some embodiments, the asserted information may provide an expected read composition value for the sequence information. In some embodiments, the asserted information may provide an expected Phred score for the sequence information. In some embodiments, the asserted information may provide an expected single nucleotide polymorphism (SNP) value for the sequence information. In some embodiments, the asserted information may relate to a GC content value for the sequence information. In some embodiments, the asserted information may comprise additional information. In some embodiments, the asserted information may comprise information relating to multiple or more than one feature of the sequence information. In some embodiments, the asserted information is any combination of the aforementioned features (e.g., determined values, properties, characteristics, etc.).

As used herein, a "feature" may be a property or characteristic, which is determined from analysis of the sequence information which provides the user with information about the sequence information, the sample from which it was taken, and/or the subject from which the sample was taken, beyond the sequence of the nucleotides of the sequence information. The sequence information may be in connection with the gene expression data obtained from a healthcare provider or a laboratory. For example, a feature may be indicative of a source (e.g., patient, subject, nucleic acid type), patient or subject identity, tissue type, tumor type, polyadenylation status, MHC sequence, protein subunits, complexity, contamination, coverage (e.g., total sequence, exon, etc.), read composition, quality and/or Phred Score, single nucleotide polymorphism (SNP) positions, and/or GC content. The feature(s) of the sequence information can then be indicative of whether the sequence information is potentially a match or mismatch to the asserted information from a healthcare provider or a laboratory.

When considering identity or source, it is important to recognize that the term not only refers to identifying a specific subject or patient as a particular individual, but also that one or more features of sequence information for one sample can be identified as being the same as the one or more features of sequence information obtained from another sample. For example, sequence information A may be compared to sequence information B which is presented and asserted to be from the same nucleic acid, subject or patient, tissue, or tumor. The identity can be corroborated or questioned by the methods herein without knowing the actual identity of the subject but can support the finding that the identity is consistent with another given sequence information. In some embodiments, the identity of the sequence information is used to compare to asserted information for a given sample, subject, tissue, or tumor. In some embodiments the identity of the sequence information is used to compare the asserted information for another nucleic acid or reference value.

In some embodiments, these determined features of the sequence information are then evaluated (e.g., determined, matched, aligned, measured, assessed) against the asserted information. This evaluation can be done to increase the confidence that the sequence information is of a particular origin (e.g., source), is identified correctly, or has a particular or specific characteristic (e.g., is from polyadenylated nucleic acids). In this respect, the methods can be used to provide checkpoints and measures to highlight any potential problems (e.g., non-matching values (e.g., for determined features and asserted information), or determined values which fall outside of accepted or established ranges). Such problems can signify or signal problems with integrity (e.g., degraded or contaminated) or source (e.g., misidentified, wrongly labeled, etc.) of the sequence data. By using the methods and processes herein, and matching determined features to asserted information for given sequence information, it lessens the possibility of incorrect or poor quality sequence data being used for analysis and raises the confidence that the sequence data is of sufficient quality to be used for diagnostic, prognostic, and/or clinical analyses.

In some embodiments, evaluating whether determined information matches asserted information involves determining whether the determined information matches asserted information exactly are within a specified threshold. More generally, in some embodiments, evaluating whether two values "match" may involve determining whether the two values match exactly or are within a specified threshold. That threshold may be 0, requiring exact matches in some embodiments. That threshold may be greater than 0 such that when numerical values are being compared, the numerical values may be said to "match" if their values are within the threshold of one another (e.g., when the absolute difference of the numerical values is less than or equal to the threshold value). In some embodiments, the threshold may be set as a function of a standard deviation (or a multiple thereof), a quantile, a percentile, or any other suitable statistical quantity. In some embodiments, evaluating whether two values "match" may involve determining, when there is a difference between the two values, whether that difference is statistically significant. Such a determination may be performed using a statistical hypothesis test, a threshold, or any other suitable statistical or mathematical technique, as aspects of the technology described herein are not limited in this respect.

In some embodiments, one or more quality control parameters are checked for the bioinformatics data. In some embodiments, tumor purity can be checked. Tumor purity, as described herein, may refer to the proportion of cancer cells in the admixture. In some embodiments, the target tumor purity for the WES is >20% (e.g., 20%, 40%, 60%). In some embodiments, the target tumor purity for the RNA-seq is >20% (e.g., 20%, 40%, 60%).

In some embodiments, depth of coverage can be checked. In some embodiments, the depth of coverage for the WES is >150× average coverage of tumor sample (e.g., 150×, 180×, 200×). In some embodiments, the target depth of coverage for the RNA-seq is >100× (e.g., 100×, 150×, 200×).

In some embodiments, alignment rate can be checked. In some embodiments, the target alignment rate for the WES is more than 90% (e.g., 91%, 95%, 99%). In some embodiments, the target alignment rate for the RNA-seq is more than 90% (e.g., 91%, 95%, 99%).

In some embodiments, base call quality scores such as Phred score can be checked. In some embodiments, the target Phred score for the WES is more than 30 (e.g., 35, 40, 50). In some embodiments, the target Phred score for the RNA-seq is more than 30 (e.g., 35, 40, 50).

In some embodiments, uniformity of coverage can be checked. In some embodiments, the target uniformity of coverage for the WES is 85% base pairs in target regions covered >20× for tumor tissue (e.g., 85%, 95%, 99%). In some embodiments, the target uniformity of coverage for the WES is 85% base pairs in target regions covered >20× for normal tissue (e.g., 85%, 95%, 99%). In some embodiments, target regions for determining uniformity of coverage may be ExonV7 target regions with the use of the coding regions from CCDS (consensus coding sequence) genes.

In some embodiments, GC bias can be checked. In some embodiments, the target GC bias for the WES is at least 50 (e.g., 50, 60, 70). In some embodiments, the acceptable range of GC bias for the WES is at least 45-65 (e.g., 45-65, 50-65, 55-65). In some embodiments, the target GC bias for the RNA-seq is at least 50 (e.g., 50, 60, 70). In some embodiments, the acceptable range of GC bias for the RNA-seq is at least 45-65 (e.g., 45-65, 50-65, 55-65).

In some embodiments, mapping quality can be checked. In some embodiments, the mapping quality for the WES is >10 (e.g., 10, 20, 30).

In some embodiments, duplication rate can be checked. In some embodiments, the duplication rate for the WES is less than 30% (e.g., 29.9%, 25%, 15%). In some embodiments, the duplication rate for the RNA-seq is less than 85% (e.g., 84.99%, 80%, 70%).

In some embodiments, insert size can be checked. In some embodiments, the acceptable median insert size for tumor tissue for the WES is about 150 (e.g., 150, 280, 250). In some embodiments, the target median insert size for tumor tissue for the WES is about 200 (e.g., 200, 250, 350). In some embodiments, the acceptable median insert size for normal tissue for the WES is about 150 (e.g., 150, 280, 250). In some embodiments, the target median insert size for normal tissue for the WES is about 200 (e.g., 200, 250, 350). In some embodiments, the acceptable median insert size for tumor tissue for the RNA seq is about 150 (e.g., 150, 280, 250). In some embodiments, the target median insert size for tumor tissue for the RNA seq is about 200 (e.g., 200, 250, 350).

In some embodiments, contamination can be checked. In some embodiments, contamination acceptable for the WES is less than 0.05% (e.g., 0.04%, 0.03%, 0.01%). In some embodiments, contamination acceptable for the RNA-seq is less than 0.05% (e.g., 0.04%, 0.03%, 0.01%).

In some embodiments, SNP concordance of a pair of tumor versus normal samples from the same patient can be checked. In some embodiments, the target SNP concordance for the WES is more than 90% (e.g., 91%, 95%, 98%). In some embodiments, the acceptable SNP concordance for the WES is more than 85% (e.g., 86%, 90%, 98%). In some embodiments, the target SNP concordance for the RNA seq is more than 90% (e.g., 91%, 95%, 98%). In some embodiments, the acceptable SNP concordance for the RNA seq is more than 85% (e.g., 86%, 90%, 98%).

In some embodiments, HLA allele concordance of a pair of tumor versus normal samples from the same patient can be checked. In some embodiments, the threshold for normal versus tumor tissue for the WES is less than 5 (e.g., 4.5, 3, 2.5). In some embodiments, the threshold for tumor RNA seq tissue versus normal WES tissue for the RNA seq is less than 5 (e.g., 4.5, 3, 2.5).

In some embodiments, sequence information can be assessed for genome contamination (e.g., non-human genome contamination). In some embodiments, the samples or sequence information are assessed to determine whether they are contaminated by determining whether they contain sequences from other species or reference genomes such as mouse, zebrafish, *drosophila*, celegans, *saccharomyces, arabidopsis*, microbiome, *mycoplasma*, adapters, UniVec, and phiX rRNA. In some embodiments, the target threshold for the ADA genomes contamination for the WES is more than 60 (e.g., 65, 70, 80). In some embodiments, the acceptable threshold for the ADA genomes contamination for the WES is more than 40 (e.g., 45, 60, 80). In some embodiments, the target threshold for the ADA genomes contamination for the RNA seq is more than 40 (e.g., 50, 60, 80). In some embodiments, the acceptable threshold for the ADA genomes contamination for the RNA seq is more than 20 (e.g., 30, 50, 70).

In some embodiments, only one feature is evaluated against an asserted information. In some embodiments, more than one feature is evaluated against an asserted information. In some embodiments, at least two or more features are evaluated against an asserted information. In some embodiments, at least three or more features are evaluated against an asserted information. In some embodiments, at least four or more features are evaluated against an asserted information. In some embodiments, at least five or more features are evaluated against an asserted information. In some embodiments, at least six or more features are evaluated against an asserted information. In some embodiments, at least seven or more features are evaluated against an asserted information. In some embodiments, at least eight or more features are evaluated against an asserted information. In some embodiments, at least nine or more features are evaluated against an asserted information. In some embodiments, at least ten or more features are evaluated against an asserted information. In some embodiments, at least eleven or more features are evaluated against an asserted information. In some embodiments, at least twelve or more features are evaluated against an asserted information. In some embodiments, at least thirteen or more features are evaluated against an asserted information. In some embodiments, at least fourteen or more features are evaluated against an asserted information. In some embodiments, at least fifteen or more features are evaluated against an asserted information.

In some embodiments, if the features or determined values are found to not meet or match the asserted information, additional steps are performed. In some embodiments, if the features or determined values are found to not meet or match the asserted information, the sequence information is rejected (e.g., is not used for subsequent analysis). In some embodiments, if the features or determined values are found to not meet or match the asserted information, the sequence information is retested, meaning that any evaluation of features or determinations are performed for at least another or second, or more (e.g., third, fourth, fifth, sixth, etc.) time. In some embodiments, if the features or determined values are found to not meet or match the asserted information, another or second, or more (e.g., third, fourth, fifth, sixth, etc.) sequence information is obtained and then tested, meaning that any evaluation of features or determinations are performed for at least one time, or second, or more (e.g., third, fourth, fifth, sixth, etc.) time, independent of the initial determinations and evaluations done on the first sequence information. In some embodiments, if the features or determined values are found to not meet or match the asserted information, the sequence information is reported to a user as such. In some embodiments, any combination of these steps may be performed in the event that features or determined values are found to not meet or match the asserted information. In some embodiments, if the features or determined values are found to not meet or match the asserted information, the sequence information can still be evaluated for characteristics related to disease (e.g., cancer), but information about the quality (e.g., the extent and nature of the one or more features of the determined sequence information that do not match the asserted information) can be provided to a user (e.g., to a physician or other medical practitioner). In some embodiments, the characteristics relate to the type of cancer, its environment, its stage, its location, its tissue of origin, its statistical likelihood of responding to various treatments or therapies, or other properties which may aid a practitioner in treating the subject. In some embodiments, if the features or determined values are found to meet or match the asserted information (e.g., match, exceed, or otherwise satisfy reference or threshold values), then additional steps may be performed. In some embodiments, if the features or determined values are found to meet or match the asserted information (e.g., match, exceed, or otherwise satisfy reference or threshold values), then additional steps may be performed. In some embodiments, if the features or determined values are found to meet or match the asserted information (e.g., match, exceed, or otherwise satisfy reference or threshold values), the sequence information is evaluated for characteristics related to cancer. In some embodiments, the characteristics relate to the type of cancer, its environment, its stage, its location, its tissue of origin, its statistical likelihood of responding to various treatments or therapies, or other properties which may aid a practitioner in treating the subject.

In some embodiments, after one or more quality control steps are performed, a report is generated for the user with the results of the quality control steps that were performed.

Accordingly, in one aspect, the disclosure relates to a method of evaluating sequence information of at least one nucleic acid, to determine at least one feature thereof. The at least one feature can be used to evaluate the quality or integrity of the sequence information, to interrogate the source of the sequence information, or to allow for analyses of other sequence information, which may or may not be from the same sequencing platform, or from the same or a different sample preparation protocol. Further the at least one feature may be used as a quality control measure to ensure subsequent analyses of a threshold quality and lower quality sequence information are omitted.

Accordingly, in one aspect, the disclosure relates to a method of evaluating sequence information by (a) obtaining sequence information which comprises: (1) sequence data from a first ribonucleic acid (RNA); or (2) sequence data from a first whole exome sequence (WES); and (b) determining one or more features of the sequence data selected from the group consisting of: (i) the identity of the subject from which the nucleic acid was obtained; (ii) a tissue of origin from which the nucleic acid obtained; (iii) a tumor type of from which the nucleic acid was obtained; (iv) a quality measure of the first RNA sequence data; (v) whether the RNA sequence data was obtained from polyadenylated (polyA) RNA or total RNA; (vi) if the first sequence data set is first WES sequence data, (vii) the sequencing platform that was used to generate the first sequence data set; and (viii) a quality measure of the first sequence data set.

In some embodiments, the method further comprises obtaining additional sequence information if the one or more features of the sequence information is below a quality control threshold suitable for further analysis.

In some embodiments, the evaluated feature is the subject identity. In some embodiments, the subject identity is determined by performing one or more of evaluations from the group comprising: a major histocompatibility complex evaluation and a SNP concordance evaluation, wherein the results of the evaluations are compared to an asserted value for the subject or a second sequence data set from the subject.

In some embodiments, the evaluated feature is the tissue of origin. In some embodiments, the tissue of origin is determined by performing one or more of evaluations from the group comprising: protein expression and biomarker analysis. In another aspect, the disclosure relates to a method of evaluating a feature comprising assigning a tissue of origin of the sample which generated the sequence information. In some embodiments, the method comprises evaluating the sequence information for markers or gene expression indicative of a tissue type from which the sequence information originated. In some embodiments, the method comprises evaluating the markers or gene expression against a database of the same for different tissue types. Different tissues throughout a subject express different proteins which create a profile of such a tissue. Accordingly, it is possible to evaluate the protein expression profile and match it to a tissue type to identify the tissue from which the sample, and by extension the sequence information, was obtained. This can be done through a variety of methods known in the art. For example, evaluating the number of a given messenger RNA (mRNA) transcript (e.g., using it as a proxy for evaluating protein expression) can be evaluated against a database of known tissue markers (e.g., protein expression profiles), it can be evaluated against a provided set of markers for a subject, or it can be evaluated against a second sequence information or set of tissue markers obtained from the subject. In some embodiments, a tissue of origin is determined by evaluating the sequence information for markers (e.g., protein expression) and matching the markers with a database of tissues. In some embodiments, a tissue of origin is determined by evaluating the sequence information for markers (e.g., protein expression) and matching the markers with a set of markers from a tissue of a subject. In some embodiments, a tissue of origin is determined by evaluating the sequence information for markers (e.g., protein expression) and matching the markers with a second sequence information obtained from a subject where the tissue of origin is known.

In some embodiments, the evaluated feature is a measure of the integrity of the sequence information. In some embodiments, the integrity measure of the first RNA sequence data is determined by performing one or more of evaluations from the group comprising: determining coverage of one or more genes in the RNA sequence data, determining relative coverage of two or more exons for at least one gene in the RNA sequence data, determining an expression ratio of two known reference genes from the RNA sequence data, or other feature or combinations of two or more thereof. In some embodiments, the integrity measure of the DNA sequence data is determined by performing one or more of evaluations from the group comprising: total coverage and/or chromosomal coverage of the DNA sequence data, or other feature or combinations of two or more thereof.

In some embodiments, the RNA sequence data is analyzed to determine whether it was obtained from polyA RNA or total RNA. In some embodiments, the RNA sequence data is analyzed by evaluating an expression level of one or more mitochondrial or histones genes from the RNA sequence data, and/or other features that are characteristic of polyA or total RNA. In some embodiments, the feature being evaluated is the sequencing platform that was used to generate the sequence. In some embodiments, the sequencing platform used for generating the WES sequence data is determined by performing one or more of evaluations from the group comprising: determining % variance for one or more reference genes in the WES sequence data, or other property of sequencing data that is characteristic of the sequencing platform that was used to generate the sequence data.

In some embodiments, methods comprise evaluating at least one of the features described herein. In some embodiments, a method comprises evaluating at least two of the features described herein. In some embodiments, a method comprises evaluating at least three of the features described herein. In some embodiments, a method comprises evaluating at least four of the features described herein. In some embodiments, a method comprises evaluating at least five of the features described herein. In some embodiments, a method comprises evaluating at least six of the features described herein. In some embodiments, a method comprises evaluating at least seven of the features described herein.

In some embodiments, the quality (e.g., source or integrity) of sequence information from one or more nucleic acid samples (e.g., at least two nucleic acid samples) is evaluated by (a) determining the sequence of two or more (e.g., 2, 3, 4, 5, 6 or more) major histocompatibility complexes (MHCs), and (b) determining whether the MHCs from the one or more samples match. In some embodiments, if the MHCs don't match (e.g., if a calculated agreement value is less than a statistically significant threshold) the sequence information from each of the nucleic acids is deemed likely from distinct sources, of insufficient quality, and is removed, discarded, retested, and/or reported as such to a user. In some embodiments, if the calculated agreement value (x) between WES normal/tumor/RNAseq is $0<x\leq2$ (e.g., 1, 1.5, 2), it represents acceptable and "warning." Warning means that the calculated agreement value is within a range that is deemed acceptable but is considered close to be not acceptable. In some embodiments, if the calculated agreement value (x) between WES normal/tumor/RNAseq is >5, it represents not acceptable or bad quality. In some embodiments, if the calculated agreement value (x) between WES normal/tumor/RNAseq is 0, it represents good quality. In some embodiments, if the MHCs match (e.g., if the agreement value is at or above the statistically significant threshold) the sequence information from each of the nucleic acid samples is deemed sufficiently likely from the same source, of sufficient quality, and is retained for further analysis and/or reported as such to a user.

In some embodiments, the quality of sequence information from one or more (e.g., at least two) nucleic acid samples is evaluated by determining a concordance value for single nucleotide polymorphisms (SNPs) in the sequence information. In some embodiments, the method further comprises evaluating the concordance value. In some embodiments, if the concordance value is less than 85%, less than 80%, or less than 75%, the sequence information from each of the nucleic acid samples is deemed likely from distinct sources, of insufficient quality, and is removed, discarded, retested, and/or reported as such to a user. In some embodiments, if the concordance value is less than 75%, the sequence information is deemed not acceptable. In some embodiments, if the concordance value is more than 80% and less than 95%, the sequence information is deemed within the ranges that are close to be not acceptable. In some embodiments, if the concordance value is more than 95%, the sequence information is deemed acceptable. In some embodiments, if the concordance value is at least 75%, at least 80%, or at least 85%, the sequence information from each of the nucleic acid samples is deemed sufficiently likely from the same source, of sufficient quality, and is retained, and/or reported as such to a user. In some embodiments, at least 5,000 SNPs can be evaluated for concordance values. In some embodiments, at least 6,000 SNPs can be evaluated for concordance values. In some embodiments, at least 7,000 SNPs can be evaluated for concordance values. In some embodiments, at least 8,000 SNPs can be evaluated for concordance values.

In some embodiments, the quality of sequence information from one or more (e.g., at least two) nucleic acid samples is evaluated by determining a contamination value for the sequence information. In some embodiments, if the contamination value is above a statistically significant threshold, the sequence information is removed, discarded, retested, and/or reported as such to a user. In some embodiments, if the contamination value is more than 0.05% (e.g., 0.06%, 1%, 2%), the sequence information is deemed to be close to not acceptable (e.g., warning). In some embodiments, if the contamination value is more than 0.1% (e.g., 0.1%, 0.5%, 1%), the sequence information is deemed to be not acceptable for blood sample and fresh frozen tissue. In some embodiments, if the contamination value is below the threshold, the sequence information is retained, and/or reported as such to a user.

In some embodiments, the quality of sequence information from one or more (e.g., at least two) nucleic acid samples is evaluated by analyzing sequence information from the one or more nucleic acid samples against a set of tumor types, determining predicted tumor type(s) from the sequence information, and determining whether the predicted tumor type(s) matches the tumor type(s) that were provided (e.g., asserted) for the one or more nucleic acid samples. In some embodiments, determining predicted tumor type(s) as a quality control step can be performed by using a computerized system or process as described herein. In some embodiments, determining predicted tumor type(s) as a quality control step can be performed by determining a cancer grade from sequence data by using machine learning techniques, as described herein and in the U.S. Provisional Patent Application Ser. No. 62/943,976, titled "Machine Learning Techniques for Gene Expression Analysis," filed on Dec. 5, 2019, which is incorporated by reference herein in its entirety. In some embodiments, if there is disagreement between the tumor type(s) (e.g., cancer grades) obtained from the sequence evaluation and an asserted information, the sequence information is identified as suspect, or insufficient quality, and is removed, discarded, retested, and/or reported as such to a user. In some embodiments, if there is agreement between the predicted tumor type(s) and expected tumor type(s) for the one or more nucleic acid samples, the sequence information is deemed of sufficient quality, and is retained, and/or reported as such to a user.

In some embodiments, matching the predicted tumor type(s) to the tumor type(s) that were provided comprise using a set of reference genes from a training data set containing a plurality of signature genes that are up-regulated or down-regulated in a certain tumor type, relative to a normal, healthy sample. For instance, if the predicted tumor type is prostate cancer (e.g., asserted information), the sample will be checked against the known reference genes of prostate cancer. In some embodiments, the predicted tumor type is also evaluated against its tumor grade, which can help determine the signature genes of the asserted cancer grade at different stages of cancer.

As described above, in some embodiments, determining predicted tumor type(s) as a quality control step may be performed by determining a cancer grade from sequence information by using a machine learning approach employing a statistical model trained using training data.

For example, in some embodiments, a statistical model may be used to predict characteristic(s) of a biological sample, using gene expression data, based on an input ranking of genes, ranked based on their respective expression levels, for a sequencing platform. Using the input ranking(s), instead of the specific values for the expression levels, allows for the same or similar data processing pipeline to be used across different expression data regardless of the specific manner in which the expression levels were obtained (e.g., regardless of which sequencing platform, sequencing conditions, sample preparation, data processing to obtain expression levels, etc.). In some embodiments, a statistical model may be used to predict cancer grade of the biological sample. In some embodiments, a statistical model may be used to predict tissue of origin of the biological sample, which also may be used for performing quality control as described herein.

For example, in some embodiments, rankings of genes based on the gene expression levels (in a biological sample) as determined by a sequencing platform may be provided as input to a statistical model trained to predict tissue of origin for the biological sample. The predicted tissue of origin may be compared against asserted tissue of origin as part of the quality control techniques described herein. As another example, in some embodiments, rankings of genes based on the gene expression levels (in a biological sample) as determined by a sequencing platform may be provided as input to a statistical model trained to predict cancer grade for the biological sample. The predicted cancer grade may be compared against asserted cancer grade as part of the quality control techniques described herein.

In some embodiments, the set of genes being ranked depends on the particular biological characteristic of interest. For example, one set of genes may be used for determining the tissue of origin and another set of genes may be used for determining the cancer grade.

In some embodiments, the expression data may be obtained for cells in the biological sample, where the subject has, is suspected of having or is at risk of having cancer. In the context where tissue of origin is a characteristic being determined, the tissue of origin is for the cells in the biological sample. The tissue of origin may refer to a particular tissue type from which the cells originate, such as lung, pancreas, stomach, colon, liver, bladder, kidney, thyroid, lymph nodes, adrenal gland, skin, breast, ovary, and prostate.

For example, some embodiments involve using a gene set for predicting tissue of origin, which may include cell of origin, for Diffuse Large B-Cell Lymphoma (DLBCL), such as germinal center B-cell (GCB) and activated B-cell (ABC). Genes in the gene set may be selected from the group consisting of: ITPKB, MYBL1, LMO2, BATF, IRF4, LRMP, CCND2, SLA, SP140, PIM1, CSTB, BCL2, TCF4, P2RX5, SPINK2, VCL, PTPN1, REL, FUT8, RPL21, PRKCB1, CSNK1E, GPR18, IGHM, ACP1, SPIB, HLA-DQA1, KRT8, FAM3C, and HLA-DMB.

In the context where cancer grade is a characteristic being determined, the cancer grade is for the cells in the biological sample. The cancer grade may refer to proliferation and differentiation characteristics of the cells in the biological sample and refer to a numerical grade that is generally determined by visual observation of cells using microscopy, such as Grade 1, Grade 2, Grade 3, and Grade 4.

For example, some embodiments involve using a gene set for predicting breast cancer grade. Genes in the gene set may be selected from the group consisting of: UBE2C, MYBL2, PRAME, LMNB1, CXCL9, KPNA2, TPX2, PLCH1, CCL18, CDK1, MELK, CCNB2, RRM2, CCNB1, NUSAP1, SLC7A5, TYMS, GZMK, SQLE, C1orf106, CDC25B, ATAD2, QPRT, CCNA2, NEK2, IDO1, NDC80, ZWINT, ABCA12, TOP2A, TDO2, S100A8, LAMP3, MMP1, GZMB, BIRC5, TRIP13, RACGAP1, ASPM, ESRP1, MAD2L1, CENPF, CDC20, MCM4, MKI67, PBK, CKS2, KIF2C, MRPL13, TTK, BUB1, TK1, FOXM1, CEP55, EZH2, ECT2, PRC1, CENPU, CCNE2, AURKA, HMGB3, APOBEC3B, LAGE3, CDKN3, DTL, ATP6V1C1, KIAA0101, CD2, KIF11, KIF20A, CDCA8, NCAPG, CENPN, MTFR1, MCM2, DSCC1, WDR19, SEMA3G, KCND3, SETBP1, KIF13B, NR4A2, NAV3, PDZRN3, MAGI2, CACNAID, STC2, CHAD, PDGFD, ARMCX2, FRY, AGTR1, MARCH8, ANG, ABAT, THBD, RAI2, HSPA2, ERBB4, ECHDC2, FST, EPHX2, FOSB, STARD13, ID4, FAM129A, FCGBP, LAMA2, FGFR2, PTGER3, NME5, LRRC17, OSBPL1A, ADRA2A, LRP2, C1orf115, COL4A5, DIXDC1, KIAA1324, HPN, KLF4, SCUBE2, FMO5, SORBS2, CARD10, CITED2, MUC1, BCL2, RGS5, CYBRD1, OMD, IGFBP4, LAMB2, DUSP4, PDLIM5, IRS2, and CX3CR1.

As another example, some embodiments involve using a gene set for predicting kidney clear cell cancer grade. Genes in the gene set may be selected from the group consisting of: PLTP, CIS, LY96, TSKU, TPST2, SERPINF1, SRPX2, SAA1, CTHRC1, GFPT2, CKAP4, SERPINA3, CFH, PLAU, BASP1, PTTG1, MOCOS, LEF1, SLPI, PRAME, STEAP3, LGALS2, CD44, FLNC, UBE2C, CTSK, SULF2, TMEM45A, FCGR1A, PLOD2, C19orf80, PDGFRL, IGF2BP3, SLC7A5, PRRX1, RARRESI, LHFPL2, KDELR3, TRIB3, IL20RB, FBLN1, KMO, ClR, CYP1B1, KIF2A, PLAUR, CKS2, CDCP1, SFRP4, HAMP, MMP9, SLC3A1, NAT8, FRMD3, NPR3, NAT8B, BBOX1, SLC5A1, GBA3, EMCN, SLC47A1, AQP1, PCK1, UGT2A3, BHMT, FMO1, ACAA2, SLC5A8, SLC16A9, TSPAN18, SLC17A3, STK32B, MAP7, MYLIP, SLC22A12, LRP2, CD34, PODXL, ZBTB42, TEK, FBP1, and BCL2.

Aspects of using statistical models for predicting tissue of origin, cancer grade, and/or any other characteristics of a biological sample are described in the U.S. Provisional Patent Application Ser. No. 62/943,976, titled "Machine Learning Techniques for Gene Expression Analysis", filed on Dec. 5, 2019, which is incorporated by reference herein in its entirety.

Returning to aspects of evaluating quality of sequence information, in some embodiments, the quality of sequence information from one or more (e.g., at least two) nucleic acid samples is evaluated by determining the presence or absence of polyadenylated RNA genes to predict whether the sequence information was obtained from polyA RNA or not. In some embodiments, if there is disagreement between the predicted and expected (e.g., asserted) polyA status of one or more samples, the sequence information for those samples is deemed as suspect, of insufficient quality, and is removed, discarded, retested, and/or reported as such to a user. In some embodiments, if there is agreement between the predicted and expected polyA status for one or more nucleic acid samples, the sequence information is deemed of sufficient quality, and is retained, and/or reported as such to a user.

In some embodiments, the quality of sequence information from one or more (e.g., at least two) nucleic acid samples is evaluated by determining a complexity value of the sequence information. In some embodiments, determining a complexity value comprises determining the number of duplications. In some embodiments, the % duplications can be determined for a DNA or RNA library. In some embodiments, if a large percentage of the library is duplicated, either a library of low complexity or over-amplification of the DNA or cDNA fragments is indicated. In some instances, differences between libraries in the complexity or amplification indicates that certain biases in the data are introduced (e.g., differing % GC content). In some embodiments, if the complexity value is less than 75%, or less than 80%, the sequence information is deemed suspect, of insufficient quality, and is removed, discarded, retested, and/or reported as such to a user. In some embodiments, if the complexity value is at least 80%, or at least 85%, the sequence information is deemed of sufficient quality for further analysis, and is retained, and/or reported as such to a user.

In some embodiments, the quality of sequence information from one or more (e.g., at least two) nucleic acid samples is evaluated by predicting a tissue source for the nucleic acid. In some embodiments, if there is disagreement between a predicted and an asserted tissue source for the nucleic acid, the sequence information is deemed suspect, of insufficient quality, and is removed, discarded, retested, or reported as such. In some embodiments, if there is agreement between the predicted and asserted tissue sources, the sequence information is deemed of sufficient quality for further analysis, and is retained, and/or reported as such to a user.

In some embodiments, the quality of sequence information from one or more (e.g., at least two) nucleic acid samples is evaluated by (a) determining a gene expression level for two different subunits of a known protein; and (b) determining an expression ratio for the two different subunits. In some embodiments, if the determined expression ratio does not match the expected expression ratio for the protein subunits, the sequence information is identified as suspect, of insufficient quality, and is removed, discarded, retested, and/or reported as such to a user. In some embodiments, if the determined expression ratio matches an expected expression ratio for the protein subunits, the sequence information is deemed of sufficient quality for further analysis, and is retained, and/or reported as such to a user.

In some embodiments, the quality of sequence information from one or more (e.g., at least two) nucleic acid samples is evaluated by determining a Phred Score for the sequence information. In some embodiments, if the Phred Score is less than 27, the sequence information is deemed suspect, of insufficient quality, and is removed, discarded, retested, and/or reported as such to a user. In some embodiments, if the Phred Score is less than 20, the sequence information is removed, discarded, retested, and/or reported as such to a user. In some embodiments, if the Phred Score is more than 20 and is less than 27, the sequence information is deemed close to be removed, discarded, retested, and/or reported as such to a user. In some embodiments, if the Phred Score is at least 27, the sequence information is deemed of sufficient quality for further analysis, and is retained, and/or reported as such to a user.

In some embodiments, the quality of sequence information from one or more (e.g., at least two) nucleic acid samples is evaluated by determining a GC content for the sequence information. In some embodiments, if the GC content is at least 30%, and less than or equal to 55%, the sequence information is deemed of sufficient information for further analysis, and is retained, and/or reported as such to a user. In some embodiments, if the GC content is in the range of 45-65%, the sequence information is deemed of sufficient information for further analysis, and is retained, and/or reported as such to a user (i.e., acceptable). In some embodiments, GC content of at least 50% (e.g., 50%, 51%, 60%) is the target value at least for human samples.

In some embodiments, at least two (e.g., 3, 4, 5, 6, 7, 8, 9, 10, or more) distinct methods for evaluating the quality (e.g., source and/or integrity) of sequence information are performed. In some embodiments, the methods performed herein evaluate sequence information from a mammal. In some embodiments, the mammal is human.

In some embodiments, the subject from which the sample which generated the sequence information has, is suspected of having, or is at risk of having a disorder. In some embodiments, the disorder is cancer.

In some embodiments, a report is generated comprising the one or more features or results of the methods described herein. In some embodiments, the report further comprises an analysis of the results of the methods described herein.

In some embodiments, the methods or processes of the disclosure may be carried out on a system or computer processor (e.g., laptop, desktop, server, or other computerized machine). The components of the system may reside in disparate places and communicate over networks, such as local area networks or wide area networks, or by internet protocols. The system may interface with the user via a web-enable browsers and graphical user interfaces (GUIs). In some embodiments, the system is under the control of the user in one place. In some embodiments, the system is comprised of components not in one place and which may not be under the direct control of the user. In some embodiments, the information of the system is stored locally.

As described herein, the term "process," "act," "step" or the variations thereof that are used in computerized processes or flow charts therein can be used interchangeably, unless indicated otherwise.

As described herein, the term "patient," "subject," "human subject" or the variations thereof can be used interchangeably, unless indicated otherwise.

Figure 6A:
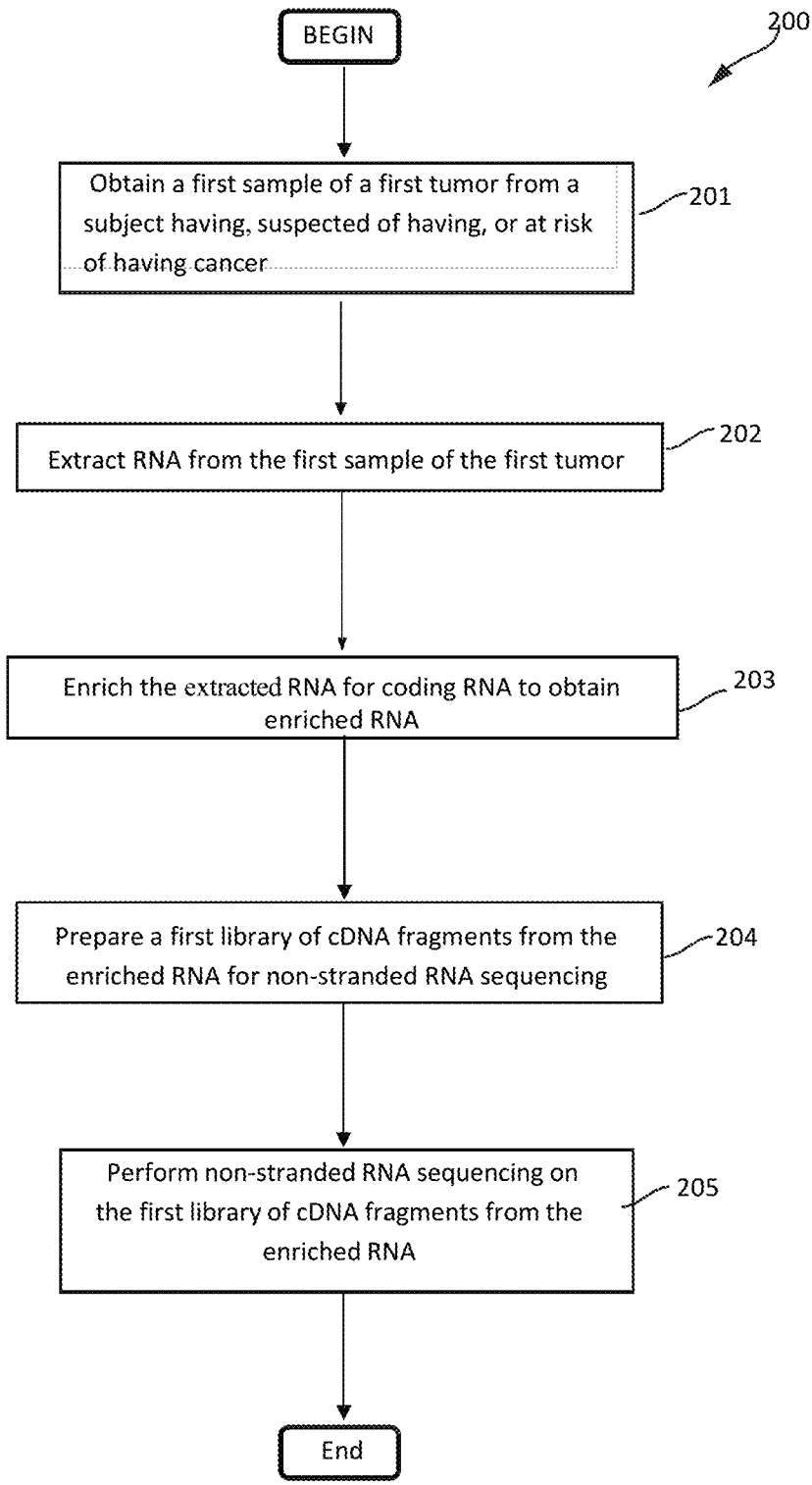
FIG. 6A is an exemplary flowchart that illustrates a process 200 for obtaining enriched RNA sequence data from a tumor of a subject having, suspected of having, or at risk of having cancer.

FIG. 6A is a flow chart showing illustrative computerized Process 200 for performing non-stranded RNA sequencing with the coding RNA enrichment. Process 200 begins at act 201, where a first sample of a first tumor from a subject having, suspected of having, or at risk of having cancer is obtained. Further aspects relating to obtaining a first sample of a first tumor from a subject having, suspected of having, or at risk of having cancer are provided in section "Biological samples."

Next process 200 proceeds to act 202, wherein RNA from the first sample of the first tumor is extracted. Aspects relating to extracting RNA from the first sample of the first tumor are described in the section called "Extraction of DNA and/or RNA."

Next the process 200 proceeds to act 203, where the extracted RNA is enriched for coding RNA to obtain enriched RNA. Aspects relating to enriching the extracted RNA for coding RNA to obtain enriched RNA are described in the section called "RNA enrichment."

Next process 200 proceeds to act 204, where a first library of cDNA fragments from the enriched RNA for non-stranded RNA sequencing is prepared. Aspects relating to preparing a first library of DNA fragments from the enriched RNA for non-stranded RNA sequencing are described in the section called "Library preparation for RNA sequencing."

Next process 200 proceeds to act 205, where non-stranded RNA sequencing is performed on the first library of cDNA fragments prepared from the enriched RNA. Aspects relating to performing non-stranded RNA sequencing on the first library of DNA fragments prepared from the enriched RNA are described in the section called "RNA sequencing." It should be appreciated that one or more acts of process 200 may be optional.

Figure 6B:
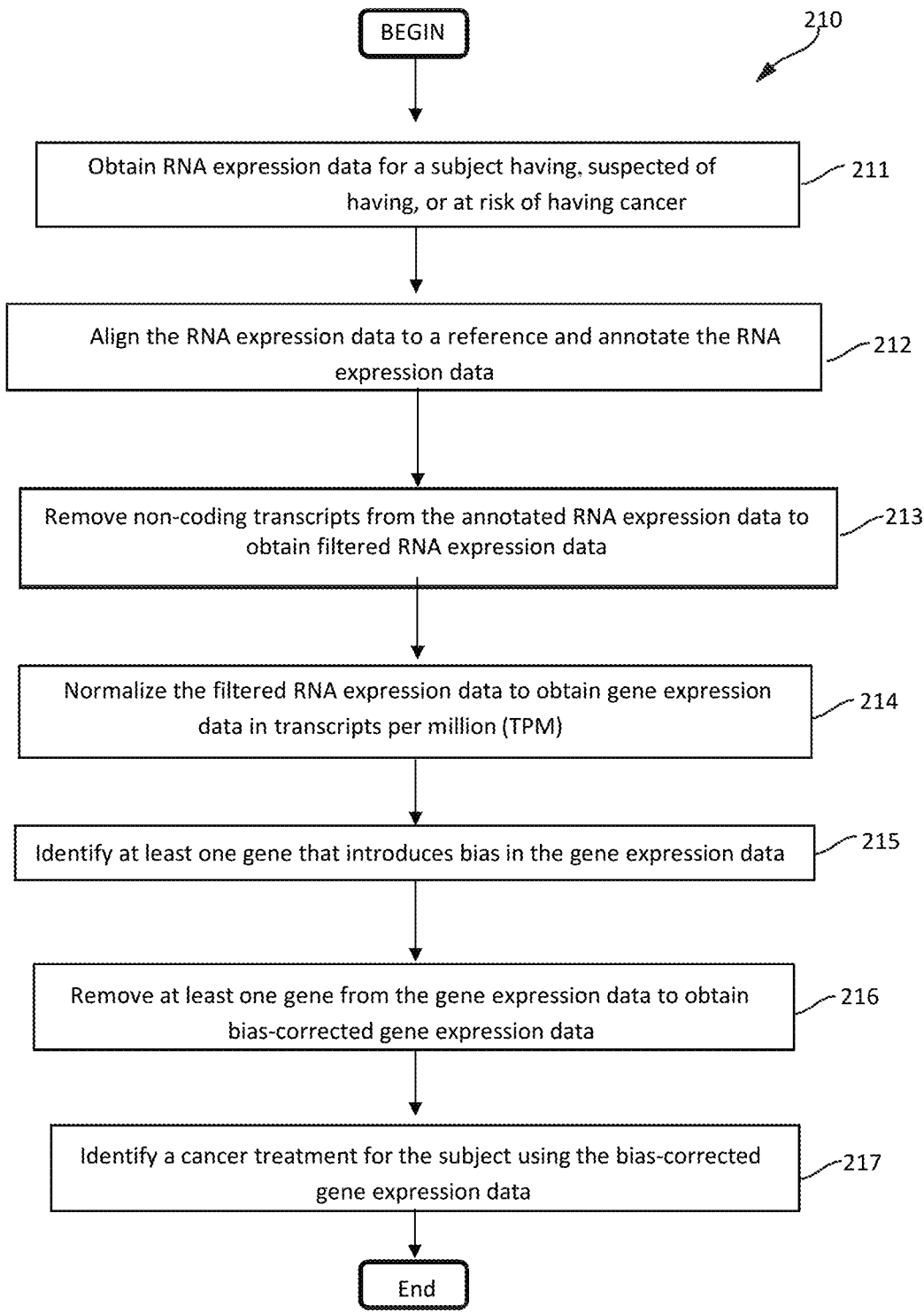
FIG. 6B is an exemplary flowchart that illustrates a process 210 for obtaining bias-corrected gene expression data from RNA expression data to identify a cancer treatment for a subject having, suspected of having, or at risk of having cancer.

FIG. 6B is a flow chart showing computerized process 210 for identifying a cancer treatment by obtaining bias-corrected gene expression data. Process 210 begins at act 211, where RNA expression data for a subject having, suspected of having, or at risk of having cancer is obtained.

Aspects relating to obtaining RNA expression data are described in the section called "Obtaining RNA expression data."

Next, process 210 proceeds to act 212, where genes in the RNA expression data are aligned to a reference and the RNA expression data is annotated. Aspects relating to aligning and annotating genes in the RNA expression data with known sequences of the human genome to obtain annotated RNA expression data are described in the section called "Alignment and annotation."

Next, process 210 proceeds to act 213, where non-coding transcripts from the annotated RNA expression data are removed to obtain filtered RNA expression data. Aspects relating to removing non-coding transcripts from the annotated RNA expression data are described in the section titled "Removing non-coding transcripts."

Next, process 210 proceeds to act 214, where the filtered RNA expression data is normalized to obtain gene expression data. The gene expression data may be in transcripts per kilobase million (TPM) format. Aspects of normalizing the filtered RNA expression data to gene expression data in transcripts per kilobase million (TPM) are described in the section called "Conversion to TPM and gene aggregation."

Next, process 210 proceeds to act 215, where at least one gene that introduces bias in the gene expression data is identified. Aspects of identifying at least one gene that introduces bias in the gene expression data are described in the section called "Removing bias."

Next, process 210 proceeds to act 216, where expression data associated with the at least one gene that introduces bias is removed from the gene expression data to obtain bias-corrected gene expression data. Aspects of removing the expression data, associated with the at least one gene that introduces bias into the gene expression data, from the gene expression data to obtain bias-corrected gene expression data are described in the section called "Removing bias."

Next, process 210 proceeds to act 217, where a cancer treatment for the subject using the bias-corrected gene expression data is identified. Aspects relating to identifying a cancer treatment for the subject using the bias-corrected gene expression data are described in the section called "Identifying a cancer treatment."

Figure 6C:
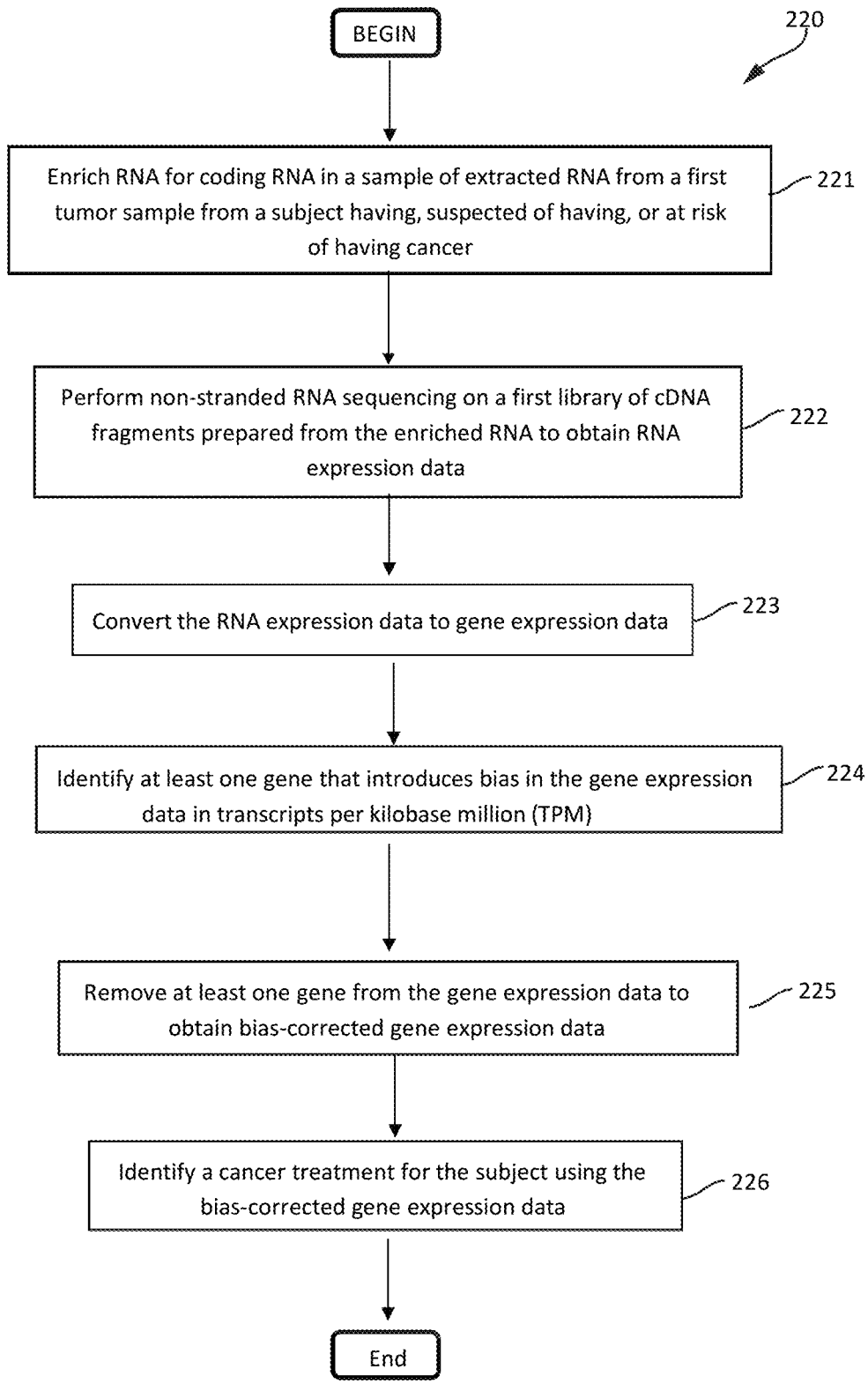
FIG. 6C is an exemplary flowchart that illustrates a process 220 for processing RNA obtained from a tumor sample to identify a cancer treatment for a subject having, suspected of having, or at risk of having cancer.

FIG. 6C is a flow chart showing computerized process 220 for identifying a cancer treatment for the subject having, suspected of having, or at risk of having cancer using the bias-corrected gene expression data. Process 220 begins at act 221, where RNA for coding RNA in a sample of extracted RNA from a first tumor sample from a subject having, suspected of having, or at risk of having cancer is enriched. Aspects relating to enriching RNA for coding RNA in a sample of extracted RNA are described in the section called "Extraction of DNA and/or RNA."

Next, process 220 proceeds to act 222, where non-stranded RNA sequencing on a first library of cDNA fragments prepared from the enriched RNA to obtain RNA expression data is performed. Aspects relating to performing non-stranded RNA sequencing on a first library of cDNA fragments prepared from the enriched RNA to obtain RNA expression data are described in the section called "RNA sequencing."

Next, process 220 proceeds to act 223, where the RNA expression data is converted to gene expression data. Next, process 220 proceeds to act 224, where at least one gene that introduces bias in the gene expression data is identified. Next, process 220 proceeds to act 225, where expression data associated with the at least one gene that introduces bias is removed from the gene expression data to obtain bias-corrected gene expression data. Aspects relating to acts 223, 224, and 225 are described in the section called "Removing bias."

Next, process 220 proceeds to act 226, where a cancer treatment for the subject using the bias-corrected gene expression data is identified. Aspects relating to identifying a cancer treatment for the subject using the bias-corrected gene expression data are described in the section called "Identifying a cancer treatment."

FIG. 7 is an exemplary flow chart showing a computerized process 300 for preparing patient samples for sequencing analysis and performing bioinformatics quality control, so that a cancer treatment suitable for the patient or subject, from which the nucleic acids are extracted for sequencing analysis, can be obtained.

In the illustrated embodiment, the process 300 comprises obtaining a first sample of a first tumor from a subject having, suspected of having, or at risk of having cancer at act 301, extracting RNA from the first sample of the first tumor at act 302, enriching the RNA for coding RNA to obtain enriched RNA at act 303, preparing a first library of cDNA fragments from the enriched RNA for non-stranded RNA sequencing at act 304, obtaining RNA expression data for the subject at act 305, aligning and annotating genes in the RNA expression data with known sequences of the human genome to obtain annotated RNA expression data at act 306, removing non-coding transcripts from the annotated RNA expression data at act 307, converting the annotated RNA expression data to gene expression data (e.g., in transcripts per kilobase million (TPM) format) at act 308, identifying at least one gene that introduces bias in the gene expression data at act 309, removing expression data for the at least one gene that introduces bias from the gene expression data to obtain bias-corrected gene expression data at act 310, obtaining sequence information and asserted information at act 311, determining one or more features from the sequence information at act 312, determining whether one or more features match asserted information at act 313, making at least one additional determination of the features at act 314, and identifying a cancer treatment for the subject using the bias-corrected gene expression data at act 315.

It should be appreciated that one or more acts of process 300 may be optional. For example, in some embodiments, acts 301 and 303 may be performed and act 303 is optional. In some embodiments, acts 301, 302, and 303 are all performed. In some embodiments, acts 301, 302, and 303 are all omitted, whereas the remaining acts are performed. This may be useful when the extracted, enriched RNA from the patient sample is already available prior to the start of process 300. In some embodiments, the one or more features at act 312 comprises one or more of the following features: source, patient, tissue type, tumor type, polyA status, MHC sequence, protein subunit ratio, complexity, contamination, coverage, exon coverage, read composition, Phred score, SNP concordance, and GC content. In some embodiments, the one or more features at act 312 further comprise strandedness of RNA sequence analysis. In some embodiments, any one or more of the features at act 312 can be determined. In some embodiments, the additional determination of the features at act 314 can include but are not limited to concordance value of SNPs, contamination value, polyA status, complexity value, Phred score, and GC content. In some embodiments, the additional determination of any one or more of the features may be performed at act 314. In some embodiments, any one or more of acts 303, process 307, and process 314 may be omitted. In some embodiments, all acts of the computerized process 300 may be performed.

Figure 8:
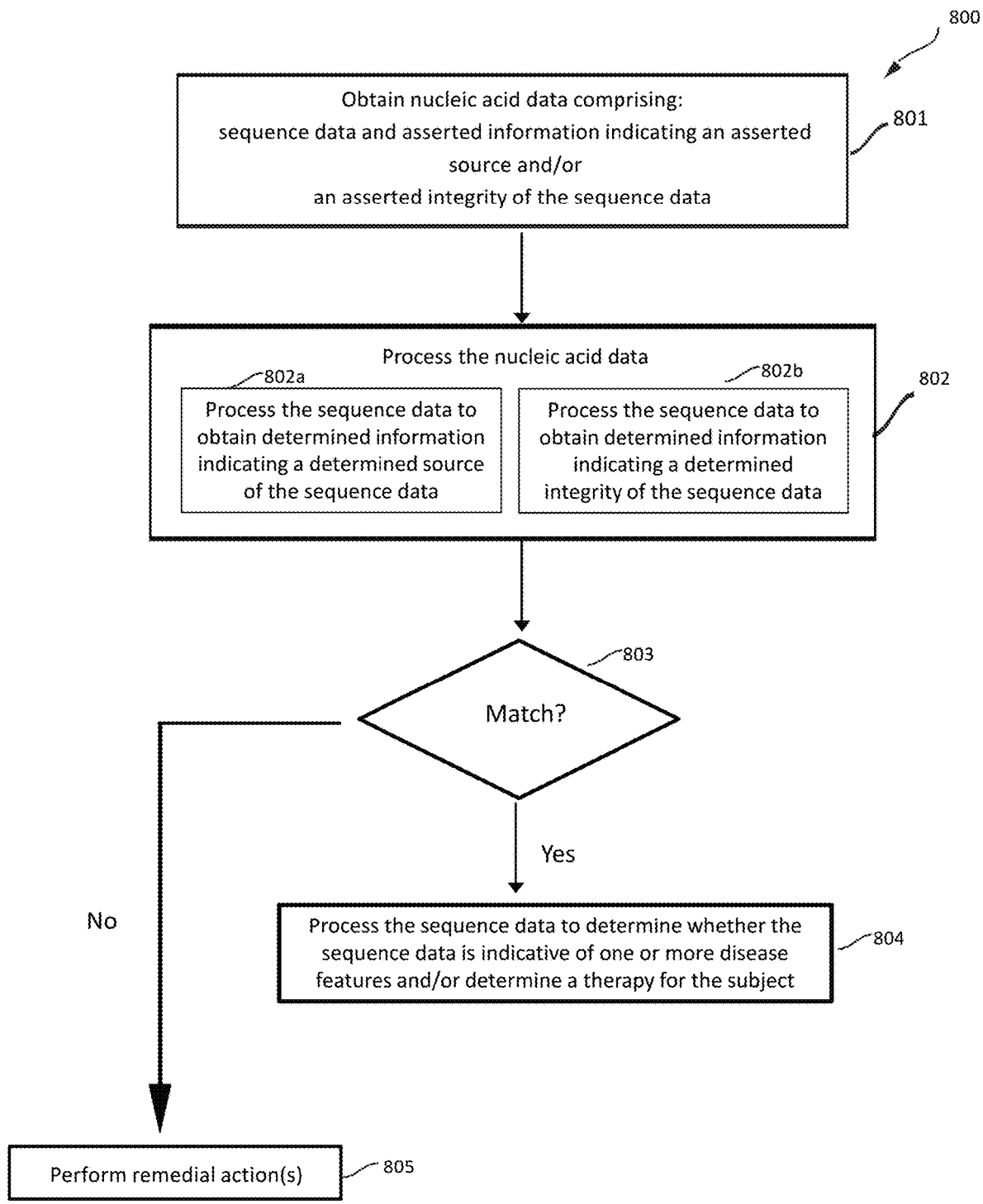
FIG. 8 is an exemplary flowchart that illustrates a process 800 showing computerized processes for processing and validating sequence data and related information.

FIG. 8 illustrates a non-limiting process pipeline 800 FIG. 8 illustrates a non-limiting process pipeline 800 for processing and validating sequence data and asserted information associated with the sequence data for subsequent analysis (e.g., for diagnostic, prognostic, therapeutic, and/or other clinical applications). Act 801 is performed by obtaining nucleic acid data comprising sequence data and asserted information indicating an asserted source for the sequence data. In some embodiments, the nucleic acid data is obtained from a biological sample that was previously processed. In some embodiments, the biological sample was previously obtained from a subject having, suspected of having, or at risk of having cancer. In some embodiments, act 801 is performed by obtaining nucleic acid data comprising an asserted integrity of the sequence data. In some embodiments, act 801 can be performed by obtaining nucleic acid data comprising sequence data and asserted information indicating an asserted source and an asserted integrity of the sequence data. In some embodiments, the asserted information indicates the asserted integrity of the sequence data. In some embodiments, the asserted information is indicative of a subject from whom the nucleic acid was obtained. For example, in some embodiments, asserted information comprises MHC allele information and/or SNP information for one or more loci of the subject. After act 801, process 800 proceeds to acts 802 and 803 where the nucleic acid data obtained at act 801 is validated. The validation comprises processing the sequence data at act 802 to obtain a determined integrity and/or a determined source and determining whether the determined integrity and/or determined source matches the asserted integrity and/or asserted source, respectively, in act 803. The sequence data is processed in act 802 to obtain determined information indicating a determined source of the sequence data in act 802a and/or determined information indicating a determined integrity of the sequence data in act 802b. In some embodiments, act 802a may comprise determining information indicative of at least one, two, three of the MHC genotype of the subject, whether the nucleic acid data is RNA data or DNA data, a tissue type of the biological sample, a tumor type of the biological sample, a sequencing platform used to generate the sequence data, SNP concordance (e.g., determining whether one or more SNPs in the sequence data match one or more SNPs in a reference sequence), and/or a whether an RNA sample is polyA enriched. In some embodiments, act 802b may comprise determining a first level of a first nucleic acid encoding a first subunit of a multimeric protein, determining a second level of a second nucleic acid encoding a second subunit of a multimeric protein, and determining whether a ratio between the first level and the second level matches an expected ratio. In some embodiments the first subunit and the second subunits are first and second CD3 subunits, first and second CD8 subunits, or first and second CD79 subunits. In some embodiments, the determined information indicative of the determined integrity is indicative of at least one, two, three of total sequence coverage, exon coverage, chromosomal coverage, a ratio of nucleic acids encoding two or more subunits of a multimeric protein, species contamination, complexity, and/or guanine (G) and cytosine (C) percentage (%) of the sequence data. In some embodiments, act 803 comprises determining one or more MHC allele sequences from the sequence data and determining whether the one or more MHC alleles sequences match the asserted MHC allele information for the subject. In some embodiments, determining MHC allele comprises determining sequences for six MHC loci from the sequence data.

In act 803 the determined integrity and/or source is evaluated by determining whether the determined source of the sequence data matches the asserted source of the sequence data and/or whether the determined integrity of the sequence data matches the asserted integrity of the sequence data.

If the asserted and determined information match in act 803 (i.e., yes), process 800 proceeds to act 804 where the sequence data is further evaluated to determine whether the sequence data is indicative a diagnostic, prognostic, therapeutic, or other clinical outcome. For example, in some embodiments the sequence data is further processed in act 804 to provide a recommendation for a cancer treatment for a subject having, suspected of having, or at risk of having cancer. In some embodiments, Act 804 is performed by determining a therapy for the subject and the therapy is subsequently administered to the subject.

In some embodiments, a process may further comprise administering the therapy to the subject. In some embodiments, the therapy is a cancer therapy.

In some embodiments, determining the therapy for the subject may include determining a plurality of gene group expression levels comprising a gene group expression level for each gene group in a set of gene groups. In some embodiments, the set of gene groups comprises at least one gene group associated with cancer malignancy, and at least one gene group associated with cancer microenvironment. The therapy for the subject is identified by using the determined gene group expression levels.

If the asserted and determined information do not match in act 803 (i.e., no), process 800 proceeds to 805, where one or more remedial action(s) are performed. In some embodiments, a remedial action comprises generating an indication that the determined information does not match the asserted information, generating an indication to not process the sequence data in a subsequent analysis, and/or generating an indication to obtain additional sequence data and/or other information about the biological sample and/or the subject.

In some embodiments, a method comprises all acts illustrated in FIG. 8. However, in some embodiments, a subset of the acts is performed and any one or more of the acts may be omitted, duplicated, and/or performed in a different order than illustrated in FIG. 8. For example, either act 802a or act 802b is performed in act 802. For example, act 803 can be performed twice to confirm the decision. For example, one or more acts in process 800 can be performed after the one or more remedial action(s) in act 805. In some embodiments, one or more acts of FIG. 8 are implemented on a computer.

In some embodiments, expression levels of one or more genes in a sample are analyzed to evaluate the origin and/or quality of the sample. For example, the expression of one or more genes that are known to be expressed in a particular cell, tissue, or tumor type is evaluated to determine whether it is at an expected expression level based on the expected cell, tissue, or tumor that is being analyzed. Similarly, the expression of one or more genes that are known not to be expressed (or not highly expressed) in a particular cell, tissue, or tumor type is evaluated to determine whether it is at an expected expression level based on the expected cell, tissue, or tumor that is being analyzed.

In some embodiments, expression levels of one or more genes are analyzed for each of a plurality of samples (e.g., 2, 3, 4, 5, 4-10, 1-50, 50-500, or more samples). If the expression of one or more genes is lower or higher than expected, this may be indicative that the quality and/or source/origin of the data being analyzed is not what was expected. In some embodiments, data from a sample that has an unexpected level (e.g., a lower or higher than expected level) of expression for one or more genes is excluded from further analysis. In some embodiments, new sequence information is obtained for a sample that has an unexpected level of expression for one or more genes, for example to confirm whether the initial data was correct. In some embodiments, a sample that has an unexpected level of expression for one or more genes can be further analyzed, for example to determine whether the sample was from a different source than initially indicated.

In some embodiments, expression levels for one or more genes were analyzed (e.g., using tSNE, PCA, or other technique) to determine whether gene expression or patterns of gene expression were similar or different in separate samples. In some embodiments, if datasets comprising the same cell type or same tissue type did not cluster within a group, or if one or more datasets were identified as statistically different from other datasets comprising the same cells or tissue, then the dataset(s) identified as different could be excluded, further analyzed, or flagged as potentially suspect. In some embodiments, additional sequence data can be obtained for a sample identified as potentially suspect.

Figure 9:
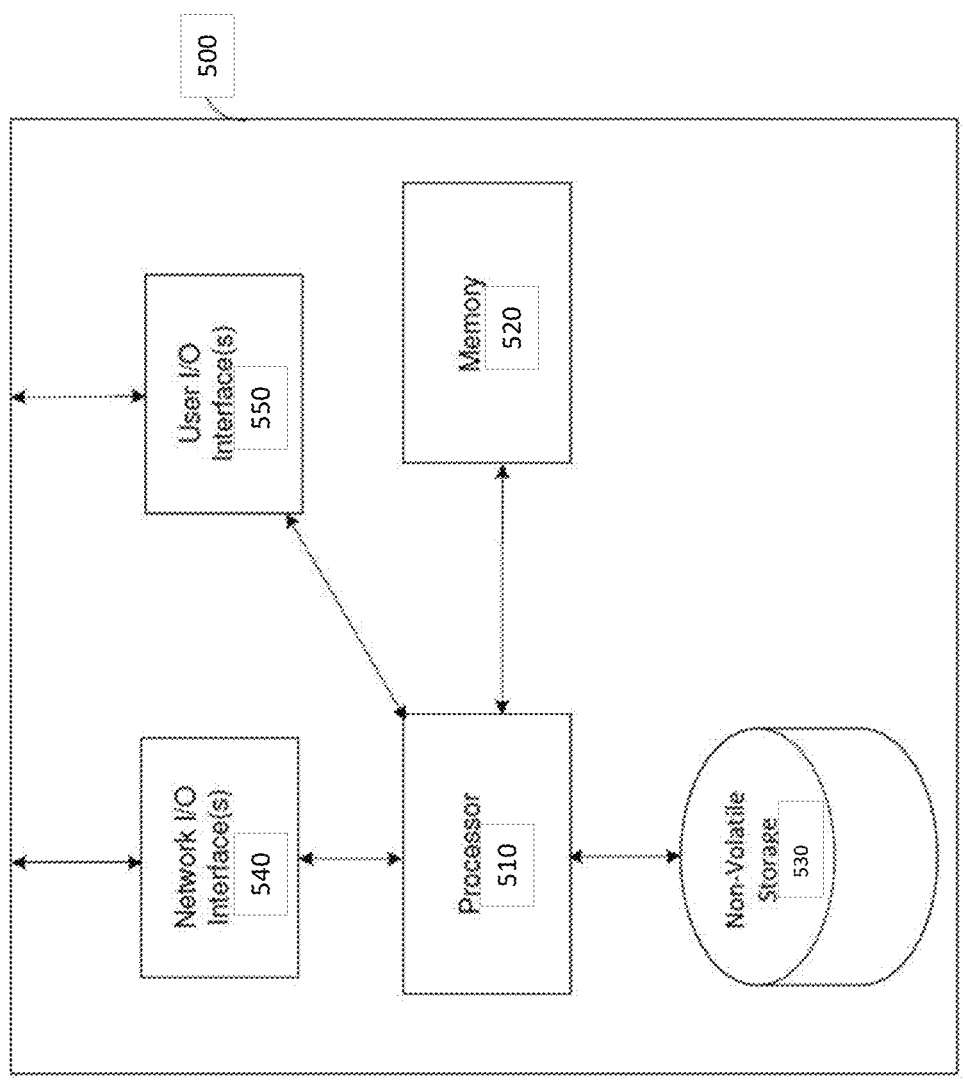
FIG. 9 is a block diagram of an illustrative computer system 500 that may be used to implement one or more embodiments of a process pipeline for preparing, assessing, and/or analyzing sequence data.

An illustrative implementation of a computer system 500 that may be used in connection with any of the embodiments of the technology described herein is shown in FIG. 9 The computer system 500 includes one or more processors 510 and one or more articles of manufacture that comprise non-transitory computer-readable storage media (e.g., memory 520 and one or more non-volatile storage media 530). The processor 510 may control writing data to and reading data from the memory 520 and the non-volatile storage device 530 in any suitable manner, as the aspects of the technology described herein are not limited in this respect. To perform any of the functionality described herein, the processor 510 may execute one or more processor-executable instructions stored in one or more non-transitory computer-readable storage media (e.g., the memory 520), which may serve as non-transitory computer-readable storage media storing processor-executable instructions for execution by the processor 510.

Computing device 500 may also include a network input/output (I/O) interface 540 via which the computing device may communicate with other computing devices (e.g., over a network), and may also include one or more user I/O interfaces 550, via which the computing device may provide output to and receive input from a user. The user I/O interfaces may include devices such as a keyboard, a mouse, a microphone, a display device (e.g., a monitor or touch screen), speakers, a camera, and/or various other types of I/O devices.

The embodiments described herein, can be implemented in any of numerous ways. For example, the embodiments may be implemented using hardware, software or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-described functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein comprises at least one computer-readable storage medium (e.g., RAM, ROM, EEPROM, flash memory or other memory technology, CD-ROM, digital versatile disks (DVD) or other optical disk storage, magnetic cassettes, magnetic tape, magnetic disk storage or other magnetic storage devices, or other tangible, non-transitory computer-readable storage medium) encoded with a computer program (i.e., a plurality of executable instructions) that, when executed on one or more processors, performs the above-described functions of one or more embodiments. The computer-readable medium may be transportable such that the program stored thereon can be loaded onto any computing device to implement aspects of the techniques described herein. In addition, it should be appreciated that the reference to a computer program which, when executed, performs any of the above-described functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques described herein.

Aspects of the technology described herein provide computer implemented methods for evaluating, generating, visualizing, and/or classifying biological characteristic(s) of sequence information of (e.g., cancer grade, tissue of origin) of subjects (e.g., cancer patients) or those having, suspected of having, or at risk of having a disorder (e.g., cancer).

In some embodiments, a software program may provide a user with a visual representation of a subject (e.g., patient)'s characteristic(s) and/or other information related to a subject (e.g., patient)'s cancer using an interactive graphical user interface (GUI). Such a software program may execute in any suitable computing environment including, but not limited to, a cloud-computing environment, a device co-located with a user (e.g., the user's laptop, desktop, smartphone, etc.), one or more devices remote from the user (e.g., one or more servers), etc.

Figure 10:
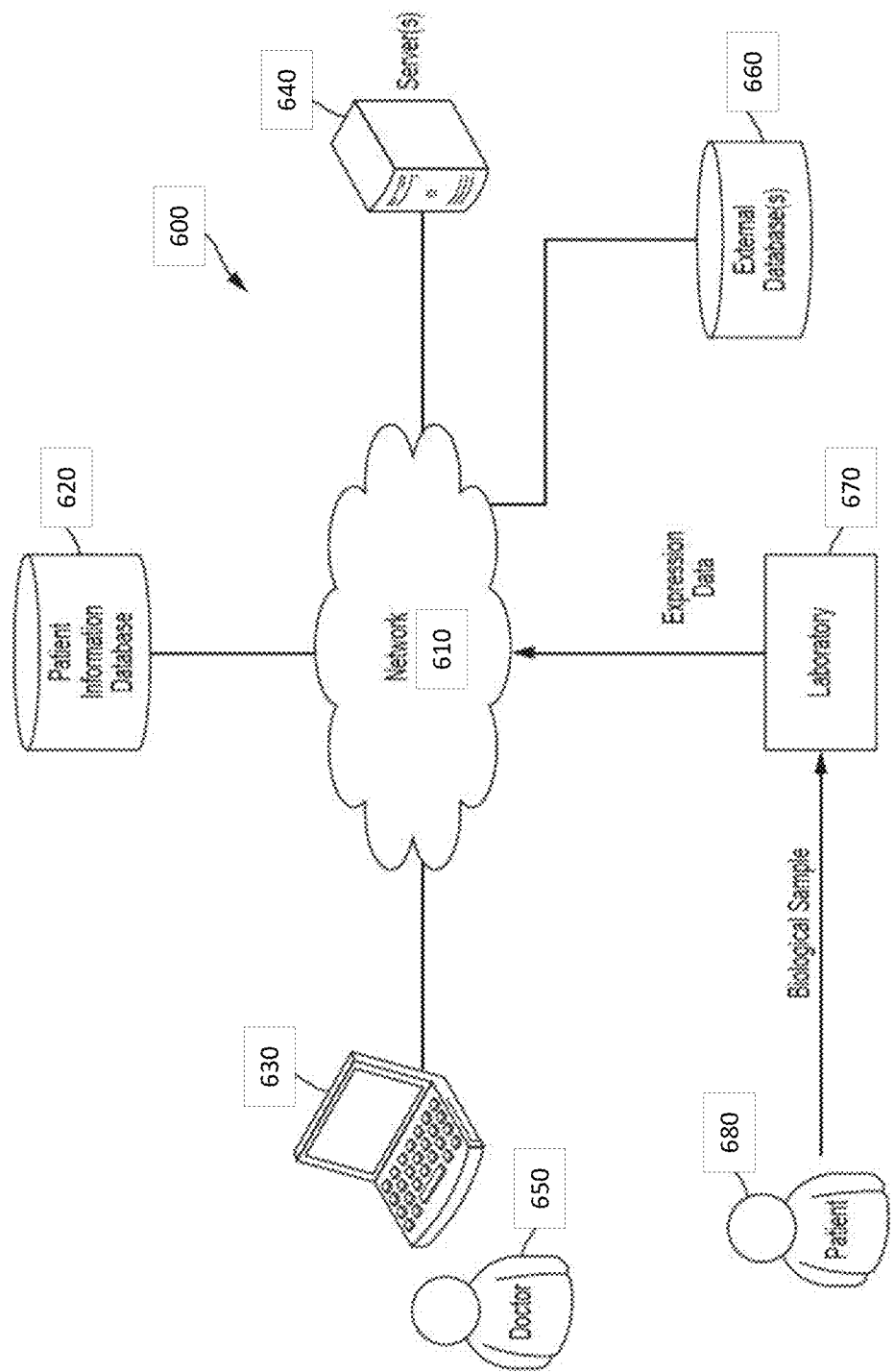
FIG. 10 is a block diagram of an illustrative environment 600 in which one or more embodiments of the technology described in this application may be implemented.

For example, in some embodiments, the techniques described herein may be implemented in the illustrative environment 600 shown in FIG. 10. As shown in FIG. 10, within illustrative environment 600, one or more biological samples of a subject 680 may be provided to a laboratory 670. Laboratory 670 may process the biological sample(s) to obtain expression data (e.g., DNA, RNA, and/or protein expression data) and/or sequence information and provide it, via network 610, to at least one database 660 that stores information about subject (e.g., patient) 680.

Network 610 may be a wide area network (e.g., the Internet), a local area network (e.g., a corporate Intranet), and/or any other suitable type of network. Any of the devices shown in FIG. 10 may connect to the network 610 using one or more wired links, one or more wireless links, and/or any suitable combination thereof.

In the illustrated embodiment of FIG. 10, the at least one database 620 may store expression data and or sequence information for the subject (e.g., patient), medical history data for the subject (e.g., patient), test result data for the subject (e.g., patient), and/or any other suitable information about the subject 680. Examples of stored test result data for the subject (e.g., patient) include biopsy test results, imaging test results (e.g., MRI results), and blood test results. The information stored in at least one database 620 may be stored in any suitable format and/or using any suitable data structure(s), as aspects of the technology described herein are not limited in this respect. The at least one database 620 may store data in any suitable way (e.g., one or more databases, one or more files). The at least one database 620 may be a single database or multiple databases.

As shown in FIG. 10, illustrative environment 600 includes one or more external databases 620, which may store information for patients other than patient 680. For example, external databases 660 may store expression data and/or sequence information (of any suitable type) for one or more patients, medical history data for one or more patients, test result data (e.g., imaging results, biopsy results, blood test results) for one or more patients, demographic and/or biographic information for one or more patients, and/or any other suitable type of information.

In some embodiments, external database(s) 660 may store information available in one or more publicly accessible databases such as TCGA (The Cancer Genome Atlas), one or more databases of clinical trial information, and/or one or more databases maintained by commercial sequencing suppliers. The external database(s) 660 may store such information in any suitable way using any suitable hardware, as aspects of the technology described herein are not limited in this respect.

In some embodiments, the at least one database 620 and the external database(s) 660 may be the same database, may be part of the same database system, or may be physically co-located, as aspects of the technology described herein are not limited in this respect.

For example, in some embodiments, server(s) 640 may access information stored in database(s) 620 and/or 660 and use this information to perform processes described herein, described with reference to FIG. 10, for determining one or more characteristics of a biological sample and/or of the sequence information.

In some embodiments, server(s) 640 may include one or multiple computing devices. When server(s) 640 include multiple computing devices, the device(s) may be physically co-located (e.g., in a single room) or distributed across multi-physical locations. In some embodiments, server(s) 640 may be part of a cloud computing infrastructure. In some embodiments, one or more server(s) 640 may be co-located in a facility operated by an entity (e.g., a hospital, research institution) with which doctor 650 is affiliated. In such embodiments, it may be easier to allow server(s) 640 to access private medical data for the patient 880.

As shown in FIG. 10, in some embodiments, the results of the analysis performed by server(s) 640 may be provided to doctor 650 through a computing device 630 (which may be a portable computing device, such as a laptop or smartphone, or a fixed computing device such as a desktop computer). The results may be provided in a written report, an e-mail, a graphical user interface, and/or any other suitable way. It should be appreciated that although in the embodiment of FIG. 10, the results are provided to a doctor 650, in other embodiments, the results of the analysis may be provided to patient 680 or a caretaker of patient 680, a healthcare provider such as a nurse, or a person involved with a clinical trial.

In some embodiments, the results may be part of a graphical user interface (GUI) presented to the doctor 650 via the computing device 630. In some embodiments, the GUI may be presented to the user as part of a webpage displayed by a web browser executing on the computing device 630. In some embodiments, the GUI may be presented to the user using an application program (different from a web-browser) executing on the computing device 630. For example, in some embodiments, the computing device 630 may be a mobile device (e.g., a smartphone) and the GUI may be presented to the user via an application program (e.g., "an app") executing on the mobile device.

The GUI presented on computing device 630 may provide a wide range of oncological data relating to both the patient and the patient's cancer in a new way that is compact and highly informative. Previously, oncological data was obtained from multiple sources of data and at multiple times making the process of obtaining such information costly from both a time and financial perspective. Using the techniques and graphical user interfaces illustrated herein, a user can access the same amount of information at once with less demand on the user and with less demand on the computing resources needed to provide such information. Low demand on the user serves to reduce clinician errors associated with searching various sources of information. Low demand on the computing resources serves to reduce processor power, network bandwidth, and memory needed to provide a wide range of oncological data, which is an improvement in computing technology. In some embodiments, the reports of the disclosure are presented to a user by means of a system or by means of a GUI.

Accordingly, in an aspect, the disclosure relates to a method of evaluating sequence information, to determine at least one feature. The evaluation can take place on a computer or other automated machine capable of carrying out programmable instructions or can be performed manually by an evaluator. The features can be used to generate a report for informing the evaluator of the at least one feature of the sequence information. In some embodiments, the feature is the sequence of the MHC alleles of the sequence information.

The major histocompatibility complex (MHC) (referred to as the Human Leukocyte Antigens (HLAs) in humans) is the mechanism by which the immune system is able to differentiate between self and nonself cells. It is a collection of glycoproteins (proteins with a carbohydrate) that exist on the plasma membranes of nearly all body cells. The (MHC) are highly polymorphic genes that are important in the immune system of biological organisms and originate from 20 genes, with more than 50 variations per gene between individuals, and allow for co-dominance between alleles. These glycoproteins are part of a pathway which enables the immune system to identify self and non-self cells by aberrations in the MHC displayed on the plasma membrane.

Due to these properties, e.g., MHCs are highly polymorphic, co-dominance, and that there are a large number of alleles that may be present in a given species, the MHC profile of a subject is highly specific and unique. Thus, it is extremely unlikely that two people, except for identical twins, will possess cells with the same set of MHC molecules. Accordingly, by evaluating the sequence of the MHC profile of sequence information, it can be used to corroborate, or disqualify, identifying information between the sequence information, an asserted information, other sequence information, or a combination thereof.

In some embodiments, one MHC allele is used for the evaluation. In some embodiments, at least two MHC alleles are used for the evaluation. In some embodiments, at least three MHC alleles are used for the evaluation. In some embodiments, at least four MHC alleles are used for the evaluation. In some embodiments, at least five MHC alleles are used for the evaluation. In some embodiments, at least six MHC alleles are used for the evaluation.

In some embodiments, the evaluated feature is a concordance value of single nucleotide polymorphisms (SNPs). "SNP" or "Single Nucleotide Polymorphism," as used herein, refers to a difference in a nucleic acid sequence (e.g., genome, sequence data set) at a single nucleotide (e.g., adenine (A), thymine (T), cytosine (C), and/or guanine (G)) shared between subjects of a species or within an individual subject on paired chromosomes. SNPs can be, or represent: changed nucleotides (e.g., A changed to T, G changed to A, etc.), known as a substitution; removed nucleotides, wherein the nucleotide is absent from the sequence entirely, known as a deletion; or added nucleotides, wherein an additional nucleotide is added to the sequence. SNPs can lead to changes in an encoded protein (e.g., nonsynonymous SNPs), or not (e.g., synonymous). Further, when the SNP is non-synonymous, it can cause a change in the encoded amino acid (e.g., missense) or cause a premature stop codon (e.g., nonsense). Synonymous SNPs can also alter the message of the nucleic acid sequence by influencing or changing the splice sites, transcription factor binding, and/or messenger RNA (mRNA) binding. These mutations (e.g., changes to the protein encoding abilities of the sequence) can cause a litany of effects including differences in phenotypes as well as various disease types. Moreover, SNPs occur in great numbers within a subject's genome, with some estimates being that a typical genome differs from the reference human genome at between 4 and 5 million sites, of which more than 99.9% are SNPs.

Since SNPs are encoded in nucleic acids which are part of the genome, they are passed from parent to progeny (both subjects, and within a subject when nucleic acids replicate). Accordingly, because of this stable inheritance, and because of the large number thereof, SNPs can be used as a genetic marker of the relatedness of subjects, and also as a measure of the identity of two nucleic acid sequences as originating from the same subject. In some embodiments, the SNP concordance value is determined between the sequence information and a reference sequence. In some embodiments, the SNP concordance value is determined between the sequence information and an asserted value. In some embodiments, the SNP concordance value must be equal to, or greater than a threshold value to be acceptable (e.g., deemed of sufficient quality and integrity) for use in further analyses. In some embodiments, the threshold value is 80%. In some embodiments, a SNP concordance value is determined between a sequence data set and a subject, wherein if the SNP concordance value is at least 70% (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9%, at least 99.95%, at least 99.99%, at least 99.999% or more), it is deemed to be sufficiently likely to be from the subject and identified as being from the subject. As described herein, in some embodiments, the determination of the concordance value is as described in the present disclosure. SNP concordance can be performed by any means available or known in the art, for example SNP concordance is performed by a variety of online tools such as Conpair (github.com/nygenome/Conpair) or GATK GenotypeConcordance (software.broadinstitute.org/gatk/documentation/tooldocs/3.8-0/org_broadinstitute_gatk_tools_walkers_variantutils_GenotypeConcordance.php) or may be calculated manually. In other examples, SNP concordance can be performed by tools as described at publicly available websites (genome.sph.umich.edu/wiki/VerifyBamID or software.broadinstitute.org/cancer/cga/contest).

In some embodiments, the evaluated feature is a quality score, for example a Phred score. A "Phred Score" (also may be known or referred to herein as a "Phred Quality Score") as used herein, refers to a measure of the quality for the identification of nucleotides sequenced by nucleic acid sequencing systems or platforms (e.g., NGS). Phred Scores are known in the art and are often generated from the sequencing platform based upon several parameters (e.g., peak shape, resolution, etc.) and a score (Q) is assigned to each nucleotide base call (For a detailed review of the calculation refer to Ewing B, Hillier L, Wendl MC, Green P. *Base-calling of automated sequencer traces using phred. L Accuracy assessment.* Genome Res. 1998 March; 8(3):175-85. and Ewing B, Green P. *Base-calling of automated sequencer traces using phred. II. Error probabilities.* Genome Res. 1998 March; 8(3):186-94.). The Phred Score of each base refers to the likelihood that a nucleotide base call is incorrect (base-calling error probability (P)) and is determined by the equation $Q=-10 \log_{10} P$. Thus, the score (e.g., Q) indicates the base call accuracy, for example a Phred Score of 10 indicates a 90% call accuracy for the base in question, while a Phred Score of 40 indicates a 99.99% call accuracy for the same base. In some embodiments, the Phred Score of the sequence information is determined and compared to a reference value. In some embodiments, the reference value is at least 27, at least 28, at least 29, at least 30, or more than 30. In some embodiments, the Phred Score is determined and compared to the Phred Score of other sequence information. In some embodiments, the Phred Score is determined and compared to an asserted score. In some embodiments, the Phred Score is used as a base level determination of quality. In some embodiments, it is used to compare a sequence with asserted information to compare identity, as if the Phred Scores are different it is unlikely they are the same sequence information or from the same sample or subject.

In some embodiments, the evaluated feature is a tumor type.

In some embodiments, the evaluated feature is a tissue type.

In some embodiments, the evaluated feature is the polyadenylation status of the sequence information. "Polyadenylated" or "PolyA" as used herein, refers to the series of multiple adenosine monophosphate nucleotides attached to the 3'-end of messenger RNA (mRNA), this 10 occurs after transcription and cleavage of the 3'-end to of the transcript to free a hydroxyl. The "polyA tail," as it is often referred, is a characteristic of fully processed mRNA and assists in various cellular processes. For example, the polyA tail is the binding site for a protein (e.g., polyA-binding protein) which promotes export from the nucleus of the cell so that translation may occur, as well as effects translation and stability of mRNA. If only transcripts of protein coding mRNA are present, it is highly likely (e.g., indicative) that the sample that generated the sequence information was generated using mRNA-Seq. In some embodiments, the polyA status indicates mRNA-Seq was not used (e.g., the whole transcriptome was used). In some embodiments, the polyA status is evaluated against an asserted information. In some embodiments, the polyA status is evaluated against a reference sequence. In some embodiments, the probability of the sequence information being generated using either mRNA-Seq or the whole transcriptome must be above a threshold. In some embodiments, the threshold is a reference value. In some embodiments, the threshold level is 90%. In some embodiments, the threshold value is an asserted information. In some embodiments, the sequence information is from a sample which contained primarily polyadenylated nucleic acids. In some embodiments, the sequence information is from a sample which contained both polyadenylated and non-polyadenylated nucleic acids In some embodiments, the evaluated feature is the GC content of the sequence information. "G/C Content" or "guanine (G)-cytosine (C) content," as used herein, refers to the percentage of nucleotides in a nucleic acid sample which are either G or C. It can be calculated by summing all of the G and C reads of given sequence information and dividing by the total nucleotides sequenced. In some embodiments, the sequence information is evaluated and the GC content is calculated by summing the number of base calls resulting in a G or C (e.g., G+C) in the sequence information and dividing by the total number of base calls in the sequence information (e.g., number of nucleotides in a sequence data set), or (G+C)/(Number of nucleotides in a sequence data set).

The GC content may also be used as a quality measure of the sequence information. Many known genomes have been sequenced, along with the respective exomes, transcriptomes, and various other portions thereof (e.g., measure of specific RNA components). Moreover, many of these sequences have been sequenced a great number of times and averages and ranges for various components thereof have been generated, for example, the GC content of the human genome. The GC content of the human genome is known to vary from approximately 35% to 60%, and has a mean value (e.g., average value) of about 41%. Accordingly, as a quality measure if a sequence information which is identified as a human genome were to be evaluated to have a GC content of 75%, the quality of the sequence information (or the sample from which it was derived) would be in question. As a result, the evaluated GC content can be compared to known ranges of GC contents expected for the sequence information, to a value provided by the sequence information donor, to a value from a database of such values, to additional sequence information, or to a reference range for sequence information of a given type to ascertain if they are consistent or if the GC content indicates a problem, which may be due to degradation, residual primers, contamination, or other complications with the sequence information.

Accordingly, in some embodiments, the GC content feature is used in a method to evaluate the integrity of the sequence information by determining a GC content for each sequence data set being evaluated; wherein, if the GC content is either: (i) less than 30%; or greater than 55%, the nucleic acid samples are deemed likely of insufficient quality, and are removed, discarded, retested, or reported as of insufficient quality, and wherein, if the GC content is: at least 30%, and less than or equal to 55%, the nucleic acid samples are deemed of sufficient quality and are retained. Additionally, in some embodiments, the GC content may be calculated and compared to asserted information. The GC content, in some embodiments, can be used to match the asserted information and thus corroborate or question the identity of the sequence information as being the same sequence information asserted, being from a given sample, subject, or specific sample or subject.

In some embodiments, the evaluated feature is a ratio of protein subunit expression (e.g., an expression ratio of nucleic acids encoding different subunits of a protein). Protein expression can be measured by any means known in the art, for example expression can be determined (e.g., quantified) by counting the number of reads that mapped to each locus in the transcriptome. By evaluating the expression of protein subunits (e.g., proteins which have multiple subunits expressed by different coding regions), and then calculating a ratio thereof, it is possible to compare the ratio with a known value, reference value, threshold value, other sequence information, or an asserted information. In some embodiments, the evaluated protein subunits are from proteins that are present in a human sample, regardless of the presence or absence of a certain type of cancer. Without wishing to be bound by any theory, such protein is encoded by a housekeeping gene (e.g., a positive or negative control of a human sample). In some embodiments, the known value, reference value, or threshold value is a fixed ratio. For example, subunit A and subunit B of a known protein has a ratio of 1:1 or 2:1. In some embodiments, the evaluated protein subunits are from proteins that are present in a human sample having or suspected of having a certain type of cancer.

In some embodiments, the ratio is compared to a known value. In some embodiments, it is compared to an asserted information. In some embodiments, it is compared to other sequence information. In some embodiments, the protein, and subunits thereof are selected for analysis due to their properties. For example, they may degrade quickly and therefore serve as a proxy for the stability and/or quality of the sample from which the sequence information was generated. In some embodiments, they may be selected for their variability between subjects, or samples, thereby allowing for comparison to corroborate or disqualify the identity of the sequence information.

In some embodiments, the evaluated feature is the coverage value. "Coverage," as used herein, refers to the number of unique reads of a given nucleotide in a reconstructed sequence. As the nucleic acid is sequenced, it is not sequenced in one entire read (e.g., start to finish in one pass), but rather is the result of multiple reads of portions or segments of the nucleic acid (e.g., RNA, exome, genome) of which have an average length (L), wherein the whole nucleic acid when reconstructed has an overall length of (G). As the number of reads of a nucleic acid increase (N), the coverage will also increase. The coverage can be calculated as N×L/G. In some embodiments, the coverage value is compared to an asserted information. In some embodiments, the coverage value is compared to a threshold or reference value. In some embodiments, the threshold or reference value is a statistically significant value. In some embodiments, the coverage value is compared to other sequence information. In some embodiments, the target value of the coverage for tumor is more than 150× (e.g., 170×, 190×). In some embodiments, the target value of the coverage for normal tissue is more than 100× (e.g., 110×, 120×, 130×). Publicly available tools can be used for determining the coverage value (github.com/brentp/mosdepth and biodatageeks.org/sequila/).

The features and evaluations described herein can be evaluated and used individually as well as in conjunction with one another. In some embodiments, at least one feature is evaluated (e.g., at least one, at least two, at least three, at least four, or more). In some embodiments, at least two features are evaluated (e.g., at least three, at least four, or more). In some embodiments, at least four features are evaluated (e.g., at least four, or more). In some embodiments, at least five features are evaluated (e.g., at least five, or more). In some embodiments, at least six features are evaluated (e.g., at least six, or more). In some embodiments, at least seven features are evaluated (e.g., at least seven, or more). In some embodiments, at least eight features are evaluated (e.g., at least eight, or more). In some embodiments, at least nine features are evaluated (e.g., at least nine, or more). In some embodiments, at least ten features are evaluated (e.g., at least ten, or more). In some embodiments, at least eleven features are evaluated (e.g., at least eleven, or more). In some embodiments, at least twelve features are evaluated (e.g., at least twelve, or more). In some embodiments, at least thirteen features are evaluated (e.g., at least thirteen, or more). In some embodiments, at least fourteen features are evaluated (e.g., at least fourteen, or more). In some embodiments, at least fifteen features are evaluated (e.g., at least fifteen, or more).

The features described herein can be evaluated sequentially, simultaneously, parallel, or a combination thereof. As it can be envisioned, the evaluations required to evaluate some features, may be useful in evaluating additional or other features. Accordingly, where such information or evaluation results are useful for other determinations, it is possible to perform evaluations of multiple features at once (e.g., simultaneous), or to use the information for a follow-on evaluations (e.g., sequential). Additionally, it can be envisioned to run multiple evaluations at the same time of different features (e.g., parallel). In some embodiments, features are evaluated sequentially. In some embodiments, features are evaluated simultaneously. In some embodiments, features are evaluated in parallel. In some embodiments, features are evaluated in a combination of methods (e.g., simultaneously as well as sequentially).

Identifying a cancer treatment

A subject's sequencing data obtained using any one of the methods described herein may be used for various clinical purposes including, but not limited to, monitoring the progress of cancer in a subject, assessing the efficacy of a treatment for cancer, identifying subjects suitable for a particular treatment, evaluating suitability of a patient for participating in a clinical trial and/or predicting relapse in a subject. Accordingly, described herein are diagnostic and prognostic methods for cancer treatment based on sequencing data obtained using methods described herein. In some embodiments, a method to process RNA expression data as described herein comprises identifying a cancer treatment (also referred to herein as an anti-cancer therapy) for the subject using the bias-corrected gene expression data.

Molecular Functional Expression Signatures

In some embodiments, identifying a cancer treatment for a subject comprises characterizing the cancer or tumor in the subject using bias-corrected gene expression data. In some embodiments, a cancer in a subject is characterized by determining a molecular functional expression signature, which may include and/or reflect information relating to the molecular characteristics of a tumor including tumor genetics, pro-tumor microenvironment factors, and anti-tumor immune response factors.

A "molecular functional expression signature (MFES)", as described herein, refers to information relating to molecular and cellular composition, and biological processes that are present within and/or surrounding the tumor. In some embodiments, the MFES of a patient includes gene express levels for each of one or more groups of genes ("gene groups"). In some embodiments, the information in the MFES may be generated using gene expression data (e.g., bias corrected gene expression data) for the gene groups obtained by sequencing normal and/or tumor tissue. Though other types of gene expression data may be used to generate an MFES, it should be appreciated that the inventors recognized that using bias-corrected gene expression data to generate a molecular functional expression signature allows the resulting MFES to more accurately and faithfully represent the molecular functional characteristics of the subject's tumor. In turn, applying an MFES determined from bias-corrected gene expression data to identifying a cancer therapy for the subject allows for the identification of more effective therapies, improved ability to determine whether one or more cancer therapies will be effective if administered to the subject, improved ability to identify clinical trials in which the subject may participate, and/or improvements to numerous other prognostic, diagnostic, and clinical applications.

Gene Groups

A "gene group" refers to a group of genes associated with molecular processes present within and/or surrounding a tumor. Examples of gene groups and techniques for determining gene group expression levels are described in International PCT Publication WO2018/231771, published on Dec. 20, 2018, entitled "Systems and Methods for Generating, Visualizing and Classifying Molecular Functional Profiles," (being a publication of PCT Application No.: PCT/US20/037017, filed Jun. 12, 2018), the entire contents of which are incorporated herein by reference. A "gene group" may be referred to herein as a "module".

Exemplary modules may include, but are not limited to, Major histocompatibility complex I (MHC I) module, Major histocompatibility complex II (MHC II) module, Coactivation molecules module, Effector cells module, Effector T cell module; Natural killer cells (NK cells) module, T cell traffic module, T cells module, B cells module, B cell traffic module, Benign B cells module, Malignant B cell marker module, M1 signatures module, Th1 signature module, Antitumor cytokines module, Checkpoint inhibition (or checkpoint molecules) module, Follicular dendritic cells module, Follicular B helper T cells module, Protumor cytokines module, Regulatory T cells (Treg) module, Treg traffic module, Myeloid-derived suppressor cells (MDSCs) module, MDSC and TAM traffic module, Granulocytes module, Granulocytes traffic module, Eosinophil signature model, Neutrophil signature model, Mast cell signature module, M2 signature module, Th2 signature module, Th17 signature module, Protumor cytokines module, Complement inhibition module, Fibroblastic reticular cells module, Cancer associated fibroblasts (CAFs) module, Matrix formation (or Matrix) module, Angiogenesis module, Endothelium module, Hypoxia factors module, Coagulation module, Blood endothelium module, Lymphatic endothelium module, Proliferation rate (or Tumor proliferation rate) module, Oncogenes module, PI3K/AKT/mTOR signaling module, RAS/RAF/MEK signaling module, Receptor tyrosine kinases expression module, Growth Factors module, Tumor suppressors module, Metastasis signature module, Antimetastatic factors module, and Mutation status module.

In some embodiments, each of one or more gene groups in an MFES may comprise at least two genes (e.g., at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same.

In some embodiments, the modules in a molecular functional expression signature may comprise or consist of: Major histocompatibility complex I (MHC I) module, Major histocompatibility complex II (MHC II) module, Coactivation molecules module, Effector cells (or Effector T cell) module, Natural killer cells (NK cells) module, T cells module, B cells module, M1 signatures module, Th1 signature module, Antitumor cytokines module, Checkpoint inhibition (or checkpoint molecules) module, Regulatory T cells (Treg) module, Myeloid-derived suppressor cells (MDSCs) module, Neutrophil signature model, M2 signature module, Th2 signature module, Protumor cytokines module, Complement inhibition module, Cancer associated fibroblasts (CAFs) module, Angiogenesis module, Endothelium module, Proliferation rate (or Tumor proliferation rate) module, PI3K/AKT/mTOR signaling module, RAS/RAF/MEK signaling module, Receptor tyrosine kinases expression module, Growth Factors module, Tumor suppressors module, Metastasis signature module, and Antimetastatic factors module. The modules may additionally include: T cell traffic module, Antitumor cytokines module, Treg traffic module, MDSC and TAM traffic module, Granulocytes or Granulocyte traffic module, Eosinophil signature model, Mast cell signature module, Th17 signature module, Matrix formation (or Matrix) module, and Hypoxia factors module. Such an MFES may be determined for a subject having a solid cancer (e.g., a melanoma) and used, for example, to identify a therapy for treating the solid cancer.

In some embodiments, the modules in a molecular functional expression signature may comprise or consist of: Effector cells (or Effector T cell) module, Natural killer cells (NK cells) module, T cells module, Malignant B cell marker module, M1 signatures module, Th1 signature module, Checkpoint inhibition (or checkpoint molecules) module, Follicular dendritic cells module, Follicular B helper T cells module, Protumor cytokines module, Regulatory T cells (Treg) module, Neutrophil signature model, M2 signature module, Th2 signature module, Complement inhibition module, Fibroblastic reticular cells module, Angiogenesis module, Blood endothelium module, Proliferation rate (or Tumor proliferation rate) module, Oncogenes module, and Tumor suppressors module. The modules may additionally include: Major histocompatibility complex I (MHC I) module, Major histocompatibility complex II (MHC II) module, Coactivation molecules module, B cell traffic module, Benign B cells module, Antitumor cytokines module, Treg traffic module, Mast cell signature module, Th17 signature module, Matrix formation (or Matrix) module, Hypoxia factors module, Coagulation module, and Lymphatic endothelium module. Such an MFES may be determined for a subject having follicular lymphoma and used, for example, to identify a therapy for treating the follicular lymphoma.

In some embodiments, the gene groups in an MFES may comprise at least two genes (e.g., at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same): Major histocompatibility complex I (MHC I) module: HLA-A, HLA-B, HLA-C, B2M, TAP1, and TAP2; Major histocompatibility complex II (MHC II) module: HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, and HLA-DRB6; Coactivation molecules module: CD80, CD86, CD40, CD83, TNFRSF4, ICOSLG, CD28; Effector cells module: IFNG, GZMA, GZMB, PRF1, LCK, GZMK, ZAP70, GNLY, FASLG, TBX21, EOMES, CD8A, and CD8B; Effector T cell module: IFNG, GZMA, GZMB, PRF1, LCK, GZMK, ZAP70, GNLY, FASLG, TBX21, EOMES, CD8A, and CD8B; Natural killer cells (NK cells) module: NKG7, CD160, CD244, NCR1, KLRC2, KLRK1, CD226, GZMH, GNLY, IFNG, KIR2DL4, KIR2DS1, KIR2DS2, KIR2DS3, KIR2DS4, KIR2DS5, EOMES, CLIC3, FGFBP2, KLRF1, and SH2D1B; T cell traffic module: CXCL9, CXCL10, CXCR3, CX3CL1, CCR7, CXCL11, CCL21, CCL2, CCL3, CCL4, and CCL5; T cells module: EOMES, TBX21, ITK, CD3D, CD3E, CD3G, TRAC, TRBC1, TRBC2, LCK, UBASH3A, TRAT1, CD5, and CD28; B cells module: CD19, MS4A1, TNFRSF13C, CD27, CD24, CR2, TNFRSF17, TNFRSF13B, CD22, CD79A, CD79B, BLK, FCRL5, PAX5, and STAP1; B cell traffic module: CXCL13 and CXCR5; Benign B cells module: CD19, MS4A1, TNFRSF13C, CD27, CD24, CR2, TNFRSF17, TNFRSF13B, CD22, CD79A, CD79B, and BLK; Malignant B cell marker module: MME, CD70, CD20, CD22, and PAX5; M1 signatures module: NOS2, IL12A, IL12B, IL23A, TNF, IL1B, and SOCS3; Th1 signature module: IFNG, IL2, CD40LG, IL15, CD27, TBX21, LTA, and IL21; Antitumor cytokines module: HMGB1, TNF, IFNB1, IFNA2, CCL3, TNFSF10, and FASLG; Checkpoint inhibition (or checkpoint molecules) module: PDCD1, CD274, CTLA4, LAG3, PDCD1LG2, BTLA, HAVCR2, and VSIR; Follicular dendritic cells module: CR1, FCGR2A, FCGR2B, FCGR2C, CR2, FCER2, CXCL13, MADCAM1, ICAM1, VCAM1, BST1, LTBR, and TNFRSF1A; Follicular B helper T cells module: CXCR5, B3GAT1, ICOS, CD40LG, CD84, IL21, BCL6, MAF, and SAP; Protumor cytokines module: IL10, TGFB1, TGFB2, TGFB3, IL22, MIF, TNFSF13B, IL6, and IL7; Regulatory T cells (Treg) module: TGFB1, TGFB2, TGFB3, FOXP3, CTLA4, IL10, TNFRSF18, TNFR2, and TNFRSF1B; Treg traffic module: CCL17, CXCL12, CXCR4, CCR4, CCL22, CCL1, CCL2, CCL5, CXCL13, and CCL28; Myeloid-derived suppressor cells (MDSCs) module: IDO1, ARG1, IL4R, IL10, TGFB1, TGFB2, TGFB3, NOS2, CYBB, CXCR4, and CD33; MDSC and TAM traffic module: CXCL1, CXCL5, CCL2, CCL4, CCL8, CCR2, CCL3, CCL5, CSF1, and CXCL8; Granulocytes module: CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, MPO, ELANE, PRTN3, CTSG, FCGR3B, CXCR1, CXCR2, CD177, PI3, FFAR2, PGLYRP1, CMA1, TPSAB1, MS4A2, CPA3, IL4, IL5, IL13, and SIGLEC8; Granulocyte traffic module: CXCL8, CXCL2, CXCL1, CCL11, CCL24, KITLG, CCL5, CXCL5, CCR3, and CCL26; Eosinophil signature model: PRG2, EPX, RNASE2, RNASE3, IL5RA, GATA1, SIGLEC8, and PRG3; Neutrophil signature model: MPO, ELANE, PRTN3, CTSG, FCGR3B, CXCR1, CXCR2, CD177, PI3, FFAR2, and PGLYRP1; Mast cell signature module: CMA1, TPSAB1, MS4A2, CPA3, IL4, IL5, IL13, and SIGLEC8; M2 signature module: IL10, VEGFA, TGFB1, IDO1, PTGES, MRC1, CSF1, LRP1, ARG1, PTGS1, MSR1, CD163, and CSF1R; Th2 signature module: IL4, IL5, IL13, IL10, IL25, and GATA3; Th17 signature module: IL17A, IL22, IL26, IL17F, IL21, and RORC; Protumor cytokines module: IL10, TGFB1, TGFB2, TGFB3, IL22, and MIF; Complement inhibition module: CFD, CFI, CD55, CD46, CR1, and CD59; Fibroblastic reticular cells module: DES, VIM, PDGFRA, PDPN, NT5E, THY1, ENG, ACTA2, LTBR, TNFRSF1A, VCAM1, ICAM1, and BST1; Cancer associated fibroblasts (CAFs) module: COL1A1, COL1A2, COL4A1, COL5A1, TGFB1, TGFB2, TGFB3, ACTA2, FGF2, FAP, LRP1, CD248, COL6A1, COL6A2, COL6A3, FBLN1, LUM, MFAP5, LGALS1, and PRELP; Matrix formation (or Matrix) module: MMP9, FN1, COL1A1, COL1A2, COL3A1, COL4A1, CA9, VTN, LGALS7, TIMP1, MMP2, MMP1, MMP3, MMP12, LGALS9, MMP7, and COL5A1; Angiogenesis module: VEGFA, VEGFB, VEGFC, PDGFC, CXCL8, CXCR2, FLT1, PIGF, CXCL5, KDR, ANGPT1, ANGPT2, TEK, VWF, CDH5, NOS3, VCAM1, MMRN1, LDHA, HIF1A, EPAS1, CA9, SPP1, LOX, SLC2A1, and LAMP3; Endothelium module: VEGFA, NOS3, KDR, FLT1, VCAM1, VWF, CDH5, MMRN1, CLEC14A, MMRN2, and ECSCR; Hypoxia factors module: LDHA, HIF1A, EPAS1, CA9, SPP1, LOX, SLC2A1, and LAMP3; Coagulation module: HPSE, SERPINE1, SERPINB2, F3, and ANXA2; Blood endothelium module: VEGFA, NOS3, KDR, FLT1, VCAM1, VWF, CDH5, and MMRN1; Lymphatic endothelium module: CCL21 and CXCL12; Proliferation rate (or Tumor proliferation rate) module: MKI67, ESCO2, CETN3, CDK2, CCND1, CCNE1, AURKA, AURKB, E2F1, MYBL2, BUB1, PLK1, PRC1, CCNB1, MCM2, MCM6, CDK4, and CDK6; Oncogenes module: MDM2, MYC, AKT1, BCL2, MME, and SYK; PI3K/AKT/mTOR signaling module: PIK3CA, PIK3CB, PIK3CG, PIK3CD, AKT1, MTOR, PTEN, PRKCA, AKT2, and AKT3; RAS/RAF/MEK signaling module: BRAF, FNTA, FNTB, MAP2K1, MAP2K2, MKNK1, and MKNK2; Receptor tyrosine kinases expression module: ALK, AXL, KIT, EGFR, ERBB2, FLT3, MET, NTRK1, FGFR1, FGFR2, FGFR3, ERBB4, ERBB3, BCR-ABL, PDGFRA, PDGFRB, and ABL1; Growth Factors module: NGF, CSF3, CSF2, FGF7, IGF1, IGF2, IL7, and FGF2; Tumor suppressors module: TP53, MLL2, CREBBP, EP300, ARID1A, HIST1H1, EBF1, IRF4, IKZF3, KLHL6, PRDM1, CDKN2A, RB1, EPHA7, TNFAIP3, TNFRSF14, FAS, SHP1, SOCS1, SIK1, PTEN, DCN, MTAP, AIM2, and MITF; Metastasis signature module: ESRP1, HOXA1, SMARCA4, TWIST1, NEDD9, PAPPA, CTSL, SNAI2, and HPSE; Antimetastatic factors module: NCAM1, CDH1, KISS1, BRMS1, ADGRG1, TCF21, PCDH10, and MITF; and Mutation status module: APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL. In certain embodiments, two or more genes from any combination of the listed modules may be used to generate a molecular functional expression signature (or a visualization thereof, termed an "MF PORTRAIT" herein) for a subject.

In some embodiments, the gene groups in an MFES may comprise at least two genes (e.g., at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same): Major histocompatibility complex I (MHC I) module: HLA-A, HLA-B, HLA-C, B2M, TAP1, and TAP2; Major histocompatibility complex II (MHC II) module; HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, and HLA-DRB6; Coactivation molecules module: CD80, CD86, CD40, CD83, TNFRSF4, ICOSLG, and CD28; Effector cells (or Effector T cell) module: IFNG, GZMA, GZMB, PRF1, LCK, GZMK, ZAP70, GNLY, FASLG, TBX21, EOMES, CD8A, and CD8B; Natural killer cells (NK cells) module: NKG7, CD160, CD244, NCR1, KLRC2, KLRK1, CD226, GNLY, KIR2DL4, KIR2DS1, KIR2DS2, KIR2DS3, KIR2DS4, KIR2DS5, EOMES, CLIC3, FGFBP2, KLRF1, and SH2D1B; T cells module: TBX21, ITK, CD3D, CD3E, CD3G, TRAC, TRBC1, TRBC2, LCK, UBASH3A, TRAT1, CD5, and CD28; B cells module: CD19, MS4A1, TNFRSF13C, CD27, CD24, CR2, TNFRSF17, TNFRSF13B, CD22, CD79A, CD79B, BLK, FCRL5, PAX5, and STAP1; M1 signatures module: NOS2, IL12A, IL12B, IL23A, TNF, IL1B, and SOCS3; Th1 signature module: IFNG, IL2, CD40LG, IL15, CD27, TBX21, LTA, and IL21; Checkpoint inhibition (or checkpoint molecules) module: PDCD1, CD274, CTLA4, LAG3, PDCD1LG2, BTLA, HAVCR2, and VSIR; Regulatory T cells (Treg) module: TGFB1, TGFB2, TGFB3, FOXP3, CTLA4, IL10, and TNFRSF1B; Myeloid-derived suppressor cells (MDSCs) module: IDO1, ARG1, IL4R, IL10, TGFB1, TGFB2, TGFB3, NOS2, CYBB, CXCR4, and CD33; Neutrophil signature model: MPO, ELANE, PRTN3, CTSG, FCGR3B, CXCR1, CXCR2, CD177, PI3, FFAR2, and PGLYRP1; M2 signature module: IL10, VEGFA, TGFB1, IDO1, PTGES, MRC1, CSF1, LRP1, ARG1, PTGS1, MSR1, CD163, and CSF1R; Th2 signature module: IL4, IL5, IL13, IL10, IL25, and GATA3; Protumor cytokines module: IL10, TGFB1, TGFB2, TGFB3, IL22, and MIF; Complement inhibition module: CFD, CFI, CD55, CD46, and CR1; Cancer associated fibroblasts (CAFs) module: COL1A1, COL1A2, COL4A1, COL5A1, TGFB1, TGFB2, TGFB3, ACTA2, FGF2, FAP, LRP1, CD248, COL6A1, COL6A2, COL6A3, FBLN1, LUM, MFAP5, and PRELP; Angiogenesis module: VEGFA, VEGFB, VEGFC, PDGFC, CXCL8, CXCR2, FLT1, PIGF, CXCL5, KDR, ANGPT1, ANGPT2, TEK, VWF, CDH5, NOS3, VCAM1, and MMRN1; Endothelium module: VEGFA, NOS3, KDR, FLT1, VCAM1, VWF, CDH5, MMRN1, CLEC14A, MMRN2, and ECSCR; Proliferation rate (or Tumor proliferation rate) module: MKI67, ESCO2, CETN3, CDK2, CCND1, CCNE1, AURKA, AURKB, E2F1, MYBL2, BUB1, PLK1, CCNB1, MCM2, MCM6, CDK4, and CDK6; PI3K/AKT/mTOR signaling module: PIK3CA, PIK3CB, PIK3CG, PIK3CD, AKT1, MTOR, PTEN, PRKCA, AKT2, and AKT3; RAS/RAF/MEK signaling module: BRAF, FNTA, FNTB, MAP2K1, MAP2K2, MKNK1, and MKNK2; Receptor tyrosine kinases expression module: ALK, AXL, KIT, EGFR, ERBB2, FLT3, MET, NTRK1, FGFR1, FGFR2, FGFR3, ERBB4, ERBB3, BCR-ABL, PDGFRA, PDGFRB, and ABL1; Growth Factors module: NGF, CSF3, CSF2, FGF7, IGF1, IGF2, IL7, and FGF2; Tumor suppressors module: TP53, SIK1, PTEN, DCN, MTAP, AIM2, RB1, and MITF; Metastasis signature module: ESRP1, HOXA1, SMARCA4, TWIST1, NEDD9, PAPPA, and HPSE; and Antimetastatic factors module: NCAM1, CDH1, KISS1, and BRMS1. In some embodiments, the gene groups may further comprise at least two genes (e.g., at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same): T cell traffic module: CXCL9, CXCL10, CXCR3, CX3CL1, CCR7, CXCL11, CCL21, CCL2, CCL3, CCL4, and CCL5; Antitumor cytokines module: HMGB1, TNF, IFNB1, IFNA2, CCL3, TNFSF10, and FASLG; Treg traffic module: CCL17, CXCL12, CXCR4, CCL4, CCL22, CCL1, CCL2, CCL5, CXCL13, and CCL28; MDSC and TAM traffic module: CXCL1, CXCL5, CCL2, CCL4, CCL8, CCR2, CCL3, CCL5, CSF1, and CXCL8; Granulocyte traffic module: CXCL8, CXCL2, CXCL1, CCL11, CCL24, KITLG, CCL5, CXCL5, CCR3, and CCL26; Eosinophil signature model: PRG2, EPX, RNASE2, RNASE3, IL5RA, GATA1, SIGLEC8, and PRG3; Mast cell signature module: CMA1, TPSAB1, MS4A2, CPA3, IL4, IL5, IL13, and SIGLEC8; Th17 signature module: IL17A, IL22, IL26, IL17F, IL21, and RORC; Matrix formation (or Matrix) module: FN1, CA9, MMP1, MMP3, MMP12, LGALS9, MMP7, MMP9, COL1A1, COL1A2, COL4A1, and COL5A1; and Hypoxia factors module: LDHA, HIF1A, EPAS1, CA9, SPP1, LOX, SLC2A1, and LAMP3. In certain embodiments, two or more genes from each of the listed modules are included. Any of the foregoing sets of modules may be used to generate an MFES (or a visualization thereof) for a subject with a solid cancer (e.g., melanoma).

In some embodiments, the gene groups may comprise at least two genes (e.g., at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same): Effector T cell module: IFNG, GZMA, GZMB, PRF1, LCK, GZMK, ZAP70, GNLY, FASLG, TBX21, EOMES, CD8A, and CD8B; Natural killer cells (NK cells) module: NKG7, CD160, CD244, NCR1, KLRC2, KLRK1, CD226, GZMH, GNLY, IFNG, KIR2DL4, KIR2DS1, KIR2DS2, KIR2DS3, KIR2DS4, and KIR2DS5; T cells module: EOMES, TBX21, ITK, CD3D, CD3E, CD3G, TRAC, TRBC1, TRBC2, LCK, UBASH3A, and TRAT1; Benign B cells module: CD19, MS4A1, TNFRSF13C, CD27, CD24, CR2, TNFRSF17, TNFRSF13B, CD22, CD79A, CD79B, and BLK; Malignant B cell marker module: MME, CD70, CD20, CD22, and PAX5; M1 signatures module: NOS2, IL12A, IL12B, IL23A, TNF, IL1B, and SOCS3; Th1 signature module: IFNG, IL2, CD40LG, IL15, CD27, TBX21, LTA, and IL21; Checkpoint inhibition (or checkpoint molecules) module: PDCD1, CD274, CTLA4, LAG3, PDCD1LG2, BTLA, and HAVCR2; Follicular dendritic cells module: CR1, FCGR2A, FCGR2B, FCGR2C, CR2, FCER2, CXCL13, MADCAM1, ICAM1, VCAM1, BST1, LTBR, and TNFRSF1A; Follicular B helper T cells module: CXCR5, B3GAT1, ICOS, CD40LG, CD84, IL21, BCL6, MAF, and SAP; Protumor cytokines module: IL10, TGFB1, TGFB2, TGFB3, IL22, MIF, TNFSF13B, IL6, and IL7; Regulatory T cells (Treg) module: TGFB1, TGFB2, TGFB3, FOXP3, CTLA4, IL10, TNFRSF18, and TNFR2; Neutrophil signature model: MPO, ELANE, PRTN3, and CTSG; M2 signature module: IL10, VEGFA, TGFB1, IDO1, PTGES, MRC1, CSF1, LRP1, ARG1, PTGS1, MSR1, CD163, and CSF1R; Th2 signature module: IL4, IL5, IL13, IL10, IL25, and GATA3; Complement inhibition module: CFD, CFI, CD55, CD46, CR1, and CD59; Fibroblastic reticular cells module: DES, VIM, PDGFRA, PDPN, NT5E, THY1, ENG, ACTA2, LTBR, TNFRSF1A, VCAM1, ICAM1, and BST1; Angiogenesis module: VEGFA, VEGFB, VEGFC, PDGFC, CXCL8, CXCR2, FLT1, PIGF, CXCL5, KDR, ANGPT1, ANGPT2, TEK, VWF, and CDH5; Blood endothelium module: VEGFA, NOS3, KDR, FLT1, VCAM1, VWF, CDH5, and MMRN1; Proliferation rate (or Tumor proliferation rate) module: MKI67, ESCO2, CETN3, CDK2, CCND1, CCNE1, AURKA, AURKB, E2F1, MYBL2, BUB1, PLK1, CCNB1, MCM2, and MCM6; Oncogenes module: MDM2, MYC, AKT1, BCL2, MME, and SYK; and Tumor suppressors module: TP53, MLL2, CREBBP, EP300, ARID1A, HIST1H1, EBF1, IRF4, IKZF3, KLHL6, PRDM1, CDKN2A, RB1, EPHA7, TNFAIP3, TNFRSF14, FAS, SHP1, and SOCS1. In some embodiments, the gene groups of the modules may further comprise at least two genes (e.g., at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same): Coactivation molecules module: TNFRSF4 and CD28; B cell traffic module: CXCL13 and CXCR5; Antitumor cytokines module: HMGB1, TNF, IFNB1, IFNA2, CCL3, TNFSF10, FASLG; Treg traffic module: CCL17, CCR4, CCL22, and CXCL13; Eosinophil signature model: PRG2, EPX, RNASE2, RNASE3, IL5RA, GATA1, SIGLEC8, and PRG3; Mast cell signature module: CMA1, TPSAB1, MS4A2, CPA3, IL4, IL5, IL13, and SIGLEC8; Th17 signature module: IL17A, IL22, IL26, IL17F, IL21, and RORC; Matrix formation (or Matrix) module: MMP9, FN1, COL1A1, COL1A2, COL3A1, COL4A1, CA9, VTN, LGALS7, TIMP1, and MMP2; Hypoxia factors module: LDHA, HIF1A, EPAS1, CA9, SPP1, LOX, SLC2A1, and LAMP3; Coagulation module: HPSE, SERPINE1, SERPINB2, F3, and ANXA2; and Lymphatic endothelium module: CCL21 and CXCL12. In certain embodiments, two or more genes from each of the listed modules are included. Any of the foregoing sets of modules may be used to generate an MFES (or a visualization thereof) for a subject with a follicular lymphoma.

In some embodiments, an MFES may include one or more gene groups associated with cancer malignancy and one or more gene groups associated with the cancer microenvironment. In some embodiments, the gene group(s) associated with cancer malignancy include the tumor properties gene group. In some embodiments, the gene group(s) associated with cancer microenvironment include the tumor-promoting immune microenvironment gene group, the anti-tumor immune microenvironment gene group, the gene angiogenesis group, and the gene fibroblasts group.

In some embodiments, the gene groups associated with cancer malignancy comprises at least three genes from the following group (e.g., at least three genes, at least four genes, at least five genes, at least six genes, at least seven genes, at least eight genes, at least nine genes, at least ten genes, or more than ten genes are selected from each group; in some embodiments all of the listed genes are selected from each group): the tumor properties group: MKI67, ESCO2, CETN3, CDK2, CCND1, CCNE1, AURKA, AURKB, CDK4, CDK6, PRC1, E2F1, MYBL2, BUB1, PLK1, CCNB1, MCM2, MCM6, PIK3CA, PIK3CB, PIK3CG, PIK3CD, AKT1, MTOR, PTEN, PRKCA, AKT2, AKT3, BRAF, FNTA, FNTB, MAP2K1, MAP2K2, MKNK1, MKNK2, ALK, AXL, KIT, EGFR, ERBB2, FLT3, MET, NTRK1, FGFR1, FGFR2, FGFR3, ERBB4, ERBB3, BCR-ABL, PDGFRA, PDGFRB, NGF, CSF3, CSF2, FGF7, IGF1, IGF2, IL7, FGF2, TP53, SIK1, PTEN, DCN, MTAP, AIM2, RB1, ESRP1, CTSL, HOXA1, SMARCA4, SNAI2, TWIST1, NEDD9, PAPPA, HPSE, KISS1, ADGRG1, BRMS1, TCF21, CDH1, PCDH10, NCAM1, MITF, APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL.

In some embodiments, the gene groups associated with cancer microenvironment includes at least three genes from each of the following groups (e.g., at least three genes, at least four genes, at least five genes, at least six genes, at least seven genes, at least eight genes, at least nine genes, at least ten genes, or more than ten genes are selected from each group; in some embodiments all of the listed genes are selected from each group): the anti-tumor immune microenvironment group: HLA-A, HLA-B, HLA-C, B2M, TAP1, TAP2, HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, HLA-DRB6, CD80, CD86, CD40, CD83, TNFRSF4, ICOSLG, CD28, IFNG, GZMA, GZMB, PRF1, LCK, GZMK, ZAP70, GNLY, FASLG, TBX21, EOMES, CD8A, CD8B, NKG7, CD160, CD244, NCR1, KLRC2, KLRK1, CD226, GZMH, GNLY, IFNG, KIR2DL4, KIR2DS1, KIR2DS2, KIR2DS3, KIR2DS4, KIR2DS5, CXCL9, CXCL10, CXCR3, CX3CL1, CCR7, CXCL11, CCL21, CCL2, CCL3, CCL4, CCL5, EOMES, TBX21, ITK, CD3D, CD3E, CD3G, TRAC, TRBC1, TRBC2, LCK, UBASH3A, TRAT1, CD19, MS4A1, TNFRSF13C, CD27, CD24, CR2, TNFRSF17, TNFRSF13B, CD22, CD79A, CD79B, BLK, NOS2, IL12A, IL12B, IL23A, TNF, IL1B, SOCS3, IFNG, IL2, CD40LG, IL15, CD27, TBX21, LTA, IL21, HMGB1, TNF, IFNB1, IFNA2, CCL3, TNFSF10, and FASLG; the tumor-promoting immune microenvironment group: PDCD1, CD274, CTLA4, LAG3, PDCD1LG2, BTLA, HAVCR2, VSIR, CXCL12, TGFB1, TGFB2, TGFB3, FOXP3, CTLA4, IL10, TNFRSF1B, CCL17, CXCR4, CCR4, CCL22, CCL1, CCL2, CCL5, CXCL13, CCL28, IDO1, ARG1, IL4R, IL10, TGFB1, TGFB2, TGFB3, NOS2, CYBB, CXCR4, CD33, CXCL1, CXCL5, CCL2, CCL4, CCL8, CCR2, CCL3, CCL5, CSF1, CXCL8, CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, CMA1, TPSAB1, MS4A2, CPA3, IL4, IL5, IL13, SIGLEC8, MPO, ELANE, PRTN3, CTSG, IL10, VEGFA, TGFB1, IDO1, PTGES, MRC1, CSF1, LRP1, ARG1, PTGS1, MSR1, CD163, CSF1R, IL4, IL5, IL13, IL10, IL25, GATA3, IL10, TGFB1, TGFB2, TGFB3, IL22, MIF, CFD, CFI, CD55, CD46, and CR1; the fibroblasts group: LGALS1, COL1A1, COL1A2, COL4A1, COL5A1, TGFB1, TGFB2, TGFB3, ACTA2, FGF2, FAP, LRP1, CD248, COL6A1, COL6A2, and COL6A3; and the angiogenesis group: VEGFA, VEGFB, VEGFC, PDGFC, CXCL8, CXCR2, FLT1, PlGF, CXCL5, KDR, ANGPT1, ANGPT2, TEK, VWF, CDH5, NOS3, KDR, VCAM1, MMRN1, LDHA, HIF1A, EPAS1, CA9, SPP1, LOX, SLC2A1, and LAMP3. In some embodiments, an unequal number of genes may be selected from each of the listed groups for use. In specific embodiments, all or almost all of the listed genes are used.

In some embodiments, gene groups associated with cancer malignancy are: the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group. In some embodiments, the gene groups associated with cancer microenvironment are: the cancer associated fibroblasts group, the angiogenesis group, the antigen presentation group, the 25 cytotoxic T and NK cells group, the B cells group, the anti-tumor microenvironment group, the checkpoint inhibition group, the Treg group, the MDSC group, the granulocytes group, and the tumor-promotive immune group.

In some embodiments, the gene groups associated with cancer malignancy comprises at least three genes from each of the following groups (e.g., at least three genes, at least four genes, at least five genes, at least six genes, at least seven genes, at least eight genes, at least nine genes, at least ten genes, or more than ten genes are selected from each group): the proliferation rate group: MKI67, ESCO2, CETN3, CDK2, CCND1, CCNE1, AURKA, AURKB, CDK4, CDK6, PRC1, E2F1, MYBL2, BUB1, PLK1, CCNB1, MCM2, and MCM6; the PI3K/AKT/mTOR signaling group: PIK3CA, PIK3CB, PIK3CG, PIK3CD, AKT1, MTOR, PTEN, PRKCA, AKT2, and AKT3; the RAS/RAF/MEK signaling group: BRAF, FNTA, FNTB, MAP2K1, MAP2K2, MKNK1, and MKNK2; the receptor tyrosine kinases expression group: ALK, AXL, KIT, EGFR, ERBB2, FLT3, MET, NTRK1, FGFR1, FGFR2, FGFR3, ERBB4, ERBB3, BCR-ABL, PDGFRA, and PDGFRB; the tumor suppressors group: TP53, SIK1, PTEN, DCN, MTAP, AIM2, and RB1; the metastasis signature group: ESRP1, CTSL, HOXA1, SMARCA4, SNAI2, TWIST1, NEDD9, PAPPA, and HPSE; the anti-metastatic factors group: KISS1, ADGRG1, BRMS1, TCF21, CDH1, PCDH10, NCAM1, and MITF; and the mutation status group: APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL.

In some embodiments, the gene groups associated with cancer microenvironment comprises at least three genes from each of the following groups (e.g., at least three genes, at least four genes, at least five genes, at least six genes, at least seven genes, at least eight genes, at least nine genes, at least ten genes, or more than ten genes are selected from each group): the cancer associated fibroblasts group: LGALS1, COL1A1, COL1A2, COL4A1, COL5A1, TGFB1, TGFB2, TGFB3, ACTA2, FGF2, FAP, LRP1, CD248, COL6A1, COL6A2, and COL6A3; the angiogenesis group: VEGFA, VEGFB, VEGFC, PDGFC, CXCL8, CXCR2, FLT1, PlGF, CXCL5, KDR, ANGPT1, ANGPT2, TEK, VWF, CDH5, NOS3, KDR, VCAM1, MMRN1, LDHA, HIF1A, EPAS1, CA9, SPP1, LOX, SLC2A1, and LAMP3; the antigen presentation group: HLA-A, HLA-B, HLA-C, B2M, TAP1, TAP2, HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, HLA-DRB6, CD80, CD86, CD40, CD83, TNFRSF4, ICOSLG, and CD28; the cytotoxic T and NK cells group: IFNG, GZMA, GZMB, PRF1, LCK, GZMK, ZAP70, GNLY, FASLG, TBX21, EOMES, CD8A, CD8B, NKG7, CD160, CD244, NCR1, KLRC2, KLRK1, CD226, GZMH, GNLY, IFNG, KIR2DL4, KIR2DS1, KIR2DS2, KIR2DS3, KIR2DS4, KIR2DS5, CXCL9, CXCL10, CXCR3, CX3CL1, CCR7, CXCL11, CCL21, CCL2, CCL3, CCL4, CCL5, EOMES, TBX21, ITK, CD3D, CD3E, CD3G, TRAC, TRBC1, TRBC2, LCK, UBASH3A, and TRAT1; the B cells group: CD19, MS4A1, TNFRSF13C, CD27, CD24, CR2, TNFRSF17, TNFRSF13B, CD22, CD79A, CD79B, and BLK; the anti-tumor microenvironment group: NOS2, IL12A, IL12B, IL23A, TNF, IL1B, SOCS3, IFNG, IL2, CD40LG, IL15, CD27, TBX21, LTA, IL21, HMGB1, TNF, IFNB1, IFNA2, CCL3, TNFSF10, and FASLG; the checkpoint inhibition group: PDCD1, CD274, CTLA4, LAG3, PDCD1LG2, BTLA, HAVCR2, and VSIR; the Treg group: CXCL12, TGFB1, TGFB2, TGFB3, FOXP3, CTLA4, IL10, TNFRSF1B, CCL17, CXCR4, CCR4, CCL22, CCL1, CCL2, CCL5, CXCL13, and CCL28; the MDSC group: IDO1, ARG1, IL4R, IL10, TGFB1, TGFB2, TGFB3, NOS2, CYBB, CXCR4, CD33, CXCL1, CXCL5, CCL2, CCL4, CCL8, CCR2, CCL3, CCL5, CSF1, and CXCL8; the granulocytes group: CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, CMA1, TPSAB1, MS4A2, CPA3, IL4, IL5, IL13, SIGLEC8, MPO, ELANE, PRTN3, and CTSG; the tumor-promotive immune group: IL10, VEGFA, TGFB1, IDO1, PTGES, MRC1, CSF1, LRP1, ARG1, PTGS1, MSR1, CD163, CSF1R, IL4, IL5, IL13, IL10, IL25, GATA3, IL10, TGFB1, TGFB2, TGFB3, IL22, MIF, CFD, CFI, CD55, CD46, and CR1. In some embodiments, an unequal number of genes may be selected from each of the listed groups for use. In specific embodiments, all or almost all of the listed genes are used.

In some embodiments, the gene groups associated with cancer malignancy are: the proliferation rate group, the PI3K/AKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group. In some embodiments, the plurality of gene groups associated with cancer microenvironment are: the cancer associated fibroblasts group, the angiogenesis group, the MHCI group, the MHCII group, the coactivation molecules group, the effector cells group, the NK cells group, the T cell traffic group, the T cells group, the B cells group, the M1 signatures group, the Th1 signature group, the antitumor cytokines group, the checkpoint inhibition group, the Treg group, the MDSC group, the granulocytes group, the M2 signature group, the Th2 signature group, the protumor cytokines group, and the complement inhibition group.

In some embodiments, the gene groups associated with cancer malignancy comprises at least three genes from each of the following groups (e.g., at least three genes, at least four genes, at least five genes, at least six genes, at least seven genes, at least eight genes, at least nine genes, at least ten genes, or more than ten genes are selected from each group): the proliferation rate group: MKI67, ESCO2, CETN3, CDK2, CCND1, CCNE1, AURKA, AURKB, CDK4, CDK6, PRC1, E2F1, MYBL2, BUB1, PLK1, CCNB1, MCM2, and MCM6; the PI3K/AKT/mTOR signaling group: PIK3CA, PIK3CB, PIK3CG, PIK3CD, AKT1, MTOR, PTEN, PRKCA, AKT2, and AKT3; the RAS/RAF/MEK signaling group: BRAF, FNTA, FNTB, MAP2K1, MAP2K2, MKNK1, and MKNK2; the receptor tyrosine kinases expression group: ALK, AXL, KIT, EGFR, ERBB2, FLT3, MET, NTRK1, FGFR1, FGFR2, FGFR3, ERBB4, ERBB3, BCR-ABL, PDGFRA, and PDGFRB; the growth factors group: NGF, CSF3, CSF2, FGF7, IGF1, IGF2, IL7, and FGF2; the tumor suppressors group: TP53, SIK1, PTEN, DCN, MTAP, AIM2, and RB1; the metastasis signature group: ESRP1, CTSL, HOXA1, SMARCA4, SNAI2, TWIST1, NEDD9, PAPPA, and HPSE; the anti-metastatic factors group: KISS1, ADGRG1, BRMS1, TCF21, CDH1, PCDH10, NCAM1, and MITF; and the mutation status group: APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL. In some embodiments, the plurality of gene groups associated with cancer microenvironment comprises at least three genes from each of the following groups: the cancer associated fibroblasts group: LGALS1, COL1A1, COL1A2, COL4A1, COL5A1, TGFB1, TGFB2, TGFB3, ACTA2, FGF2, FAP, LRP1, CD248, COL6A1, COL6A2, and COL6A3; the angiogenesis group: VEGFA, VEGFB, VEGFC, PDGFC, CXCL8, CXCR2, FLT1, PIGF, CXCL5, KDR, ANGPT1, ANGPT2, TEK, VWF, CDH5, NOS3, KDR, VCAM1, MMRN1, LDHA, HIF1A, EPAS1, CA9, SPP1, LOX, SLC2A1, and LAMP3; the MHCI group: HLA-A, HLA-B, HLA-C, B2M, TAP1, and TAP2; the MHCII group: HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, and HLA-DRB6; the coactivation molecules group: CD80, CD86, CD40, CD83, TNFRSF4, ICOSLG, and CD28; the effector cells group: IFNG, GZMA, GZMB, PRF1, LCK, GZMK, ZAP70, GNLY, FASLG, TBX21, EOMES, CD8A, and CD8B; the NK cells group: NKG7, CD160, CD244, NCR1, KLRC2, KLRK1, CD226, GZMH, GNLY, IFNG, KIR2DL4, KIR2DS1, KIR2DS2, KIR2DS3, KIR2DS4, and KIR2DS5; the T cell traffic group: CXCL9, CXCL10, CXCR3, CX3CL1, CCR7, CXCL11, CCL21, CCL2, CCL3, CCL4, and CCL5; the T cells group: EOMES, TBX21, ITK, CD3D, CD3E, CD3G, TRAC, TRBC1, TRBC2, LCK, UBASH3A, and TRAT1; the B cells group: CD19, MS4A1, TNFRSF13C, CD27, CD24, CR2, TNFRSF17, TNFRSF13B, CD22, CD79A, CD79B, and BLK; the M1 signatures group: NOS2, IL12A, IL12B, IL23A, TNF, IL1B, and SOCS3; the Th1 signature group: IFNG, IL2, CD40LG, IL15, CD27, TBX21, LTA, and IL21; the antitumor cytokines group: HMGB1, TNF, IFNB1, IFNA2, CCL3, TNFSF10, and FASLG; the checkpoint inhibition group: PDCD1, CD274, CTLA4, LAG3, PDCD1LG2, BTLA, HAVCR2, and VSIR; the Treg group: CXCL12, TGFB1, TGFB2, TGFB3, FOXP3, CTLA4, IL10, TNFRSF1B, CCL17, CXCR4, CCR4, CCL22, CCL1, CCL2, CCL5, CXCL13, and CCL28; the MDSC group: IDO1, ARG1, IL4R, IL10, TGFB1, TGFB2, TGFB3, NOS2, CYBB, CXCR4, CD33, CXCL1, CXCL5, CCL2, CCL4, CCL8, CCR2, CCL3, CCL5, CSF1, and CXCL8; the granulocytes group: CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, CMA1, TPSAB1, MS4A2, CPA3, IL4, IL5, IL13, SIGLEC8, MPO, ELANE, PRTN3, and CTSG; the M2 signature group: IL10, VEGFA, TGFB1, IDO1, PTGES, MRC1, CSF1, LRP1, ARG1, PTGS1, MSR1, CD163, and CSF1R; the Th2 signature group: IL4, IL5, IL13, IL10, IL25, and GATA3; the protumor cytokines group: IL10, TGFB1, TGFB2, TGFB3, IL22, and MIF; and the complement inhibition group: CFD, CFI, CD55, CD46, and CR1. In some embodiments, an unequal number of genes may be selected from each of the listed groups for use. In specific embodiments, all or almost all of the listed genes are used.

A molecular functional expression signature may include any suitable number of gene groups. In some embodiments, an MFES comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, or at least 28 modules. In some embodiments, an MFES comprises up to 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, up to 26, up to 27, or up to 28 gene groups.

Tumor Microenvironment Types

The inventors have recognized that a molecular functional expression signature for a subject having, suspected of having, or at risk of having cancer may provide valuable information about the microenvironment of the subject's cancer. The inventors have recognized that a subject's MFES may be used to classify the subject's microenvironment as being one of multiple types. For example, in some embodiments, the MFES may be used to classify the subject's microenvironment as being one of four different types of microenvironment (e.g., "1st MF profile" or "type A" microenvironment, "2nd MF profile" or "type B" microenvironment, "3rd MF profile" or "type C" microenvironment, "4th MF profile" or "type D" microenvironment, which are described in International PCT Publication WO2018/231771, which is incorporated by reference herein in its entirety). In turn, the identified microenvironment type be used to identify a cancer therapy and/or determine the effectiveness (or lack thereof) for one or more cancer therapies. Examples of identifying cancer therapies based on a type of cancer microenvironment (e.g., determined from gene group expression data, for example, part of a molecular functional expression signature or a molecular functional profile) are described in International PCT Publication WO2018/231771.

First MF profile cancers may also be described as "inflamed/vascularized" and/or "inflamed/fibroblast-enriched"; Second MF profile cancers may also be described as "inflamed/non-vascularized" and/or "inflamed/non-fibroblast-enriched"; Third MF profile cancers may also be described as "non-inflamed/vascularized" and/or "non-inflamed/fibroblast-enriched"; and Fourth MF profile cancers may also be described as "non-inflamed/non-vascularized" and/or "non-inflamed/non-fibroblast-enriched" and/or "immune desert."

In some embodiments, "inflamed" refers to the level of compositions and processes related to inflammation in a cancer (e.g., a tumor). In some embodiments, inflamed cancers (e.g., tumors) are highly infiltrated by immune cells, and are highly active with regard to antigen presentation and T-cell activation. In some embodiments, "vascularized" refers to the formation of blood vessels in a cancer (e.g., a tumor). In some embodiments, vascularized cancers (e.g., tumors) comprise high levels of cellular compositions and process related to blood vessel formation. In some embodiments, "fibroblast enriched" refers to the level or amount of fibroblasts in a cancer (e.g., a tumor). In some embodiments, fibroblast enriched tumors comprise high levels of fibroblast cells.

Predicting Therapy Response

In some embodiments, sequencing data obtained using systems and methods described herein (e.g., bias-corrected gene expression data, data processed using the quality control techniques described herein, etc.) may be used for identifying subjects suitable for a particular treatment, and/or predicting likelihood of a patient's response or lack thereof to a particular treatment and/or predicting whether a patient may or may not have one or more adverse reactions to a particular therapy as described in International PCT Publication WO2018/231771, published on Dec. 20, 2018, entitled "Systems and Methods for Generating, Visualizing and Classifying Molecular Functional Profiles," (being a publication of PCT Application No.: PCT/US2018/037017, filed Jun. 12, 2018), the entire contents of which are incorporated herein by reference.

In some embodiments, sequencing data obtained as described herein (e.g., bias-corrected gene expression data, data processed using the quality control techniques described herein, etc.) is useful for identifying a subject suitable for a particular treatment. In some embodiments, sequencing data (e.g., bias-corrected gene expression data, data processed using the quality control techniques described herein, etc.) obtained as described herein is useful for predicting likelihood of a patient's response or lack thereof to a particular treatment. In some embodiments, sequencing data obtained as described herein (e.g., bias-corrected gene expression data, data processed using the quality control techniques described herein, etc.) is useful for predicting whether a patient may or may not have one or more adverse reactions to a particular therapy.

In some embodiments, predicted efficacy of an immune checkpoint blockade therapy may be determined using sequencing data obtained as described herein (e.g., bias-corrected gene expression data, data processed using the quality control techniques described herein, etc.) as described in International PCT Publication WO2018/231772, published on Dec. 20, 2018, entitled "Systems and Methods for Identifying Responders and Non-Responders to Immune Checkpoint Blockade Therapy" (being a publication of International patent application number PCT/US2018/037018, filed Jun. 12, 2018), the entire contents of which are incorporated herein by reference.

In some embodiments, sequencing data obtained as described herein (e.g., bias-corrected gene expression data, data processed using the quality control techniques described herein, etc.) is useful for determining a biomarker, a biomarker score, a normalized biomarker score, a therapy score, and/or an impact score as described in International PCT Publication WO2018/231762, published on Dec. 20, 2018, entitled "Systems and Methods for Identifying Cancer Treatments from Normalized Biomarker Scores" (being a publication of International patent application number PCT/US2018/037008, filed Jun. 12, 2018), the entire contents of which are incorporated herein by reference.

Methods of Treatment

In certain methods described herein, an effective amount of anti-cancer therapy described herein may be administered or recommended for administration to a subject (e.g., a human) in need of the treatment via a suitable route (e.g., intravenous administration).

The subject to be treated by the methods described herein may be a human patient having, suspected of having, or at risk for a cancer. Examples of a cancer include, but are not limited to, melanoma, lung cancer, brain cancer, breast cancer, colorectal cancer, pancreatic cancer, liver cancer, prostate cancer, skin cancer, kidney cancer, bladder cancer, or prostate cancer. The subject to be treated by the methods described herein may be a mammal (e.g., may be a human). Mammals include but are not limited to: farm animals (e.g., livestock), sport animals, laboratory animals, pets, primates, horses, dogs, cats, mice, and rats.

A subject having a cancer may be identified by routine medical examination, e.g., laboratory tests, biopsy, PET scans, CT scans, or ultrasounds. A subject suspected of having a cancer might show one or more symptoms of the disorder, e.g., unexplained weight loss, fever, fatigue, cough, pain, skin changes, unusual bleeding or discharge, and/or thickening or lumps in parts of the body. A subject at risk for a cancer may be a subject having one or more of the risk factors for that disorder. For example, risk factors associated with cancer include, but are not limited to, (a) viral infection (e.g., herpes virus infection), (b) age, (c) family history, (d) heavy alcohol consumption, (e) obesity, (f) genetics, and (g) chemical or toxin exposure, and (h) tobacco use.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons, or for virtually any other reasons.

Empirical considerations, such as the half-life of a therapeutic compound, generally contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally (but not necessarily) based on treatment, and/or suppression, and/or amelioration, and/or delay of a cancer. Alternatively, sustained continuous release formulations of an anti-cancer therapeutic agent may be appropriate. Various formulations and devices for achieving sustained release are known in the art.

In some embodiments, dosages for an anti-cancer therapeutic agent as described herein may be determined empirically in individuals who have been administered one or more doses of the anti-cancer therapeutic agent. Individuals may be administered incremental dosages of the anti-cancer therapeutic agent. To assess efficacy of an administered anti-cancer therapeutic agent, one or more aspects of a cancer (e.g., tumor formation, tumor growth, tumor type, MF expression signature) may be analyzed.

Generally, for administration of any of the anti-cancer antibodies described herein, an initial candidate dosage may be about 2 mg/kg. For the purpose of the present disclosure, a typical daily dosage might range from about any of 0.1 µg/kg to 3 µg/kg to 30 µµg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression or amelioration of symptoms occurs or until sufficient therapeutic levels are achieved to alleviate a cancer, or one or more symptoms thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner (e.g., a medical doctor) wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy may be monitored by conventional techniques and assays and/or by monitoring cancer Types A-D as described herein. The dosing regimen (including the therapeutic used) may vary over time.

When the anti-cancer therapeutic agent is not an antibody, it may be administered at the rate of about 0.1 to 300 mg/kg of the weight of the patient divided into one to three doses, or as described herein. In some embodiments, for an adult patient of normal weight, doses ranging from about 0.3 to 5.00 mg/kg may be administered. The particular dosage regimen, e.g., dose, timing, and/or repetition, will depend on the particular subject and that individual's medical history, as well as the properties of the individual agents (such as the half-life of the agent, and other considerations well known in the art).

For the purpose of the present disclosure, the appropriate dosage of an anti-cancer therapeutic agent will depend on the specific anti-cancer therapeutic agent(s) (or compositions thereof) employed, the type and severity of cancer, whether the anti-cancer therapeutic agent is administered for preventive or therapeutic purposes, previous therapy, the patient's clinical history and response to the anti-cancer therapeutic agent, and the discretion of the attending physician. Typically the clinician will administer an anti-cancer therapeutic agent, such as an antibody, until a dosage is reached that achieves the desired result.

Administration of an anti-cancer therapeutic agent can be continuous or intermittent, depending, for example, upon the recipient's physiological condition, whether the purpose of the administration is therapeutic or prophylactic, and other factors known to skilled practitioners. The administration of an anti-cancer therapeutic agent (e.g., an anti-cancer antibody) may be essentially continuous over a preselected period of time or may be in a series of spaced dose, e.g., either before, during, or after developing cancer.

As used herein, the term "treating" refers to the application or administration of a composition including one or more active agents to a subject, who has a cancer, a symptom of a cancer, or a predisposition toward a cancer, with the purpose to cure, heal, alleviate, relieve, alter, remedy, ameliorate, improve, or affect the cancer or one or more symptoms of the cancer, or the predisposition toward a cancer.

Alleviating a cancer includes delaying the development or progression of the disease, or reducing disease severity. Alleviating the disease does not necessarily require curative results. As used therein, "delaying" the development of a disease (e.g., a cancer) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detected and assessed using clinical techniques known in the art. Alternatively or in addition to the clinical techniques known in the art, development of the disease may be detectable and assessed based on the cancer types described herein. However, development also refers to progression that may be undetectable. For purpose of this disclosure, development or progression refers to the biological course of the symptoms. "Development" includes occurrence, recurrence, and onset. As used herein "onset" or "occurrence" of a cancer includes initial onset and/or recurrence.

In some embodiments, the anti-cancer therapeutic agent (e.g., an antibody) described herein is administered to a subject in need of the treatment at an amount sufficient to reduce cancer (e.g., tumor) growth by at least 10% (e.g., 20%, 30%, 40%, 50%, 60%, 70%, 80%, 90% or greater). In some embodiments, the anti-cancer therapeutic agent (e.g., an antibody) described herein is administered to a subject in need of the treatment at an amount sufficient to reduce cancer cell number or tumor size by at least 10% (e.g., 20%, 30%, 40%, 50%, 60%, 70%, 80%, 90% or more). In other embodiments, the anti-cancer therapeutic agent is administered in an amount effective in altering cancer type. Alternatively, the anti-cancer therapeutic agent is administered in an amount effective in reducing tumor formation or metastasis.

Conventional methods, known to those of ordinary skill in the art of medicine, may be used to administer the anti-cancer therapeutic agent to the subject, depending upon the type of disease to be treated or the site of the disease. The anti-cancer therapeutic agent can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, an anti-cancer therapeutic agent may be administered to the subject via injectable depot routes of administration such as using 1-, 3—, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (e.g., glycerol, propylene glycol, liquid polyethylene glycol, and the like). For intravenous injection, water soluble anti-cancer therapeutic agents can be administered by the drip method, whereby a pharmaceutical formulation containing the antibody and a physiologically acceptable excipients is infused. Physiologically acceptable excipients may include, for example, 5% dextrose, 0.9% saline, Ringer's solution, and/or other suitable excipients. Intramuscular preparations, e.g., a sterile formulation of a suitable soluble salt form of the anti-cancer therapeutic agent, can be dissolved and administered in a pharmaceutical excipient such as Water-for-Injection, 0.9% saline, and/or 5% glucose solution.

In one embodiment, an anti-cancer therapeutic agent is administered via site-specific or targeted local delivery techniques. Examples of site-specific or targeted local delivery techniques include various implantable depot sources of the agent or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568, the contents of each of which are incorporated by reference herein for this purpose.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., *Gene Therapeutics: Methods And Applications Of Direct Gene Transfer* (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338. The contents of each of the foregoing are incorporated by reference herein for this purpose.

Therapeutic compositions containing a polynucleotide may be administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol.

Therapeutic polynucleotides and polypeptides can be delivered using gene delivery vehicles. The gene delivery vehicle can be of viral or non-viral origin (e.g., Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). The contents of each of the foregoing are incorporated by reference herein for this purpose. Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed. The contents of each of the foregoing are incorporated by reference herein for this purpose.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No.

5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581. The contents of each of the foregoing are incorporated by reference herein for this purpose.

It is also apparent that an expression vector can be used to direct expression of any of the protein-based anti-cancer therapeutic agents (e.g., anti-cancer antibody). For example, peptide inhibitors that are capable of blocking (from partial to complete blocking) a cancer causing biological activity are known in the art.

In some embodiments, more than one anti-cancer therapeutic agent, such as an antibody and a small molecule inhibitory compound, may be administered to a subject in need of the treatment. The agents may be of the same type or different types from each other. At least one, at least two, at least three, at least four, or at least five different agents may be co-administered. Generally anti-cancer agents for administration have complementary activities that do not adversely affect each other. Anti-cancer therapeutic agents may also be used in conjunction with other agents that serve to enhance and/or complement the effectiveness of the agents. Treatment efficacy can be assessed by methods well-known in the art, e.g., monitoring tumor growth or formation in a patient subjected to the treatment. Alternatively or in addition to, treatment efficacy can be assessed by monitoring tumor type over the course of treatment (e.g., before, during, and after treatment).

Combination Therapy

Compared to monotherapies, combinations of treatment approaches showed higher efficacy in many studies, but the choice of remedies to be combined and designing the combination therapy regimen remain speculative. Given that the number of possible combinations is now extremely high, there is great need for a tool that would help to select drugs and combinations of remedies based on objective information about a particular patient. Use of patient specific information (e.g., a patient's sequencing data) for designing or electing a specific combination therapy establishes a scientific basis for choosing the optimal combination of preparations.

Also provided herein are methods of treating a cancer or recommending treating a cancer using any combination of anti-cancer therapeutic agents or one or more anti-cancer therapeutic agents and one or more additional therapies (e.g., surgery and/or radiotherapy). The term combination therapy, as used herein, embraces administration of more than one treatment (e.g., an antibody and a small molecule or an antibody and radiotherapy) in a sequential manner, that is, wherein each therapeutic agent is administered at a different time, as well as administration of these therapeutic agents, or at least two of the agents or therapies, in a substantially simultaneous manner.

Sequential or substantially simultaneous administration of each agent or therapy can be affected by any appropriate route including, but not limited to, oral routes, intravenous routes, intramuscular, subcutaneous routes, and direct absorption through mucous membrane tissues. The agents or therapies can be administered by the same route or by different routes. For example, a first agent (e.g., a small molecule) can be administered orally, and a second agent (e.g., an antibody) can be administered intravenously.

As used herein, the term "sequential" means, unless otherwise specified, characterized by a regular sequence or order, e.g., if a dosage regimen includes the administration of an antibody and a small molecule, a sequential dosage regimen could include administration of the antibody before, simultaneously, substantially simultaneously, or after administration of the small molecule, but both agents will be administered in a regular sequence or order. The term "separate" means, unless otherwise specified, to keep apart one from the other. The term "simultaneously" means, unless otherwise specified, happening or done at the same time, i.e., the agents of the invention are administered at the same time. The term "substantially simultaneously" means that the agents are administered within minutes of each other (e.g., within 10 minutes of each other) and intends to embrace joint administration as well as consecutive administration, but if the administration is consecutive it is separated in time for only a short period (e.g., the time it would take a medical practitioner to administer two agents separately). As used herein, concurrent administration and substantially simultaneous administration are used interchangeably. Sequential administration refers to temporally separated administration of the agents or therapies described herein.

Combination therapy can also embrace the administration of the anti-cancer therapeutic agent (e.g., an antibody) in further combination with other biologically active ingredients (e.g., a vitamin) and non-drug therapies (e.g., surgery or radiotherapy).

It should be appreciated that any combination of anti-cancer therapeutic agents may be used in any sequence for treating a cancer. The combinations described herein may be selected on the basis of a number of factors, which include but are not limited to the effectiveness of altering identified tumor type, reducing tumor formation or tumor growth, and/or alleviating at least one symptom associated with the cancer, or the effectiveness for mitigating the side effects of another agent of the combination. For example, a combined therapy as provided herein may reduce any of the side effects associated with each individual members of the combination, for example, a side effect associated with an administered anti-cancer agent.

In some embodiments, an anti-cancer therapeutic agent is an antibody, an immunotherapy, a radiation therapy, a surgical therapy, and/or a chemotherapy.

Examples of the antibody anti-cancer agents include, but are not limited to, alemtuzumab (Campath), trastuzumab (Herceptin), Ibritumomab tiuxetan (Zevalin), Brentuximab vedotin (Adcetris), Ado-trastuzumab emtansine (Kadcyla), blinatumomab (Blincyto), Bevacizumab (Avastin), Cetuximab (Erbitux), ipilimumab (Yervoy), nivolumab (Opdivo), pembrolizumab (Keytruda), atezolizumab (Tecentriq), avelumab (Bavencio), durvalumab (Imfinzi), and panitumumab (Vectibix).

Examples of an immunotherapy include, but are not limited to, a PD-1 inhibitor or a PD-L1 inhibitor, a CTLA-4 inhibitor, adoptive cell transfer therapy, therapeutic cancer vaccines, oncolytic virus therapy, T-cell therapy, and immune checkpoint inhibitors. In some embodiments, an immunotherapy may include a chimeric antigen receptor (CAR) T-cell therapy. A CAR is designed for a T-cell and is a chimera of a signaling domain of the T-cell receptor (TcR) complex and an antigen-recognizing domain (e.g., a single chain fragment (scFv) of an antibody) (Enblad et al., *Human Gene Therapy.* 2015; 26(8):498-505). In some embodiments, an antigen binding receptor is a chimeric antigen receptor (CAR). A T cell that expressed a CAR is referred to as a "CAR T cell." A CAR T cell receptor, in some embodiments, comprises a signaling domain of the T-cell receptor (TcR) complex and an antigen-recognizing domain (e.g., a single chain fragment (scFv) of an antibody) (Enblad et al., *Human Gene Therapy.* 2015; 26(8):498-505).

Examples of radiation therapy include, but are not limited to, ionizing radiation, gamma-radiation, neutron beam radiotherapy, electron beam radiotherapy, proton therapy, brachytherapy, systemic radioactive isotopes, and radiosensitizers.

Examples of a surgical therapy include, but are not limited to, a curative surgery (e.g., tumor removal surgery), a preventive surgery, a laparoscopic surgery, and a laser surgery.

Examples of the chemotherapeutic agents include, but are not limited to, Carboplatin or Cisplatin, Docetaxel, Gemcitabine, Nab-Paclitaxel, Paclitaxel, Pemetrexed, and Vinorelbine.

Additional examples of chemotherapy include, but are not limited to, Platinating agents, such as Carboplatin, Oxaliplatin, Cisplatin, Nedaplatin, Satraplatin, Lobaplatin, Triplatin, Tetranitrate, Picoplatin, Prolindac, Aroplatin and other derivatives; Topoisomerase I inhibitors, such as Camptothecin, Topotecan, irinotecan/SN38, rubitecan, Belotecan, and other derivatives; Topoisomerase II inhibitors, such as Etoposide (VP-16), Daunorubicin, a doxorubicin agent (e.g., doxorubicin, doxorubicin hydrochloride, doxorubicin analogs, or doxorubicin and salts or analogs thereof in liposomes), Mitoxantrone, Aclarubicin, Epirubicin, Idarubicin, Amrubicin, Amsacrine, Pirarubicin, Valrubicin, Zorubicin, Teniposide and other derivatives; Antimetabolites, such as Folic family (Methotrexate, Pemetrexed, Raltitrexed, Aminopterin, and relatives or derivatives thereof); Purine antagonists (Thioguanine, Fludarabine, Cladribine, 6-Mercaptopurine, Pentostatin, clofarabine, and relatives or derivatives thereof) and Pyrimidine antagonists (Cytarabine, Floxuridine, Azacitidine, Tegafur, Carmofur, Capacitabine, Gemcitabine, hydroxyurea, 5-Fluorouracil (5FU), and relatives or derivatives thereof); Alkylating agents, such as Nitrogen mustards (e.g., Cyclophosphamide, Melphalan, Chlorambucil, mechlorethamine, Ifosfamide, mechlorethamine, Trofosfamide, Prednimustine, Bendamustine, Uramustine, Estramustine, and relatives or derivatives thereof); nitrosoureas (e.g., Carmustine, Lomustine, Semustine, Fotemustine, Nimustine, Ranimustine, Streptozocin, and relatives or derivatives thereof); Triazenes (e.g., Dacarbazine, Altretamine, Temozolomide, and relatives or derivatives thereof); Alkyl sulphonates (e.g., Busulfan, Mannosulfan, Treosulfan, and relatives or derivatives thereof); Procarbazine; Mitobronitol, and Aziridines (e.g., Carboquone, Triaziquone, ThioTEPA, triethylenemalamine, and relatives or derivatives thereof); Antibiotics, such as Hydroxyurea, Anthracyclines (e.g., doxorubicin agent, daunorubicin, epirubicin and relatives or derivatives thereof); Anthracenediones (e.g., Mitoxantrone and relatives or derivatives thereof); Streptomyces family antibiotics (e.g., Bleomycin, Mitomycin C, Actinomycin, and Plicamycin); and ultraviolet light.

EXAMPLES

In order that the invention described herein may be more fully understood, the following examples are set forth. The examples described in this application are offered to illustrate the methods, compositions, and systems provided herein and are not to be construed in any way as limiting their scope.

Example 1: Workflow for WES and RNA Sequencing

Provided below is an example of specimen collection from a subject having or suspected of having cancer, DNA and/or RNA extraction therefrom, DNA library preparation (cDNA in the case of library preparation from RNA), and data processing.

Specimen collection Prior to collection of biological samples from a subject having or suspected of having a cancer, sufficient quantities of sterilized instruments, consumables, and reagents (e.g., digest buffer) were verified.

For tumor tissue (bulk), 30 mg of tumor tissue was collected from a subject and put into a 2 ml cryogenic tube with RNA-later, the contents of which were then snap frozen. The specimens were shipped on dry ice as needed.

For blood samples (which are considered "normal tissue" (or non-cancerous)), 0.5-1 mL of whole blood was collected in an EDTA vacutainer collection tube (plastic preferred) labeled with at least the sample ID and date/time collected. The vacutainer tube was then placed into a sealed biohazard bag with absorbent materials. Whole blood in EDTA was frozen on dry ice as needed and sent to a laboratory with other specimen(s) as needed. FIG. 1B illustrates an embodiment of a process that includes the sample collection process.

Creation of Single Cell Suspension for CYTOF and RNA-seq (SCS, optional, validation)

The following steps were used to create single-cells suspensions (SCS) from tumor samples that were collected in 50 mL of cold L-15 medium (lx).

1) Transfer the container with tumor sample from an operating room on ice to a biological safety hood for dissection, wherein it takes approximately 60-90 min from surgical resection to the bench.
2) Transfer the tumor sample into a 100×15 mm petri dish containing fresh L-15 medium. Using a curved scissor, dissect the tumor into fragments of 1-2 mm$^3$ on a sterile petri dish with L-15 to keep the tissue moist. To 50 mL conical tube containing 25 mL of enzyme cocktail add 0.5 μm of tumor tissue.
3) Place the tube on a shaker at a speed of 85 rpm for 45 min at 37° C.
4) After 45 min, vigorously pipette the contents using a 10 mL pipette. Incubate for another 45 min under the same conditions.
5) After the incubation, filter the sample through a 70 μm cell strainer into a new 50 mL conical tube. Using the back of a 3 mL syringe, gently apply pressure on the cell strainer to disaggregate any remaining tissue.
6) Add 25 mL of warm (37° C.) L-15 media containing 10% FBS through the cell strainer, into the 50 mL conical tube.
7) Centrifuge at 300 g at room temperature for 5 min. Decant the supernatant.
8) Add 10 mL of warm (37° C.) 1× eBioscience multi species RBC lysis buffer. Incubate in the dark for 5 min at room temperature.
9) After the incubation add 40 mL of cold 1X PBS to the tube. Centrifuge at 300 g for 5 min at 4° C. Decant supernatant. Add 10 mL of cold DMEM with 10% FBS, and resuspend the pellet gently.
10) Centrifuge at 300 g for 5 min at 4° C. Decant the supernatant. Resuspend cells in 1 mL of cold L-15 with 10% FBS.
11) Filter the sample through a 70 um cell strainer into a new 50 mL conical tube.

12) Count cells using Trypan blue. Also assess viability using MoxiFlow (4 μL cells +196 μl MoxiFlow Viability Reagent, use 75 μL to test). 2,000,000 cells were aliquoted into a 15 mL conical tube. Once the cells have been pelleted (more then 2*10$^6$), each lysate was resuspended in 500-750 μl of RNAlater/RNA Protect in a 1.5 ml microcentrifuge tube. The 1.5 ml tube was placed into a 50 mL conical tube with tissue paper/paper towels on top to secure the 1.5mLtubes. The 50 ml tube can then be shipped with the tumor specimen(s) on dry ice.

DNA and RNA extraction from bulk biopsy

Extraction of normal DNA and RNA. DNA from biopsy specimens was extracted using DSP DNA Midi Kit (Qiagen®) using an automated process on the QIAsymphony (giagen.com/us/shop/automated-solutions/sample-preparation/qiasymphony-spas-instruments/).

A minimum of 1000-2000ng of total DNA mass in at least 10 μl volumes (e.g., 100-200ng/ul in 10 μl minimum) for each DNA sample was collected. Moreover, the extracted DNA solutions had 260/280 ratios of ~ 1.8.

A minimum of 1000-6000ng of total RNA mass was collected. RNA Integrity Number (RIN) scores obtained via Agilent's BioAnalyzer or Tape Station were of at least 7. Extraction of tumor DNA and tumor RNA. DNA and RNA were extracted from 30 mg of tissue using AllPrep DNA/RNA Mini Kit by Qiagen® (using the manual process described by the manufacturer).

DNA/RNA extraction and CYTOF for SCSs

Extraction: RNeasy Micro Plus Kit by Qiagen® (manual process) was used. A minimum of 2,000,000 cells were used for extraction. Table 1 below shows that the RNA concentration, yield, and quality drops substantially if RNA is extracted from a total of less than 2 million cells. It was found that 2 million cells provided at least 1.8 μg of RNA, which is sufficient for good quality RNAseq data (i.e., less noise and better correlation between RNA expression within different isoforms of the same protein coding RNA). It is recommended to have more than 1 ug of RNA for better quality.

TABLE 1

RNA quantity and quality as a function of the number of cells from which RNA is extracted.

| Sample ID | Number of Cells | RNA Concentration (ng/uL) | Volume (uL) | Total Yield (ng) | RIN |
|---|---|---|---|---|---|
| BG002 | 2 million | 70.2 | 26 | 1825 | 8.5 |
| BG020 | 1 million | 8.0 | 57.5 | 460 | 8.3 |
| BG005 | 0.5 million | 8.2 | 26 | 213 | 8.7 |
| BG008 | 0.5 million | 8.0 | 26 | 208 | 8.4 |

CyTOF: Resuspend cells that are not going to be used for RNAseq (minimum 5 million), in cold cell staining buffer (CSB) and place on ice in preparation for antibody labeling.

Library preparation, RNA sequencing, and WES

Illumina libraries were made and subjected to quality control (e.g., using Tapestation D1000 High Sensitivity DNA screen tape) to evaluate their integrity and peak size. The analysis consumed up to 1 ng library in 2 μL.

Whole Exome Sequencing (WES) on DNA samples (tumor tissue and germline blood) was performed using Agilent Human All Exon V6 Capture (48.2 Mb) or Clinical Research Exome (54.6 Mb). WES Illumina deep sequencing was performed with standard NextSeq RNA-seq configuration, Paired-End 100 bp Reads with an estimated coverage >100x.

RNA Sequence on RNA samples (tumor tissue and SCS) was performed using Ilumina TruSeq RNA Library Prep PCR enrichment of captured DNA (Poly-A mRNA-seq), non-stranded (to compared data with that of The Cancer Genome Atlas (TCGA)) paired-end 100 bp Reads (75+75) with an estimated coverage >50 million paired-end reads.

PolyA enrichment

Different RNA enrichment methods provide various enrichment of RNA transcripts. riboRNA depletion retains 10-50% of non-coding transcripts (e.g., rRNA, miRNA, long non-coding RNA (LncRNA)) in the library. So, the percentages of protein-coding reads strongly vary depending on the method of RNA enrichment. In clinical settings the focus was on expression of protein coding transcripts. PolyA enrichment, compared to rRNA depletion, provided more stable and controllable percent of protein coding transcripts (FIG. 2).

Figure 2B:
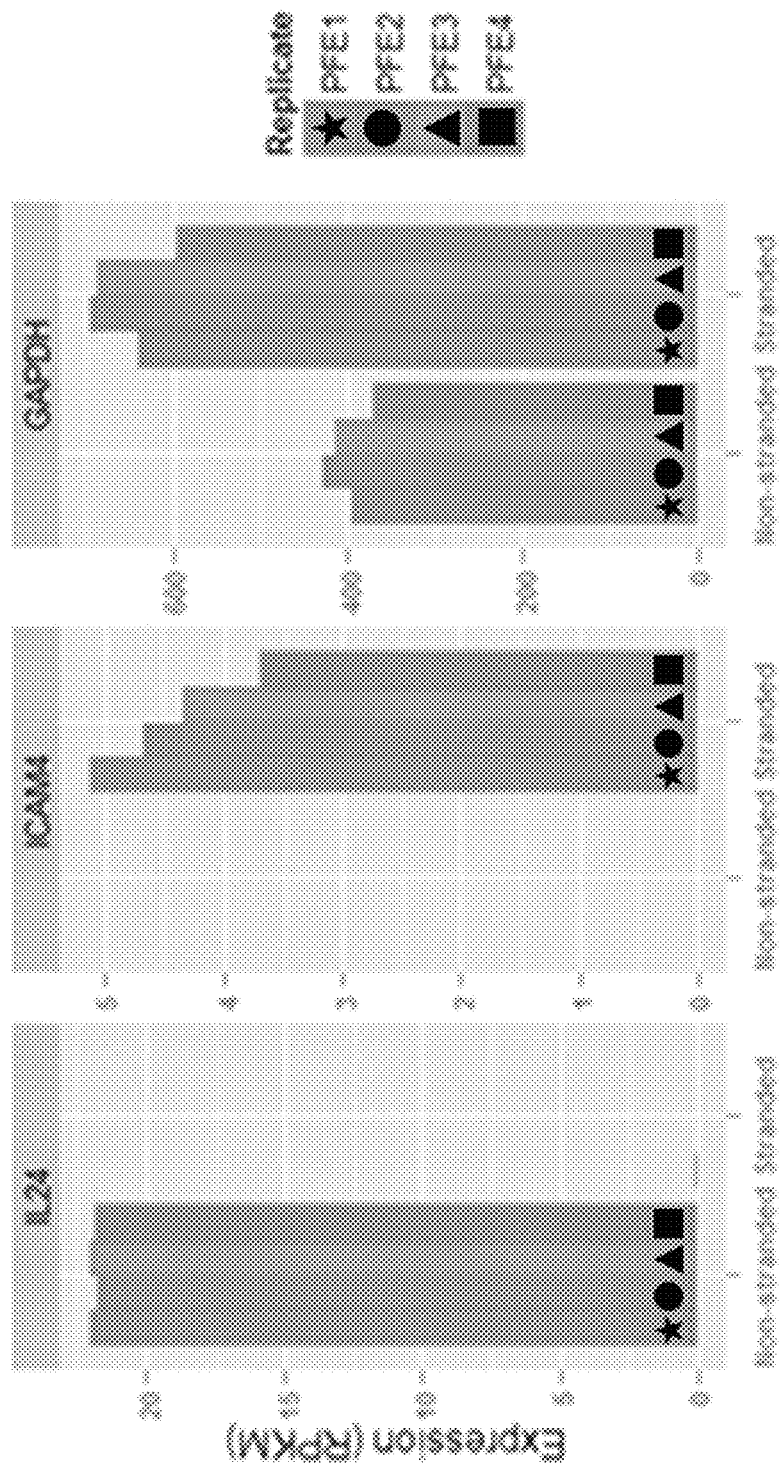

Further, because PolyA enrichment was used, and it was known that protein-coding RNA was enriched, RNA sequencing was performed on non-stranded RNA. FIG. 2B demonstrates that differences in RNA expression levels of IL24, ICAM4, and GAPDH RNA seen when either stranded or non-stranded RNA is used for sequencing.

FASTQ files processing, and RNA expression assessment

The raw data in the NextSeq BCL file format was converted to the standard Illumina FASTQ format. As described herein, any type of format that is suitable for further analysis can be used. In this example, the FASTQ data was subjected to quality control using standard quality control algorithms (e.g., FastQ Screen (bioinformatics.babraham.ac.uk/projects/fastqc/), RSeQC (rseqc.sourceforge.net/), and then processed to obtain expression per gene in TPM with no or minimal batch effects across samples. Data in the form of FASTQ files was delivered via a secure SFTP server or Illumina BaseSpace.

Quality Control Steps assuring quality of FASTQ files

The following are steps involved in assuring quality control of the data in FASTQ files:

(1) Remove low-quality reads. This can be performed by using any suitable software or tool to evaluate and/or remove reads that are deemed of low-quality such as based on positional information. In some embodiments, low-quality reads can be removed by using FILTERBYTILE (e.g., filterbytile.sh (from BBmap)). In some embodiments, low-quality reads (e.g., bad tiles) are removed from sequence files (e.g., FASTQ files). In some embodiments, the data analysis pipeline may be stopped if the quality of the reads is too low for further analysis with sufficient confidence. For example, in some embodiments, if bad tiles represent greater than a threshold percentage (e.g., 50%) of the sample, the analysis pipeline is terminated.

(2) Assure quality control based on various parameters. This can be performed by using any suitable software or tool to evaluate the confidence of the quality control. In some embodiments, quality control can be assured by using FastQC (e.g., bioinformatics.babraham.ac.uk/projects/fastqc/). In some embodiments, quality control can be assured by reviewing read counts as a measure of the complexity of the library. In some embodiments, quality control can be assured by reviewing per base Phred quality score as a measure of sequencing quality of the platform. In some embodiments, quality control can be assured by reviewing per tile quality score. In some embodiments, quality control can be assured by reviewing per sequence GC content to identify contamination. In some embodiments, quality control can be assured by reviewing per base sequencing content to identify adapter and other contamination. In some embodiments, quality control can be assured by reviewing sequence duplication levels as a measure of a quality of RNA/DNA selection and PCR. In some embodiments, quality control can be assured by reviewing adapter content.

In some embodiments, the data analysis pipeline may be stopped if the quality control cannot be assured for further analysis with sufficient confidence. For example, in some embodiments, if read counts represent greater than a threshold value (e.g., >20 mln) or Phred score represent greater than a threshold percentage (e.g., >50% green zone), the analysis pipeline is terminated.

(3) Determine cross-species contamination. This can be performed by using any suitable software or tool to evaluate the cross-species contamination. In some embodiments, cross-species contamination can be determined by using Fastq Screen (e.g., bioinformatics.babraham.ac.uk/projects/fastq_screen/_build/html/index.html). In some embodiments, cross-species contamination can comprise contamination from various species such as mouse, zebrafish, drosophila, C. elegans, Saccharomyces, Arabidopsis, microbiome, adapters, vectors, and phiX. In some embodiments, the data analysis pipeline may be stopped if the cross-species contamination is too severe for further analysis with sufficient confidence. For example, in some embodiments, if contamination represents greater than a threshold percentage (e.g., >20%), the analysis pipeline is terminated.

(4) Assure quality of the data based on various parameters. This can be performed by using any suitable software or tool to evaluate the quality. In some embodiments, quality control can be assured by using Mosdepth (e.g., github.com/brentp/mosdepth). In some embodiments, quality can be assured by determining per chromosome coverage distribution (as a sex prediction algorithm). In some embodiments, quality can be assured by determining o specific regions coverage distribution (e.g., Collaborative Consensus Coding Sequence (CCDS), exons, etc.). In some embodiments, the data analysis pipeline may be stopped if the quality of the data is too low for further analysis with sufficient confidence. For example, in some embodiments, if the confirmation of coverage of clinically important genome regions is failed, the analysis pipeline is terminated.

(5) Assure the presence and the quality of certain characteristics of the data. This can be performed by using any suitable software or tool. In some embodiments, the presence or quality of certain characteristics of the data can be assured by using Picard (broadinstitute.github.io/picard/). In some embodiments, certain characteristics can be the number of the percentage of the duplicities. In some embodiments, certain characteristics can be mapped regions. In some embodiments, certain characteristics can be properly paired regions.

(6) Assure quality control based on various parameters. This can be performed by using any suitable software or tool to evaluate the confidence of the quality control. In some embodiments, quality control can be assured by using RseQC (e.g., rseqc.sourceforge.net/). In some embodiments, quality control can be assured by reviewing strandedness analysis to prove stranded or non-stranded RNA-seq protocol. In some embodiments, quality control can be assured by reviewing gene body coverage to detect coverage bias due to the extraction protocol (polyA/total RNA-seq) and RIN. In some embodiments, quality control can be assured by reviewing read distribution of exons, introns, transcription end sites (TES), and transcription start sites (TSS). In some embodiments, the data analysis pipeline may be stopped if the quality control cannot be assured for further analysis with sufficient confidence. For example, in some embodiments, if duplicates represent greater than a threshold percentage (e.g., <60%) for RNA or less than a threshold percentage (e.g., <20%) for adapter contamination, the analysis pipeline is terminated.

(7) Check cross-individual contamination by determining concordance of a pair of samples (e.g., tumor/normal from the same patient). This can be performed by using any suitable software or tool. In some embodiments, cross-individual contamination can be determined by using Conpair (e.g., github.com/nygenome/Conpair). In some embodiments, the data analysis pipeline may be stopped if the cross-individual contamination is too severe for further analysis with sufficient confidence. For example, in some embodiments, if normal DNA does not match tumor DNA, the analysis pipeline is terminated. In some embodiments, if large cross-individual contamination is detected, the analysis pipeline is terminated.

(8) Run a tumor type classifier. This can be performed by using any suitable software or tools. In some embodiments, a gene expression-based classifier can be used. For example, a gene expression-based classifier trained on RNAseq of previously sequenced tumors of different tissue types can be used to classify tumor type. Examples of such classifiers are described herein and in U.S. Provisional Patent Application Ser. No. 62/943,976, titled "Machine Learning Techniques for Gene Expression Analysis," filed on Dec. 5, 2019, which is incorporated by reference herein in its entirety. In some embodiments, this allows the prediction of the tumor type from RNA-seq data on the basis of the gene expression data. In some embodiments, the data analysis pipeline may be stopped if the tumor type is a mismatch for further analysis with sufficient confidence. For example, in some embodiments, if the asserted tumor type from clinicians does not match the determined tumor type, the analysis pipeline is terminated.

(9) Predict library type. This can be performed by using any suitable software or tools. In some embodiments, RNA-seq type classifier can be used. In some embodiments, the RNA-seq type classifier can be a gene expression-based classifier on XGboost (e.g., xgboost.readthedocs.io/en/latest/) trained model. In some embodiments, the prediction of library type is based on expression of specific genes from the RNA-seq data. In some embodiments, the data analysis pipeline may be stopped if the library type is a mismatch for further analysis with sufficient confidence. For example, in some embodiments, if the asserted library type does not match the determined library type (e.g., total RNA-seq, or polyA-RNA-seq), the analysis pipeline is terminated.

(10) Check concordance of HLA allele. This can be performed by using any suitable software or tools. In some embodiments, MHC allele composition can be determined. In some embodiments, the data analysis pipeline may be stopped if the HLA allele is a mismatch for further analysis with sufficient confidence. For example, in some embodiments, if the HLA allele from a sample does not confirm the source of the samples, the analysis pipeline is terminated.

(11) Perform distribution analysis of expression for different transcripts types. This can be performed by using any suitable software or tools. In some embodiments, the transcripts type can be Mt rRNA, Mt tRNA, lincRNA, miRNA, misc RNA, protein coding, rRNA, snRNA, snoRNA, ribozyme, Ig, processed, NMD, or retained intron. In some embodiments, one or more transcripts type can be determined. In some embodiments, the data analysis pipeline may be stopped if the transcript type is not suitable for further analysis with sufficient confidence. For example, in some embodiments, if the transcripts represent a greater threshold percentage (e.g., >70% transcripts are protein-coding transcripts), the analysis pipeline is terminated.

Alignment

Alignment can be performed by using any suitable software or tools. For example, a program for quantifying transcripts, for example from bulk and single-cell RNA-Seq data, using high-throughput sequencing reads (e.g., Kalliso available from Github, github.com, for example as described in Nicolas L Bray, Harold Pimentel, Pill Melsted and Lior Pachter, Near-optimal probabilistic RNA-seq quantification, Nature Biotechnology 34, 525-527 (2016), doi:10.1038/nbt.3519) was performed with input FASTQ files. Kalisto indexing was performed based on:
 a. GRCh38 genome assembly (no alt analysis) with overlapping genes from the PAR locus removed.
 b. Gene annotation based on GENCODE V23 comprehensive annotation (regions ALL) (gencodegenes.org)

Files with transcript expression in TPM (Transcripts Per Kilobase Million) were obtained thereafter.

Removing of Non-Coding Transcripts for the Data and Other Biases

The Transcripts Per Million (TPM) expression allows presentation of gene expression in the format of concentration (in 1 million of transcripts). This allows comparison of samples with different coverage and RNA sequencing depth.

Figure 3:
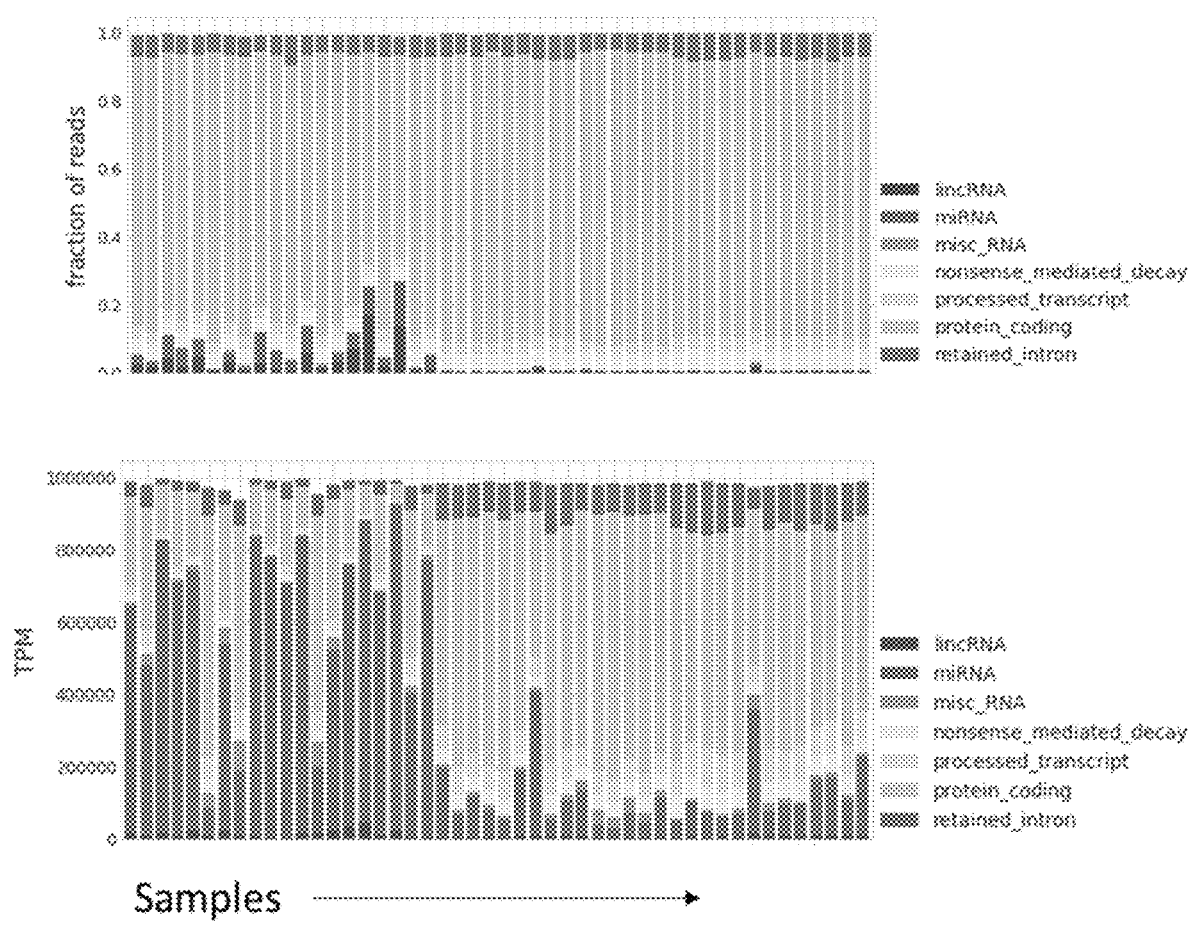
FIG. 3 is a graphical representation of the distribution of different RNA transcripts for different types of RNA as shown in the legend. Each column represents a unique sample. All samples were prepared from the same tissue type, using the same RNA enrichment method and the same sequencing service. The bottom panel shows the data in the top panel in Transcripts per Kilobase Million (TPM).

TPM uses correction of the read counts by the length of each gene in bases, so it can create a great bias in the samples with uneven distribution of non-coding transcripts after TPM calculation because some non-coding transcripts (miRNA, snRNA, snoRNA) have very small transcript length. FIG. 3 shows the biases that are created upon TPM calculation.

To remove batches based on uneven distribution of non-coding transcripts in RNA library, non-coding transcripts were removed from the data before further RNA expression quantification.

Excluded types included:
 {pseudogene, polymorphic_pseudogene, processed_pseudogene,
  transcribed_processed_pseudogene, unitary_pseudogene, unprocessed_pseudogene,
  transcribed_unitary_pseudogene, IG_C_pseudogene, IG_J_pseudogene, IG_V_pseudogene,
  transcribed_unprocessed_pseudogene, translated_unprocessed_pseudogene TR_J_pseudogene,
  TR_V_pseudogene
  snRNA, snoRNA, miRNA
  Ribozyme, rRNA, Mt_tRNA, Mt_rRNA, scaRNA
  retained_intron, sense_intronic, sense_overlapping
  nonsense_mediated_decay, non_stop_decay
  Antisense, lincRNA, macro_lncRNA
  processed_transcript, 3prime_overlapping_ncrna
  sRNA, misc_RNA, vaultRNA, TEC}
 Retained types:
 {protein_coding,
  Ig (IG_C_gene, IG_D_gene, IG_J_gene, IG_V_gene)
  TCR (TR_C_gene, TR_D_gene, TR_J_gene, TR_V_gene)}

In addition to removing non-coding transcripts, genes that were found to have the highest variance between PolyA RNA sequencing and total RNA sequencing were also removed. Such genes included (1) histone-encoding genes, and (2) mitochondria-related genes, having very long or very short PolyA tails, which result in uneven enrichment of the transcripts.

Figure 4A:
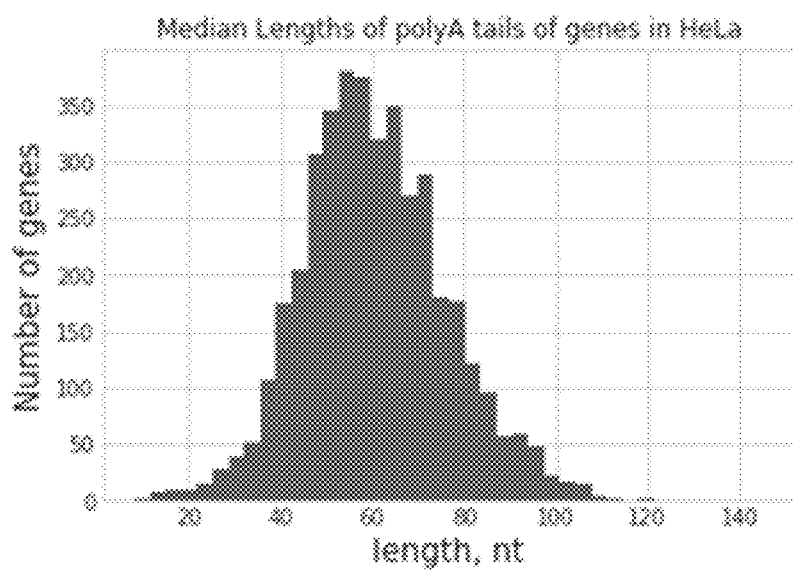
FIG. 4A shows the distribution of poly-A tails of RNA transcripts from HeLa cell samples, and several examples of poly-A tails for histone family genes.
Figure 4B:
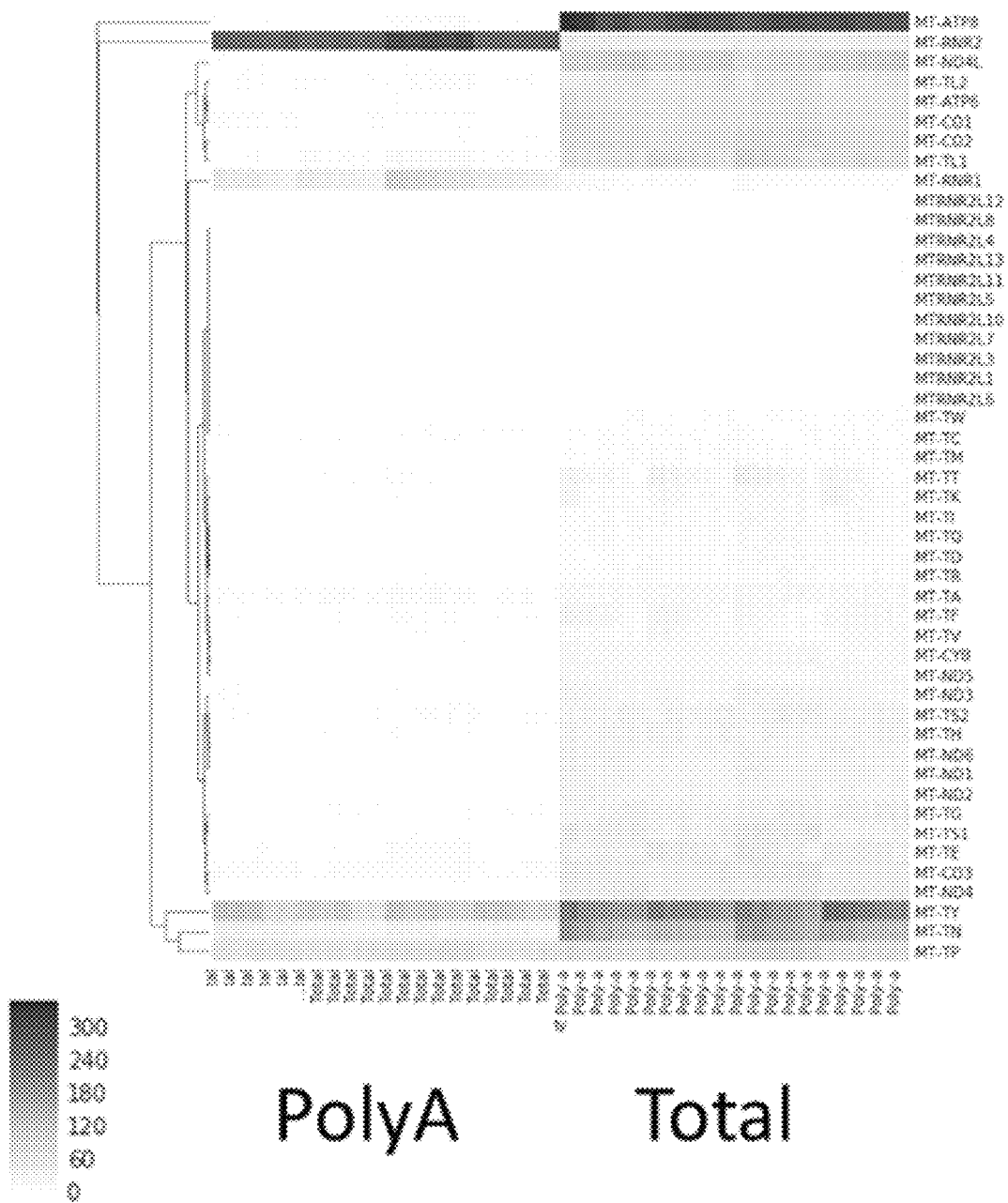
FIG. 4B shows a comparison of expression of mitochondrial RNA for samples that are either poly-A-enriched or enriched by rRNA depletion (denoted by total RNA).
Figure 4C:
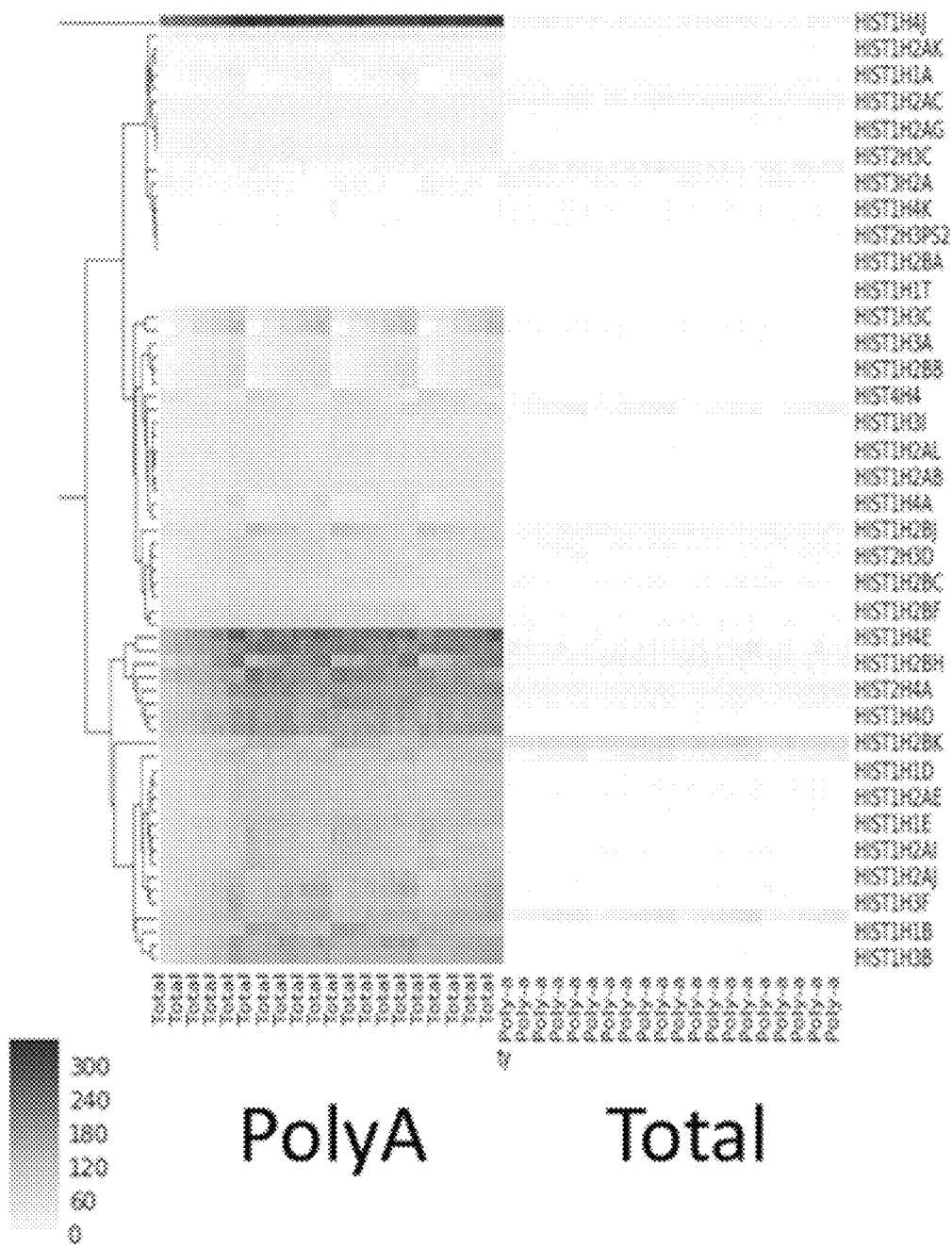
FIG. 4C shows a comparison of expression of Histone coding RNA for samples that are either poly-A-enriched or enriched by rRNA depletion (denoted by total RNA).

FIG. 4A shows the variation in the length of PolyA tails for different histone-encoding genes. FIG. 4B shows a comparison of expression of histone coding and mitochondrial genes within samples in which RNA was enriched by either polyA enrichment or by ribo-RNA depletion (total RNA). Genes that are excluded are described in the present disclosure (e.g., transcripts from protein non-coding regions, histone-encoding genes, and mitochondria-related genes).

Gene aggregation and TPM normalization

Figure 5:
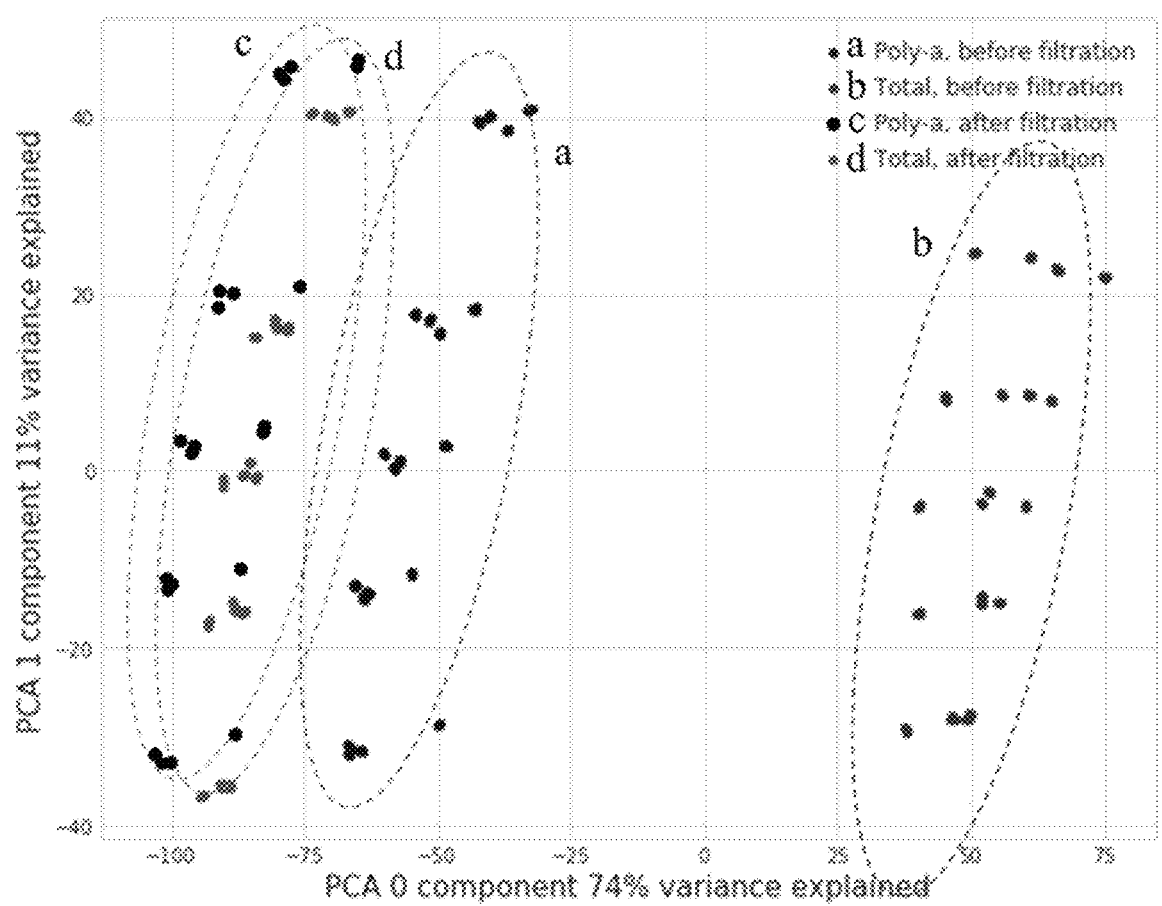
FIG. 5 shows a principal component analysis (PCA) of RNA expression of cell samples containing different percentages of HeLa cells, either with or without polyA enrichment, and with or without data filtration. Data filtration included removal of non-coding RNA transcripts, histone-coding transcripts, and mitochondrial transcripts. The PCA0—component describes major differences between poly-A and total-RNA sequencing. The PCA1 component describes different cell line ratios. Samples were prepared as a mixture of two different cell lines in 5 different ratios.

Expression per gene was calculated as a sum of the expression of the transcripts for the gene. Gene expression data was normalized to the total number of transcripts (in the million). This procedure allows correction for major batch effects associated with library preparation, uneven RNA transcript distribution between samples, and correction for RNA enrichment method (FIG. 5).

Example 2: DNA and RNA Extraction from Peripheral Blood Mononuclear Cells (PBMC) or Cell Suspensions To prepare nucleic acid materials for downstream sequencing analysis, DNA and/or RNA was extracted from a single PBMC cell pellet or suitable cell suspensions. In brief, AllPrep DNA/RNA assay kits (Qiagen®) were used for purifying genomic DNA and total RNA simultaneously from a single biological sample. Biological samples were first lysed and homogenized in a highly denaturing guanidine-isothiocyanate-containing buffer, which immediately inactivated DNases and RNases to ensure isolation of intact DNA and RNA. The lysate was then passed through an AllPrep DNA spin column. This column, in combination with the high-salt buffer, allowed selective and efficient binding of genomic DNA. The column was washed and the DNA was then eluted. Alternatively, the lysate that passed through the AllPrep DNA spin column went through an RNeasy spin column to selectively isolate RNA.

In some circumstances, for further improving the quality of the starting RNA, ethanol was added to the flow-through from the AllPrep DNA spin column to provide appropriate binding conditions for RNA. The sample was then applied to an RNeasy spin column, where total RNA was bound to the membrane and contaminants were washed away. High-quality RNA was then eluted in water. Some of the steps and/or the entire procedure can be managed and conducted by lab personnel. In the event that quality control related issues arise, lab personnel will notify the provider (e.g., healthcare provider) of the cells or tissue (e.g., PMBCs or cell suspensions).

Preparation of reagents

Reagents for the extraction of DNA and/or RNA from a sample were prepared according to the manufacturer's instruction, including AllPrep DNA/RNA Mini handbook and AllPrep DNA/RNA Micro handbook, the contents of which are incorporated by reference herein. Some of the processes may be customized based on the requirements of the nucleic acids of a given sequencing platform. In general, B-mercaptoethanol (β-ME) was added to Buffer RLT Plus before use. 10 μL R-ME per 1 mL Buffer RLT Plus was added. The lab personnel who conducted the preparation of the reagents wore appropriate Personal Protective Equipment (PPE) and the reagents were dispensed in a fume hood. Buffer RLT Plus was generally stable at room temperature for 1 month after addition of β-ME. The date of the addition of β-ME and the 1-month expiration date were marked on the bottle.

Buffer RPE, Buffer AW1, and Buffer AW2 were each supplied as a concentrate by the manufacturer. Before using for the first time, appropriate volume of 100% ethanol was added, as indicated on the bottle, to obtain a working solution. The solutions were appropriately labeled per the Solutions and Reagent Labeling Standard Operating Procedure (SOP) as described herein. Buffer RLT Plus may form a precipitate during storage. If necessary, the precipitates formed in Buffer RLT Plus were dissolved by warming in a 37° C. water bath until precipitates were dissolved. The Buffer RLT Plus without precipitates was then place at room temperature. Prolonged incubation in the water bath was not recommended. It was noted that Buffer RLT Plus, Buffer RW1, and Buffer AW1 contained a guanidine salt.

Preparation of material for extraction

Before the start of extraction, tubes and columns were labeled with a specimen ID for each sample being processed. Frozen cell pellets were thawed slightly, so they were dislodged by flicking the tube. Cell lysates were incubated at 37° C. in a water bath until completely thawed. Prolonged incubation was discouraged, due to its potential compromise on RNA integrity. For pelleted cells, the cell pellet was loosened thoroughly by flicking the tube. This was an important step for properly preparing the nucleic acid materials because incomplete loosening of the cell pellet may lead to inefficient lysis and reduced nucleic acid yields. Appropriate volume of Buffer RLT Plus was added, followed by vortexing or pipetting to mix. In general, for $<5\times10^5$ cells, 350 µL Buffer RLT Plus was added. For $5\times10^5$-$1\times10^7$ cells, 600 µL Buffer RLT Plus was added.

The lysate was homogenized by using QIAshredder. In brief, the lysate was pipetted directly into a QIAshredder spin column placed in a 2 mL collection tube. The lysate was then pipetted and centrifuged for 2 minutes at maximum speed (18,565×g). The homogenized lysate was transferred to an AllPrep DNA spin column placed in a 2 mL collection tube. The lid was closed gently, and the spin column was centrifuged for 30s at >8000×g. After centrifugation, any remaining liquid on the column membrane was checked and removed. If necessary, the centrifugation step was repeated until all liquid was passed through the membrane. The AllPrep DNA spin column was placed in a new 2 ml collection tube and was stored at room temperature or at 4° C. (not in the freezer) for later DNA purification. The flow-through for RNA purification was used.

Total RNA purification

For purifying RNA, 600 µL of 70% ethanol was added to the flow through from the previous step, and was mixed well by pipetting. Up to 700 µL of the sample was immediately transferred, including any precipitate that was formed which might be visible, to an RNeasy spin column placed in a 2 ml collection tube. The lid of the collection tube was closed gently and was centrifuged for 15 s at ≥8000× g. The flow-through was discarded. In the event that the sample volume exceeded 700 µL, successive aliquots were centrifuged in the same RNeasy spin column. The flow-through was discarded after each centrifugation. The collection tube was re-used in the following step.

700 µL Buffer RW1 was added to the RNeasy spin column. The lid was closed gently, and was centrifuged for 15 s at ≥8000× g to wash the spin column membrane. The flow-through was discarded. The collection tube was re-used in the following step. 500 µL Buffer RPE was added to the RNeasy spin column. The lid was closed gently, and was centrifuged for 15 s at ≥8000× g to wash the spin column membrane. The flow-through was discarded.

In general, if $<5\times10^5$ cells were processed, 500 µL of 80% ethanol was added to the RNeasy MinElute spin column. The lid was closed gently, and the spin column was centrifuged for 2 min at ≥8000× g to wash the spin column membrane. The collection tube with the flow-through was discarded. The RNeasy MinElute spin column was placed in a new 2 mL collection tube. The lid of the spin column was opened, and the spin column was centrifuged at full speed (18,565×g) for 5 minutes. The collection tube with the flow-through was discarded. The RNeasy MinElute spin column was placed in a new 1.5 mL collection tube. 14 µL RNase-free water was directly added to the center of the spin column membrane. The lid was closed gently, and was centrifuged for 1 min at full speed (18,565×g) to elute the RNA. The spin column was discarded, and the 1.5 mL tube was stored with extracted RNA at −80° C. until further processing.

If $>5\times10^5$ cells were processed, 500 µL Buffer RPE was added to the RNeasy spin column. The lid was closed gently, and was centrifuged for 2 min at ≥8000× g to wash the spin column membrane. The RNeasy spin column was placed in a new 2 mL collection tube. The old collection tube with the flow-through was discarded. The collection tube was then centrifuged at full speed (18,565×g) for 1 min. The RNeasy spin column was placed in a new 1.5 mL collection tube. 30-50 µL of RNase-free water was added directly to the spin column membrane. The lid was closed gently, and was centrifuge for 1 min at ≥8000× g to elute the RNA.

Genomic DNA purification

500 µL Buffer AW1 was added to the AllPrep DNA spin column (previously placed in a new 2 ml collection tube and stored at room temperature or at 4° C.). The lid was closed gently, and the spin column was centrifuged for 15 s at ≥8000× g. The flow-through was discarded. The spin column was re-used in the following step. 500 µL Buffer AW2 was added to the AllPrep DNA spin column. The lid was closed gently, and was centrifuged for 2 min at full speed (18,565×g) to wash the spin column membrane. After centrifugation, the AllPrep DNA spin column was carefully removed from the collection tube. If the column contacted the flow-through, the collection tube was emptied and the spin column was centrifuged again for 1 min at full speed.

If $<5\times10^5$ cells were processed, the AllPrep DNA spin column was placed in a new 1.5 mL collection tube. 50 µL Buffer EB was added (preheated to 70° C.) directly to the spin column membrane and the lid was closed and was incubated at room temperature for 2 min. The spin column was centrifuged for 1 min at ≥8000× g to elute the DNA. Repeat addition of Buffer EB was conducted and centrifugation to elute further DNA. A new 1.5 mL collection tube was used to collect the second DNA eluate, and then was combined with the first eluate. The spin column was discarded, and was stored in the 1.5 mL tube with extracted DNA at 4° C. until further processing.

If $>5\times10^5$ cells were processed, the AllPrep DNA spin column was placed in a new 1.5 mL collection tube. 50 µL Buffer EB was added directly to the spin column membrane and the lid was closed. The spin column was incubated at room temperature for 1 min was centrifuged for 1 min at ≥8000× g to elute the DNA. Repeat addition of Buffer EB was conducted and centrifugation to elute further DNA. A new 1.5 mL collection tube was used to collect the second DNA eluate, and then was combined with the first eluate. The spin column was discarded, and was stored in the 1.5 mL tube with extracted DNA at 4° C. until further processing.

Troubleshooting processes included, but were not limited to the following in Table 3.

TABLE 3

Troubleshooting Steps for AllPrep DNA/RNA Procedure

| Incident | Troubleshooting steps |
| --- | --- |
| Clogged AllPrep DNA and RNeasy spin column | Clogged column can be caused by the following:<br>a) Inefficient disruption and/or homogenization<br>1. Increase g-force and centrifugation time if necessary<br>2. In subsequent preparations, reduce the amount of starting material and/or increase the homogenization time.<br>b) Too much starting material<br>1. Reduce the amount of starting material. It is essential to use the correct amount.<br>c) Centrifugation temperature too low<br>1. The centrifugation temperature should be 20-25° C. Some centrifuges may cool |
| Low nucleic acid yield | Low nucleic acid yield can be caused by the following:<br>a) Inefficient disruption and/or homogenization<br>1. In subsequent preparations, reduce the amount of starting material and/or increase the homogenization time.<br>b) Too much starting material<br>1. Reduce the amount of starting material. It is essential to use the correct amount.<br>c) RNA still bound RNeasy spin column membrane<br>1. Repeat RNA elution, but incubate the RNeasy spin column on the benchtop for 10 min with RNase-free water before centrifuging<br>d) DNA still bound to AllPrep DNA spin column membrane<br>1. Repeat DNA elution, but incubate the AllPrep DNA spin column on the benchtop for 10 minutes with Buffer EB before centrifuging.<br>e) Ethanol carryover<br>1. During the second wash with Buffer RPE, be sure to centrifuge at ≥8000 × g for 2 min at 20-25° C. to dry the RNeasy spin column membrane.<br>2. Perform the optional centrifugation to dry the RNeasy spin column membrane if any flow-through is present on the outside of the column. |
| DNA contaminated with RNA | This can be caused by the following:<br>a) Lysate applied to the AllPrep DNA spin column contains ethanol<br>1. Add ethanol to the lysate after passing the lysate through the AllPrep DNA spin column.<br>b) Sample is affecting pH of homogenate<br>1. The final homogenate should have a pH of 7. Make sure that the sample is not highly acidic or basic. |
| Contamination of RNA with DNA affects downstream applications | This can be caused by the following:<br>a) Cell number too high<br>1. For some cell types, the efficiency of DNA binding to the AllPrep DNA spin column may be reduced when processing very high cell numbers.<br>b) Tissue has high DNA content<br>1. For certain tissues with extremely high DNA content (e.g., thymus), some DNA will pass through the AllPrep DNA spin column. Try using smaller samples. Alternatively, perform DNase digestion on the RNeasy spin column membrane, or perform DNase digestion of the eluted RNA followed by RNA cleanup. |
| Low $A_{260}/A_{280}$ value in RNA eluate | Use 10 mM Tris HCl, pH 7.5, not RNase-free water, to dilute the sample before measuring purity. |
| RNA degraded | RNA degradation can be caused by the following:<br>a) Inappropriate handling of starting material<br>1. Ensure that tissue samples are properly stabilized and stored in RNAlater RNA Stabilization Reagent.<br>2. Ensure that frozen tissue was flash-frozen immediately in liquid nitrogen and properly stored at −70° C. Perform the AllPrep DNA/RNA procedure quickly, especially the first few steps.<br>b) RNase contamination<br>1. Although all AllPrep buffers have been tested and are guaranteed RNase-free, RNases can be introduced during use. Be certain not to introduce any RNases during the AllPrep DNA/RNA procedure or later handling. |
| DNA fragmented | This can happen when homogenization is too vigorous. The length of purified DNA depends strongly on the homogenization conditions. If longer DNA fragments are required, keep the homogenization time to a minimum or use a gentler homogenization method if possible. |
| Nucleic acid concentration too low | The elution volume may be too high. Elute nucleic acids in a smaller volume. Do not use less than 50 μL Buffer EB for the AllPrep DNA spin column, or less than 1 × 30 μL of water for the RNeasy spin column. Although eluting in smaller volumes results in increased nucleic acid concentrations, yields may be reduced. |
| Nucleic acids do not perform well in downstream experiments | a) Salt carryover during elution<br>1. Ensure that buffers are at 20-30° C.<br>2. Ensure that the correct buffer is used for each step of the procedure.<br>3. When reusing collection tubes between washing steps, remove residual flow-through from the rim by blotting on clean paper towels.<br>b) Ethanol carryover<br>1. During the second wash with Buffer RPE, be sure to centrifuge at ≥8000 × g for 2 min at 20-25° C. to dry the RNeasy spin column membranes. After centrifugation, carefully remove the column from the collection tube so that the column does not contact the flow-through. Otherwise, carryover of ethanol will occur.<br>2. Perform the optional centrifugation to dry the RNeasy spin column membrane if any flow-through is present on the outside of the column. |

Example 3: The Constructions of DNA Libraries for Sequencing

DNA libraries were prepared before performing the downstream sequencing. In brief, library Construction (LC) consisted of shearing extracted genomic DNA to a predetermined size (e.g., 200 base pairs), and then prepared the libraries for Hybrid Capture. Fragmented DNA was repaired, and unique molecular barcodes were added to each DNA sample, so that each DNA sample could be identified during sequencing. DNA samples were purified before amplifying the barcoded libraries with Polymerase Chain Reaction (PCR). The DNA samples were then purified again before the amount and quality of each library was assessed using Quality Control (QC) steps described according to manufacturer instructions.

In general, library Construction consisted of four main steps. First, genomic DNA was sheared to about 200 base pairs using the SureSelect XT HS Enzymatic Fragmentation Kit. The shearing resulted in DNA fragments that needed to undergo blunt end repair. The second step was the repairing and dA-tailing of the DNA ends. This step added an "A" base to the 3' end of a blunt phosphorylated DNA fragment. This treatment created compatible overhangs for the next step of DNA sample preparation. In the third step, specific molecular-barcoded adaptors were ligated to each sample using the "A" base overhang created in the last step. Adapters were platform-specific sequences for fragment recognition by the sequencer: for example, the P5 and P7 sequences enabled library fragments to bind to the flow cells of Illumina platforms. The molecular barcode was unique to each sample being run and allowed multiple samples to be subsequently mixed together, with the barcode used to identify each sample at sequencing. The samples were then purified using AMPure XP beads. In the final step, the adaptor-ligated libraries were amplified with PCR, and then purified a second time using AMPure XP beads. Some or all of the procedures were managed and conducted by lab personnel. In the event that quality control related issues arise, lab personnel will notify the provider (e.g., healthcare provider) of the biopsy sample or the extracted DNA.

Normalization of samples for Library Construction

Samples were normalized to 10-200 ng in 7 µL, using low TE. The maximum amount of DNA available was used for each sample, within the range provided. The lab personnel then navigated to the normalization spreadsheet, which was located in the Clinical Lab Documents folder in the shared Google Drive. The tab labeled "LC Normalization" was selected. The Sample ID was entered into column A. The measured concentration was entered into column B. The spreadsheet automatically calculated the volumes of sample and low TE required for normalization in columns G and H. If the concentration of a sample was on the lower side, the spreadsheet calculated a volume of sample >7 µL and a volume of low TE<0 µL. If this occurred, only 7 µL of sample was used and was not diluted. The volumes calculated in the spreadsheet were used for normalizing the appropriate volumes into a 96 well semi-skirted PCR plate.

Enzymatic DNA shearing

In some embodiments, DNA is fragmented using an endonuclease (e.g., using an enzymatic fragmentation kit from SureSelect). In some embodiments, a SureSelect Fragmentation Buffer and Enzyme were thawed on ice. Fragmentation Buffer was vortexed and spun down before use. A 3 µL Fragmentation master mix for each sample was prepared using 2 µL of 5× SureSelect Fragmentation Buffer mixed with 1 µL SureSelect Fragmentation Enzyme. In some embodiments, larger volumes can be prepared for multiple reactions (e.g., 18 µL of 5× SureSelect Fragmentation Buffer mixed with 9 µL SureSelect Fragmentation Enzyme for 8 reactions including excess). 3 µL Fragmentation master mix was added to each sample well and was mixed by pipetting up and down 20 times. The plate was immediately placed on the thermal cycler on the Enzymatic Fragmentation program (step 1: 37° C. for 15 minutes; step 2: 65° C. for 5 minutes and step 3: 4° C. on hold).

Repair and dA-Tail the Fragmented DNA ends

In some embodiments, fragmented DNA is repaired and dA-tailed, for example using a kit from SureSelect. In some embodiments, reagents were first thawed on ice (e.g., from −20° C. storage) and Agencourt AMPure XP beads were equilibrated to room temperature for at least 30 minutes. End Repair A-Tailing Buffer, Ligation Buffer, End Repair A-Tailing Enzyme Mix, T4 DNA Ligase, and Adaptor Oligo Mix (all from SureSelect XT HS Library Preparation Kit for ILM) were mixed by vortexing.

In some embodiments, a ligation master mix was prepared. The thawed vial of Ligation Buffer was vortexed for 15 seconds at high speed to ensure homogeneity. The Ligation Buffer used in this step was viscous and was mixed thoroughly by vortexing at high speed for 15 seconds before removing an aliquot for use. When combined with other reagents, the Ligation Buffer was mixed well by pipetting up and down 15-20 times using a pipette set to at least 80% of the mixture volume or by vortexing at high speed for 10-20 seconds. A flat-top vortex mixer was used when vortexing strip tubes or plates throughout the protocol. When reagents were mixed by vortexing, the occurrence of adequate mixing was visually verified.

In some embodiments, an appropriate volume of Ligation master mix was prepared by combining reagents as follows: a 25 µL reaction volume for 1 reaction containing 23 µL of Ligation Buffer and 2 µL of T4 DNA Ligase, a 225 µL reaction volume for 8 reactions (including excess) containing 207 µL of Ligation Buffer and 18 µL of T4 DNA Ligase, a 625 µL reaction volume for 24 reactions (including excess) containing 575 µL of Ligation Buffer and 50 µL of T4 DNA Ligase.

The Ligation Buffer was slowly pipetted into a 1.5 mL Eppendorf tube, ensuring that the full volume was dispensed. The T4 DNA Ligase was slowly added, rinsing the enzyme tip with buffer solution after addition and was mix well by slowly pipetting up and down 15-20 times or sealed the tube and vortexed at high speed for 10-20 seconds. The liquid was spun briefly to collect the liquid, which was kept at room temperature for a minimum of 30 minutes, but not more than 45 minutes before use.

The thawed vial of End Repair-A Tailing Buffer was thawed for 15 seconds at high speed to ensure homogeneity. The solution was visually inspected. If any solids were observed, vortexing was continued until all solids were dissolved. The appropriate volume of End Repair/dA-Tailing master mix was prepared by combining the following reagents: a 20 µL reaction volume for 1 reaction containing 16 µL of End Repair A-Tailing Buffer and 4 µL of End Repair A-Tailing Enzyme Mix, a 180 µL reaction volume for 8 reactions (including excess) containing 144 µL of End Repair A-Tailing Buffer and 36 µL of End Repair A-Tailing Enzyme Mix, a 500 µL reaction volume for 24 reactions (including excess) containing 400 µL of End Repair A-Tailing Buffer and 100 µL of End Repair A-Tailing Enzyme Mix.

The End Repair-A Tailing Buffer was slowly pipetted into a 1.5 mL Eppendorf tube, ensuring that the full volume was dispensed. The End Repair-A Tailing Enzyme Mix was slowly added, rinsing the enzyme tip with buffer solution after addition and was mixed well by pipetting up and down 15-20 times or sealed the tube and vortexed at high speed for 5-10 seconds. The liquid was spun briefly to collect and was kept on ice. 20 µL of the End Repair/dA-Tailing master mix was added to each sample well containing approximately 50 µL of fragmented DNA and was mixed by pipetting up and down 15-20 times using a pipette set to 60 µL or capped the wells and vortexed at high speed for 5-10 seconds. The samples were briefly spun and then the plate or strip tube was immediately placed in the Thermal cycler and started the End Repair/dA-Tailing program (step 1: 20° C. for 15 minutes; step 2: 72° C. for 15 minutes and step 3: 4° C. on hold).

Ligate the molecular-barcoded adaptor

Once the thermal cycler reached the 4° C. Hold step, the samples were transferred to ice while setting up this step. To each end-repaired/dA-tailed DNA sample (approximately 70 µL), 25 µL of the Ligation master mix that was prepared previously was added, kept at room temperature, and was mixed by pipetting up and down at least 10 times using a pipette set to 85 µL or capped the wells and vortexed at high speed for 5-10 seconds. The samples were briefly spun. 5 µL of Adaptor Oligo Mix (white capped tube) was added to each sample and was mixed by pipetting up and down 15-20 times using a pipette set to 85 µL or capped the wells and vortexed at high speed for 5-10 seconds. The Ligation master mix and the Adaptor Oligo Mix were added to the samples in separate addition steps as directed in the steps above, mixing after each addition. The samples were briefly spun and the plate or strip tube was then immediately placed in the thermal cycler and bean the Ligation program (step 1: 20° C. for 30 minutes; step 2: 4° C. on hold). The sample wells were sealed and were stored overnight at either 4° C. or −20° C. if next steps were not continued.

Purify the samples using AMPure XP beads

The AMPure XP beads were verified and held at room temperature for at least 30 minutes before use. The beads were not frozen at any time. 400 μL of 70% ethanol per sample was prepared, plus excess, for use in the following steps. The freshly-prepared 70% ethanol may be used for subsequent purification steps run on the same day. The complete Library Preparation protocol required 0.8 ml of fresh 70% ethanol per sample. The AMPure XP bead suspension was mixed well so that the reagent appeared homogeneous and consistent in color. 80 μL of homogeneous AMPure XP beads were added to each DNA sample (approximately 100 μL) in the PCR plate or strip tube and were pipetted up and down 15-20 times or capped the wells and vortexed at high speed for 5-10 seconds to mix. Samples were incubated for 5 minutes at room temperature. The plate or strip tube was put into a magnetic separation device (DynaMag −96 Side Magnet) and was waited for the solution to clear (approximately 5 to 10 minutes). The plate or strip tube was placed in the magnetic stand. The cleared solution from each well was carefully removed and discarded. The beads were not touched while removing the solution. The plate or strip tube was continued to keep in the magnetic stand while 200 μL of freshly-prepared 70% ethanol in each sample well was dispensed. Any disturbed beads were allowed to settle after 1 minute and the ethanol was removed. The plate or strip tube was placed in the magnetic stand while you dispense another 200 μL of freshly-prepared 70% ethanol in each sample well. Any disturbed beads were allowed to settle after 1 minute and the ethanol was removed. The wells were sealed with strip caps, and the samples were then briefly spun to collect the residual ethanol. The plate or strip tube was returned to the magnetic stand for 30 seconds. The residual ethanol was removed with a P20 pipette. The samples were air dried for 5 minutes. The bead pellet was not dried to the point that the pellet appeared cracked during any of the bead drying steps in the protocol. Elution efficiency was significantly decreased when the bead pellet was excessively dried. 35 μL nuclease-free water was added to each sample well. The wells were sealed with strip caps, then were mixed well on a vortex mixer and the plate or strip tube was briefly spun to collect the liquid and was incubated for 2 minutes at room temperature. The plate or strip tube was put in the magnetic stand and was left for approximately 5 minutes, until the solution was clear. The cleared supernatant (approximately 34.5 μL) was removed to a fresh PCR plate or strip tube sample well and was kept on ice. The beads could be discarded at this time. It was noted that it may not be possible to recover the entire 34.5 μL supernatant volume at this step. The maximum possible amount of supernatant was transferred for further processing. To maximize recovery, the cleared supernatant was transferred to a fresh well in two rounds of pipetting, using a P20 pipette set at 17.25 μL.

Amplify the adaptor-ligated library

The following PCR reagents from the SureSelect XT HS Library Preparation Kit for ILM (PrePCR) were thawed, mixed and kept on ice. Herculase II Fusion DNA Polymerase was mixed by pipetting up and down 15-20 times. 5× Herculase II Reaction Buffer was mixed by vortexing. 100Mm dNTP Mix was mixed by vortexing. Forward Primer and SureSelect XT HS Index Primers A01 through H04 were separately mixed by vortexing. The appropriate index assignments for each sample were determined. The SureSelect XT HS Index Primers were provided in single-use aliquots. To avoid cross-contamination of libraries, each vial was discarded after use in one library preparation reaction. Residual volume was not re-used or retained for subsequent experiments.

Appropriate volume of pre-capture PCR reaction mix was prepared as described below on ice and then was mixed well on a vortex mixer. For example, a 13.5 μL reaction volume for 1 reaction contained 10 μL of 5× Herculase II Reaction Buffer, 0.5 μL of 100 mM dNTP Mix, 2 μL of Forward Primer, and lpL of 5× Herculase II Fusion DNA, a 121 μL reaction volume for 8 reactions (including excess) contained 90 μL of 5× Herculase II Reaction Buffer, 4.5 μL of 100 mM dNTP Mix, 18 μL of Forward Primer, and 9 μL of 5× Herculase II Fusion DNA, or a 337 μL reaction volume for 24 reactions (including excess) contained 250 μL of 5× Herculase II Reaction Buffer, 12.5 μL of 100 mM dNTP Mix, 50 μL of Forward Primer, and 25 μL of 5× Herculase II Fusion DNA.

13.5 μL of the PCR reaction mixture was added to each purified DNA library sample (34.5 μL) in the PCR plate wells. 2 μL of the appropriate SureSelect XT HS Index Primer was added to each reaction. The wells were capped and were then vortex at high speed for 5 seconds. The plate or strip tube was spun briefly to collect the liquid and any bubbles were released. Before adding the samples to the thermal cycler, the Pre-Capture PCR program was started according to the conditions below to bring the temperature of the thermal block to 98° C. Once the thermal cycler reached 98° C., the sample plate or strip tube was immediately placed in the thermal block and the following temperature cycling protocol was performed.

| Segment | Number of Cycles | Temperature | Time |
|---------|------------------|-------------|------|
| 1 | 1 | 98° C. | 2 minutes |
| 2 | 8 | 98° C. | 30 seconds |
|   |   | 60° C. | 30 seconds |
|   |   | 72° C. | 1 minute |
| 3 | 1 | 72° C. | 5 minutes |
| 4 | 1 | 4° C. | Hold |

Purify the Amplified Library with AMPure XP Beads

The AMPure XP beads were verified to be held at room temperature for at least 30 minutes before use. 400 μL of 70% ethanol per sample was prepared, plus excess. The AMPure XP bead suspension was mixed well, so that the reagent appeared homogeneous and consistent in color. 50 μL of homogenous AMPure XP beads were added to each amplification reaction in the PCR plate or strip tube and was pipetted up and down 15-20 times to mix. Samples were incubated for 5 minutes at room temperature. The plate was out into a magnetic separation device (DynaMag −96 Side Magnet) and was waited up to 5 minutes for the solution to clear. The plate or strip tube was put on the magnetic stand and the cleared solution from each well was carefully removed and discarded. The beads were touched while removing the solution. The plate or strip tube was continued to be kept in the magnetic stand while dispensing 200 μL of freshly-prepared 70% ethanol into each sample well. Disturbed beads were allowed to settle after the wait for 1 minute, then removed the ethanol. The ethanol wash was repeated once. The wells were sealed with strip caps, then the samples were briefly spun to collect the residual ethanol. The plate or strip tube was returned to the magnetic stand for 30 seconds. The residual ethanol was removed with a P20 pipette. The samples were dried by keeping the unsealed plate or strip tube at room temperature for up to 5 minutes, until the residual ethanol was just evaporated. 15 μL nuclease-free water was added to each sample well. The wells were sealed with strip caps, then were mixed well on a vortex mixer and the plate or strip tube was briefly spun to collect the liquid and was incubate for 2 minutes at room temperature. The plate or strip tube was put in a magnetic stand and was left for 3 minutes, until the solution was clear. 15 µL of the cleared supernatant was removed to a fresh PCR plate or strip tube sample well and was kept on ice. The new PCR plate was sealed containing libraries. The beads were discarded. The quality of sample libraries was checked using the an electrophoresis device, for example an automated electrophoresis device (e.g., a TapeStation System available from Agilent, agilent.com) and a spectrophotometer, for example a small volume full-spectrum, UV-visible spectrophotometer (e.g., Nanodrop spectrophotometer available from ThermoFisher Scientific, thermofisher.com), or the plate was stored at −20° C.

Resources from the manufacturers, including Agilent SureSelect XT HS Target Enrichment System for Illumina Paired-End Multiplexed Sequencing Library protocol and Agilent SureSelect XT HS and XT Low Input Enzymatic Fragmentation Kit protocol, were incorporated by reference herein.

Example 4: Hybridization-Capture and Target Enrichment of DNA Libraries

Hybridization-Capture based target enrichment was used directly after Library Construction described in Example 3. This protocol described the steps to hybridize the prepared gDNA libraries with a target-specific capture probes. Target enrichment worked by mixing target-specific biotinylated probes with the DNA Library. The probes were bound to the targets which were then isolated by streptavidin coated magnetic bead pulldown, leaving uncaptured DNA (the areas of the genome that we do not want) behind. The steps to hybridize the prepared DNA libraries with a target-specific capture library were provided. After library preparation, the libraries were denatured and biotin-labeled probes specific to targeted regions were used for hybridization. The pool was enriched for regions of interest by adding streptavidin-coated beads that were bound to the biotinylated probes. DNA fragments bound to the streptavidin-coated beads via biotinylated probes were magnetically pulled down from the solution. The enriched fragments were then eluted from the beads. Each DNA library sample must be hybridized and captured individually. Some or all of the procedures were managed and conducted by lab personnel. In the event that quality control related issues arise, lab personnel will notify the provider (e.g., healthcare provider) of the biopsy sample or the extracted DNA. As a general work procedure, before beginning the procedure, work surfaces and pipettes were thoroughly disinfected by wiping down with 10% bleach, followed by 70% ethanol. The same cleaning process was followed after completion of work procedure.

Normalization of samples for Hybrid Capture

12 µL nuclease-free water was used to normalize samples to 500-1000 ng. The maximum amount of DNA available was used for each sample, within the range provided. The lab personnel then navigated to the normalization spreadsheet, located in the Clinical Lab. Documents folder in the shared Google Drive. The tab labeled "HC Normalization" was selected. The Sample ID was entered into column A and the measured concentration was entered into column B. The spreadsheet automatically calculated the volumes of sample and low TE required for normalization in columns G and H. If the concentration of a sample was on the lower side, the spreadsheet calculated a volume of sample >12 µL and a volume of nuclease-free water <0 µL. If this occurred, only 12 µL of sample was used, and the sample was not diluted. Using the volumes calculated in the spreadsheet, appropriate volumes were normalized into a 96 well semi-skirted PCR plate.

Hybridize DNA Samples to the Capture Library

In some embodiments, the component reagents for hybridization using a SureSelect kit were thawed, according to the thawing conditions described below. Each reagent was vortexed to mix, then tubes were spun briefly to collect the liquid.

To each DNA library sample well, 5 µl SureSelect XT HS and XT Low Input Blocker Mix (previously thawed on ice) were added. The wells were capped and then vortexed at high speed for 5 seconds. The plate was spun briefly to collect the liquid and any bubbles were released. The sealed sample plates were transferred to the thermal cycler and the Hybridization program was started. The thermal cycler was programmed to pause during Segment 3 of the Hybridization program to allow additional reagents to be added to the Hybridization wells, as described in the next sections. During Segments 1 and 2 of the thermal cycling program, the additional reagents were prepared as described in the next section. If needed, these steps could be finished after the thermal cycler program pauses in Segment 3. A 25% solution of SureSelect RNase Block (e.g., previously thawed on ice) was prepared and was mixed well by vortexing, and the mix was briefly centrifuged and then kept on ice.

Further, a Capture Library Hybridization Mix was prepared as follow for one or more reactions. For example, a 13 µL reaction volume for 1 reaction contained 2 µL of 25% RNase Block solution, 5 µL of Capture Library >3 Mb (e.g., previously thawed on ice), and 6 µL of SureSelect Fast Hybridization Buffer (e.g., previously thawed and kept at room temperature), a 117 µL reaction volume for 8 reactions (including excess) contained 18 µL of 25% RNase Block solution, 45 µL of Capture Library >3 Mb, and 54 µL of SureSelect Fast Hybridization Buffer, or a 325 µL reaction volume for 24 reactions (including excess) contained 50 µL of 25% RNase Block solution, 125 µL of Capture Library >3 Mb, and 150 µL of SureSelect Fast Hybridization Buffer.

The listed reagents were combined at room temperature, mix well by vortexing at high speed for 5 seconds, and then were spun down briefly. The mixture was just prepared before pausing the thermal cycler in Segment 3. The mixture was kept at room temperature briefly until the mixture was added to the DNA samples on the cycler. Solutions containing the Capture Library were not kept at room temperature for extended periods.

The thermal cycler was pauses at Segment 3 of the Hybridization program (1 minute at 65° C.). With the cycler paused, and while keeping the DNA+Blocker samples in the cycler, 13 µl of the room-temperature Capture Library Hybridization Mix was transferred to each sample well and was mixed well by pipetting up and down slowly 10 times. The wells were sealed with fresh domed strip caps and that all wells were made sure to completely sealed. A compression pad was placed on the plate to prevent evaporation during hybridization. The Play button was pushed to resume the thermal cycling program to allow hybridization of the prepared DNA samples to the Capture Library. Wells were adequately sealed to minimize evaporation to prevent results from being negatively impacted.

Prepare Streptavidin-Coated Magnetic Beads

In some embodiments, the bead preparation steps began approximately one hour after starting hybridization. Reagents for capture from the SureSelect XT HS Target Enrichment Kit ILM Hyb Moedule included the SureSelect Binding Buffer, the SureSelect Wash Buffers 1 and 2 (e.g., all kept at room temperature), and Dynabead MyOne Streptavidin T1 (e.g., stored at 2° C. to 8° C.). Dynabeads MyOne Streptavidin T1 magnetic beads were brought to room temperature for at least 30 minutes. The Dynabeads MyOne Streptavidin T1 magnetic beads were vigorously resuspend on a vortex mixer. The magnetic beads settled during storage. For each hybridization sample, 50 µl of the resuspended beads was added to wells of a fresh PCR plate. The beads were washed by adding 200 µl of SureSelect Binding Buffer, mixing by pipetting up and down 20 times or capping the wells and vortexing at high speed for 5-10 seconds. The plate was put into a magnetic separator device and waited for the solution to clear, approximately 5 minutes. The supernatant was removed and discarded. The wash steps were repeated two more times, for a total of three washed. The beads were resuspended in 200 µl of SureSelect Binding Buffer.

Capture the Hybridized DNA using Streptavidin-Coated Beads

After the hybridization step was complete on the thermal cycler, the samples were transferred to room temperature. The entire volume (approximately 30 µl) was immediately transferred of each hybridization mixture to the wells containing 200 µl of washed streptavidin beads using a multichannel pipette. The mixture was pipetted up and down 5-8 times to mix and then the wells were sealed with fresh caps. The capture plate was incubated on a 96-well plate mixer and was mixed at 1500 rpm for 30 minutes at room temperature. The samples were properly mixed in the wells. During the 30-minute incubation for capture, SureSelect Wash Buffer 2 was pre-warmed in the thermal cycler at 70° C. by placing 200 µL aliquots of Wash Buffer 2 in wells of a fresh 96-well plate and aliquot 6 wells of buffer for each DNA sample in the run.

The wells were capped and then incubated in the thermal cycler, with heated lid ON, held at 70° C. until time for use. When the 30-minute sample incubation period was complete, the samples were briefly spun to collect the liquid. The plate was put in a magnetic separator to collect the beads and was waited until the solution was clear, then the supernatant was removed and discarded. The beads were resuspended in 200 µl of SureSelect Wash Buffer 1 and were mixed by pipetting up and down 15-20 times, until beads were fully resuspended. The plate was put in the magnetic separator and was waited for the solution to clear (approximately 1 minute), and then the supernatant was removed and discarded. The plate was removed from the magnetic separator and was transferred to room temperature. The beads were washed with Wash Buffer 2, using the steps below: 1) resuspend the beads in 200 µl of 70° C. pre-warmed Wash Buffer 2; 2) pipetted up and down 15-20 times, until beads were fully resuspended; 3) incubated the samples for 5 minutes at 70° C. on the thermal cycler with the heated lid on; 4) After the 5 minute incubation, the plate was put in the magnetic separator at room temperature; 5) the solution was waited to clear (approximately 1 minute), then the supernatant was removed and discarded; and 6) the wash steps were repeated five more times for a total of 6 washes.

After verifying that all wash buffer was removed, 25 µl of nuclease-free water was added to each sample well and then pipetted up and down 8 times to resuspend the beads. The plate was sealed and the samples were kept on ice until they were used later. Captured DNA was retained on the streptavidin beads during the post-capture amplification step.

Amplify the captured libraries

In some embodiments, reagents for post-capture PCR amplification were thawed and kept on ice, and included a Herculase II Fusion DNA Polymerase (mixed by pipetting up and down), a 5× Herculase II Reaction Buffer, 100 mM dNTP Mix, and SureSelect Post-Capture Primer Mix (e.g., all mixed by vortexing).

The Post-Capture PCR thermal cycler program was started to preheat the cycler. Appropriate volumes of PCR reaction mix were prepared, on ice, and mixed well on a vortex mixer. For example, a 25 µL reaction volume for 1 reaction contained 12.5 µL of nuclease-free water, 10 µL of 5× Herculase II Reaction Buffer, 1 µL of Herculase II Fusion DNA Polymerase, 0.5 µL of 100 mM dNTP Mix, and 1 µL of SureSelect Post-Capture Primer Mix.

For each reaction, 25 µl of the PCR reaction mix was added to each sample well containing bead-bound target-enriched DNA. The PCR reactions were mixed well by pipetting up and down until the bead suspension was homogeneous. Splashing samples onto well walls was avoided and the samples were not spun at this step. The plate was sealed well. The plate was placed in the thermal cycler and compression pad was placed on the plate to prevent evaporation. The Play button was pressed to resume the Post-Capture PCR thermal cycler program. When the PCR amplification program was complete, the plate was spun briefly. The streptavidin-coated beads were removed by placing the plate on the magnetic stand at room temperature. The solution was waited to clear (approximately 2 minutes), and then each supernatant (approximately 50 µl) was transferred to wells of a fresh plate. The beads could be discarded at this time.

Purify the Amplified Capture Libraries using AMPure XP beads

In brief, the AMPure XP beads were come to room temperature for at least 30 minutes. The beads were not frozen at any time. 400 µl of fresh 70% ethanol per sample was prepared for later use in step as described herein. The AMPure XP bead suspension was mixed well so that the suspension appeared homogeneous and consistent in color. 50 µl of the homogeneous AMPure XP bead suspension was added to each amplified DNA sample (approximately 50 µl) in the PCR plate and was mixed well by pipetting up and down 15-20 times, or the wells were capped and vortexed at high speed for 5-10 seconds. The beads were made sure to be in a homogeneous suspension in the sample wells. Each well had a uniform color with no layers of beads or clear liquid present. The samples were then incubated for 5 minutes at room temperature. The plate was put on the magnetic stand at room temperature and was waited for the solution to clear (approximately 3 to 5 minutes). While keeping the plate on the magnetic stand, the cleared solution from each well was carefully removed and discarded. The beads were not disturbed while removing the solution. The plate was continued to be placed on the magnetic stand while dispensing 200 µl of freshly-prepared 70% ethanol in each sample well and waited for 1 minute to allow any disturbed beads to settle, then the ethanol was removed.

The ethanol wash was repeated once for a total of two washes. All of the ethanol at each wash step was carefully removed. The wells with then sealed with strip caps, and then were briefly spin to collect the residual ethanol. The plate was returned to the magnetic stand for 30 seconds. The residual ethanol was removed with a P20 pipette. Next, the samples were dried by keeping them at room temperature until the wells were dry (about 5-10 minutes). The bead pellet was ensured to not start to crack, as this was a sign of over drying. 25 µl of nuclease-free water was then added to each sample well. The sample wells were sealed, mixed well on a vortex mixer and then briefly spun to collect the liquid without pelleting the beads. The wells were incubated for 2 minutes at room temperature. The plate was put on the magnetic stand and left until the solution was clear. A new PCR plate was labeled with the Run ID. The cleared supernatant (approximately 25 µl) was transferred to the fresh plate. The beads could be discarded at this time. Then, the quality of captured libraries was checked by qPCR methods by using the Roche LightCycler SOP, or stored at −20° C.

Example 5: The Constructions of RNA Libraries for Sequencing

RNA libraries were prepared before performing the downstream sequencing. In brief, this protocol explained how to convert cDNA was synthesized from mRNA in a total RNA sample, into a library of DNA for hybridization capture prior to sequencing. The reagents provided in an Illumina TruSeq Stranded mRNA library prep workflow were used.

The process involved the adenylation of the 3' ends of blunt ended fragments by the addition of one adenine nucleotide. This prevented them from ligating to each other during adapter ligation reaction. One corresponding thymine nucleotide on the 3' end of the adapter provided a complementary overhang for ligating the adapter to the fragment. This strategy ensured a low rate of chimera (concatenated template) formation. In the next step, multiple indexing adapters were ligated to the ends of the ds cDNA fragments, which prepared them for hybridization onto a flow cell. Fragments with no adapters were not hybridized to surface-bound primers on the flow cell. Fragments with an adapter on one end can hybridize to surface bound primers, but did not form clusters. The DNA fragment enrichment process used PCR to selectively enrich those DNA fragments that had adapter molecules on both ends and to amplify the amount of DNA in the library. PCR was performed with a PCR Primer Cocktail that annealed to the ends of the adapters. RNA Library Construction consisted of three steps as described herein. Introduction above followed by a library clean up and library quantitation by qPCR per the protocol of using a nucleic acid amplification device (e.g., a PCR system), for example a real-time PCR system (e.g., a LightCycler Instrument 480 available from Roche, lifescience.roche.com) by Roche Life Science. Accurate quantification achieved by qPCR allowed to create optimum cluster densities across all four lanes of the flow cell.

Some or all of the procedures were managed and conducted by lab personnel. In the event that quality control related issues arise, lab personnel will notify the provider (e.g., healthcare provider) of the biopsy sample or the extracted RNA.

Adenylate 3' Ends

The reagents were prepared according to the conditions below. In brief, 2.5 µL Resuspension buffer was added to each well containing sample (Resuspension Buffer is typically stored at −25° C. to −15° C. and let stand for 30 minutes to bring to room temperature before use). 12.5 µL A-Tailing Mix was added to each well, and then was mixed thoroughly by pipetting up and down 10 times (A-Tailing Mix is typically stored at −25° C. to −15° C. and thawed at room temperature). The plate was sealed and centrifuged at 280×g for 1 minute. The plate was incubated on the ATAIL70 program of the thermal cycler. The ATAIL70 program was as the following steps: 1) preheat lid: 100° C. hold time, 2) step 1: 37° C. for 30 minutes, 3) step 2: 70° C. for 5 minutes, and 4) step 3: 4° C. hold time. The plate was then centrifuged at 280×g for 1 minute.

Ligate Adapters

The reagents were prepared according to the conditions below. In brief, the RNA Adapter tubes were centrifuged at 600×g for 5 seconds. Ligation Mix was removed from −25° C. to −15° C. storage. The following reagents were added in the order listed to each well: 1) 2.5 µL Resuspension Buffer, 2) 2.5 µL Ligation Mix, and 3) 2.5 µL RNA Adapter Indexes. The mixed reagents were then mixed thoroughly by pipetting up and down 10 times and were centrifuged at 280×g for 1 minute. The plate was placed on the thermal cycler and the LIG program was run. The LIG program was as the following: 1) preheat lid: 100° C. hold time, 2) step 1: 30° C. for 10 minutes, and 3) step 2: 4° C. hold time. The Stop Ligation Buffer was centrifuged at 600×g for 5 seconds. Once the LIG program stopped, the plate was removed from thermal cycler and 5 µL Stop Ligation Buffer was added to each well, and was mixed thoroughly by pipetting up and down. The plate was then centrifuged at 280×g for 1 minute. Ligation Mix from storage was not removed until instructed to do so in the procedure. RNA Adapter Indexes are typically stored at −25° C. to −15° C. and thawed at room temperature for 10 minutes prior to use. Resuspension Buffer and AMPure XP Beads are typically stored at 2° C. to 8° C. and let stand for 30 minutes to bring to room temperature before use. Stop Ligation Buffer is typically stored at −25° C. to −15° C. and thawed at room temperature before use.

Clean Up Ligated Fragments

In brief, 42 µL AMPure XP beads were added to each well and mixed thoroughly by pipetting up and down before incubated at room temperature for 15 minutes. After incubation, the mix was centrifuged at 280×g for 1 minute. The wells were then placed on a magnetic stand and waited until the liquid is clear (about 2-5 minutes). While waiting for the liquid to clear, fresh 80% EtOH was made for use in the two washes step above. After the liquid was cleared, all supernatant was removed and discarded from each well, and was wash two times as the following: 1) added 200 µL fresh 80% EtOH to each well, 2) incubated on the magnetic stand for 30 seconds, and 3) removed and discarded all supernatant from each well. 20 µL pipette was used to remove residual EtOH from each well.

The magnetic stand was air-dried for 5 minutes. The bead pellet did not start to crack, as this was a sign of over drying. The magnetic stand was then removed. 52.5 µL Resuspension buffer was added to each well and mixed thoroughly by pipetting up and down before incubating at room temperature for 2 minutes. The mixed buffer was centrifuged at 280×g for 1 minute. A magnetic stand was placed and waited until the liquid was clear (about 2-5 minutes). 50 µL supernatant was transferred to the corresponding well of a newly labeled PCR plate. 50 µL AMPure XP beads were added to the plate and mixed thoroughly by pipetting up and down before incubating at room temperature for 15 minutes. The plate was centrifuged at 280×g for 1 minute. A magnetic stand was placed and waited until the liquid was clear (2-5 minutes). All supernatant was removed and discarded from each well. The well was washed two times as following: 1) added 200 µL fresh 80% EtOH to each well, 2) incubated on the magnetic stand for 30 seconds, and 3) removed and discarded all supernatant from each well.

After that, 20 µL pipette was used to remove residual EtOH from each well. The magnetic stand was air-dried for 5 minutes. The bead pellet was ensured to not starting to crack, as this would be a sign of over drying. The bead pellet was then removed from the magnetic stand. 22.5 µL Resuspension Buffer was added to each well and mixed thoroughly by pipetting up and down before incubating at room temperature for 2 minutes. The wells then were centrifuged at 280×g for 1 minute. A magnetic stand was placed and waited until the liquid was clear (2-5 minutes). 20 µL supernatant was transferred to the corresponding well of a newly labeled PCR plate. The beads were not disturbed during the process. Alternatively, this step was a safe stopping point. The plate could be sealed and stored at −25° C. to −15° C. for up to 7 days.

Enrich DNA Fragments

The reagents were prepared according to the conditions below. In brief, the PCR plate was placed on ice and 5 µL PCR primer cocktail was added to each well. 25 µL PCR Master Mix was added to each well, and then mixed thoroughly by pipetting up and down 10 times. The sample wells were sealed and centrifuged at 280×g for 1 minute. The sample wells were placed on the thermal cycler and the mRNA PCR program was performed. The mRNA PCR program was as the following: 1) preheat lid: 100° C. hold time, 2) step 1: 98° C. for 30 seconds, 3) step 2 (15 cycles): 98° C. for 10 seconds, 60° C. for 30 seconds, and 72° C. for 30 seconds, 4) step 3: 72° C. for 5 minutes, and step 4) 4° C. hold time.

Once the program was complete and the plate was centrifuged at 280×g for 1 minute. AMPure XP beads were mixed by thorough vortexing and 50 µL was added to each well and mixed thoroughly by pipetting up and down 10 times before incubating at room temperature for 15 minutes. The sample wells were centrifuged at 280×g for 1 minute. A magnetic stand was placed and waited until the liquid was clear (2-5 minutes). All supernatant was removed and discarded from each well. The wells were washed two times as the following: 1) added 200 µL fresh 80% EtOH to each well, 2) incubated on the magnetic stand for 30 seconds, and 3) removed and discarded all supernatant from each well. A 20 µL pipette was used to remove residual EtOH from each well. The magnetic stand was air-dried for 5 minutes. The bead pellet was ensured to not start to crack, which was a sign of over drying. The magnetic stand was removed next. 32.5 µL Resuspension buffer was added to each well, and was mixed thoroughly by pipetting up and down 10 times before incubating at room temperature for 2 minutes. The wells were centrifuged at 280×g for 1 minute. A magnetic stand was placed and waited until the liquid was clear (2-5 minutes). 30 µL supernatant was suspended to the corresponding well of a newly labeled PCR plate. The lab personnel then proceeded with library QC using the a nucleic acid amplification device (e.g., a PCR system), for example a real-time PCR system (e.g., a LightCycler Instrument 480 available from Roche, lifescience.roche.com), or the plate was sealed and stored at −20° C. for up to 7 days. PCR Primer Cocktail is typically stored at −25° C. to −15° C. and thawed at room temperature before use. PCR Master Mix is typically stored at −25° C. to −15° C. and thawed on ice before use. Resuspension Buffer and AMPure XP Beads are typically stored at 2° C. to 8° C. and let stand for 30 minutes to bring to room temperature before use.

Resource from the manufacturers, including TruSeq Stranded mRNA Reference Guide, is incorporated by reference herein.

Example 6: Quality Control Concerning the DNA/RNA Library Preparation Process based on DNA and RNA from Fresh Frozen Tissue Library Sequencing For library preparation, extracts of DNA and RNA from the tissue were obtained by using the AllPrep DNA/RNA Mini Kit. Any suitable extraction kit known in the art could also be used. Library construction from purified DNA was carried out with Agilent SureSelect XT HS and Agilent SureSelect Human All Exon V7 exome kits. Library construction from purified RNA was carried out with Illumina TruSeq mRNA stranded kit. Quality control (QC) metrics were carried out after each stage of library preparation. All QC metrics were prepared with a spectrophotometer, for example a small volume full-spectrum, UV-visible spectrophotometer (e.g., Nanodrop spectrophotometer available from ThermoFisher Scientific, thermofisher.com), a fluorometer, for example for quantification of DNA or RNA (e.g., a Qubit Flex fluorometer available from ThermoFisher Scientific, thermofisher.com), a nucleic acid amplification device (e.g., a PCR system), for example a real-time PCR system (e.g., a LightCycler Instrument 480 II available from Roche, lifescience.roche.com) and an electrophoresis device, for example an automated electrophoresis device (e.g., a, Agilent TapeStation System 4150 available from Agilent, agilent.com). All measurement content carried purity, concentrations and size of DNA/RNA fragments.

QC metrics during the next generation sequencing experiment were a set of individual parameters that evaluated the overall quality of the data set. The following metrics were evaluated: cluster density, percentage of clusters passing filters that were assigned to an index, quality score of 30 (Q30) and error rate. The next stage was to estimate quality metrics used in the bioinformatics pipeline (Bioinformatics QC). It was divided into two processes: WES (DNA sequencing) and RNA sequencing (RNA-seq). The following metrics were taken into account: tumor purity, depth of coverage, alignment rate, base call quality scores or Phred score, uniformity of coverage, GC content, mapping quality, duplication rate, insert size, contamination, SNP concordance, HLA allele concordance and ADA genomes contamination.

In general, the protocol described in the present example provides the metrics for QC methods used in the library preparation stages and in the bioinformatic pipeline of whole-exome sequencing (WES) and RNA-seq analysis. Bioinformatic pipeline was divided into two components: QC from sequencing platform and Bioinformatics QC. On a sequencer platform and in Bioinformatics QC, a table with estimated metrics for WES and RNA-seq data was provided. For some metrics within a targeted range, which were the most appreciable value and acceptable range, the sample data could be used. If the values of the obtained metrics fell outside of the acceptable range, the corresponding sample was considered having poor quality.

In any given experiment or project, one or more of the quality control processes can be used. In some experiment or project, all of the quality control processes can be used. Some or all of the procedures were managed and conducted by lab personnel. In the event that quality control related issues arise, lab personnel will notify the provider (e.g., healthcare provider) of the biopsy sample or the extracted DNA/RNA.

Quality control steps in the process of DNA and RNA library preparation

Table 4—Table 6 describe embodiments of DNA and RNA library preparation including one or more quality control steps at each phase: extraction, library construction, and hybridization and capture. Measuring the concentrations of extracts, primary libraries and libraries after hybridization and capture, the quality of products from the samples were identified. Based on the determination of the quality of DNA or RNA in the tested sample, a decision was made to either go forward to the next step or to repeat the processes. A spectrophotometer, for example a small volume full-spectrum, UV-visible spectrophotometer (e.g., Nanodrop spectrophotometer available from ThermoFisher Scientific, thermofisher.com), a fluorometer, for example for quantification of DNA or RNA (e.g., a Qubit fluorometer available from ThermoFisher Scientific, thermofisher.com), an electrophoresis device, for example an automated electrophoresis device (e.g., a TapeStation System available from Agilent, agilent.com) and a nucleic acid amplification device (e.g., a PCR system), for example a real-time PCR system (e.g., a LightCycler Instrument available from Roche, lifescience.roche.com) were used for measuring purity, concentrations and size of DNA/RNA fragments. The acceptable and the targeted ranges of DNA and RNA for the respective devices for each phase are indicated in the tables below. The results of the quality control can be confirmed by performing electrophoresis. The results of the quality control can be confirmed by the determination of the size distribution of the nucleic acids.

The present Example provides troubleshooting protocols. For example, if an additional peak at 150 bp at the electropherogram from the TapeStation on the LC or HC stage was observed. An additional step of washing with AMPure beads (library to beads 1: 0.8 volume ratio) were made.

TABLE 4

Quality Control: Extraction of DNA or RNA for Library Preparation
Extraction

| Device | DNA (Acceptable\|Target) | RNA (Acceptable\|Target) | Comments |
|---|---|---|---|
| | Total amount for next step 20-200 ng \| 30-200 ng | Total amount for next step 100-1000 ng \| >200-1000 ng | |
| Nanodrop | concentration >4 ng/ul \| >5.5 ng/ul | concentration >3 ng/ul \| >5 ng/ul | If the metrics are out of range you have to repeat extraction process |
| | 260/280   >1.5 \| 1.8-2.0 | 260/280   >1.5 \| 1.8-2.0 | |
| | 260/230   >1.5 \| 2.0-2.2 | 260/230   >1.5 \| 2.0-2.2 | |
| Qubit | Concentration >3 ng/ul \| >4.5 ng/ul | Concentration >2 ng/ul \| >4 ng/ul | |
| Tapestation | Concentration >2.5 ng/ul \| >4 ng/ul | Concentration >1.5 ng/ul \| >3 ng/ul | |
| | | RIN >5 \| >8 | |

TABLE 5

Quality Control: DNA or RNA for Library Construction
Library construction

| Device | DNA (Acceptable\|Target) | RNA (Acceptable\|Target) | Comments |
|---|---|---|---|
| | Total amount for next step 200-1000 ng \| 500-1000 ng | Total amount for next step 0.5-4 nmol/l \| 0.5-4 nmol/l | |
| Qubit | Concentration >17 ng/ul \| >42 ng/ul | Concentration >0.1 ng/ul \| >0.1 ng/ul | If the metrics are out of range, extraction process can be repeated. |
| Tapestation | Concentration >15 ng/ul \| >40 ng/ul | Concentration >0.1 ng/ul \| >0.1 ng/ul | If an electropherogram with an additional peak at 150 bp is observed, the troubleshooting as described in the present Example would provide guidance. |
| | | Concentration >0.5 nmol/l \| >0.5 nmol/l | |
| | | Average 370-440 \| 370-440 | |
| LightCycler | Not required | Concentration >0.5 nmol/l \| >0.5 nmol/l | |

TABLE 6

Quality Control: DNA or RNA for Library after Hybridization and Capture

| Device | DNA (Acceptable|Target) Final concentration for pooling | Comments |
|---|---|---|
| | 0.5-4 nmol/l | 0.5-4 nmol/l | |
| Qubit | Concentration >0.1 ng/ul | >0.1 ng/ul | If the metrics are out of range, extraction process can be repeated. |
| Tapestation | Concentration >0.1 ng/ul | >0.1 ng/ul | If you see an electropherogram with an additional peak at 150 bp is observed, look in the troubleshootinglist (#1) as described in the present Example would provide guidance. |
| | Concentration >0.5 nmol/l | >0.5 nmol/l | |
| | Average 380-440 | 380-440 | |
| LightCycler | Concentration >0.5 nmol/l | >0.5 nmol/l | |

Quality control steps afterDNA and RNA library preparation

The main quality control metrics for the sequencing process occurred on the Illumina NextSeq® 500/550 sequencer. Table 7 shows the QC parameters of the sample run for whole-genome sequencing (WES) and RNA-sequencing.

TABLE 7

Quality Control: Sequencing Processes Sample run

| QC parameter | Targeted values WES | Targeted values RNA-seq | Comments |
|---|---|---|---|
| Cluster density CLUSTER PF (%) | Targeted range 170-220 Acceptable range <280 | Targeted range 170-220 Acceptable range <280 | Cluster density and Alignment rate should be monitored in every run. |
| Actual Yield | >15 Gbp | | The yield that's been received |
| % ≥Q30 | Targeted range >85% Acceptable range >75% | Targeted range >85% Acceptable range >75% | The percentage of bases with a quality score of 30 or higher Quality scores and quality of signal/noise ratio should be monitored in every run. |
| ERROR RATE % | Targeted <0.7% Acceptable <1% | Targeted <0.7% Acceptable <1% | Refers to the percentage of bases called incorrectly at any one cycle. It is calculated from the reads that are aligned to Illumina's PhiX control. If this was not used then % Q30 would be the best tool to check base quality. Error rate increases along the length of the read. |

Bioinformatics QC

After the performance of sequencing (e.g., RNA seq), quality control can be performed for bioinformatics pipeline. In brief, the software was created and generated by the following parameters for measurements: single nucleotide variants (SNVs; somatic plus germline variants), small indels, copy number alterations (CNAs) (plus loss of heterozygosity (LOH)), focal amplifications/deletions, gene fusions rearrangement (mRNA expressed), fusion protein expression, RNA expression (for biomarker proteins), and tumor mutational burden (TMB).

In any given experiment or project, one or more paramaters could be used for quality control. For example, only SNV detection was performed for certain bioinformatic analysis. Only in/del detection was performed for certain bioinformatic analysis. Only CNA detection was performed for certain bioinformatic analysis. Only fusion detection was performed for certain bioinformatic analysis. Only RNA expression measurement detection was performed for certain bioinformatic analysis. Only TMB measurement detection was performed for certain bioinformatic analysis. In other examples, SNV detection and CAN detection can be performed for certain bioinformatic analysis.

Table 8 provides a lists of quality control parameters for bioinformatics analysis.

TABLE 8

| QC parameter | Targeted values WES | Targeted values RNA-seq | Comments |
| --- | --- | --- | --- |
| Tumor purity | >=20% | >=20% | In case of failure - inform the physician if to proceed with sample below LOD |
| Depth of coverage | >=150x average coverage - tumor sample >=100x average coverage of normal tissue | >50 mln pair-end reads | In case of failure - resequence the sample |
| Alignment rate | >90% | >90% | |
| Base call quality scores | Phred score >30 | Phred score >30 | Quality scores and quality of signal/noise ratio should be monitored in every run. Low-quality scores can lead to increased false-positive variant calls; thus, results must be interpreted with caution and repeat testing may be indicated. |
| Uniformity of coverage | 85% of base pairs in target regions covered >=20x for tumor tissue 85% of base pairs in target regions covered >=20x for normal tissue | Not applicable | — |
| GC bias | Targeted value 50 Acceptable range: 45-65 | Targeted value 50 Acceptable range: 45-65 | GC bias should be monitored with every run to detect changes in test performance or sample quality issues. In the last assembly of the reference human genome, the GC composition for the entire genome is ~40%, 48.9% for the RNA encoding. We use ExonV7 kit, the mean GC content for the targets there is 47.9%. |
| Mapping quality | MapQ >=10 | Not applicable | The proportion of reads that do not map to target regions must be monitored during each run. Poor mapping quality may be a result of non-specific amplification, capture of off target DNA, or contamination. Reads with MapQ = 0 are obtained with simultaneous alignment to several regions. |
| Duplication rate | <30% | <85% | The duplication rate should be monitored in every run and for each sample independently to monitor library diversity. |
| Insert size | Median insert size for tumor tissue~[150; 200] Median insert size for normal tissue~[150; 200] | Median insert size~[150; 200] | Insert size is the length of the sequencing DNA (or RNA) that is "inserted" between the adapters. |
| Contamination | <0.05% | <0.05% | Contamination - Percentage of sequence segments of foreign origin in sample. |

TABLE 8-continued

Quality Control: Bioinformatics
Bioinformatics

| QC parameter | Targeted values WES | Targeted values RNA-seq | Comments |
| --- | --- | --- | --- |
| SNP concordance of a pair of samples tumor/nomial from the same patient | Targeted >90% Acceptable >85% | Targeted >90% Acceptable >85% | A contaminated sequence is one that does not faithfully represent the genetic information from the biological source In case of failure, investigate where the mix-up could have happened. Stop the bioinformatics analysis until the troubleshooting and sample concordance |
| HLA allele concordance of a pair of samples tumor/normal from the same patient | Threshold for normal vs tumor tissue <5 | Threshold for tumor RNAseq vs normal WES tissue <5 | In case of failure - Investigate where the mix-up could have happened. Stop the bioinformatics analysis until the troubleshooting and sample concordance |
| ADA genomes contamination | Targeted threshold >60 Acceptable threshold >40 (with WARNING sign) | Targeted threshold >40 Acceptable threshold >20 (with WARNING sign) | For One hit one genome, GRCh38.d1.vd1 In case of failure - report to lab personnel |

The present Example provides troubleshooting protocols. For example, if the quality control of HLA allele concordance of tumor/normal pair failed, it was an indicator that the tissues from different patients were potentially mixed up. The lab personnel should proceed to confirm the potential mix up and investigate the reason of the potential mix up. The lab personnel should reach out to the physician if the mix up was not due to the internal errors in the laboratory.

Figures 11, 12:
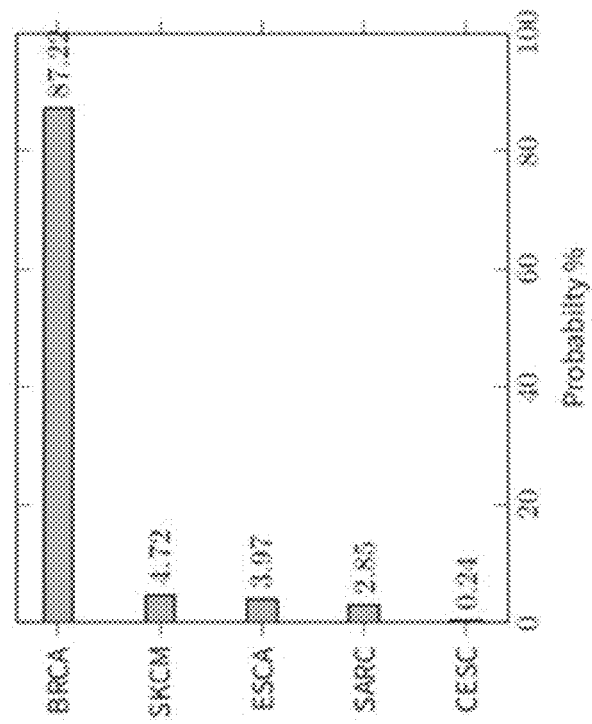
FIG. 11 shows the results of MHC allele analysis for sequence information obtained from three nucleic acids (RNA-Seq, WES Tumor, and WES Normal) for two subjects (103 and 105).
FIG. 12 shows an example of a bar graph representing the probability of sequence information being from a particular type of tumor (e.g., BRCA related to breast cancer).

Example 7: Determining the Sequence of Major Histocompatibility Complexes (MHC) can be used to Assess Sequence Data Identity and/or Integrity MHC genes are highly polymorphic, with large numbers of alleles for the genes of each class (e.g., Class I, II, and III) of MHC (e.g., human leukocyte antigens (HLAs) in humans). The combination of the number of potential alleles in a population with the number of genes in each individual result in a large number of unique MHC profiles. These can be used to assess the likelihood that sequence data is from a given source or subject (or if sequence data from multiple samples are from the same subject). Sequences corresponding to one or more MHC loci can be used to determine an MHC allele combination for a particular nucleic acid sample. The result of the sequencing one or more MHC loci can be evaluated against asserted information (e.g., an asserted HLA allele combination) which is expected to be consistent with the sequence data. If the determined MHC combination matches the asserted information, the sequence data is consistent. If the determined MHC combination does not match the asserted information, the sequence data is inconsistent and this can indicate a problem with the sample and/or sequence data. For example, the sample and/or sequence data may have been contaminated, misidentified, degraded, or otherwise corrupted. This can prompt investigation into the origin of the inconsistency. Such investigation may entail determining the sequence of the sequence data at the MHC loci at least one additional time, obtaining a second sequence data from the sample and determining the sequences of the sequence data at the MHC loci at least one additional time, reporting the sequence data as inconsistent, and/or a combination thereof. FIG. 11 illustrates an example of MHC data validation. In FIG. 11, six HLA alleles are determined from each of three sequence data sets (RNA-Seq data, WES tumor data, and WES normal data) from two subjects (e.g., 103 and 105). As can be seen from FIG. 11, all three samples share all six alleles for subject 105, indicating they are consistent and likely from the same subject. In the case of subject 103 however, there is consistency for two sequence data sets (between whole exome sequence data from a tumor sample (WES Tumor) and whole exome sequence data from a normal sample (WES Normal)), but an inconsistency for a third sequence data set (RNA sequence data allegedly from the same subject 103).

In some embodiments, the sequence of at least one MHC locus is determined and verified against at least one MHC sequence of the same locus from a reference sequence data set (e.g., from a sample asserted to be from the same subject). In some embodiments, two or more MHC alleles loci are sequenced (e.g., at least three, four, or five MHC loci are sequenced). In some embodiments, six MHC loci are sequenced. In some embodiments, more than six MHC loci are sequenced In some embodiments, the sequence data is from a human subject. In some embodiments, the MHC is human leukocyte antigens (HLA). Accordingly, in some embodiments two or more HLA loci are sequenced (e.g., three, four, five, or more HLA loci). In some embodiments, six HLA loci are sequenced. In some embodiments, more than six HLA loci are sequenced.

In some embodiments, the results are displayed to a user in a report (e.g., via a GUI).

Example 8: Predicted Tumor Type can be used to Assess Sequence Data Identity and/or Integrity Various techniques can be used to predict, based on nucleic acid sequence data, the type of tumor from which a sample was taken (e.g., breast, colon, prostate, bladder, kidney, rectal, lung, lymphoma, melanoma, oral, oropharyngeal, pancreatic, thyroid, uterine, eye, gastrointestinal, etc.). Many existing tools rely on large data sets of known samples with evaluated biomarkers, thereby allowing for the comparison of biomarkers from a sequence data set to be evaluated against an existing known data set. Other methods of prediction utilize neural networks and deep learning systems to analyze data sets and perform the data analysis. The sequence data can be trained against an existing network or data set to predict the type of tumor from which the sequence data was obtained.

The result of a tumor type prediction (e.g., determined information) can then be evaluated against asserted information (e.g., a tumor type) which is believed to be consistent with the sequence data. If the determined information matches the asserted information, the sequence data is consistent and believed to be identified correctly. If the determined information matches the asserted information, the sequence data can be processed to determine whether the sequence data is indicative of one or more disease features. If the determined information does not match the asserted information, the sequence data is inconsistent and may indicate a problem with the sample or sequence data. For example, the sample and/or sequence data may have been contaminated, misidentified, degraded, or otherwise corrupted. This can prompt investigation into the origin of the inconsistency. Such investigation may entail predicting the tumor type from the sequence data at least one additional time, obtaining a second sequence data set from the sample and performing the prediction at least one additional time, reporting the sequence data as inconsistent, and/or a combination thereof.

As can be seen in FIG. 12, a tumor type can be predicted (e.g., BRCA associated breast cancer) and evaluated in the context of an asserted tumor type or in the context of at least one additional sequence data set (e.g., reference sequence data, or sequence data from the same subject and/or the same tumor sample). If the asserted information matches the determined information, the data is consistent. If they do not match, it signals a possible inconsistency which may be evaluated and/or reported to the user. Further, when the determined value is evaluated in the context of additional sequence data, it can be used to evaluate whether the sequence data are from the same subject or source, or from different sources.

Accordingly, in some embodiments a predicted tumor type is determined from the sequence information and evaluated against an asserted tumor type. In some embodiments, the results are displayed to a user in a report (e.g., via a GUI).

Example 9: Ratio of Protein Subunits can be used to Assess Sequence Data Identity and/or Quality Multi-subunit proteins encoded by the nucleic acid can be used to evaluate the sequence data. The expression levels of different subunits of a protein can be evaluated by determining the expression of each subunit (e.g., by determining DNA or RNA levels encoding each subunit) and determining a ratio of the subunits (e.g., by determining a ratio of DNA or RNA levels encoding different protein subunits in a nucleic acid sample). This ratio (determined information) can then be validated against either asserted information (e.g., an expected ratio) or additional sequence data. If the ratio matches an expected ratio (e.g., a ratio either believed to be accurate based on other sequence data obtained from the subject, or a known ratio for the protein and its constituent subunits), the sequence information can be validated. If the determined ratio does not match the expected ratio, the sequence data is inconsistent and may indicate a problem with the sample or sequence data. For example, the sample and/or sequence data may have been contaminated, misidentified, degraded, or otherwise corrupted. This can prompt an investigation into the origin of the inconsistency. Such investigation may entail determining a new ratio from the sequence data at least one additional time, obtaining a second sequence data set from the sample and determining the ratio at least one additional time, reporting the sequence data as inconsistent, and/or a combination thereof.

Figure 13A:
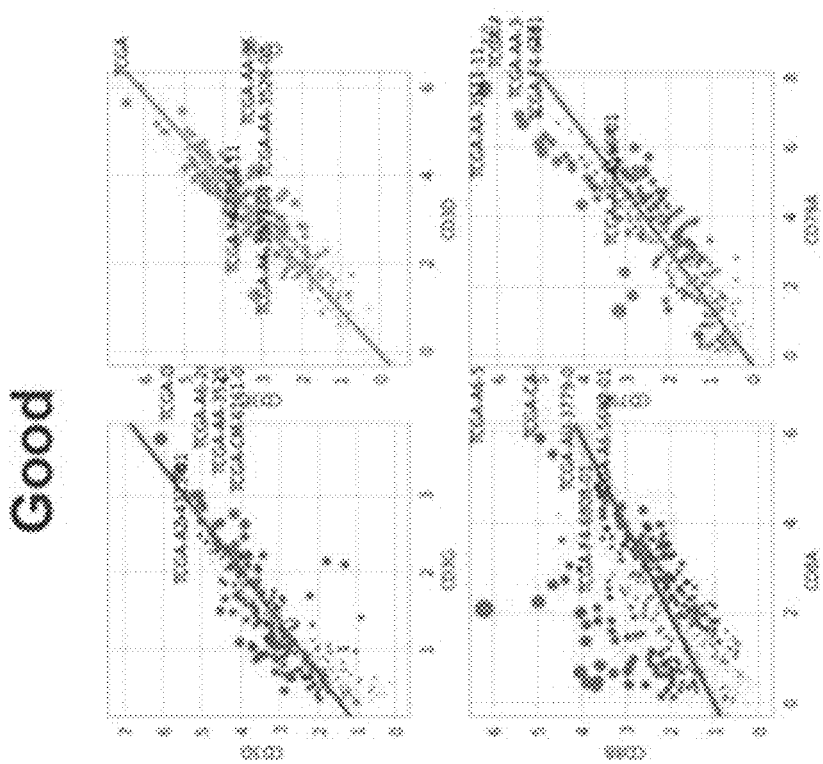
FIGS. 13A-13B show graphs representing an example of the relationship between protein subunit expression levels.
Figure 13B:
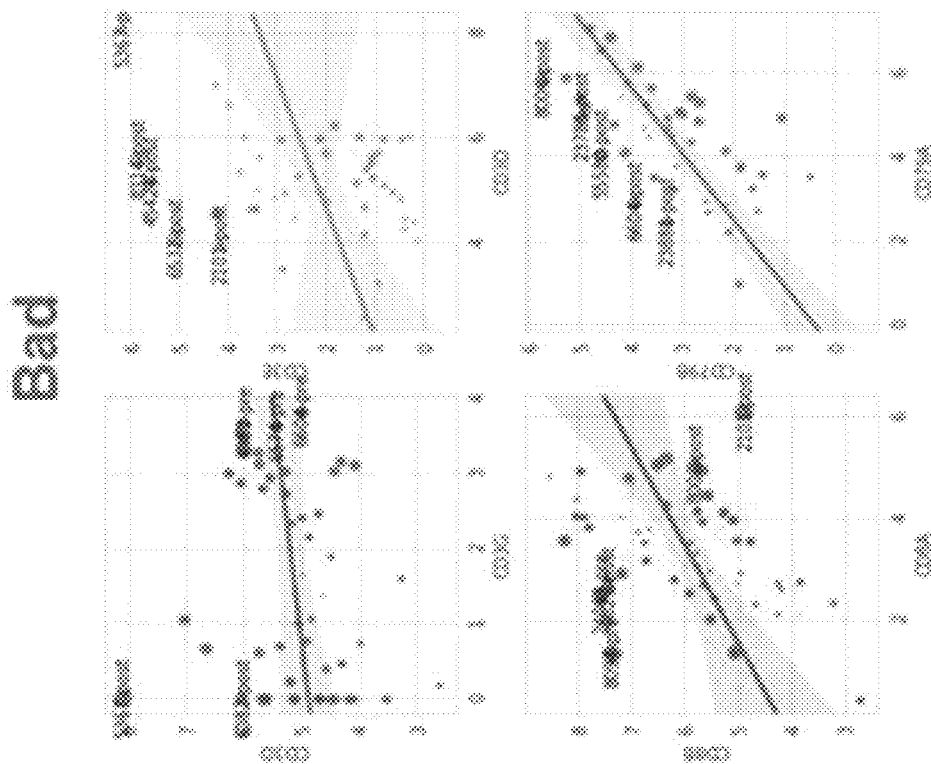

FIG. 13A shows a graph representing expression levels of subunits which agree with a predicted or known value for the subunits being evaluated or are within an acceptable or determined threshold for such ratio. FIG. 13B shows a graph representing expression levels of subunits which disagree with the predicted or known value for the subunits being evaluated or are outside an acceptable or determined threshold for such ratio.

As can be seen in FIG. 13A, nucleic acids encoding protein subunits can be evaluated against a known ratio (e.g., an existing measured value, or a theoretical value based on sequences known in the art) or can be evaluated against measured data from known samples (e.g., fit to a line as shown). When the ratio falls within accepted or established thresholds for variability and deviation, it is identified as consistent. As can be seen in FIG. 13B, nucleic acids encoding protein subunits can evaluated against a known ratio (e.g., existing measured value, or theoretical value based on sequences known in the art), or can be evaluated against measured data from known samples (e.g., fit against a line as shown). When the ratio falls outside accepted or established thresholds for variability and deviation, it can be identified as inconsistent. In some embodiments, at least one ratio is determined. In some embodiments, nucleic acids encoding a second protein and/or its subunits are evaluated to determine a second ratio. In some embodiments, nucleic acids encoding a third protein and/or its subunits are evaluated to determine a third ratio. In some embodiments, nucleic acids encoding a fourth protein and/or its subunits are evaluated to determine a fourth ratio. In some embodiments, nucleic acids encoding at least one additional protein and/or its subunits are used to determine at least one additional ratio.

In some embodiments, the subunits used to determine the ratio are CD3 subunits CD3D and CD3G. In some embodiments, the subunits used to determine the ratio are CD3 subunits CD3E and CD3D. In some embodiments, the subunits used to determine the ratio are CD3 subunits CD3G and CD3E. In some embodiments, the subunits used to determine the ratio are CD8 subunits CD8B and CD8A. In some embodiments, the subunits used to determine the ratio are the CD79 subunits CD79A and CD79B.

In some embodiments, the results are displayed to a user in a report (e.g., via a GUI).

Example 10: Polyadenylation Status can be used to Assess Sequence Data Identity and/or Integrity PolyA status can be used to evaluate the sequence data. The sequence data can evaluated to determine whether different genes are polyadenylated are present or not (e.g., histone genes, mitochondrial genes). This analysis can be used to evaluate and or assess the likelihood that an asserted sample preparation protocol is correct (e.g., to validate whether an RNA sample is a polyA or a total RNA sample). If the determined polyA status matches the asserted polyA status, the sequence data is validated as consistent. If the determined polyA status does not match the asserted polyA status, the sequence data is identified as inconsistent and may indicate a problem with the sample or sequence data. Additionally, in the instance where ambiguous results are returned for the polyA status (e.g., where polyadenylated genes are found, but others are not, or where unanticipated expression is found, or where less than expected expression is found (e.g., partial expression)), it may indicate problems with the sample preparation, degradation of the sample from which the sequence data was prepared, or other quality issues. For example, the sample and/or sequence data may have been contaminated, misidentified, degraded, or otherwise corrupted. This can prompt an investigation into the origin of the inconsistency. Such investigation may entail determining a polyA status from the sequence data at least one additional time, obtaining a second sequence data from the sample and determining the polyA status at least one additional time, reporting the sequence data as inconsistent, and/or a combination thereof.

Figure 14A:
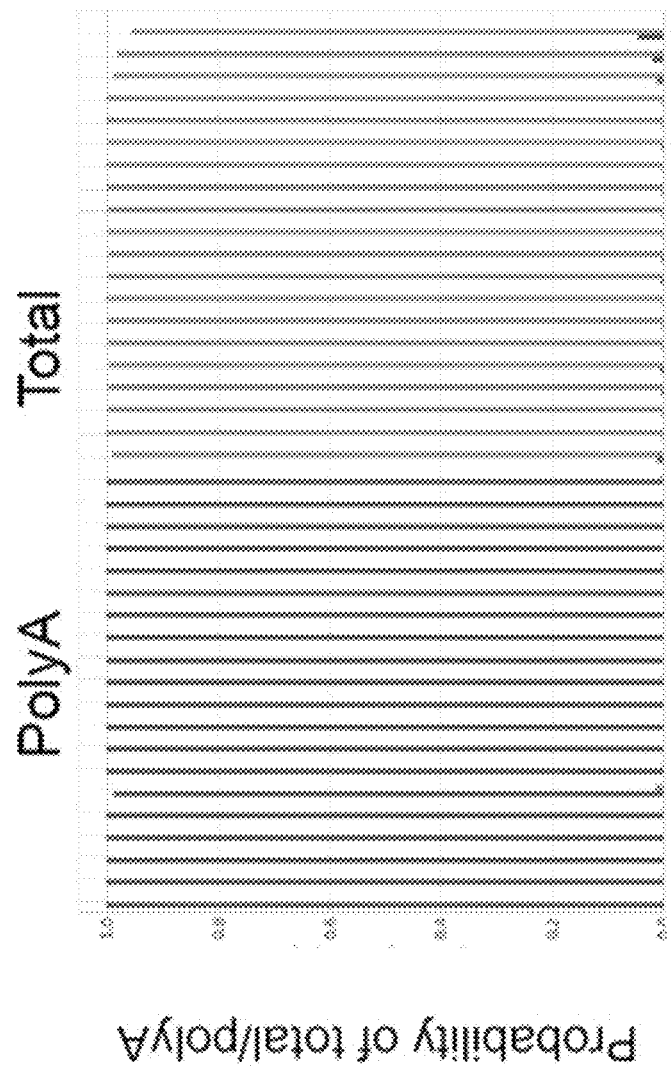
FIGS. 14A-14B show examples of bar graphs representing the probability that sequence information was obtained from samples that contained only polyadenylated RNA or from samples that contained total or all RNA (total RNA).
Figure 14B:
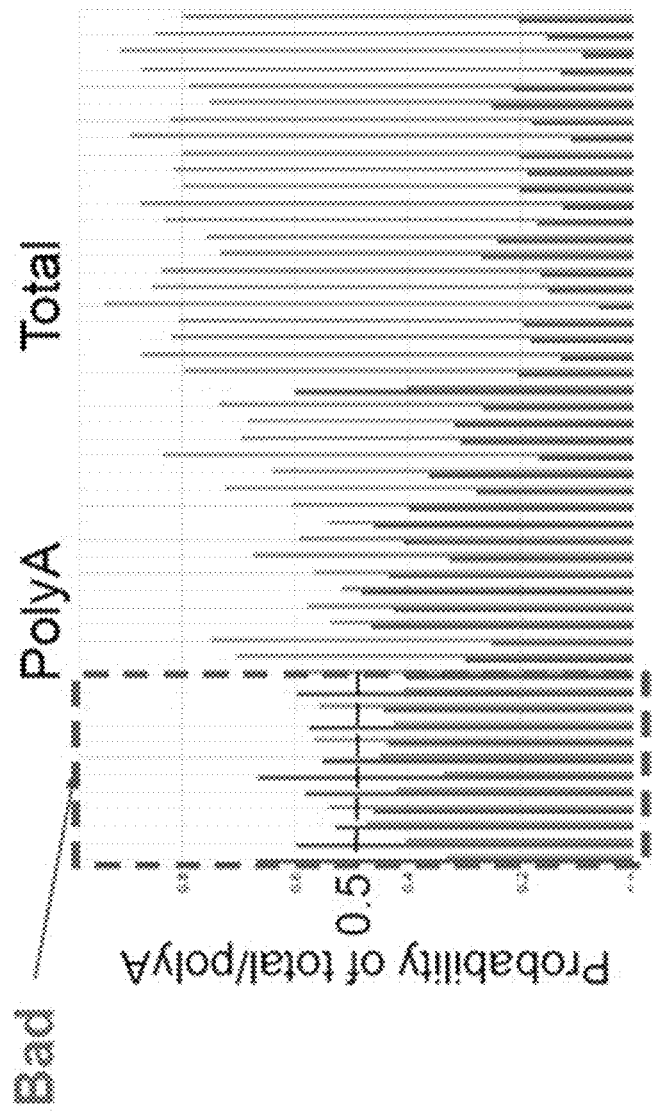

FIGS. 14A-14B show examples of bar graphs representing the probability that sequence information was obtained from samples that contained only polyadenylated RNA or from samples that contained total or all RNA (total RNA). FIG. 14A shows positive results (indicating sequences which appear uniform) from the analysis of two different sequences. The left set of bars (bars 1-20, as read left to right) show results from a sequence which has a high probability of being from samples which contained primarily polyadenylated RNA. The right set of bars (bars 21-40, as read left to right) show results from a sequence which has a high probability of being from samples which contained primarily total RNA. FIG. 14B shows poor results (indicating, for example, possible contamination or degradation) from the analysis of two different sequences. The outlined box, tagged "Bad," shows probability of the sequences as being from polyadenylated RNA about 50%, indicating it is indeterminate that the sequences are uniform.

As can be seen in FIG. 14A, the sequence data can be evaluated and a polyA status can be determined as either polyadenylated or total RNA in some embodiments. FIG. 14B shows an example where the determination falls below a threshold of either polyadenylated or total RNA (e.g., 50% polyA, 50% total RNA). In this case, the sequence data can be identified as inconsistent and/or of poor quality and may signal a problem with the nucleic acid sample. Accordingly, in some embodiments the sequence data is identified as polyadenylated sequence data. In some embodiments, the sequence data is identified as total RNA sequence data. In some embodiments, the threshold for identifying a sample as polyA is when the percent polyA RNA in a sample is above 50%. In some embodiments, the threshold is 60%. In some embodiments, the threshold is 70%. In some embodiments, the threshold is 80%. In some embodiments, the threshold is 90%. In some embodiments, the threshold is 95%. In some embodiments, the threshold is 96%. In some embodiments, the threshold is 97%. In some embodiments, the threshold is 98%. In some embodiments, the threshold is 99%. In some embodiments, the results are displayed to a user in a report (e.g., via a GUI).

Example 11: Exon Coverage can be used to Assess Sequence Data Identity and/or Integrity Various techniques can be used for evaluating the consistency of data and/or to group data points for analysis (e.g., in some embodiments principal component analysis (PCA) can be used). Such techniques can be useful in evaluating sequence data for identity and/or integrity. For instance, exon coverage can be determined from the sequence information and evaluated to determine whether there is a consistent level of coverage when compared to other sequence information or to an asserted (e.g., expected) coverage level. An inconsistency in the coverage (e.g., higher or lower coverage than expected) could indicate that the sequence data is from a different source than expected (e.g., than asserted), or that there is a problem with the sequence data or the sample from which it was obtained.

Exon coverage can be determined for different batches of sequence data reads from a given subject and plotted against sequence data from other subjects. In some embodiments, the results of the evaluation are presented to a user in a report (e.g., via a GUI).

Example 12: RNAseq Read Distribution and Composition can be used to Assess Sequence Data Identity and/or Integrity In some embodiments, read composition can be evaluated in the context of the number of reads of a given component (e.g., protein coding sequence) of the sequence data in terms of either total number of reads for that component and/or as a relative percentage of that component calculated against the total number of reads). These can be compared against a threshold established for each parameter (e.g., total number of reads, and/or reads of a component relative to the total number of reads).

In some embodiments, a threshold is 20 million total reads per protein coding region. In some embodiments, a threshold for the relative number of reads of a protein coding region compared to the total number of reads in a sample is 50% or more. In some embodiments, the results are displayed to a user in a report (e.g., via a GUI).

Example 13: Biomarkers can be used to Assess Sequence Identity and/or Integrity

Figure 15:
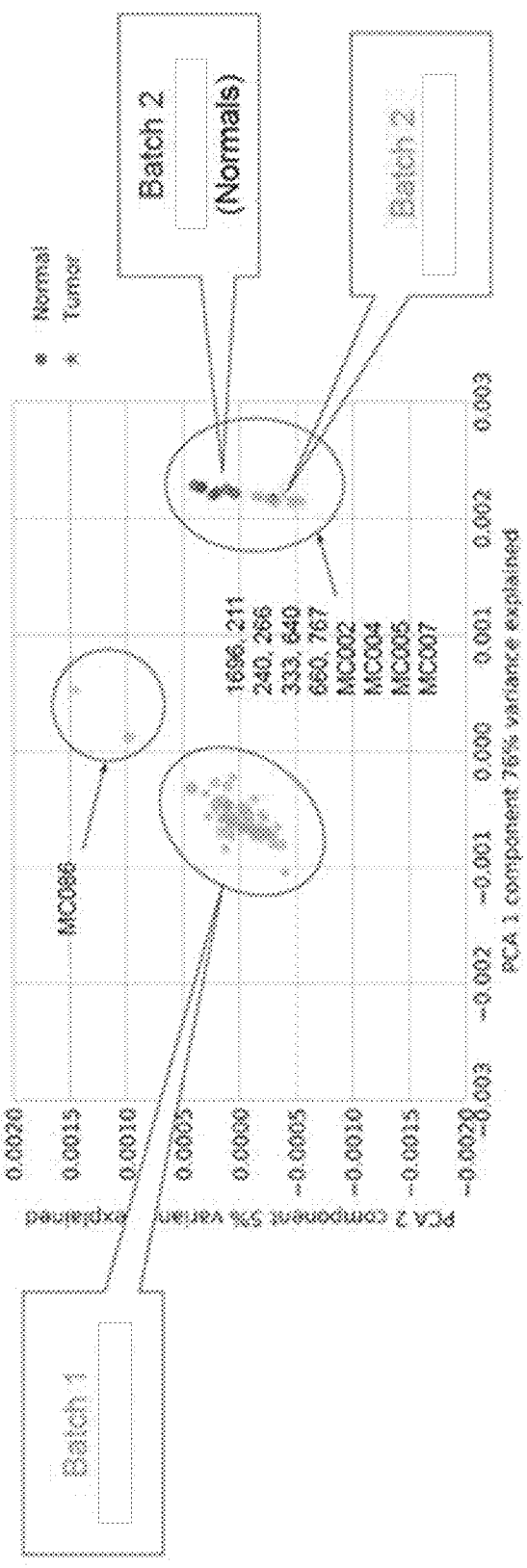
FIG. 15 shows an example of a principal component analysis and illustrates the analysis of three batches of gene expression data including tumor and normal samples.

Biomarkers can also be assessed to evaluate the quality and/or identity of the sequence data. As shown in FIG. 15, PCA can be performed to evaluate the expression of biomarkers. The results can be compared or trained against existing data sets of similar cohorts. The evaluation can be used to help validate an asserted information and/or one or more additional sequence data sets. In some embodiments, this will be useful to determine with increased likelihood that the sequence information is from a given source or subject. In contrast, inconsistency (e.g., if the evaluation does not match the asserted information and/or one or more additional sequence data sets) may indicate that there is a potential quality issue related to the data that should be further investigated to identify the source of the inconsistency (and/or that that the data should not be used for further analysis).

In some embodiments, the biomarker is for follicular lymphoma. In some embodiments, the results are displayed to a user in a report (e.g., via a GUI).

Example 14: Non-Limiting Examples of Quality Control Metrics for Assessing Sequence Data Identity and/or Integrity In some embodiments, the disclosure relates to a method wherein at least one of the following additional features is determined: (1) mean quality score; (2) contamination value; (3) GC content; (4) duplication level; (5) gene body coverage; and (6) per chromosome coverage. One or more of these determinations can be used to further assess the source or integrity of the sequence data by comparison with a reference, or by comparison with at least one additional sequence data set.

In some embodiments, at least one additional feature is determined. In some embodiments, at least two additional features are determined. In some embodiments, at least three additional features are determined. In some embodiments, at least four additional features are determined. In some embodiments, at least five additional features are determined. In some embodiments, at least six additional features are determined.

In some embodiments, evaluation of a concordance value of single nucleotide polymorphisms (SNPs) comprises: (a) determining a concordance value of single nucleotide polymorphisms (SNPs) from the sequence data; and (b) determining whether the concordance value of the sequence data matches or exceeds a reference concordance value. In some embodiments, the reference concordance value is 80%.

In some embodiments, evaluation of a contamination value comprises; (a) determining a contamination value of the sequence data; and (b) determining whether the contamination value is less than a reference contamination value. In some embodiments, the reference contamination value is 10%.

In some embodiments, evaluation of a complexity value comprises: (a) determining a complexity value of the sequence data; and (b) determining whether the complexity value matches a reference complexity value.

In some embodiments, evaluation of a Phred Score comprises: (a) determining a Phred Score of the sequence data; and (b) determining whether the Phred Score matches or exceeds a reference Phred Score.

In some embodiments, evaluation of a GC content comprises: (a) determining a GC content of the sequence data; and (b) determining if the GC content matches a reference GC content.

In some embodiments, the methods further comprise generating a report to display the results of the at least one additional determination to a user (e.g., via a GUI).

Example 15: Non-Limiting Protocol for Assessing Sequencing Data Quality Control

In some embodiments, a quality protocol for sequence data (e.g., for WES and/or RNAseq data) comprises one or more of the following steps:
  i) In some embodiments, low-quality reads (for example, based on positional information) are removed. In some embodiments, low-quality sequences (e.g., reads from low-quality areas of a sequencing flow cell) are removed from sequence data (e.g., from a FASTQ file). In some embodiments, if a significant fraction of the sequence reads are of low-quality (e.g., if bad tiles represent more than 30%, more than 40%, or more than 50% of a sequence data file).
  ii) In some embodiments, quality control tool for sequence data (e.g., FastQC as an example) is used to evaluate one or more of library complexity (e.g., read counts); quality of the sequencing platform (e.g., based on a per base Phred quality score); per tile quality score; per sequence GC content (for example to detect contamination based on an unexpected GC content), per base sequencing content (e.g., to detect adapter or other contamination); sequence duplication levels (e.g., to evaluate the quality of RNA/DNA selection and/or PCR amplification); and/or adapter content. In some embodiments, a quality threshold for further analysis includes greater than 10 million read counts (e.g., greater than 20 million read counts), and/or a Phred score of greater than 25 (e.g., 28 or greater than 28) in more than 30% of reads (e.g., in 50% of reads or more than 50% reads). In some embodiments, a quality control pipeline is stopped if the quality threshold is not met.
  iii) In some embodiments, sequence data is screened against a library of sequences (e.g., using FastQ Screen, from Babraham Bioinformatics), for example to detect cross-species contamination (e.g., from other sources such as mouse, zebrafish, *drosophila, C. elegans, Saccharomyces, Arabidopsis*, microbiome, adapters, vectors, phiX, or other source). In some embodiments, a quality control threshold for further analysis based on cross-species contamination is set at around 10%, around 20%, around 30%, or higher. For example, in some embodiments, a quality control pipeline is stopped if sequence data comprises 30% or greater than 30% contamination (e.g., with bacterial sequence).
  iv) In some embodiments, per chromosome coverage distribution and/or coverage distribution is determined for one or more specific regions (e.g., one or more CCDS protein coding regions, exons, etc.) using an analytical tool (e.g., Mosdepth). In some embodiments, a quality control threshold for further analysis involves confirming that sequence data covers clinically important genomic regions. In some embodiments, a quality control pipeline is stopped if sequence coverage does not include one or more target genomic regions of interest.
  v) In some embodiments, an analytical tool (e.g., Picard) is used to evaluate one or more sequence data parameters such as insert size, duplicates, mapping, pairing, or other parameter(s).
  vi) In some embodiments, an analytical tool for evaluating RNA sequence data (e.g., RseQC as an example) is used, for example, to determine insert size (e.g., inner distance between paired RNA reads), strandedness (e.g., to determine or confirm whether a stranded or non-stranded RNA sequence protocol was used), and/or gene body coverage (e.g., to determine coverage bias, for example associated with an RNA extraction protocol, for example to distinguish polyA versus total RNA sequence data).
  vii) In some embodiments, a quality threshold for RNA analysis comprises determining the percentage duplicates and/or adapter contamination and proceeding with further analysis for RNA sequence data that has less than 70% (for example less than 60%, or less than 50%) duplicates and/or less than 25% (for example less than 20%, less than 15%, or less than 10%) adapter contamination. Accordingly, an analysis protocol is terminated, in some embodiments, when RNA sequence data that has more than 50% (e.g., 60% or more than 60%, or more than 70%) duplicates and/or more than 10% (e.g., more than 15%, 20% or more than 20%, or more than 30%) adapter contamination.
  viii) In some embodiments, cross-individual contamination is evaluated (e.g., using a concordance and/or contamination estimator such as Conpair), for example to determine the concordance of a pair of samples (e.g., tumor and normal) obtained from the same patient. In some embodiments, further analysis is performed if the normal and tumor samples (e.g., normal and tumor DNA) are identified as being from the same subject.

ix) In some embodiments, a tumor-type classifier is used to predict a tumor type from gene expression data of a sample, and the predicted tumor type is compared to the asserted tumor type (e.g., the tumor type provided along with the nucleic acid data). In some embodiments, further analysis is performed if the predicted and asserted tumor types match.

x) In some embodiments, an RNA sequence type classifier is used to predict the library type from RNA sequence data (e.g., based on specific gene expression levels or patterns). In some embodiments, further analysis is performed if the predicted library type matches an asserted library type for the sample being analyzed.

xi) In some embodiments, an MHC allele composition is determined for two or more samples (e.g., from tumor and/or normal tissue) from the same subject. In some embodiments, further analysis is performed if the MHC allele compositions for the two or more samples match.

In some embodiments, one or more of the steps described above are performed. If sequence data (e.g., RNA and/or DNA sequence data) fails to satisfy one or more of these quality control steps, the sequence data can be excluded from further analysis. In some embodiments, additional sequence data can be obtained for a subject for which an initial set of sequence data did not satisfy one or more quality control criteria.

Example Embodiments

Some embodiments provide for a method comprising: obtaining a first sample of a first tumor from a subject having, suspected of having, or at risk of having cancer; extracting RNA from the first sample of the first tumor; enriching the RNA for coding RNA to obtain enriched RNA; preparing a first library of DNA fragments from the enriched RNA for non-stranded RNA sequencing; and performing non-stranded RNA sequencing on the first library of DNA fragments prepared from the enriched RNA.

In some embodiments, the method further comprises extracting DNA from the first sample of the tumor; preparing a second library of DNA fragments from the extracted DNA; and performing whole exome sequencing (WES) on the second library of DNA fragments.

In some embodiments, the method further comprises: obtaining a first sample of blood from the subject; extracting DNA from the first sample of blood; preparing a third library of DNA fragments from the DNA extracted from the first sample of blood; and performing whole exome sequencing (WES) on the third library of DNA.

In some embodiments, the method further comprises obtaining a second sample of a second tumor from the subject. In some embodiments, the first tumor and the second tumor are a same tumor. In some embodiments, the first and second tumors are different tumors.

In some embodiments, the method further comprises combining the first and second tumor samples to form a combined tumor sample, and extracting the RNA comprises extracting the RNA from the combined tumor sample.

In some embodiments, the method further comprises: extracting RNA from the second sample; and combining the RNA extracted from the second sample with the RNA extracted from the first sample to form combined extracted RNA, and wherein enriching the RNA for coding RNA comprises enriching the combined extracted RNA for coding RNA. In some embodiments, the method further comprises: extracting DNA from the second tumor sample; and combining the DNA extracted from the second tumor sample with the DNA extracted from the first tumor sample to form combined extracted DNA, and preparing a second library of DNA fragments from the extracted DNA comprises preparing a library of DNA fragment from the combined extracted DNA.

In some embodiments, the method further comprises placing the first sample in a first cryogenic tube, the first cryogenic tube comprising a composition that is able to penetrate the sample and protect DNA and/or RNA therein from degradation. In some embodiments, the method further comprises snap freezing the contents of the first cryogenic tube.

In some embodiments, the method further comprises placing the first sample of blood in a vacutainer comprising an anticoagulant. In some embodiments, the method further comprises snap freezing the contents of the vacutainer. In some embodiments, the snap-frozen contents of the cryogenic tube and/or vacutainer are stored for up to 7 months at −65° C. to −80° C.

In some embodiments, the first tumor sample is at least 20 mg in weight, consist of at least $2 \times 10^6$ cells, or provides at least 1pg of RNA upon RNA extraction.

In some embodiments, the method further comprises: forming a single-cell suspension of cells from the first sample of tumor; and performing mass cytometry on at least a first part of the single-cell suspension, the at least the first part of the single-cell suspension comprising at least $5 \times 10^6$ cells.

In some embodiments, the method further comprises forming a lysate from at least a second part of the single-cell suspension, the at least the second part of the single-cell suspension comprising at least $2 \times 10^6$ cells; extracting RNA from the lysate; performing RNA sequencing on the extracted RNA to obtain RNA expression data; and/or determining whether the first tumor is heterogeneous based on the RNA expression data.

In some embodiments, forming the single-cell suspension of cells comprises: dissecting the first tumor sample to obtain tumor sample fragments; incubating the tumor sample fragments in an enzyme cocktail, the enzyme cocktail comprising penicillin and/or streptomycin, collagenase I, and collagenase IV; and filtering the enzyme cocktail through a 70 µm cell strainer.

In some embodiments, the first sample of blood is at least 0.5-1.0 ml in volume.

In some embodiments, the RNA extracted from either the first sample or the second sample is at least 1000-6000 ng in total mass, has a purity corresponding to a ratio of absorbance at 260 nm to absorbance at 280 nm of at least 2.0.

In some embodiments, the DNA extracted from the first sample is at least 1000-2000 ng in total mass, in at least 10 µl of solution, of a concentration of 100-200 ng/µl, and has a purity corresponding to a ratio of absorbance at 260 nm to absorbance at 280 nm of at least 1.8.

In some embodiments, enriching the RNA for coding RNA comprises performing polyA enrichment.

In some embodiments, the WES performed on the second library of DNA fragments, and the WES performed on the third library of DNA fragments have at least 100 bp paired-end reads, and an estimated coverage of at least 100×.

In some embodiments, the WES has an estimated coverage of at least 150×.

In some embodiments, the RNA sequencing on the first library of DNA fragments has at least 100 bp paired-end reads, and an estimated total number of reads of at least 50 million paired-end reads.

In some embodiments, the RNA sequencing on the first library of DNA fragments at least 100 bp paired-end reads, and an estimated total number of reads of at least 100 million paired-end reads.

In some embodiments, the method further comprises subjecting a sample of any one of the prepared libraries of DNA fragments to quality control tests to evaluate their integrity and/or peak size, wherein each sample of the prepared libraries comprises up to 1 ng of a library.

In some embodiments, the subject is human.

Some embodiments provide for a kit, comprising: a composition that is able to penetrate tissue and protect DNA and/or RNA therein from degradation; at least one tool for dissecting a sample of tumor and preparing a single-cell suspension therefrom; at least one reagent for snap-freezing of biological samples; an anticoagulant; at least one vacutainer; at least one reagent for extracting DNA and RNA from tissue samples and blood; and at least one reagent for preparing DNA libraries from DNA and/or RNA samples.

Some embodiments provide for a kit for use in a method according to any of the preceding examples.

Some embodiments provide for a system comprising at least one computer hardware processor and at least one non-transitory computer-readable storage medium storing processor-executable instructions that, when executed by the at least one computer hardware processor, cause the at least one computer hardware processor to perform a method for processing RNA expression data. The method comprises using at least one computer hardware processor to perform: obtaining RNA expression data for a subject having, suspected of having, or at risk of having cancer; aligning and annotating genes in the RNA expression data with known sequences of the human genome to obtain annotated RNA expression data; removing non-coding transcripts from the annotated RNA expression data; converting the annotated RNA expression data to gene expression data in transcripts per kilobase million (TPM); identifying at least one gene that introduces bias in the gene expression data; removing the at least one gene from the gene expression data to obtain bias-corrected gene expression data; and identifying a cancer treatment for the subject using the bias-corrected gene expression data.

Some embodiments provide for at least one non-transitory computer-readable storage medium storing processor-executable instructions that, when executed by at least one computer hardware processor, cause the at least one computer hardware processor to perform a method for processing RNA expression data. The method comprises using at least one computer hardware processor to perform: obtaining RNA expression data for a subject having, suspected of having, or at risk of having cancer; aligning and annotating genes in the RNA expression data with known sequences of the human genome to obtain annotated RNA expression data; removing non-coding transcripts from the annotated RNA expression data; converting the annotated RNA expression data to gene expression data in transcripts per kilobase million (TPM); identifying at least one gene that introduces bias in the gene expression data; removing the at least one gene from the gene expression data to obtain bias-corrected gene expression data; and identifying a cancer treatment for the subject using the bias-corrected gene expression data.

Some embodiments provide for a method for processing RNA expression data, the method comprising using at least one computer hardware processor to perform: obtaining RNA expression data for a subject having, suspected of having, or at risk of having cancer; aligning and annotating genes in the RNA expression data with known sequences of the human genome to obtain annotated RNA expression data; removing non-coding transcripts from the annotated RNA expression data; converting the annotated RNA expression data to gene expression data in transcripts per kilobase million (TPM); identifying at least one gene that introduces bias in the gene expression data; removing the at least one gene from the gene expression data to obtain bias-corrected gene expression data; and identifying a cancer treatment for the subject using the bias-corrected gene expression data.

In some embodiments, identifying the at least one gene from the gene expression data comprises identifying at least one gene having an average transcript length at least a threshold amount higher or lower than an average length of transcripts in the gene expression data.

In some embodiments, identifying the at least one gene from the gene expression data comprises identifying at least one gene having at least a threshold variation in average transcript expression level based on transcript expression levels in reference samples.

In some embodiments, identifying the at least one gene from gene expression data comprises identifying one or more genes having a polyA tail that is at least a threshold amount smaller in length compared to an average length of polyA tails of genes from a sample from which the RNA expression data was obtained.

In some embodiments, the at least one gene belongs to a family of genes selected from the group consisting of: histone-encoding genes, mitochondrial genes, interleukin-encoding genes, collagen-encoding genes, B-cell receptor-encoding genes, and T cell receptor-encoding genes.

In some embodiments, the at least one gene comprises at least one histone-encoding gene selected from the group consisting of: HIST1H1A, HIST1H1B, HIST1H1C, HIST1H1D, HIST1H1E, HIST1H1T, HIST1H2AA, HIST1H2AB, HIST1H2AC, HIST1H2AD, HIST1H2AE, HIST1H2AG, HIST1H2AH, HIST1H2A1, HIST1H2AJ, HIST1H2AK, HIST1H2AL, HIST1H2AM, HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2BO, HIST1H3A, HIST1H3B, HIST1H3C, HIST1H3D, HIST1H3E, HIST1H3F, HIST1H3G, HIST1H3H, HIST1H3I, HIST1H3J, HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L, HIST2H2AA3, HIST2H2AA4, HIST2H2AB, HIST2H2AC, HIST2H2BE, HIST2H2BF, HIST2H3A, HIST2H3C, HIST2H3D, HIST2H3PS2, HIST2H4A, HIST2H4B, HIST3H2A, HIST3H2BB, HIST3H3, and HIST4H4.

In some embodiments, the at least one gene comprises at least one mitochondrial gene selected from the group consisting of: MT-ATP6, MT-ATP8, MT-CO1, MT-C02, MT-C03, MT-CYB, MT-ND1, MT-ND2, MT-ND3, MT-ND4, MT-ND4L, MT-ND5, MT-ND6, MT-RNR1, MT-RNR2, MT-TA, MT-TC, MT-TD, MT-TE, MT-TF, MT-TG, MT-TH, MT-TI, MT-TK, MT-TL1, MT-TL2, MT-TM, MT-TN, MT-TP, MT-TQ, MT-TR, MT-TS1, MT-TS2, MT-TT, MT-TV, MT-TW, MT-TY, MTRNR2L1, MTRNR2L10, MTRNR2L11, MTRNR2L12, MTRNR2L13, MTRNR2L3, MTRNR2L4, MTRNR2L5, MTRNR2L6, MTRNR2L7, and MTRNR2L8.

In some embodiments, the RNA expression data is characterized by at least 100 bp paired-end reads, and an estimated coverage of at least 50 million paired-end reads.

In some embodiments, the RNA expression data is characterized by at least 100 bp paired-end reads, and an estimated total number of reads of at least 100 million paired-end reads.

In some embodiments, aligning genes in the RNA expression data is performed using a GRCh38 genome assembly.

In some embodiments, annotating the genes in the RNA expression data is based on GENCODE V23 comprehensive annotation (gencodegenes.org).

In some embodiments, the removed non-coding transcripts belong to groups selected from the list consisting of: pseudogenes, polymorphic pseudogenes, processed pseudogenes, transcribed processed pseudogenes, unitary pseudogenes, unprocessed pseudogenes, transcribed unitary pseudogenes, constant chain immunoglobulin (IG C) pseudogenes, joining chain immunoglobulin (IG J) pseudogenes, variable chain immunoglobulin (IG V) pseudogenes, transcribed unprocessed pseudogenes, translated unprocessed pseudogenes, joining chain T cell receptor (TR J) pseudogenes, variable chain T cell receptor (TR V) pseudogenes, small nuclear RNAs (snRNA), small nucleolar RNAs (snoRNA), microRNAs (miRNA), ribozymes, ribosomal RNA (rRNA), mitochondrial tRNAs (Mt tRNA), mitochondrial rRNAs (Mt rRNA), small Cajal body-specific RNAs (scaRNA), retained introns, sense intronic RNA, sense overlapping RNA, nonsense-mediated decay RNA, non-stop decay RNA, antisense RNA, long intervening noncoding RNAs (lincRNA), macro long non-coding RNA (macro lncRNA), processed transcripts, 3prime overlapping non-coding RNA (3prime overlapping nerna), small RNAs (sRNA), miscellaneous RNA (misc RNA), vault RNA (vaul-tRNA), and TEC RNA.

In some embodiments, the RNA expression data has been obtained by performing RNA sequencing on one or more samples of a subject's tumor.

In some embodiments, identifying the cancer treatment for the subject using the bias-corrected gene expression data comprises: determining, using the bias-corrected gene expression data, a gene group expression level for each gene group in a set of gene groups, wherein the set of gene group comprises at least one gene group associated with cancer malignancy, and at least one gene group associated with cancer microenvironment; and identifying the cancer treatment using the determined gene group expression levels. In some embodiments, the method further comprises: administering the cancer treatment to the subject.

Some embodiments provide for a method comprising: enriching RNA for coding RNA in a sample of extracted RNA from a first tumor sample from a subject having, suspected of having, or at risk of having cancer; performing non-stranded RNA sequencing on a first library of cDNA fragments prepared from the enriched RNA to obtain RNA expression data; converting the RNA expression data to gene expression data in transcripts per kilobase million (TPM); identifying at least one gene that introduces bias in the gene expression data; removing, from the gene expression data, expression data associated with the at least one gene to obtain bias-corrected gene expression data; and identifying a therapy for the subject using the bias-corrected gene expression data. In some embodiments, the method further comprises administering to the subject the identified therapy.

In some embodiments, identifying the therapy for the subject using the bias-corrected gene expression data comprises: determining, using the bias-corrected gene expression data, a plurality of gene group expression levels comprising a gene group expression level for each gene group in a set of gene groups, wherein the set of gene groups comprises at least one gene group associated with cancer malignancy, and at least one gene group associated with cancer microenvironment; and identifying the therapy using the determined plurality of gene group expression levels.

In some embodiments, identifying the at least one gene that introduces bias in the gene expression data comprises identifying at least one gene having an average transcript length at least a threshold amount higher or lower than an average length of transcripts in the gene expression data.

In some embodiments, identifying the at least one gene that introduces bias in the gene expression data comprises identifying at least one gene having at least a threshold variation in average transcript expression level based on transcript expression levels in reference samples.

In some embodiments, identifying the at least one gene comprises identifying one or more genes having a polyA tail that is at least a threshold amount smaller in length compared to an average length of polyA tails of genes from a sample from which the RNA expression data was obtained.

In some embodiments, the at least one gene belongs to a family of genes selected from the group consisting of: histone-encoding genes, mitochondrial genes, interleukin-encoding genes, collagen-encoding genes, B-cell receptor-encoding genes, and T cell receptor-encoding genes.

In some embodiments, the at least one gene comprises at least one histone-encoding gene selected from the group consisting of: HIST1H1A, HIST1H1B, HIST1H1C, HIST1H1D, HIST1H1E, HIST1H1T, HIST1H2AA, HIST1H2AB, HIST1H2AC, HIST1H2AD, HIST1H2AE, HIST1H2AG, HIST1H2AH, HIST1H2A1, HIST1H2AJ, HIST1H2AK, HIST1H2AL, HIST1H2AM, HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, 20 HIST1H2BK, HIST1H2BL, HIST1H2BM, HIST1H2BN, HIST1H2BO, HIST1H3A, HIST1H3B, HIST1H3C, HIST1H3D, HIST1H3E, HIST1H3F, HIST1H3G, HIST1H3H, HIST1H3I, HIST1H3J, HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L, HIST2H2AA3, HIST2H2AA4, HIST2H2AB, HIST2H2AC, HIST2H2BE, HIST2H2BF, HIST2H3A, HIST2H3C, HIST2H3D, HIST2H3PS2, HIST2H4A, HIST2H4B, HIST3H2A, HIST3H2BB, HIST3H3, and HIST4H4.

In some embodiments, the at least one gene comprises at least one mitochondrial gene selected from the group consisting of: MT-ATP6, MT-ATP8, MT-CO1, MT-CO2, MT-CO3, MT-CYB, MT-ND1, MT-ND2, MT-ND3, MT-ND4, MT-ND4L, MT-ND5, MT-ND6, MT-RNR1, MT-RNR2, MT-TA, MT-TC, MT-TD, MT-TE, MT-TF, MT-TG, MT-TH, MT-TI, MT-TK, MT-TL1, MT-TL2, MT-TM, MT-TN, MT-TP, MT-TQ, MT-TR, MT-TS1, MT-TS2, MT-TT, MT-TV, MT-TW, MT-TY, MTRNR2L1, MTRNR2L10, MTRNR2L11, MTRNR2L12, MTRNR2L13, MTRNR2L3, MTRNR2L4, MTRNR2L5, MTRNR2L6, MTRNR2L7, and MTRNR2L8.

In some embodiments, the RNA expression data is characterized by at least 100 bp paired-end reads, and an estimated read depth of at least 50 million paired-end reads.

In some embodiments, the method further comprises: aligning and annotating genes in the RNA expression data with known sequences of the human genome to obtain annotated RNA expression data before identifying at least one gene that introduces bias in the gene expression data, aligning genes in the RNA expression data is performed using a GRCh38 genome assembly, and annotating the genes in the RNA expression data is performed using a GEN-CODE V23 comprehensive annotation (gencodegenes.org).

In some embodiments, the method further comprises: removing non-coding transcripts from the RNA expression data, wherein the removed non-coding transcripts belong to groups selected from the list consisting of: pseudogenes, polymorphic pseudogenes, processed pseudogenes, transcribed processed pseudogenes, unitary pseudogenes, unprocessed pseudogenes, transcribed unitary pseudogenes, constant chain immunoglobulin (IG C) pseudogenes, joining chain immunoglobulin (IG J) pseudogenes, variable chain immunoglobulin (IG V) pseudogenes, transcribed unprocessed pseudogenes, translated unprocessed pseudogenes, joining chain T cell receptor (TR J) pseudogenes, variable chain T cell receptor (TR V) pseudogenes, small nuclear RNAs (snRNA), small nucleolar RNAs (snoRNA), microRNAs (miRNA), ribozymes, ribosomal RNA (rRNA), mitochondrial tRNAs (Mt tRNA), mitochondrial rRNAs (Mt rRNA), small Cajal body-specific RNAs (scaRNA), retained introns, sense intronic RNA, sense overlapping RNA, nonsense-mediated decay RNA, non-stop decay RNA, antisense RNA, long intervening noncoding RNAs (lincRNA), macro long non-coding RNA (macro lncRNA), processed transcripts, 3prime overlapping non-coding RNA (3prime overlapping ncrna), small RNAs (sRNA), miscellaneous RNA (misc RNA), vault RNA (vaultRNA), and TEC RNA.

In some embodiments, the method further comprises: obtaining a first sample of a first tumor from a subject having or suspected of having cancer, and extracting RNA from the first sample of the first tumor to obtain the sample of extracted RNA; before enriching the RNA for coding RNA. In some embodiments, the method further comprises obtaining a second sample of a second tumor from the subject.

In some embodiments, the method further comprises: combining the first and second samples to form a combined tumor sample, and extracting the RNA comprises extracting the RNA from the combined tumor sample.

In some embodiments, the method further comprises: extracting RNA from the second sample; combining the RNA extracted from the second sample with the RNA extracted from the first sample to form combined extracted RNA, and enriching the RNA for coding RNA comprises enriching the combined extracted RNA for coding RNA.

In some embodiments, the sample of extracted RNA comprises at least 1 μg of RNA upon RNA extraction.

In some embodiments, the extracted RNA is at least 1000-6000 ng in total mass, has a purity corresponding to a ratio of absorbance at 260 nm to absorbance at 280 nm of at least 2.0.

In some embodiments, enriching the RNA for coding RNA comprises performing polyA enrichment.

Some embodiments provide for a system, comprising: at least one computer hardware processor; and at least one non-transitory computer-readable storage medium storing processor-executable instructions that, when executed by the at least one computer hardware processor, cause the at least one computer hardware processor to perform: a method, comprising: (a) obtaining nucleic acid data comprising: (i) sequence data comprising at least 5 kilobases (kb) of DNA and/or RNA, the sequence data obtained by sequencing a biological sample of a subject having, suspected of having, or at risk of having a disease; and (ii) asserted information indicating an asserted source and/or an asserted integrity of the sequence data; and (b) validating the nucleic acid data by: (i) processing the sequence data to obtain determined information indicating a determined source and/or a determined integrity of the sequence data; and (ii) determining whether the determined information matches the asserted information.

Some embodiments provide for at least one non-transitory computer-readable storage medium storing processor-executable instructions that, when executed by at least one computer hardware processor, cause the at least one computer hardware processor to perform: a method, comprising: (a) obtaining nucleic acid data comprising: (i) sequence data comprising at least 5 kilobases (kb) of DNA and/or RNA, the sequence data obtained by sequencing a biological sample of a subject having, suspected of having, or at risk of having a disease; and (ii) asserted information indicating an asserted source and/or an asserted integrity of the sequence data; and (b) validating the nucleic acid data by: (i) processing the sequence data to obtain determined information indicating a determined source and/or a determined integrity of the sequence data; and (ii) determining whether the determined information matches the asserted information.

Some embodiments provide for a method, comprising: (a) obtaining nucleic acid data comprising: (i) sequence data comprising at least 5 kilobases (kb) of DNA and/or RNA, the sequence data obtained by sequencing a biological sample of a subject having, suspected of having, or at risk of having a disease; and (ii) asserted information indicating an asserted source and/or an asserted integrity of the sequence data; and (b) validating the nucleic acid data by: (i) processing the sequence data to obtain determined information indicating a determined source and/or a determined integrity of the sequence data; and (ii) determining whether the determined information matches the asserted information.

In some embodiments, when it is determined that the asserted information matches the determined information: (i) accessing a database of disease features; and (ii) processing the sequence data to determine whether it is indicative of one or more of the disease features; and (d) when it is determined that the asserted information does not match the determined information: (i) indicating to a user that the determined and asserted information do not match; (ii) excluding the sequence data from further analysis; and/or (iii) obtaining additional sequence data and/or other information about the biological sample and/or the subject.

In some embodiments, the asserted information for the sequence data is based on (one, at least two, at least three, between 2 and 10, between 5 and 10 pieces of) information selected from the group consisting of: MHC allele sequence information; nucleic acid type; subject identity; sample identity; tissue type from which the sample was obtained; tumor type from which the sample was obtained; sequencing platform used to generate the sequence data; sequence integrity; polyA status of an RNA sample (e.g., indicating whether the RNA sample was polyA enriched); total sequence coverage; exon coverage; chromosomal coverage; ratio of expression levels of nucleic acids encoding two or more subunits of the same protein; contamination; single nucleotide polymorphisms (SNPs); complexity; and/or guanine (G) and cytosine (C) percentage (%).

In some embodiments, the determined information for the sequence data is based on (one, at least two, at least three, between 2 and 10, between 5 and 10 pieces of) information selected from the group consisting of: MHC allele sequence information; nucleic acid type; subject identity; sample identity; tissue type from which the sample was obtained; tumor type from which the sample was obtained; sequencing platform used to generate the sequence data; sequence integrity; polyA status of an RNA sample (e.g., indicating whether the RNA sample was polyA enriched); total sequence coverage; exon coverage; chromosomal coverage; ratio of expression levels of nucleic acids encoding two or more subunits of the same protein; contamination; single nucleotide polymorphisms (SNPs); complexity; and/or guanine (G) and cytosine (C) percentage (%).

In some embodiments, the disease is cancer. In some embodiments, the subject is human.

In some embodiments, the source of the sequence data is a subject, a tissue type, a tumor type, an RNA sequence type, or a DNA sequence type.

In some embodiments, the subject from which the sequence data is obtained is evaluated by determining one or more MHC sequences, for example, by determining MHC sequences for six MHC loci.

In some embodiments, the source of one or more nucleic acid sequence data sets is evaluated by determining a SNP concordance for the nucleic acid sequence data sets.

In some embodiments, the integrity of the sequence data is evaluated by determining exon coverage, one or more ratios of protein subunit encoding nucleic acids, and/or gene coverage of the sequence data.

In some embodiments, the integrity of RNA sequence data is evaluated by determining coverage of one or more genes in the RNA sequence data.

In some embodiments, the integrity of RNA sequence data is evaluated by determining a relative coverage of two or more exons for at least one gene in the RNA sequence data.

In some embodiments, the integrity of RNA sequence data is evaluated by determining an expression ratio of two known reference genes in the RNA sequence data.

In some embodiments, the method further comprises determining a level of nucleic acid degradation, contamination, and/or GC content.

In some embodiments, determining whether RNA sequence data is polyA RNA sequence data or total RNA sequence data comprises determining the expression level of one or more mitochondrial and/or histone genes in the RNA sequence data.

In some embodiments, the sequencing platform that was used for generating WES sequence data is identified by determining a percent (%) variance for one or more reference genes in the WES sequence data.

In some embodiments, the method further comprises generating a report that indicates an extent of a match between one or more features that are determined from the sequence data and one or more corresponding asserted features in the asserted information.

Equivalents and Scope

All of the features described in this specification may be combined in any combination. Each feature described in this specification may be replaced by an alternative feature serving the same, equivalent, or similar purpose. Thus, unless expressly stated otherwise, each feature described is only an example of a generic series of equivalent or similar features.

All of the features described in this specification may be combined in any combination. Each feature described in this specification may be replaced by an alternative feature serving the same, equivalent, or similar purpose. Thus, unless expressly stated otherwise, each feature described is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

The terms "program" or "software" are used herein in a generic sense to refer to any type of computer code or set of processor-executable instructions that can be employed to program a computer or other processor (physical or virtual) to implement various aspects of embodiments as described above. Additionally, according to one aspect, one or more computer programs that when executed perform methods of the technology described herein need not reside on a single computer or processor, but may be distributed in a modular fashion among different computers or processors to implement various aspects of the technology described herein.

Processor-executable instructions may be in many forms, such as program modules, executed by one or more computers or other devices. Generally, program modules include routines, programs, objects, components, data structures, etc. that performs particular tasks or implement particular abstract data types. Typically, the functionality of the program modules may be combined or distributed.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, for example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements);etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as an example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the described methods and systems encompass all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also described, and any element(s) can be removed from the group. It should it be understood that, in general, where the systems and methods described herein (or aspects thereof) are referred to as comprising particular elements and/or features, certain embodiments of the systems and methods or aspects of the same consist, or consist essentially of, such elements and/or features. For purposes of simplicity, those embodiments have not been specifically set forth in haec verba herein.

It is also noted that the terms "including," "comprising," "having," "containing", "involving", are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the described systems and methods, to the tenth of the unit of the lower limit of the range, unless the context clearly dictates otherwise.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

Additionally, as used herein the terms "patient" and "subject" may be used interchangeably. Such terms may include, but are not limited to, human subjects or patients. Such terms may also include non-human primates or other animals.

The terms "approximately", "substantially," and "about" may be used to mean within ±20% of a target value in some embodiments, within ±10% of a target value in some embodiments, within ±5% of a target value in some embodiments, and within ±2% of a target value in some embodiments. The terms "approximately" and "about" may include the target value.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that fall within the prior art may be explicitly excluded from any one or more of the claims. Because such embodiments are deemed to be known to one of ordinary skill in the art, they may be excluded even if the exclusion is not set forth explicitly herein. Any particular embodiment of the systems and methods described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

Subject matter of international PCT publication WO2018/231771

MF Profiles

A "molecular functional tumor portrait (MF profile)," as described herein, refers to a graphical depiction of a tumor with regard to molecular and cellular composition, and biological processes that are present within and/or surrounding the tumor, Related compositions and processes present within and/or surrounding a tumor are presented in functional modules (also described herein as "gene groups") of a MF profile.

Figure 16A:
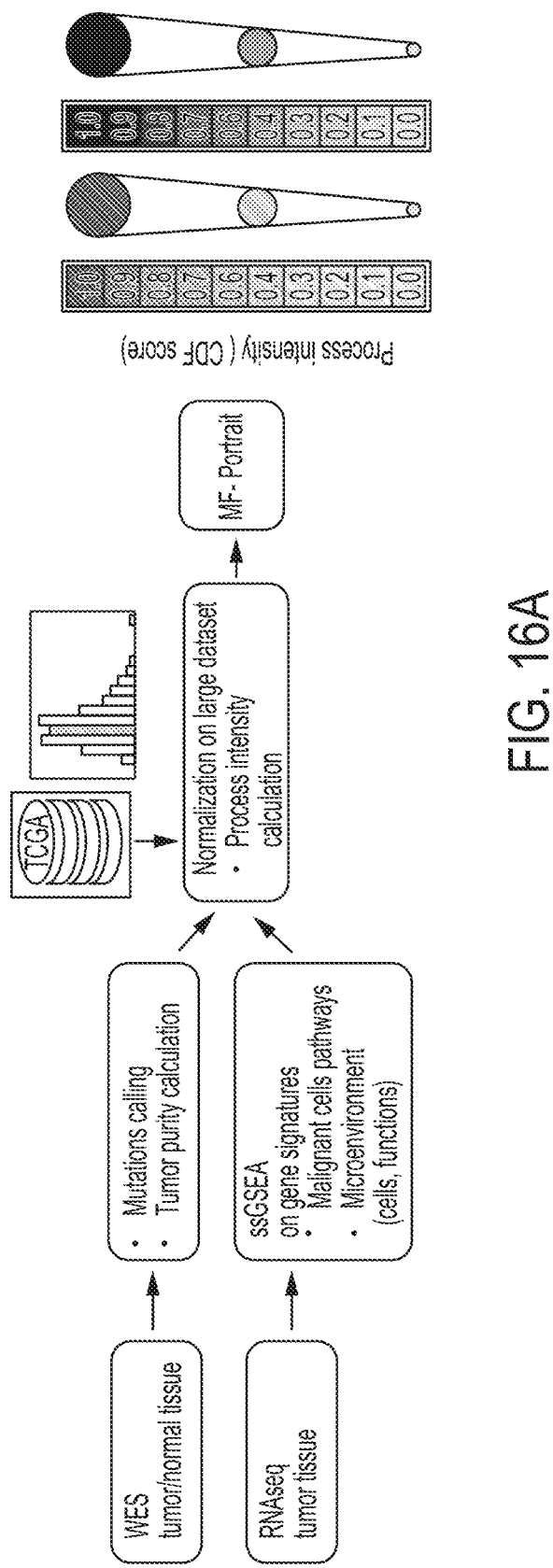
FIG. 16A is a graphical representation of an exemplary bioinformatics pipeline for determining tumor functional properties in a molecular functional profile (MF profile), in accordance with some embodiments of the technology described herein.
Figure 16B:
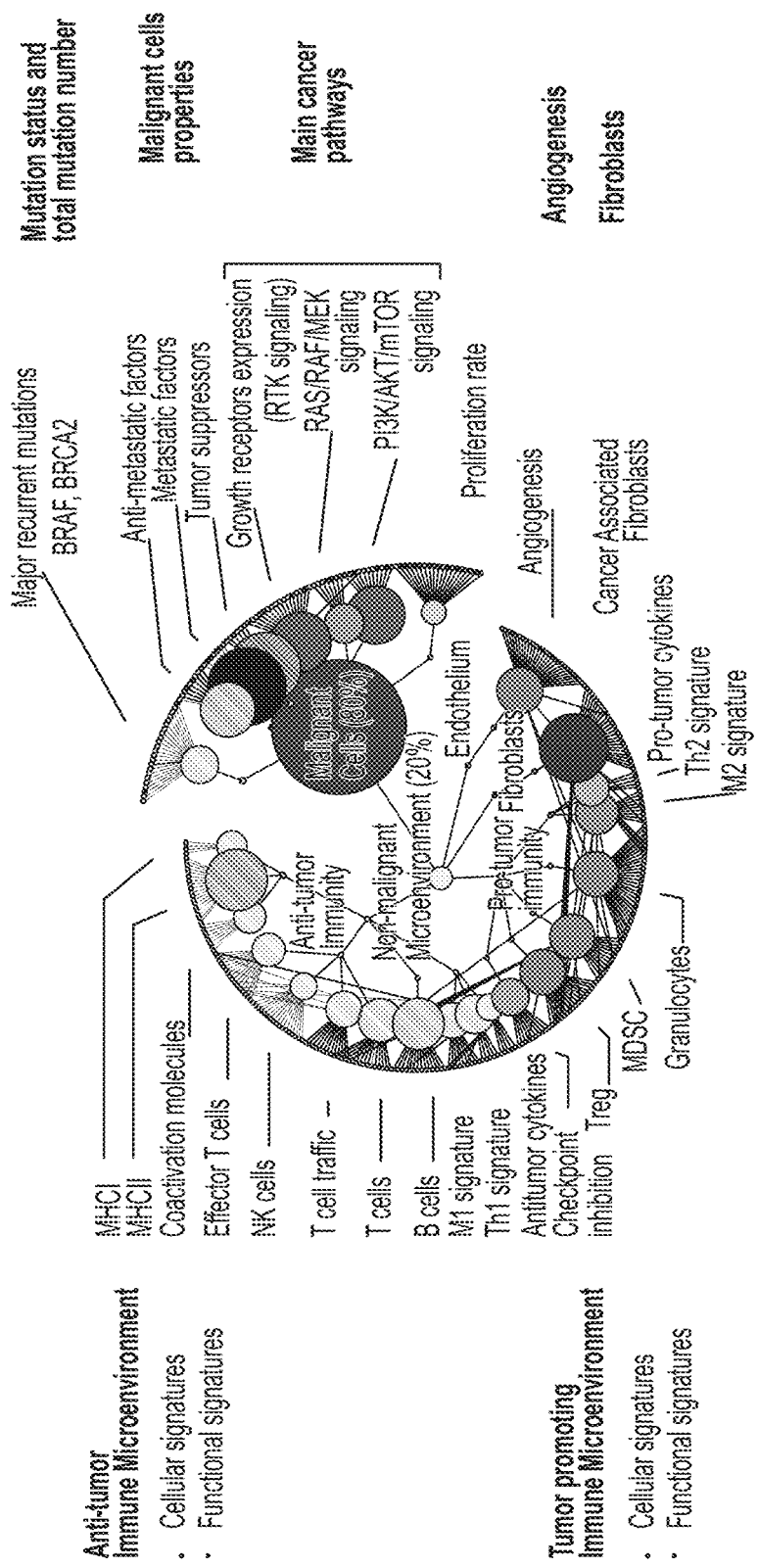
FIG. 16B is a graphical representation of tumor functional properties in a MF profile comprising 28 functional modules, in accordance with some embodiments of the technology described herein. The size of the modules correspond to their intensity rate. Colors reflect the module pro- or anti-cancer activity. Solid shades without cross-marking are assigned to the modules that promote tumor growth, while shades of with cross-marking are assigned to those having anticancer activity. The malignancy modules are collected in the Tumor Burden sector, which are located in the right top quarter of the graphical representation.

MF profiles may be constructed, in some embodiments, from gene expression data (for example sequencing data, e.g, whole exome sequencing data, RNA sequencing data, or other gene expression data) of normal tissue and/or tumor tissue. FIG. 16A shows an exemplary bioinformatics pipeline for constructing a tumor portrait from sequencing data. MF profiles produced in accordance with the bioinformatics pipeline in FIG. 16A may comprise functional modules depicted as circles and arrange in an circular pattern as shown in FIG. 16B. Each circle of the MF profile in FIG. 1613 represents a functional module, which are labeled using lines. Related functional modules may be combined into a single functional module. For example, FIG. 1613 shows that the anti-metastatic factors module, the metastatic factors module, and the tumor suppressors module may be combined into the malignant cell properties module.

Figure 16C:
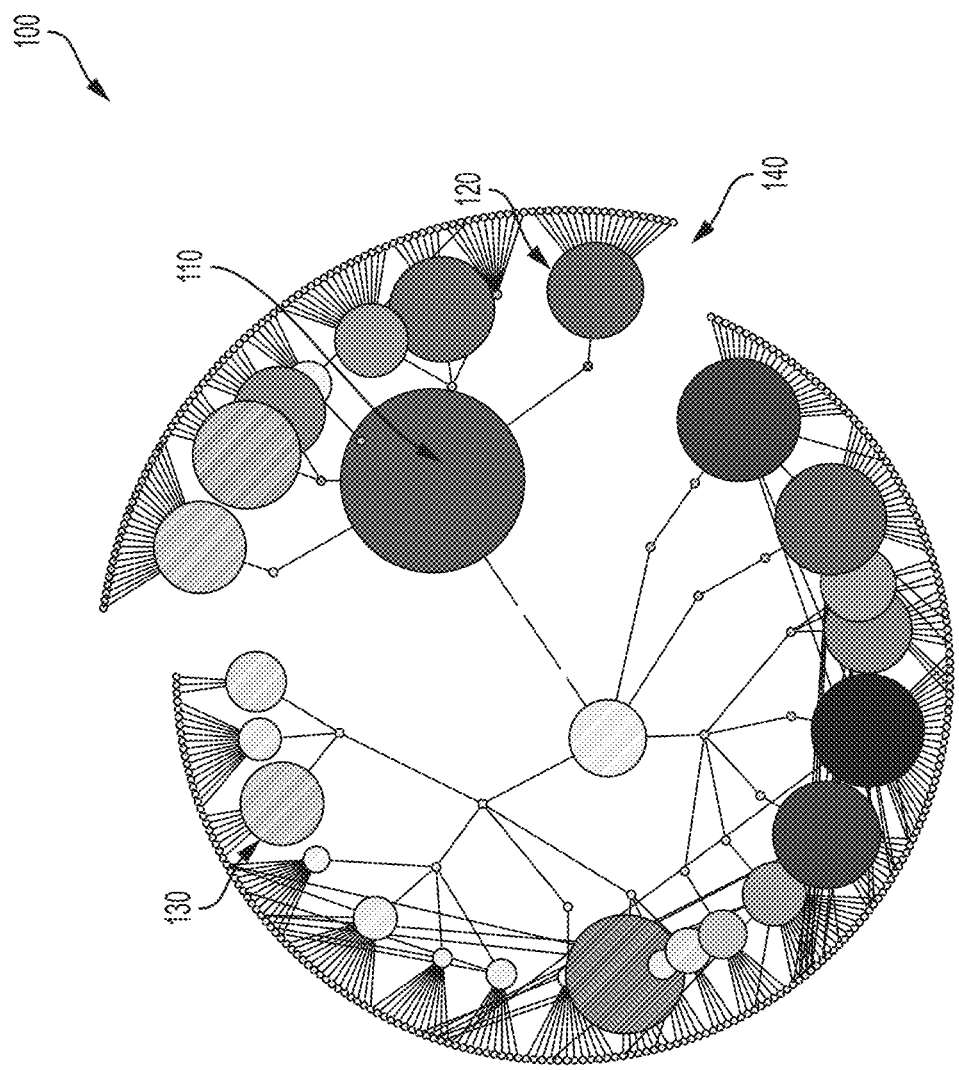
FIG. 16C shows an exemplary MF profile, in accordance with some embodiments of the technology described herein.

FIG. 16C shows one embodiment of an MF profile as provided herein. As shown in FIG. 16C, the MF profile 100 comprises 28 functional modules, three of which are labeled as 110, 120 and 130. Module size indicates module intensity. For example, module 110 is larger than module 120 indicating that module 110 has increased module intensity as compared to module 120. The presence or absence of cross-hatching of the module indicates whether the module is a pro-tumor module or an anti-tumor module. Pro-tumor modules (e.g. module 120) are shown in solid shades without cross-marking thereof, and anti-tumor modules (e.g. module 130) are shown with cross-marking thereof. The depth of shading of the module indicates module intensity. Modules relating to tumor malignancy 140 are depicted in the top right quarter of the circle.

MF Profile Modules

A "functional module" or "gene group," as described herein, refers to related compositions and processes present within and/or surrounding a tumor.

For example, an immune response/inflammation module provides information related to immune system composition and activity within a tumor. Examples of immune system composition and activity within a tumor presented in the immune response/inflammation module include, but are not limited to, the number of unique tumor antigens, MI-IC-restricted antigen presentation, expression of co-stimulatory compounds that are involved in T cell activation, intensities of activation and effector phases of adaptive and innate immune responses, proportions of different lymphoid and myeloid cell populations within a tumor, expression rates of cancer-promoting and anti-cancer cytokines, and intensities of immune response processes (e.g. activities of immunosuppressive cells and expression of immune checkpoint inhibitory molecules).

Exemplary modules in a MF profile may include, but are not limited to, Major histocompatibility complex I (MICI) module, Major histocompatibility complex II (MHCII) module, Coactivation molecules module, Effector cells module, Effector T cell module; Natural killer cells (NK cells) module, T cell traffic module, T cells module, B cells module, B cell traffic module, Benign 13 cells module, Malignant B cell marker module, Ml signatures module, Th1 signature module, Antitumor cytokines module, Checkpoint inhibition (or checkpoint molecules) module, Follicular dendritic cells module, Follicular B helper T cells module, Protumor cytokines module, Regulatory T cells (Treg) module, Treg traffic module, Myeloid-derived suppressor cells (MDSCs) module, MDSC and TAM traffic module, Granulocytes module, Granulocytes traffic module, Eosinophil signature model, Neutrophil signature model, Mast cell signature module, M2 signature module, Th2 signature module, Th17 signature module, Protumor cytokines module, Complement inhibition module, Fibroblastic reticular cells module, Cancer associated fibroblasts (CAFs) module, Matrix formation (or Matrix) module, Angiogenesis module, Endothelium module, Hypoxia factors module, Coagulation module, Blood endothelium module, Lymphatic endothelium module, Proliferation rate (or Tumor proliferation rate) module, Oncogenes module, PI3K/AKT/mTOR signaling module, RAS/RAF/MEK signaling module, Receptor tyrosine kinases expression module, Growth Factors module, Tumor suppressors module, Metastasis signature module, Antimetastatic factors module, and Mutation status module. In certain embodiments, the modules may be described as "gene groups".

In some embodiments, the gene groups of the modules may comprise at least two genes (e.g. at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same.

In some embodiments, the modules in a MF profile may comprise or consist of: Major histocompatibility complex I (MIICI) module, Major histocompatibility complex II (MHCII) module, Coactivation molecules module, Effector cells (or Effector T cell) module, Natural killer cells (NK cells) module, T cells module, B cells module, MI signatures module, Th1 signature module, Antitumor cytokines module, Checkpoint inhibition (or checkpoint molecules) module, Regulatory T cells (Treg) module, Myeloid-derived suppressor cells (MDSCs) module, Neutrophil signature model, M2 signature module, Th2 signature module, Protumor cytokines module, Complement inhibition module, Cancer associated fibroblasts (CAFs) module, Angiogenesis module, Endothelium module, Proliferation rate (or Tumor proliferation rate) module. PI3K/AKT/mTOR signaling module, RAS/RAF/MEK signaling module, Receptor tyrosine kinases expression module, Growth Factors module, Tumor suppressors module, Metastasis signature module, and Antimetastatic factors module. The MF profile may additionally include: T cell traffic module, Antitumor cytokines module, Treg traffic module, MDSC and TAM traffic module, Granulocytes or Granulocyte traffic module, Eosinophil signature model, Mast cell signature module, Th17 signature module, Matrix formation (or Matrix) module, and Hypoxia factors module. Such an MF profile could be useful for a subject with a solid cancer (e.g. a melanoma).

In some embodiments, the modules in a MF profile may comprise or consist of: Effector cells (or Effector T cell) module, Natural killer cells (NK cells) module, T cells module, Malignant B cell marker module, MI signatures module, Th1 signature module, Checkpoint inhibition (or checkpoint molecules) module, Follicular dendritic cells module, Follicular B helper T cells module, Protumor cytokines module, Regulatory T cells (Treg) module, Neutrophil signature model, M2 signature module, Th2 signature module, Complement inhibition module, Fibroblastic reticular cells module, Angiogenesis module, Blood endothelium module, Proliferation rate (or Tumor proliferation rate) module, Oncogenes module, and Tumor suppressors module. The MF profile may additionally include: Major histocompatibility complex I (MHCI) module, Major histocompatibility complex II (MHII) module. Coactivation molecules module, B cell traffic module, Benign B cells module, Antitumor cytokines module, Treg traffic module, Mast cell signature module, Th17 signature module, Matrix formation (or Matrix) module, Hypoxia factors module, Coagulation module, and Lymphatic endothelium module. Such an MF profile could be useful for a subject with follicular lymphoma.In some embodiments, the gene groups of the modules may comprise at least two genes (e.g. at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same): Major histocompatibility complex I (MHCI) module: HLA-A, HLA-B, ILA-C, B2M, TAP1, and TAP2; Major histocompatibility complex II (MHCII) module: HLA-DRA. HLA-DRB1, HLA-DOB. HLA-DPB2, HLA-DMA, HLA-DOA, HLA-DPA1, HLA-DPB 1, HLA-DMB, HILA-DQB1, HLA-DQA1, ILA-DRB5, LA-DQA2, HLA-DQB2, and HLA-DRB6; Coactivation molecules module: CD80, CD86, CD40, CD83, TNFRSF4, ICOSLG, CD28; Effector cells module: IFNG, GZMA, GZMB, PRF1, LCK, GZMK, ZAP70, GNLY, FASLG, TBX21, EOMES, CD8A, and CD8B; Effector T cell module: IFNG, GZMA, GZMB, PRFI, LCK, GZMK, ZAP70, GNLY, FASLG, TBX21, EOMES, CD8A, and CD8B; Natural killer cells (NK cells) module: NKG7, CD160, CD244, NCRI, KLRC2, KLRK1, CD226, GZMH, GNLY, IFNG, KIR2DL4, KIR2DS 1, KIR2DS2, KIR2DS3, KIR2DS4, KIR2DS5, EOMES, CLIC3, FGFBP2, KLRFI, and SH2DIB; T cell traffic module: CXCL9, CXCL10, CXCR3, CX3CL1, CCR7, CXCL11, CCL21, CCL2, CCL3, CCL4, and CCL5; T cells module: EOMES, TBX21, ITK, CD3D, CD3E, CD3G, TRAC, TRBC1, TRBC2, LCK, UBASH3A, TRAT1, CD5, and CD28; B cells module: CD19, MS4A1, TNFRSF13C, CD27, CD24, CR2, TNFRSF17, TNFRSF13B, CD22, CD79A, CD79B, BLK, FCRL5, PAX5, and STA I; B cell traffic module: CXCL13 and CXCR5; Benign B cells module: CD19, MS4AI. TNFRSF13C, CD27, CD24, CR2, TNFRSFI7, TNFRSF13B, CD22, CD79A, CD79B, and BLK; Malignant B cell marker module: MME, CD70, CD20, CD22, and PAX5; MI signatures module: NOS2, I_12A, IL12B, IL23A, TNF, IL1B, and SOCS3; Th1 signature module: IFNG, IL2, CD40LG, IL15, CD27, TBX21, LTA, and IL21; Antitumor cytokines module: HMGB 1, TNF, IFNB 1, IFNA2, CCL3, TNFSF10, and FASLG; Checkpoint inhibition (or checkpoint molecules) module: PDCD1, CD274, CTLA4, LAG3, PDCD1LG2, BTLA, HAVCR2, and VSIR; Follicular dendritic cells module: CR1, FCGR2A, FCGR2B, FCGR2C, CR2, FCER2, CXCL13, MADCAMI1, ICAM1, VCAM1, BST1, LTBR, and TNFRSFA; Follicular B helper T cells module: CXCR5, B3GAT1, ICOS, CD40LG, CD84, IL21, BCL6, MAF, and SAP; Protumor cytokines module: I-10, TGF3 μl, TGFB2, TGF33, IL22, MIF, TNFSF133, IL6, and IL7; Regulatory T cells (Treg) module: TGFB 1, TGFB2, TGFB3, FOXP3, CTLA4, IL10, TNFRSF18, TNFR2, and TNFRSFIB; Treg traffic module: CCLI1, CXC12, CXCR-4, CCR4, CCL22, CCL1, CCL2, CCL5, CXCL13, and CCL28; Myeloid--derived suppressor cells (MDSCs) module: IDOL, ARGI, IL4R, IL10, TGFB 1, TGFB2, TGFB3, NOS2, CYBB, CXCR4, and CD33; MDSC and TAM traffic module: CXCL1, CXCL5, CCL2, CCL4, CCL8, CCR2, CCL3, CCL5, CSF1, and CXCL8; Granulocytes module: CXCL8, CXCL2, CXCL1, CCL24, KITLG, CCL5, CXCL5, CCR3, CCL26, IPRG2, EPX, RNASE2, RNASE3, IL5RA, GATA1, SIGLEC8, PRG3, MPO, ELANE, PRTN3, CTSG, FCGR3B, CXCR1, CXCR2, CD177, P13, FFAR2, PGLYRPL, CMA1, TPSAB 1, MS4A2, CPA3, IL4, IL5, IL13, and SIGLEC8; Granulocyte traffic module: CXCL8, CXCL2, CXCL1, CCLI1, CCL24, KITLG, CCL5, CXCL5, CCR3, and CCL26; Eosinophil signature model: PRCG2, EPX, RNASE2, RNASE3, IL5RA, GATA1, SIGLEC8, and PRG3; Neutrophil signature model: MPO, ELANE, PRTN3, CTSG, FCGR3B, CXCR1, CXCR2, CD177, P13, FFAR2, and PGLY RPI1; Mast cell signature module: CMIIA1, TPSAB 1, MS4A2, CPA3, IL4. IL5, 1L13, and SIGLEC8; M2 signature module: IL10, VEGFA, TGFB 1, IDOL, PTGES, MRCI, CSF1, LRPI, ARG1, PTGS 1, MSRI, CD163, and CSF1R; Th2 signature module: IL4, 1L5, IL13, IL10, IL25, and GAT A3; Th17 signature module: IL17A, IL22, IL26, IL17F, IL21, and RORC; Protumor cytokines module: 1110, TGFB 1, TGFB2, TGFB3, 1L22, and MIF; Complement inhibition module: CFD, CFI, CD55, CD46, CR1, and CD59; Fibroblastic reticular cells module: DES, VIM11, PDGFRA, PDPN, NT5E, THY1, ENG, ACTA2, LTBR, TNFRSF1A, VCAM1, ICAM1, and BST1; Cancer associated fibroblasts (CAFs) module: COL1A1, COL1A2, COL4A1, COL5A1, TGFB 1, TG FB2, TGFB3, ACTA2, FGF2, FAP, LRP1, CD248, COL6A1, COL6A2, COL6A3, FBLN1, LUM, MFAP5, LGALS 1, and PRELP; Matrix formation (or Matrix) module: MMP9, FNI, COL1A1, COL1A2, COL3A1, COL4A1, CA9, VTN, LGALS7, TIMPI1, MMP2, MMP1, MMP$^3$, MMP12, LGALS9, MMP7, and COL5A1; Angiogenesis module: VEGFA, VEGFB, VEGFC, PDGFC, CXCL8, CXCR2, FLT1, PIGF, CXCL5, KDR, ANGPT1, ANGPT2, TEK, VWF, CDH5, NOS3, VCAM1, MMRNI, LDHA, HIF1A. EPAS 1, CA9, SPP1, LOX, SLC2A1, and LAM P3; Endothelium module: VEGFA, NOS3, KDR, FLT1, VCAM 1, VWF, CDH5, MMRNI, CLEC 14A, MMRN2, and ECSCR; Hypoxia factors module: LDHA, HIF1A, EPAS 1, CA9, SPP1, LOX, SLC2A1, and LAMP3; Coagulation module: HPSE, SERPINE1, SERPINB2, F3, and ANXA$^2$; Blood endothelium module: VEGFA. NOS3, KDR, FLTi, VCAM1, VWF, CDH5, and MMRNI; Lymphatic endothelium module: CCL21 and CXCL12; Proliferation rate (or Tumor proliferation rate) module: MK167, ESC02, CETN3, CDK2, CCND1, CCNE1, AUR KA, AURKB, E2F1, MYBL2, BUB 1, PLKi, PRC 1, CCNB 1, MCM2, MCM6, CDK4, and CDK6; Oncogenes module: MDM2, M YC, AKT1, BCL2, MME, and SYK; P13 K/AKT/mTOR signaling module: PIK3CA, PIK3CB, PIK3CG, PIK3CD, AKT1, MTOR, PTEN, PRKCA, AKT2, and A KT3;

RAS/RAF/MEK signaling module: BRAF, FNTA, FNTB, MAP2K1, MAP2K2, MKNK1, and MKNK2; Receptor tyrosine kinases expression module: ALK, AXL, KIT, EGFR, ERBB2, FLT3, MET, NTRK1, FGFR1, FGFR2, FGFR3, ERBB4, ERBB3, BCR-ABL, PDGFRA, PDGFRB, and ABL1; Growth Factors module: NGF, CSF3, CSF2, FGF7, IGF1, IGF2, IL7, and FGF2; Tumor suppressors module: TP53, MLL2, CREBBP, EP300, ARIDIA, HIST1H1, EBF1, IRF4, IKZF3, KLHL6, PRDM1, CDKN2A, RB 1, EPHA7, TNFAIP3, TNFRSF14, FAS, SHP1, SOCS 1, SIK1, PTEN, DCN, MTAP, AIM2, and MITF; Metastasis signature module: ESRP1, HOXA1, SMARCA4, TWIST 1, NEDD9, PAPPA, CTSL, SNAI2, and HPSE; Antimetastatic factors module: NCAM1, CDH1, KISS 1, BRMS 1, ADGRG1, TCF21, PCDH10, and MITF; and Mutation status module: APC, ARIDIA, ATM, ATRX, BAP1, BR_AF, BRCA2, CDH1, CDKN2A, CTCF, CTNNB 1, DNMT3A, EGFR, FBXW 7, FLT3, GAT A3, HRAS, IDH1, KRAS, MAP3K1, MTOR, NAV3, NCOR1, NF1, NOTCH 1, NPM1, NRAS, PBRM1, PIK3CA, PIK3R1, PTEN, RB I, RUNX1, SETD2, STAG2, TAF1, TP53, and VHL. In certain embodiments, two or more genes from any combination of the listed modules may be included in an MF portrait.

In some embodiments, the gene groups of the modules may comprise at least two genes (e.g. at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same): Major histocompatibility complex I (MHCI) module: HLA-A, HLA-B, HLA-C, B2M, TAP1, and TAP2; Major histocompatibility complex II (MHCII) module; HLA-DRA, HLA-DRB 1, HLA-DOB. HLA-DPB2, HLA-DMA, HLA-DOA, HLA-DPA1, HLA-DPB 1, HLA-DMB, HLA-DQB 1, HFILA-DQA1, -1LA-DR35, HLA-DQA2, HILA-DQB2, and ILA-DRB6; Coactivation molecules module: CD80, CD86, CD40, CD83, TNFRSF4, ICOSLG, CD28; Effector cells (or Effector T cell) module: IFNG, GZMA, GZMB. PRFI, LCK, GZMK, ZAP70, GNLY, FASLG, TBX21, EOMES, CD8A, and CD8B; Natural killer cells (NK cells) module: NKG7, CD160, CD244, NCRI, KIRC2, KLRK1, CD226, GNLY, KIR2DL4, KIR2DS 1, lKIR2DS2, KIR2DS3, KIR2DS4, KIR2DS5, EOMES, CLIC3, FGFBP2, KLRF1, and SH2DlB; T cells module: TBX21, ITK, CD3D, CD3E, CD3G, TRAC, TRBC1, TRBC2, LCK, UB3AS13A, TRAT1, CD5, and CD28; B cells module: CD19, MS4A1, TNFRSF13C, CD27, CD24, CR2, TNFRSF17, TNFRSF13B, CD22, CD79A, CD79B, BLK, FCRL5, PAX5, and STAPI; MI signatures module: NOS2, IL12A, IL12B, IL23A, TNF, IL1B, and SOCS3; Th1 signature module: IFNG, IL2, CD40LG, 1L15, CD27, TBX21, LTA, and 1L21; Checkpoint inhibition (or checkpoint molecules) module: PDCD 1, CD274, CTLA4, LAG3, PDCD1LG2, BTLA, HAVCR2, and VSIR; Regulatory T cells (Treg) module: TGFB 1, TGFB2, TGFB3, FOXP3, CTLA4, IL10, and TNFRSF1B; Myeloid-derived suppressor cells (MDSCs) module: IDO1, A RGI, IL4R, IL10, TGFB 1, TGFB2, TGFB3, NOS2, CYBB, CXCR4, and CD33; Neutrophil signature model: MPO, ELANE, PRTN3, CTSG, FCGR33, CXCR1, CXCR2, CD177, P13, FFAIR2, and PGLYRP1; M2 signature module: IL10, VEGFA, TGFB 1, IDO1, PTGES, MRC1, CSF1, LRP1, ARG1, PTGS 1, MSR1, CD163, and CSF1R; Th2 signature module: 1L4, IL5, 1L13, IL10, 1L25, and GATA3; Protumor cytokines module: IL10, TGFB 1, TGFB2, TGFB3, IL22, and MIF; Complement inhibition module: CFD, CFI, CD55, CD46, and CR1; Cancer associated fibroblasts (CAFs) module: COL1A1, COL1A2, COL4A1, COL5A1, TGFB 1, TGFB2, TGFB3, ACTA2, FGF2, FAP, LRP1, CD248, COL6A1, COL6A2, COL6A3, FBLN1, LUM, MFAP5, and PRELP; Angiogenesis module: VEGFA, VEGFB, VEGFC, PDGFC, CXCL8, CXCR2, FLT1, PIGF, CXCL5, KDR, ANGPT1, ANGPT2, TEK, VWF, CDH5, NOS3, VCAM1, and MMRN1; Endothelium module: VEGFA, NOS3, KDR, FLT1, VCAM1, VWF, CDH5, MMRN1, CLECI4A, MMRN2, and ECSCR; Proliferation rate (or Tumor proliferation rate) module: MKI67, ESC02, CETN3, CDK2, CCND1, CCNE1, AURKA, AURKB, E2F1, MYBL2, BUB 1, PLK1, CCNB 1, MCM2, MCM6, CDK4, and CDK6; P13 K/AKT/mTOR signaling module: PIK3CA, PIK3CB, PI1K3CG, PIIK3CD, AKT1, MTOR, PTEN, PRKCA, AKT2, and AKT3; RAS/RAF/MEK signaling module: BRAF, FNTA, FNTB, MAP2K1, MAP2IK2, MKNK1, and MKNK2; Receptor tyrosine kinases expression module: ALK, AXL, KIT, EGFR, ERBB2, FLT3, MET, NTRKI, FGFR1, FGFR2, FGFR3, ERBB4, ERBB3, BCR-ABL, PDGFR_A, PDGFRB, and ABL1; Growth Factors module: NGF, CSF3, CSF2, FGF7, IGF1, IGF2, IL7, and FGF2; Tumor suppressors module: TP53, SIK1, PTEN, DCN, MTAP, AIM2, RB 1, and MITF; Metastasis signature module: ESRP1, 1-OXA1, SMARCA4, TWIST 1, NEDD9, PAPPA, and HPSE; and Antimetastatic factors module: NCAM1, CDH1, KISS 1, and BRMS 1, In some embodiments, the gene groups of the modules may further comprise at least two genes (e.g., at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same): T cell traffic module: CXCL9, CXCL10, CXCR3, CX3CLI, CCR7, CXCL11, CCL21, CCL2, CCL3, CCL4, and CCL5; Antitumor cytokines module: HMGB 1, TNF, IFNB 1, IFN A2, CCL3, TNFSF10, and FASLG; Treg traffic module: CCL17, CXCL12, CXCR4, CCR4, CCL22, CCL1, CCL2, CCL5, CXCL13, and CCL28; MDSC and TAM traffic module: CXCL1, CXCL5, CCL2, CCL4, CCL8, CCR2, CCL3, CCL5, CSF1, and CXCL8; Granulocyte traffic module: CXCL8, CXCL2, CXCL1, CCL11, CCL24, KITLG, CCL5, CXCL5, CCR3, and CCL26; Eosinophil signature model: PRG2, EPX, R_NASE2, RNASE3, IL5RA, GATA1, SIGLEC8, and PRG3; Mast cell signature module: CMA1, TPSAB 1, MS4A2, CPA3, IL4, IL5, 1L13, and S1GLEC8; Th17 signature module: IL17A, IL22, 1L26, IL17F, IL21, and RORC; Matrix formation (or Matrix) module: FN1, CA9, MMP1, MMP3, MMP12, LGA LS9, MIMP7, MMNP9, COL1A1, COL1A2, COL4A1, and COL5A1; and Hypoxia factors module: LDHA, HIF1A, EPAS 1, CA9, SPP1, LOX, SLC2A1, and LAMP3. In certain embodiments, two or more genes from each of the listed modules are included. Any of the foregoing sets of modules may be used in a MF portrait for a subject with a solid cancer (e,g., melanoma).

In some embodiments, the gene groups of the modules may comprise at least two genes (e.g., at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same): Effector T cell module: IFNG, GZMA, GZMB, PRFI, LCK, GZMK, ZAP70, GNLY, FASLG, TBX21, EOMES, CD8A, and CD8B; Natural killer cells (NK cells) module: NKG7, CD160, CD244, NCR1, KLRC2, KLRK1, CD226, GZMH, GNLY, IFNG, KIR2DL4, KIR2DS 1, KIR2DS2, KIR2DS3, KIR2DS4, and KIR2DS5; T cells module: EOMES, TBX21, ITK, CD3D, CD3E, CD3G, TRAC, TRBC1, TR I3C2, LCK, UBASH3A, and TRAT1; Benign B cells module: CD19, MS4A1, TNFRSF13C. CD27, CD24, CR2, TNFRSF17, TNFRSF13B, CD22, CD79A, CD7913, and BLK; Malignant B cell marker module: MME, CD70, CD20, CD22, and PAX5; MI signatures module: NOS2, ILI2A, IL12B, IL23A, TNF, IL1B, and SOCS3; Thi signature module: IFNG, 1L2, CD40LG, IL15, CD$^2$7, TBX21, LTA, and IL21; Checkpoint inhibition (or checkpoint molecules) module: PDCD1, CD274, CTLA4, LAG3, PDCD1LG2, BTLA, and HAVCR2; Follicular dendritic cells module: CR1, FCGR2A, FCGR2B, FCGR2C, CR2, FCER2, CXCL13, MADCAM1, ICAM1, VCAM1,BST1, LTBR, and TNFRSF1A; Follicular B helper T cells module: CXCR5, B3GAT1, ICOS, CD)40LG, CD84, HL21, BCL6, MAF, and SAP; Protumor cytokines module: IL10, TGFB 1. TGFB2, TGFB3, IL22, MIF, TNFSF13B, 1L6, and IL7; Regulatory T cells (Treg) module: TGFB1, TGFB2, TGF33, FOXP3, CTLA4, I110, TNFRSF18, and TNFR2; Neutrophil signature model: MPO, ELANE, PRTN3, and CTSG: M2 signature module: IL1, VEGFA, TGFB 1, IDOl, PTGES, MRCl, CSF1, LRPI, ARGI, PTGS 1, MSR1, CD163, and CSF1R: Th2 signature module: IL4, IL5, 1L13, IL10, IL25, and GAT A3; Complement inhibition module: CFD, CFI, CD55, CD46, CR1, and CD59; Fibroblastic reticular cells module: DES, VIM, PDGFRA, PDPN, NT5E, THY1, ENG, ACTA2, LTBR, TNFRSFIA, VCAMI1, ICAM1, and BST1; Angiogenesis module: VIEGFA, VEGFiB, VEG FC, PDGFC, CXCL8, CXCR2, FLTl, PIGF, CXCL5, KDR, ANGPT1, ANGPT2, TEK, VWF, and CDH5; Blood endothelium module: VEGFA, NOS3, KDR, FLT1, VCAM1, VWF, CDH5, and MMRNI; Proliferation rate (or Tumor proliferation rate) module: MKK167, ESC02, CETN3, CDK2, CCND1, CCNE1, AURKA, AURKB, E2F1, MYBL2, BUB 1, PLK1, CCNB 1, MCM2, and MCM6; Oncogenes module: MDM2, MYC, AKT1, BCL2, MME, and SYK; and Tumor suppressors module: TP53, MLL2, CREBBP, EP300, ARID I A, HIST1H1, EBFI, IRF4, IKZF3, KLHL6, PRDMI1, CDKN2A, RB I, EP1HA7, TNFAIP3, TNFRSF14, FAS, SHP1, and SOCS 1. In some embodiments, the gene groups of the modules may further comprise at least two genes (e.g., at least two genes, at least three genes, at least four genes, at least five genes, at least six genes, at least seven genes, at least eight genes, at least nine genes, at least ten genes, or more than ten genes as shown in the following lists; in some embodiments all of the listed genes are selected from each group; and in some embodiments the numbers of genes in each selected group are not the same): Coactivation molecules module: TNFRSF4 and CD28; B cell traffic module: CXCL13 and CXCR5; Anti-tumor cytokines module: HMGB 1, TNF, IFNB 1, IFNA2, CCL3, TNFSFl0, FASLG; Treg traffic module: CCL17, CCR4, CCL22, and CXCL13; Eosinophil signature model: PRG2, EPX. RNASE2, RNASE3, IL5RA, GATA1, SIGLEC8, and PRG3; Mast cell signature module: CMA1, TPSAB 1, MS4A2, CPA3, 1L4, IL.5, 1L13, and SIGLEC8; Th17 signature module: IL17A, IL22, IL26, ILI 7F, IL21, and RORC; Matrix formation (or Matrix) module: MMP9, FNI, COL1A1, COL1A2, COL3A1, COL4A1, CA9, VTN, LGALS7, TIMPI, and MMP2; Hypoxia factors module: LDHA, HIF1A, EPAS 1, CA9, SPPI, LOX, SLC2A1, and LAMP3; Coagulation module: HPSE, SERPINE1, SERPINB2, F3, and ANXA2; and Lymphatic endothelium module: CCL2I and CXCL12. In certain embodiments, two or more genes from each of the listed modules are included. Any of the foregoing sets of modules may be used in a MF portrait for a subject with a follicular lymphoma.

In some embodiments, the plurality of gene groups (or modules) associated with cancer malignancy is the tumor properties group. In some embodiments, the plurality of gene groups associated with cancer microenvironment are the tumor--promoting immune microenvironment group, the anti-tumor immune microenvironment group, the angiogenesis group, and the fibroblasts group.

In certain embodiments, the plurality of gene groups associated with cancer malignancy comprises at least three genes from the following group (e.g., at least three genes, at least four genes, at least five genes, at least six genes, at least seven genes, at least eight genes, at least nine genes, at least ten genes, or more than ten genes are selected from each group; in some embodiments all of the listed genes are selected from each group): the tumor properties group: MKI67, ESCO2, CETN3, CDK2, CCND1, CCNEI, AURKA, AURKB, CDK4, CDK6, PRC 1, E2FI, MYBL2, BUB 1, PLK1, CCNB 1, MCM2, MCM6, PIK3CA, PIK3CB. PIK3CG, PIK3CD, AKTI, MTOR, PTEN, PRKCA, AKT2, AKT3, BRAF, FNTA, FNTB, MAP2K1, MAP2K2, MKNK1, MKNK2, ALK, AXL, KIT, EGFR, ERBB2, FLT3, MET, NTRKI, FGFRI, FGFR2, FGFR3, ER13B4, ERB33, BCR-ABL, PDGFRA, PDGFRB, NGF, CSF3, CSF2, FGF7, IGF1, IGF2, 1L7, FGF2, TP53, SIK1, PTEN, DCN, MTAP, AIM2, RB I, ESRPI, CTSL, HOXA1, SMARCA4, SNAI2, TWIST1, NEDD9, PAPPA, HPSE, KISS 1, ADGRG,I BRMS 1, TCF21, CDH1, PCDH10, NCAM1, MITF, APC, ARID 1 A, ATM, ATRX, BAP1, BRAF, BRCA2, CDH1, CDK_N2A, CTCF, CTNNB 1, DNMT3A, EGFR, FBXW7, FLT3, GAT A3, HRAS, IDH1, KRAS, MAP3K1, MTOR, NAV3, NCOR1, NF1, NOTCH1, NPM1, NRAS, PBRM1, PIK3CA, PIK3RI, PTEN, RB I, RUNX1, SETD2, STAG2, TAF1, TP53, and VFIL. In certain embodiments, the plurality of gene groups associated with cancer microenvironment includes at least three genes from each of the following groups (e.g., at least three genes, at least four genes, at least five genes, at least six genes, at least seven genes, at least eight genes, at least nine genes, at least ten genes, or more than ten genes are selected from each group; in some embodiments all of the listed genes are selected from each group): the anti-tumor immune microenvironment group: HLA-A, HLA-B, HLA-C, B2M, TAP1, TAP2, HLA-DRA, HLA-DRB 1, HLA-DOB, HLA-DPB2, HLA-DMA, HLA-DOA, HLA-DPA1, HLA-DPB1, HLA-DMB,1-1LA-DQBB1, HILA-DQA1, HiL-A-DRB5, HLA-DQA2, HLA-DQB2, HLA-DRB6, CD80, CD86, CD40, CD83. TNFRSF4, COSLG, CD28, IFNG, GZMA, GZMB, PRF1, LCK, GZ.MPK, ZAP70, GNLY, FASLG, TBX21, EOMES, CD8A, CD8B, NKG7, CD160, CD244, NCRI, KLRC2, KLRK1, CD226, GZMH, GNLY, IFNG, KIR2DL4, KIR2DS 1, KIR2DS2, KIR2DS3, KIR_2DS4, KIR2DS5, CXCL9, CXCL10, CXCR3, CX3CL1, CCR7, CXCL11, CCL21, CCL2, CCL3, CCL4, CCL5, EOMES, TBX21, ITK, C_D3D, CD3E, CD3G, TRAC, TR3C1, TRBC2, LCK, UBASH3A, TRAT1, CD19, MS4A1, TNFRSF13C, CD27, CD24, CR2, TNFRSF17, TNFRSF13B, CD22, CD79A, CD79B, BLK, NOS2, IL12A, IL12B, IL23A, TNF, IL1B, SOCS3, IFNG, IL2, CD40LG, IL15, CD27, TBX21, LTA, IL21, HMGB 1, TNF, IFNB 1, IFNA2, CCL3, TNFSF10, and FASLG; the tumor-promoting immune microenvironment group: PDCD1, CD274, CTLA4, LAG3, PDCD1LG2, BTLA, HAVCR2, VSIR, CXCL 12, TGFB 1, TGFB2, TGFB3, FOXP3, CTLA4, IL10, TNFRSF1B, CCL17, CXCR4, CCR4, CCL22, CCL1, CCL2, CCL5, CXCL13, CCL28, IDO1, ARGI, IL4R, IL10, TGFB 1, TGFB2, TGFB3, NOS2-CYBB, CXCR4, CD33, CXCLI, CXCL5, CCL2, CCL4, CCL8, CCR2, CCL3, CCL5, CSF1, CXCL8, CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, CMAI, TPSAB 1, MS4A2, CPA3, 1L4, IL5, 1L13, SIGLEC8, MPO, ELANE, PRTN3, CTSG, IL10, VEGFA, TGFB 1, IDO1, PTGES, MRC 1, CSF1, LRP1, ARG1, PTGS 1, MSR1, CD163, CSF1R, 1L4, IL5, L13, IL, 1L25, GAT A3, 1I10, TGFB 1, TGFB2, TGFB3, IL22, MIF, CFD, CFI, CD55, CD46, and CR1: the fibroblasts group: LGALS 1, CO1IAI, COL1A2, COL4A1, COL5A1, TGFB 1, TGFB2, TGFB3, ACTA2, FGF2, FAP, LRP1, CD248, COL6A1, COL6A2, and COL6A3; and the angiogenesis group: VEGFA, VEGFB, VEGFC, PDGFC, CXCL8, CXCR2, FLT1, PIGF, CXCL5, KDR, ANGPT1, ANGPT2, TEK, VWF, CDH5, NOS3, KDR, VCAM1, MMRN1, LDHA, HIF1A, EPAS 1, CA9, SPP1, LOX, SLC2A1, and LAMP3. In some embodiments, an unequal number of genes may be selected from each of the listed groups for use. In specific embodiments, all or almost all of the listed genes are used.

In some embodiments, the plurality of gene groups associated with cancer malignancy are: the proliferation rate group, the PI13K/AKT/mTOR signaling group, the RAS/RAF/MEK signaling group, the receptor tyrosine kinases expression group, the tumor suppressors group, the metastasis signature group, the anti-metastatic factors group, and the mutation status group. In some embodiments, the plurality of gene groups associated with cancer microenvironment are: the cancer associated fibroblasts group, the angiogenesis group, the antigen presentation group, the cytotoxic T and NK cells group, the B cells group, the anti-tumor microenvironment group, the checkpoint inhibition group, the Treg group, the MDSC group, the granulocytes group, and the tumor-promotive immune group.

In some embodiments, the plurality of gene groups associated with cancer malignancy comprises at least three genes from each of the following groups (e.g., at least three genes, at least four genes, at least five genes, at least six genes, at least seven genes, at least eight genes, at least nine genes, at least ten genes, or more than ten genes are selected from each group): the proliferation rate group: MK167, ESC02, CETN3, CDK2, CCND1, CCNEI, AURKA, AURKB, CDK4, CDK6, PRC 1, E2F1, MYBL2, BUB 1, PLK1, CCNB 1, MCM/2, and MCNM6; the PI3 K/AKT/mTOR signaling group: PIK3CA, PIK3CB, PIK3CG, PIK3CD, AKT1, MTOR, PTEN, PRKCA, AKT2, and AKT3; the RAS/RAF/MEK signaling group: BRAF, FNTA, FNTB, MAP2K1, MAP2K2, MKNK1, and MKNK2; the receptor tyrosine kinases expression group: ALIK, AXL, KIT, EGFR, ERBB2, FLT3, MET, NTR1K1, FGFRi, FGFR2, FGFR$^3$, ERBB4, ERBB3, BCR-ABL, PDGFRA, and PDGFRB; the tumor suppressors group: TP53, SIK1, PTEN, DCN, MTAP, AEV12, and RB 1; the metastasis signature group: ESRP1, CTSL, HOXA1, SMARCA4, SNAI2, TWIST 1, NEDD9, PAPPA, and HPSE; the anti-metastatic factors group: KISS 1, ADGRG1, BRMS 1, TCF2I, CDH1, PCDHIO, NCAM1, and MITF; and the mutation status group: APC, ARIDIA, ATM, ATRX, BAPI, BRAF, BRCA2, CDH1, CDKN2A, CTCF, CTNNB I, DNMT3A, EGFR, FBXW7, FLT3, GAT A3, HRAS, IDH1, KRAS, MAP3K1, MTOR, NAV3, NCOR1, NF1, NOTCH1, NPM1, NRAS, PBRM1, PIK3CA, PIK3R1, PTEN, RB I, RUNX1, SETD2, STAG2, TAF1, TP53, and VHL In some embodiments, the plurality of gene groups associated with cancer microenvironment comprises at least three genes from each of the following groups (e.g., at least three genes, at least four genes, at least five genes, at least six genes, at least seven genes, at least eight genes, at least nine genes, at least ten genes, or more than ten genes are selected from each group): the cancer associated fibroblasts group: LGALS 1, COL1A1, COL1A2, COL4A1, COL5A1, TGFB 1, TGFB2, TGFB3, ACTA2, FGF2, FAP, LRPI, CD248, COL6A1, COL6A2, and COL6A3; the angiogenesis group: VEGFA, VEGFB, VEGFC, PDG FC, CXCL8, CXCR2, FLT1, PIGF, CXCL5, KDR, ANGPT1, ANGPT2, TEK, VWF, CDH5, NOS3, KDR. VCAM1, MMRN1, LDHA, HIF1A, EPAS 1, CA9, SPP1, LOX, SLC2A1, and LA MP3; the antigen presentation group: HLA-A, HLA--B, HLA-C, B2M, TAP1, TAP2, HLA-DRA, HLA-DRB 1, HLA-DOB, HLA-DPB2, HLA-DMA, HLA-DOA, HLA-DPA1, HLA-DPB 1, HLA-DMB, HLA-DQB 1, HLA-DQA1, HLA-DRB5, HLA-DQA2, HLA-DQB2, HLA-DRB6, CD80, CD86, CD40, CD83, TNFRSF4, ICOSLG, and C1D28; the cytotoxic T and N1K cells group: IFNG, GZMA, GZMB, PRF1, LCK, GZMK, ZAP70, GNLY, FASLG, TBX21, EOMES, CD8A, CD8B, NKG7, CD160, CD244, NCR1, KLRC2, KLR IK1I, CD226, GZMH, GNLY, IFNG, KIR2DL4, KIR2DS 1, KIR2DS2, KIR2DS3, KIR2DS4, KIR2DS5, CXCL9, CXCL10, CXCR_3, CX3CL1, CCR7, CXCLI1, CCL21, CCL2, CCL, CCL4, CCL5, EOMES, TBX21, ITK, CD3D, CD3E, CD3G, TRAC, TR_BC1, TRBC2, LCK, UBASH3A, and TRAT1; the B cells group: CD19, MS4A1, TNFRSFI3C, CD27, CD24, CR2, TNFRSF17, TNFRSFl3B, CD22, CD79A, CD79B, and BLK; the anid-tumor microenvironment group: NOS2, IL12A, ILl2B, IL23A, TNF, IL1B, SOCS3, IFNG, IL2, CD40LG, IL15, CD27, TBX21, LTA, IL21, HMGB 1, TNF, IFNB 1, IFNA2, CCL3, TNFSF10. and FASLG; the checkpoint inhibition group: PDCDI, CD274, CTLA4, LAG3, PDCD2I 2, BTLA, HA VCR2, and VSIR; the Treg group: CXCL12, TGFB 1, TGFB2, TGFB3, FOXP3, CTLA4, IL10, TNFRSF1B, CCL17, CXCR4, CCR4, CCL22, CCL1, CCL2, CCL5, CXCL13, and CCL28; the MDSC group: IDOl, ARGI, IL4R, IL10, TGFB 1, TGFB2, TGFB3, NOS2, CYBB, CXCR4, CD33, CXCL1, CXCL5, CCL2, CCL4, CCL8, CCR2, CCL3, CCL5, CSF1, and CXCL8; the granulocytes group: CXCL8, CXCL2, CXCL1, CCLI1, CCL24, KITLG, CCL5, CXCL5, CCR3, CCL26, PRG2, EPX, RNASE2, RNASE3, IL5RA, GATA1, SIGLEC8, PRG3, CMAI, TPSAB 1, MS4A2, CPA3, IL4, IL5, IL13, SIGLEC8, MPO, ELANE, PRTN3, and CTSG; the tumor-promotive immune group: IL10, VEGFA, TGFB1, IDO1, PTGES, MRCI, 20 CSF1, LRPI, ARGI, PTGS 1, MSRI, CD163, CSFIR. IL4, IL5, IL13, IL10, IL25, GAT A3. IL10, TGFB 1, TGFB2, TGFB3, 1L22, MIF, CFD, CFI, CD55, CD46, and CR1. In some embodiments, an unequal number of genes may be selected from each of the listed groups for use, In specific embodiments, all or almost all of the listed genes are used.

In some embodiments, the plurality of gene groups associated with cancer malignancy are: the proliferation rate group, the PI3K/AKT/MTOR signaling group, the RAS/RAF/MEK signaling group, the receptor tyrosine kinases expression group, the growth factors group, the tumor suppressors group, the metastasis signature group, the antimetastatic factors group, and the mutation status group, In some embodiments, the plurality of gene groups associated with cancer microenvironment are: the cancer associated fibroblasts group, the angiogenesis group, the MHCI group, the MHCII group, the coactivation molecules group, the effector cells group, the NK cells group, the T cell traffic group, the T cells group, the B cells group, the MI signatures group, the Th1 signature group, the antitumor cytokines group, the checkpoint inhibition group, the Treg group, the MDSC group, the granulocytes group, the M2 signature group, the Th2 signature group, the protumor cytokines group, and the complement inhibition group.

In some embodiments, the plurality of gene groups associated with cancer malignancy comprises at least three genes from each of the following groups (e.g., at least three genes, at least four genes, at least five genes, at least six genes, at least seven genes, at least eight genes, at least nine genes, at least ten genes, or more than ten genes are selected from each group): the proliferation rate group: MKI67, ESC02, CETN3, CDK2, CCND1, CCNE1, AURKA, AURKB, CDK4, CDK6, PRC 1, E2F1, MYBL2, BUB 1, PLK1, CCNB 1, MCM2, and MCM6; the P13 K/AKT/mTOR signaling group: PIK3CA, PIK3CB, P1IK3CG, P1IK3CD, AIKT1, MTOR, PTEN, PRKCA, AKT2, and AKT3; the RAS/RAF/MEK signaling group: BRAF, FNTA, FNTB, MAP2K1, MAP2K2, MKNK1, and M4IKNK2; the receptor tyrosine kinases expression group: ALK, AXL, KIT, EGFR, ERBB2, FLT3, MET, NTRK1, FGFRI, FGFR2, FGFR3, ERBB4, ERBB3, BCR-ABL, PDGFRA, and PDGFRB; the growth factors group: NGF, CSF3, CSF2, FGF7, IGF1, IGF2, IL7, and FGF2; the tumor suppressors group: TP53, SIK1, PTEN, DCN, MTAP, AIM2, and RB I; the metastasis signature group: ESRP1, CTSL, HOXA1, SMARCA4, SNAI2, TWIST 1, NEDD9, PAPPA, and HPSE; the antimetastatic factors group: KISS 1, ADGRG1, BRMS 1, TCF21, CDH1, PCDH10, NCAM1, and MITF; and the mutation status group: APC, ARID 1 A, ATM, ATRX, BAP1, BRAF, B3RCA2, CDH1, CDKN2A, CTCF, CTNNB 1, DNMT3A, EGFR, FBXW7, FLT3, GAT A3, HRAS, IDH1, KRAS, MAP3K1, MTOR, NAV3, NCOR1, NF1, NOTCH1, NPM1, NRAS, PBRM1, PIK3CA, PIK3R1, PTEN, RB I, RUNX1, SETD2, STAG2, TAF1, TP53, and VHL. In some embodiments, the plurality of gene groups associated with cancer microenvironment comprises at least three genes from each of the following groups: the cancer associated fibroblasts group: LGALS 1, COL1A1, COL1A2, COL4A1, COL5A1, TGFB 1, TGFB2, TGFB3, ACTA2, FGF2, FAP, LRP1, CD248, COL6A1, COL6A2, and COL6A3; the angiogenesis group: VEGFA, VEGF3, VEGFC, PDGFC, CXCL8, CXCR2, FLT1, PIGF, CXCL5, KDR, ANGPT1, ANGPT2, TEK, VWF, CDH5, NOS3, KDR, VCAM1, MMRN1, LDHA, HIF1A, EPAS 1, CA9, SPP1, LOX, SLC2A1, and LAMP3; the MHCI group: HLA-A, HLA-B, H1LA-C, B2M, TAP1, and TAP2; the MHCII group: HLA-DR_A, HLA-DRB 1, H1LA-DOB, HLA-DPB2, HLA-DMA, HLA-DOA, HLA-DPA1, HLA-DPB 1, HLA-DMB, HLA-DQB 1, HLA-DQA1, HLA-RB5, HLA-DQA2, HLA-DB2, and HLA-DRB6; the coactivation molecules group: CD80, CD86, CD40, CD83. TNFRSF4, ICOSLG, and CD28; the effector cells group: IFNG, GZMA, GZM B, PRF1, LCK, GZMK, ZAP70, GNLY, FASLG, TBX21, EOMES, CD8A, and CD8B; the NK cells group: NKG-7, CD160, CD244, NCR1, KLRC2, KLRK1, CD226, GZMH, GNLY, IFNG, KIR2DL4, KIR2DS 1, KIR2DS2, KIR2DS3, KIR2DS4, and KIR2DS5; the T cell traffic group: CXCL9, CXCL10, CXCR3, CX3CLI, CCR7, CXCL1I1, CCL21, CCL2, CCL3, CCL4, and CCL5; the T cells group: EOMES, TBX21, ITK, CD3D, CD3E, CD3G, TRAC, TRBC1, TRBC2, LCK, UBASH3A, and TRAT1; the B cells group: CD19, MS4AI, TNFRSFI3C. CD27, CD24, CR2, TNFRSF17, TNFRSF13B, CD22, CD79A, CD79B, and 13L K; the MI signatures group: NOS2, ILI2A, ILI2B, 1L23A, TNF, IL1B, and SOCS3; the Th1 signature group: IFNG, IL2, CD40LG, IL15, CD27, TBX21, LTA, and 1L21; the antitumor cytokines group: HMGB 1, TNF, IFNB 1, IFNA2, CCL3, TNFSFI0, and FASLG; the checkpoint inhibition group: PDCD, CD274, CTLA4, LAG3, PDCD1LG2, BTLA, HAVCR2, and VSIR; the Treg group: CXCL12, TGFB 1, TGFB2, TGFB3, FOXP3, CTLA4, IL10, TNFRS-FIB, CCL17, CXCR4, CCR4, CCL22, CCL1, CCL2, CCL5, CXCL13, and CCL28; the MDSC group: IDOl, ARGI, IL4R, ILI0, TGFB 1, TGFB2, TGFB3, NOS2, CYBB, CXCR4, CD33, CXCL1, CXCL5, CCL2, CCL4, CCL8, CCR2, CCL3, CCL5, CSF1, and CXCL8; the granulocytes group: CXCL8, CXCL2, CXCL1, CCLI1, CCL24, KITLG, CCL5, CXCL5, CCR3, CCL26, PRG2, EPX, RNASE2, RNASE3, IL5RA, GATA1, SIGLEC8, PRG3, CMAI, TPSAB 1, MS4A2, CPA3, 1L4, IL5, IL13, SIGLEC8, MPO, ELANE, PRTN3, and CTSG; the M2 signature group: IL10, VEGFA, TGFB 1, IDOl, PTGES, MRC1, CSF1, LRP1, ARG1, PTGS 1, MSR1, CD163, and CSFIR; the Th2 signature group: IL4, IL5, IL13, IL10, I_25, and GAT A3; the proturnor cytokines group: IL10, TGFB 1, TGFB2, TGFB3, IL22, and M IF; and the complement inhibition group: CFD, CFI, CD55, CD46, and CR1. In some embodiments, an unequal number of genes may be selected from each of the listed groups for use. In specific embodiments, all or almost all of the listed genes are used.

MF profiles may depict the intensity (e.g., amount) of a module or gene group using a distinguishing feature (e.g., color, shading or pattern, size, and/or shape). As used herein, "intensity" refers to an amount of a gene group expression level within a MF profile. For example, 2MF profile type cancers have an intense proliferation rate module indicative of a high proliferation rate of such cancers. Accordingly, in $2^{nd}$ MF profile type cancers, the proliferation rate module is depicted in a larger size as an indication that this module is more abundant in the tumor than other modules. In some embodiments, the MF profile comprises modules of various sizes in which module size is indicative of module intensity. In some embodiments, the MF profile comprises modules of increasing sizes in which increasing module size is indicative of increasing module intensity.

MF profiles may depict a module as a pro-tumor module or anti-tumor module using a distinguishing feature (e.g., color, shading or pattern, size, and/or shape). In some embodiments, the MF profile comprises a pro-tumor module as one color or pattern and an anti-tumor module as another color or pattern. In some embodiments, the MF profile comprises a pro-tumor module as burgundy or a shade thereof and an anti-tumor module as blue or a shade thereof, In some embodiments, the MF profile comprises a pro-tumor module as solid shades without cross-marking and an anti-tumor module as shades with cross--marking.

MF profiles may comprise any number of functional modules, In some embodiments, the M F profile comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, or at least 28 modules. In some embodiments, the MF profile comprises up to 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, up to 26, up to 27, or up to 28 modules, MF Profile Types The present disclosure is based, in part, on the finding that various cancers (e.g., tumors) can be categorized into four types (i.e., first MF profile type or "$1^{st}$ MF profile," second MF profile type or "$2^{nd}$ MF profile," third MF profile type or "$3^{rd}$ MF profile," and fourth MF profile type or "$4^{th}$ MF profile" cancers) based on certain properties of the cancer or tumor (e.g., expression data).

As used herein, the term "cancer type," "tumor type," or "MF profile type" refers to a cancer (e.g. a tumor) having certain features including certain molecular and cellular compositions, and biological processes. MF profile type, in some embodiments, may provide information relating to a level of immune cells within and/or surrounding a tumor. For example, an "inflamed" or "hot" MF profile type includes a cancer (e.g., a tumor) that is highly infiltrated by immune cells, a "non-inflamed" or "cold" MF profile type describes a cancer (e.g., a tumor) that is poorly infiltrated by immune cells. In some embodiments, describing a cancer as a $1^{st}$ MF profile type cancer indicates that the cancer (e.g., a tumor) is inflamed. In some embodiments, describing a cancer as a $2^{nd}$ MF profile type cancer indicates that the cancer (e.g., a tumor) is rd inflamed. In some embodiments, describing a cancer as a 3 MF profile type cancer indicates that the cancer (e.g., a tumor) is non-inflamed, In some embodiments, describing a cancer as a $4^{th}$ MF profile type cancer indicates that the cancer (e.g., a tumor) is non-inflamed. MF profile type, in some embodiments, provides information relating to an average ratio of malignant to nonmalignant cells of a tumor (e.g., tumor purity). In some embodiments, the average ratio of malignant to nonmalignant cells increases with MF profile type. For example, $4^{th}$ MF profile >3$^{rd}$ MF profile >2$^{nd}$ MF profile >1$^{st}$ MF profile with respect to an average ratio of malignant to nonmalignant cells.

In some embodiments, describing a cancer as a 1$^{st}$ MF profile type cancer indicates that the tumor has about 2 times (twice) as many nonmalignant cells as malignant cells. In some embodiments, describing a cancer as a 1$^{st}$ MF profile type cancer indicates that the tumor has an average ratio of malignant to nonmalignant cells of between 0.4 to 0.6. In some embodiments. describing a cancer as a 1$^{st}$ MF profile type cancer indicates that the cancer has an average ratio of malignant to nonmalignant cells of about 0.5.

In some embodiments, describing a cancer as a 2$^{nd}$ MF profile type cancer indicates that the cancer has about 1.5 times as many nonmalignant cells as malignant cells. In some embodiments, describing a cancer as a 2$^{nd}$ MF profile type cancer indicates that the cancer has an average ratio of malignant to nonmalignant cells between 0.6 to 0.7, In some embodiments, describing a cancer as a 2$^{nd}$ MF profile type cancer indicates that the cancer has an average ratio of malignant to nonmalignant cells of about 0.65. rd In some embodiments, describing a cancer as a 3 MF profile type cancer indicates that the cancer has about 1.3 times as many nonmalignant cells as malignant cells. In some d embodiments, describing a cancer as a 3 MF profile type cancer indicates that the cancer has an average ratio of malignant to nonmalignant cells between 0.7 to 0.8, In some d embodiments, describing a cancer as a 3 MF profile type cancer indicates that a tumor has an average ratio of malignant to nonmalignant cells of about 0.8.

In some embodiments, describing a cancer as a 4 MF profile type cancer indicates that the cancer has about 1.1 times as many nonmalignant cells s malignant cells. In some embodiments, describing a cancer a 4$^{th}$MF profile type cancer indicates that the cancer has an average ratio of malignant to nonmalignant cells between 0,8 to 0.9. In some embodiments, describing a cancer as a 4$^{th}$ MF profile type cancer indicates that the cancer has an average ratio of malignant to nonmalignant cells of about 0.85.

MF profile type, in some embodiments, provides information relating to tumor vascularization. In some embodiments, describing a cancer as a 1$^{st}$ MF profile type cancer indicates that the cancer (e.g., the tumor) is vascularized. In some embodiments, describing a cancer as a 2$^{nd}$ MF profile type cancer indicates that the cancer (e.g,, the tumor) is non- rd vascularized. In some embodiments, describing a cancer as a 3 MF profile type cancer indicates that the cancer (e.g., the tumor) is vascularized. In some embodiments, describing a cancer as a 4$^{th}$ MF profile type cancer indicates that the cancer (e.g., the tumor) is non-vascularized.

MF profile type, in some embodiments, provides information relating to levels of cancer associated fibroblasts (CAFs) within and/or surrounding a tumor, In some embodiments, describing a cancer as a 1MF profile type cancer indicates that the cancer (e.g; the tumor) comprises CAFs, In some embodiments, describing a cancer as a 2$^{nd}$ MF profile type cancer indicates that the cancer (e.g., the tumor) is devoid of CAFs. In some rd embodiments, describing a cancer as a 3 MF profile type cancer indicates that the cancer (e.g. the tumor) comprises CAFs. In some embodiments, describing a cancer as a 4$^{th}$ MF profile type cancer indicates that the cancer (e.g., the tumor) is devoid of CAFs.

MF profile type, in some embodiments, provides information relating to tumor proliferation rates. In some embodiments, describing a cancer as a 1$^{th}$ MF profile type cancer indicates that the cancer (e.g., the tumor) has an average proliferation rate. In some embodiments, describing a cancer as a 2$^{nd}$ r MF profile type cancer indicates that the cancer (e.g., the tumor) has a high proliferation rate. In some embodiments, describing a cancer as a d 3 MF profile type cancer indicates that the cancer (e.g., the tumor) has an average proliferation rate. In some embodiments, describing a cancer as a 4$^{th}$ MF profile type cancer indicates that the cancer (e.g., the tumor) has a high proliferation rate.

MF profile type, in some embodiments, provides information relating to patient survival rate. In some embodiments, the patient survival rate increases with MF profile type. For example, 1$^{st}$ MF profile >2$^{nd}$ MF profile >3$^{rd}$ MF profile >4$^{th}$ MF profile with respect to patient survival rate. In some embodiments, describing a cancer as a P MF profile type cancer indicates a good patient survival rate. In some embodiments, describing a cancer as a 2$^{th}$ MF profile type cancer indicates an optimal patient survival rate. In some embodiments, describing a rd cancer as a 3 MF profile type cancer indicates that a poor patient survival rate. In some embodiments, describing a cancer as a 4$^{th}$ MF profile type cancer indicates that a poor patient survival rate.

MF profile type, in some embodiments, provides information relating to patient treatment. In some embodiments, the MF profile type provides information relating to an expected treatment outcome of a therapy. In some embodiments, the MF profile indicates that a specific treatment option is recommended. In some embodiments, the MF profile indicates that a specific treatment option is non-curative. In some embodiments, the MF profile indicates that a specific treatment option is dependent on a certain feature of a tumor, for example, mutational status of the tumor. In some embodiments, identifying a cancer as a 1$^{st}$ MF profile type cancer indicates that a treatment selected from the group consisting of an angiogenesis inhibitor, a CAFs inhibitor, an immunosuppressive factor inhibitor, a MDSC inhibitor, a Treg inhibitor, a metastatic activity inhibitor, and an immunotherapy should be recommended or used. In some embodiments, identifying a cancer as a 1$^{st}$ MF profile type cancer indicates that treatment using a growth factor inhibitor dependent on a certain feature of a tumor (e.g., mutational status) should be recommended or used.

In some embodiments, identifying a cancer as a 2$^{nd}$ d MF profile type cancer indicates that a treatment selected from the group consisting of an immnosuppressive factor inhibitor, a MDSC inhibitor, a Treg inhibitor, a metastatic activity inhibitor, a checkpoint inhibitor, and an immunotherapy should be recommended or used. In some embodiments, identifying a cancer as a 2$^{nd}$ MF profile type cancer indicates that treatment using a growth factor inhibitor dependent on a certain feature of a tumor (e.g., mutational status) should be recommended or used. rd In some embodiments, identifying a cancer as a 3 MF profile type indicates that a treatment selected from the group consisting of an angiogenesis inhibitor, a CAFs inhibitor, an immunosuppressive factor inhibitor, a M2 macrophage inhibitor, a MDSC inhibitor, and a Treg inhibitor should be recommended or used. In some embodiments, identifying a cancer d as a 3 MF profile type indicates that a checkpoint inhibitor should be recommended or used. In some embodiments, identifying a cancer as a 4$^{o}$MF profile type cancer indicates that a treatment such as an angiogenesis inhibitor and/or an immunotherapy should be recommended or used. In some embodiments, identifying a cancer as a 4 MF profile type indicates that a non-curative treatment option may be selected from the group consisting of a kinase inhibitor, a radiotherapy, and a chemotherapy.

Computer Implemented Methods For Generating, Visualizing and Classifying MF Profiles Aspects of the technology described herein provide computer implemented methods for generating, visualizing and classifying molecular-functional (MF) profiles of cancer patients. In some embodiments, a software program may provide a user with a visual representation of a 20 patient's MF profile and/or other information related to a patient's cancer using an interactive graphical user interface (GUI). Such a software program may execute in any suitable computing environment including, but not limited to, a cloud-computing environment, a device co-located with a user (e.g., the user's laptop, desktop, smartphone, etc.), one or more devices remote from the user (e.g., one or more servers), etc.

Figure 17A:
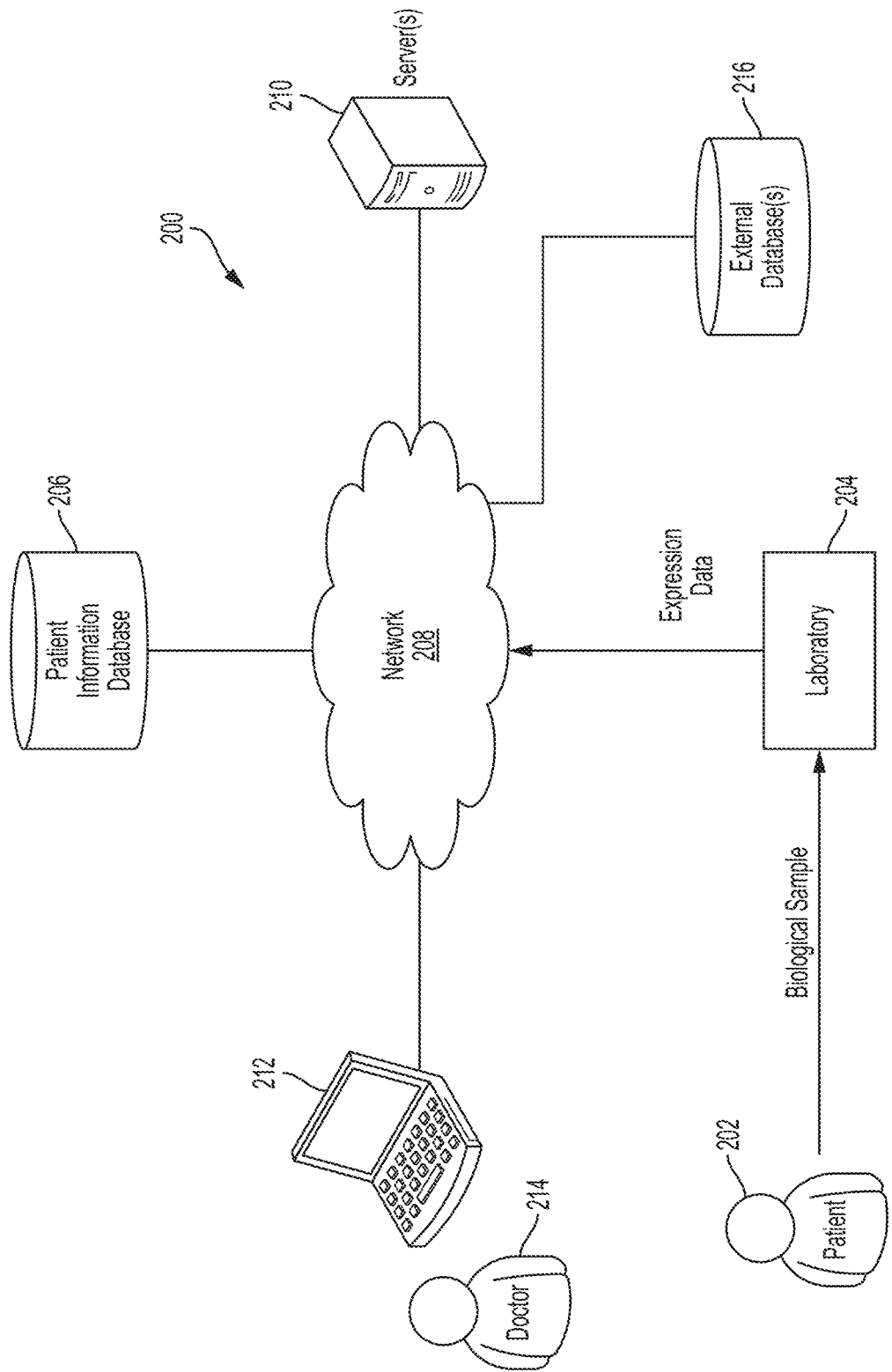
FIG. 17A is a block diagram of an illustrative environment 200 in which some embodiments of the technology described herein may be implemented.

For example, in some embodiments, the techniques described herein may be implemented in the illustrative environment 200 shown in FIG. 17A. As shown in FIG. 17A, within illustrative environment 200, one or more biological samples of a patient 202 may be provided to a laboratory 204. Laboratory 204 may process the biological sample(s) to obtain expression data (e.g., DNA, RNA, and/or protein expression data) and provide it, via network 208, to at least one database 206 that stores information about patient 202. Network 208 may be a wide area network (e.g., the Internet), a local area network (e.g., a corporate Intranet), and/or any other suitable type of network. Any of the devices shown in FIG. 17A may connect to the network 208 using one or more wired links, one or more wireless links, and/or any suitable combination thereof.

In the illustrated embodiment of FIG. 17A, the at least one database 206 may store expression data for the patient, medical history data for the patient, test result data for the patient, and/or any other suitable information about the patient 202. Examples of stored test result data for the patient include biopsy test results, imaging test results (e.g., MRI results), and blood test results. The information stored in at least one database 206 may be stored in any suitable format and/or using any suitable data structure(s), as aspects of the technology described herein are not limited in this respect. The at least one database 206 may store data in any suitable way (e.g., one or more databases, one or more files). The at least one database 206 may be a single database or multiple databases.

As shown in FIG. 17A, illustrative environment 200 includes one or more external databases 216, which may store information for patients other than patient 202. For example, external databases 216 may store expression data (of any suitable type) for one or more patients, medical history data for one or more patients, test result data (e.g., imaging results, biopsy results, blood test results) for one or more patients, demographic and/or biographic information for one or more patients, and/or any other suitable type of information. In some embodiments, external database(s) 216 may store information available in one or more publically accessible databases such as TCGA (The Cancer Genome Atlas), one or more databases of clinical trial information, and/or one or more databases maintained by commercial sequencing suppliers. The external database(s) 216 may store such information in any suitable way using any suitable hardware, as aspects of the technology described herein are not limited in this respect. In some embodiments, the at least one database 206 and the external database(s) 216 may be the same database, may be part of the same database system, or may be physically co-located, as aspects of the technology described herein are not limited in this respect.

In some embodiments, information stored in patient information database 206 and/or in external database(s) 216 may be used to perform any of the techniques described herein related to determining whether a subject is likely to respond positively or not likely to respond positively to an immune checkpoint blockade therapy. For example, the information stored in the database(s) 206 and/or 216 may be accessed, via network 208, by software executing on server(s) 210 to perform any one or more of the techniques described herein including with reference to FIGS. 54A, 54B, 54C, 54D, 55A and 55B.

For example, in some embodiments, server(s) 210 may access information stored in database(s) 206 and/or 216 and use this information to perform process 3900, described with reference to FIG. 54A, for identifying a MF profile cluster with which to associate an MF profile for a subject.

As another example, in some embodiments, server(s) 210 may access information stored in database(s) 206 and/or 216 and use this information to perform process 3920, described with reference to FIG. 54B, for generating MF profile clusters using RNA expression data obtained from subjects having a particular type of cancer.

As another example, in some embodiments, server(s) 210 may access information stored in database(s) 206 and/or 216 and use this information to perform process 3940, described with reference to FIG. 54C, for identifying an MF profile cluster with which to associate an M F profile determined for a subject at least in part by determining the subject's expression levels for multiple gene groups.

As another example, in some embodiments, server(s) 210 may access information stored in database(s) 206 and/or 216 and use this information to perform process 3960, described with reference to FIG. 54D, for generating MF profile clusters using RNA expression data obtained from subjects having a particular type of cancer, and associating a subject with one of the generated MF clusters based on the subject's M F profile.

As another example, in some embodiments, server(s) 210 may access information stored in database(s) 206 and/or 216 and use this information to perfom process 4000, described with reference to FIG. 55A, for generating an MF profile for a subject and generating an MF portrait for visualizing the MF profile in a graphical user interface.

As another example, in some embodiments, server(s) 210 may access information stored in database(s) 206 and/or 216 and use this information to perform process 4020, described with reference to FIG. 55B, for presenting a generated personalized graphical user interface (GUI) to a user.

In some embodiments, server(s) 210 may include one or multiple computing devices, When server(s) 210 include multiple computing devices, the device(s) may be physically co-located (e.g., in a single room) or distributed across multi-physical locations. In some embodiments, server(s) 210 may be part of a cloud computing infrastructure. In some embodiments, one or more server(s) 210 may be co-located in a facility operated by an entity (e.g., a hospital, research institution) with which doctor 214 is affiliated. In such embodiments, it may be easier to allow server(s) 210 to access private medical data for the patient 202.

As shown in FIG. 17A, in some embodiments, the results of the analysis performed by server(s) 210 may be provided to doctor 214 through a computing device 214 (which may be a portable computing device, such as a laptop or smartphone, or a fixed computing device such as a desktop computer). The results may be provided in a written report, an e-mail, a graphical user interface, and/or any other suitable way. It should be appreciated that although in the embodiment of FIG. 17A, the results are provided to a doctor, in other embodiments, the results of the analysis may be provided to patient 202 or a caretaker of patient 202, a healthcare provider such as a nurse, or a person involved with a clinical trial.

In some embodiments, the results may be part of a graphical user interface (GUI) presented to the doctor 214 via the computing device 212. In some embodiments, the GUI may be presented to the user as part of a webpage displayed by a web browser executing on the computing device 212. In some embodiments, the GUI may be presented to the user using an application program (different from a web-browser) executing on the computing device 212. For example, in some embodiments, the computing device 212 may be a mobile device (e.g., a smartphone) and the GUI may be presented to the user via an application program (e.g., an app") executing on the mobile device.

The GUI presented on computing device 212 provides a wide range of oncological data relating to both the patient and the patient's cancer in a new way that is compact and highly informative. Previously, oncological data was obtained from multiple sources of data and at multiple times making the process of obtaining such information costly from both a time and financial perspective. Using the techniques and graphical user interfaces illustrated herein, a user can access the same amount of information at once with less demand on the user and with less demand on the computing resources needed to provide such information. Low demand on the user serves to reduce clinician errors associated with searching various sources of information. Low demand on the computing resources serves to reduce processor power, network bandwidth, and memory needed to provide a wide range of oncological data, which is an improvement in computing technology.

FIG. 17I3 shows a block diagram of an illustrative GUI 250 containing information about patient 202. GUI 250 may include separate portions providing different types of information about patient 202. Illustrative GUI 150 includes the following portions: Patient Information Portion 252, Molecular-Functional (MF) Portrait Portion 260, Clinical Trial Information Portion 262, Immunotherapy Portion 254, Efficacy Predictor Portion 256, and Targeted Therapy Selection Portion 258.

Patient Information Portion 252 may provide general information about the patient and the patient's cancer. General information about the patient may include such information as the patient's name and date of birth, the patient's insurance provider, and contact information for the patient such as address and phone number. General information about the patient's cancer may include the patient's diagnosis, the patient's history of relapse and/or remission, and information relating to stage of the patient's cancer. Patient Information Portion 252 may also provide information relating to potential treatment options for the patient and/or previously administered treatments.

Molecular-Functional (MF) Portrait Portion 260 may include a molecular functional tumor portrait (MF profile) which refers to a graphical depiction of a tumor with regard to its molecular and cellular composition, and biological processes that are present within and/or surrounding the tumor. Further aspects relating to a patient's MF profile are provided herein.

Clinical Trial Information Portion 262 may include information relating to a clinical trial for a therapy that may be and/or will be administered to the patient. Clinical Trial Information Portion 262 may provide information about an ongoing clinical trial or a completed clinical trial. Information that may be provided in Clinical Trial Information Portion 262 may include information related to a therapy used in the clinical trial such as dosage and dosage regimen, number and diagnosis of patients participating in the clinical trial, and patient outcomes.

Immunotherapy Portion 254 may include patient specific information as it relates to an immunotherapy. Immunotherapy Portion 254 may provide such information for different immunotherapies, for example, immune checkpoint blockade therapies, anti-cancer vaccine therapies, and T cell therapies. Patient specific information relating to an immunotherapy may include information about the patient such as the patient's biomarkers associated with an immunotherapy and/or information about the patient's cancer such as composition of immune cells in the patient's tumor.

Efficacy Predictor Portion 256 may include information indicative of the patient's predicted response to an immunotherapy based on patient specific information presented in Immunotherapy Portion 254.

Targeted Therapy Selection Portion 258 may include patient specific information as it relates to a targeted therapy. Targeted Therapy Selection Portion 258 may provide such information for different targeted therapies, for example, a kinase inhibitor therapy, a chemotherapy, and anti-cancer antibody therapy. Patient specific information relating to an a targeted therapy may include information about the patient such as the patient's biomarkers associated with a targeted therapy and/or information about the patient's cancer such as whether a mutation is present in the patient's tumor.

Figure 17B:
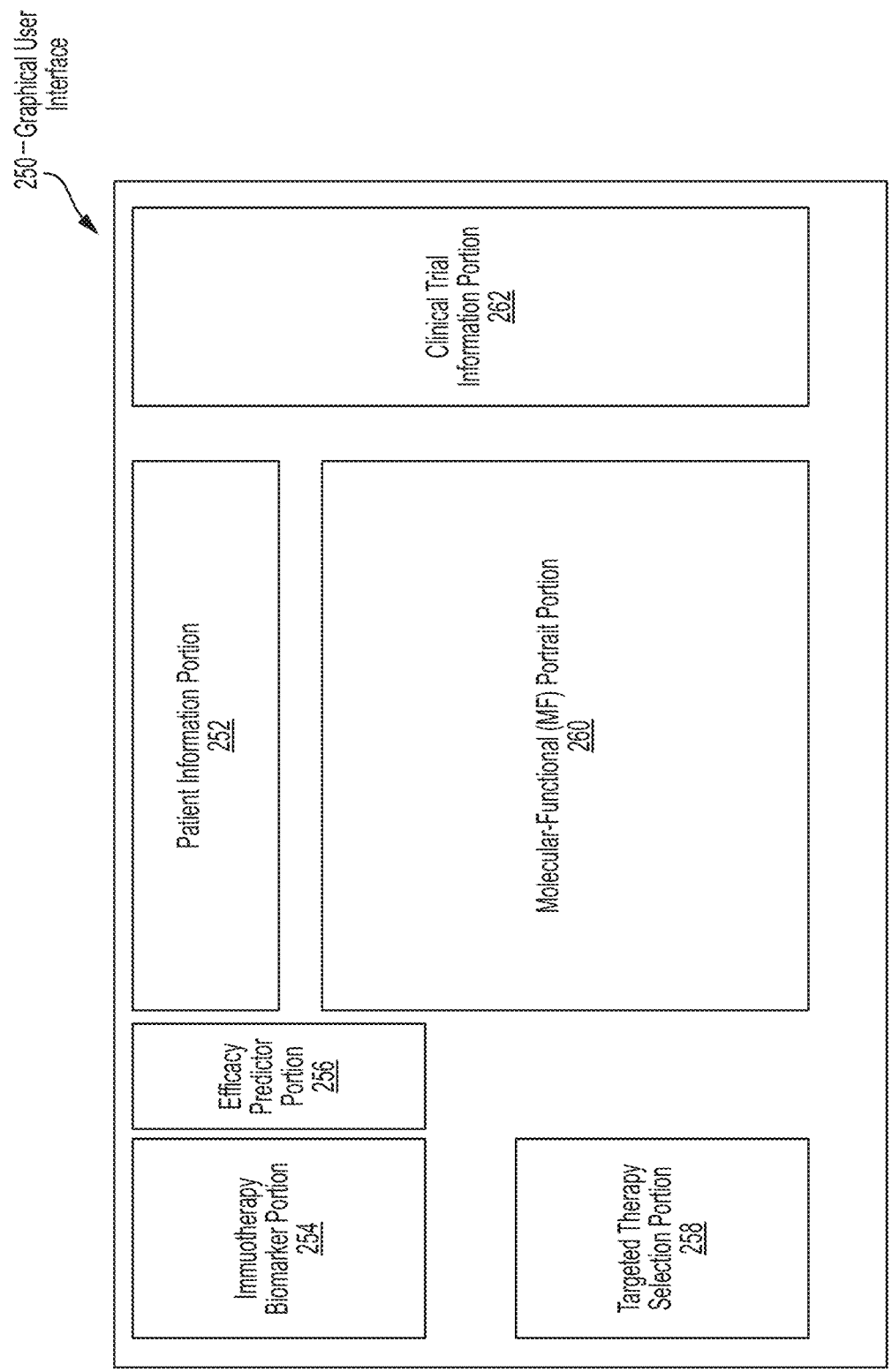
FIG. 17B is a block diagram of an illustrative graphical user interface 250 including patient data that may be presented to a user (e.g., a doctor), in accordance with some embodiments of the technology described herein.
Figure 17C:
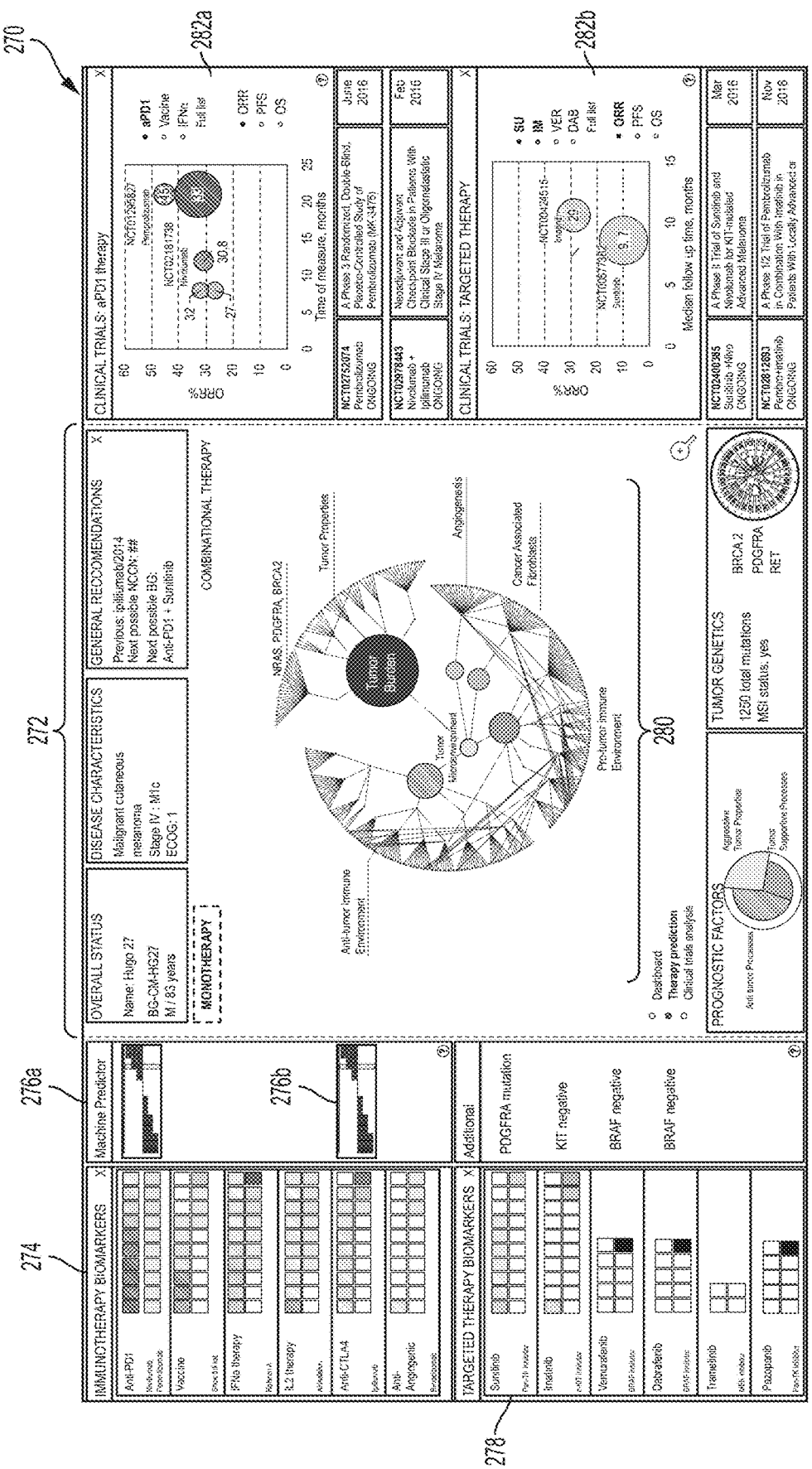
FIG. 17C is an illustrative example of the graphical user interface 250 of FIG. 17B, in accordance with some embodiments of the technology described herein.

An illustrative example of the graphical user interface 250 of FIG. 17B is shown as graphical user interface 270 of FIG. 17C. As shown in FIG. 17C, Patient Information Portion 272 may provide different information in different panels, for example, Overall Status panel, Disease Characteristics panel, and General Recommendations panel. Overall Status panel, in some embodiments, may provide general information about the patient such as patient name and patient age. Disease Characteristics panel, in some embodiments, may provide information about the patient's cancer such as type of cancer and stage of cancer. General Recommendations panel, in some embodiments, may provide previous treatments and possible treatment options for the patient.

Clinical Trial Information Portion 282*a* provides information relating to a clinical trial for anti-PD1 therapy. Clinical Trial Information Portion 282*a* (as shown in the upper portion) shows a graph providing patient overall response rate (ORR) for anti-PD1 therapy and other therapies such as vaccine or IFNα therapies. A user may select portions of the Clinical Trial Information Portion 282*a* to access information related to patient progression-free survival (PFS) and/or patient overall survival (OS), Clinical Trial Information Portion 282*a* (as shown in the lower portion) provides information relating to different clinical trials that may be presented to a user including a brief description of the clinical trial.

Clinical Trial Information Portion 282*b* provides information relating to a clinical trial for different targeted therapies. Clinical Trial Information Portion 282*b* (as shown in the upper portion) shows a graph providing patient overall response rate (ORR) for different targeted therapies including sunitinib (SU), imatinib (EVI), vemurafenib (VER) and dabrafenib (DAB). A user may select portions of the Clinical Trial Information Portion 282*b* to access information related to patient progression-free survival (PFS) and/or patient overall survival (OS). Clinical Trial Information Portion 282*b* (as shown in the lower portion) provides information relating to different clinical trials that may be presented to a user including a brief description of the clinical trial.

Immunotherapy Portion 274 provides patient specific information associated with an immunotherapy and information indicative of the patient's predicted response to that immunotherapy. Immunotherapy Portion 274 provides such information for anti-PD1 therapy, a therapeutic cancer vaccine, IFNαc therapy, IL2 therapy, anti-CTLA4 therapy, and anti-angiogenic therapy. Patient specific information shown in Immunotherapy Portion 274 includes the patient's biomarker information relating to various immunotherapies and the patient's therapy scores calculated from their biomarkers, Efficacy Predictor Portion 276a provides information indicative of the patient's predicted response to anti-PD1 therapy based on patient specific information presented in Immunotherapy Portion 274. Efficacy Predictor Portion 276b provides information indicative of the patient's predicted response to ani-CTLA4 therapy based on patient specific information presented in Immunotherapy Portion 274.

Targeted Therapy Selection Portion 278 provides patient specific information associated with a targeted therapy and information indicative of the patient's predicted response to the targeted therapy. Targeted Therapy Selection Portion 278 provides such information for sunitinib (SU), imatinib (IM), vemurafenib (VER), dabrafenib (DAB), trametinib, and pazopanib. Patient specific information shown in Targeted Therapy Selection Portion 278 includes a patient's biomarker information relating to various targeted therapies and the patient's therapy scores calculated from their biomarkers.

An illustrative implementation of a computer system 3800 that may be used in connection with any of the embodiments of the technology described herein is shown in FIG. 53. The computer system 600 may include one or more computer hardware processors 3800 and one or more articles of manufacture that comprise non-transitory computer-readable storage media (e.g; memory 3820 and one or more non-volatile storage devices 3830). The processor(s) 3810 may control writing data to and reading data from the memory 3820 and the non-volatile storage device(s) 3830 in any suitable manner. To perform any of the functionality described herein, the processor(s) 3810 may execute one or more processor-executable instructions stored in one or more non-transitory computer-readable storage media (e.g., the memory 3820), which may serve as non-transitory computer-readable storage media storing processor-executable instructions for execution by the processor(s) 3810.

Systems and methods described herein provide for calculating an MF profile of a subject and 10 associating the MF profile with an existing MF profile cluster, For example, computer-implemented processes for calculating a MF profile of a subject and associating the calculated MF profile with an existing MF profile cluster are described with reference to FIGS. 54A and 54C.

FIG. 54A is a flowchart of an illustrative computer-implemented process 3900 for identifying a MF profile cluster with which to associate an MF profile for a subject (e.g., a cancer patient), in accordance with some embodiments of the technology described herein, Process 3900 may be performed by any suitable computing device(s). For example, may be performed by a laptop computer, a desktop computer, one or more servers, in a cloud computing environment, or in any other suitable way.

Process 3900 begins at act 3902, where RNA expression data and/or whole exome sequencing (WES) data for a subject is obtained, RNA expression data may be acquired using any method known in the art, e.g., whole transcriptome sequencing, total RNA sequencing, and mRNA sequencing. In some embodiments, obtaining RNA expression data and/or whole exome sequencing (WES) data comprises obtaining expression data from a biological sample from a patient and/or from a database storing such expression data. Further aspects relating to obtaining expression data are provided in section titled "Obtaining Expression Data".

Next, process 3900 proceeds to act 3904, where the MF profile for the subject is determined by determining a set of expression levels for a respective set of gene groups that includes gene groups associated with cancer malignancy and cancer microenvironment. The MF profile may be determined for a subject having any type of cancer, including any of the types described herein. The MF profile may be determined using any number of gene groups that relate to compositions and processes present within and/or surrounding the subject's tumor. Gene group expression levels, in some embodiments, may be calculated as a gene set enrichment (GSEA) score for the gene group. Further aspects relating to determining MF profiles are provided in section titled "MF Profiles".

Next, process 3900 proceeds to act 3906, where a MF profile cluster with which to associate the MF profile of the subject is identified. The MF profile of the subject may be associated with any of the types of MF profile clusters types described herein, A subject's MF profile may be associated with one or multiple of the MF profile clusters in any suitable way. For example, an MF profile may be associated with one of the MF profile clusters using a similarity metric (e.g; by associating the MF profile with the MF profile cluster whose centroid is closest to the MF profile according to the similarity metric). As another example, a statistical classifier (e.g., k-means classifier or any other suitable type of statistical classifier) may be trained to classify the MF profile as belonging to one or multiple of the M F clusters. Further aspects relating to determining MF profiles are provided in section "MF Profiles".

Optionally, process 3900 proceeds to act 3908, where a therapy for the subject is identified based on the identified MF profile cluster. The identified therapy may be any type of anti-cancer therapy depending on the patient's cancer and their identified MF profile cluster. A single anti-cancer therapy or a combination of anti-cancer therapies may be identified in act 3908.

Identifying a therapy based on the MF profile cluster includes excluding those therapies that may be ineffective or harmful to the subject in order to identify a suitable therapy for the subject.

Further aspects related to using a patient's identified MF profile cluster for clinical purposes are provided in section "Applications".

The MF profile of the subject may be output to a user, in some embodiments, by displaying the MF profile to the user in a graphical user interface (GUI), including the information about the MF profile in a report, sending an email to the user, and/or in any other suitable way. For example, the M F profile of the subject and other patient related information may be provided to a user in a GUI as shown in FIGS. 18-52.

In this way, a patient's MIF profile can be identified and used for various clinical purposes including assessing the efficacy of a treatment for cancer and/or evaluating suitability of a patient for participating in a clinical trial. FIG. 54C is a flowchart of an illustrative computer-implemented process 3940 for identifying an existing MF profile cluster with which to associate a MF profile for a subject (e.g., a cancer patient), in accordance with some embodiments of the technology described herein. Process 3940 may be performed by any suitable computing device(s). For example, may be performed by a laptop computer, a desktop computer, one or more servers, in a cloud computing environment, or in any other suitable way.

Process 3940 begins at act 3942, where RNA expression data and/or whole exome sequencing (WES) data for a subject having a particular type of cancer is obtained. RNA expression data may be acquired using any method known in the art, e.g., whole transcriptome sequencing, total RNA sequencing, and mRNA sequencing, In some embodiments, obtaining RNA expression data and/or whole exome sequencing (WES) data comprises obtaining expression data from a biological sample from a patient and/or from a database storing such expression data. Further aspects relating to obtaining expression data are provided in section "Obtaining Expression Data", Next, process 3940 proceeds to act 3944, where the MF profile for the subject is determined by determining a set of expression levels for a respective set of gene groups that includes at least one gene group associated with cancer malignancy and at least four gene groups associated with cancer microenvironment. The at least one gene group associated with cancer malignancy, in some embodiments, consists of a tumor properties gene group. The at least four gene groups associated with cancer microenvironment, in some embodiments, consists of tumor-promoting immune microenvironment group, anti-tumor immune microenvironment group, angiogenesis group, and fibroblasts group.

It should be appreciated that act 3944 may be performed using any number of gene groups associated with cancer malignancy and cancer microenvironment. For example, MF profiles may be determined using set of gene groups that includes 19 gene groups where the gene groups associated with cancer malignancy consists of the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, and the mutation status group, and the gene groups associated with cancer microenvironment consists of the antigen presentation group, the cytotoxic T and NK cells group, the B cells group, the anti-tumor microenvironment group, the checkpoint inhibition group, the Treg group, the MDSC group, the granulocytes group, the cancer associated fibroblasts group, the angiogenesis group, and the tumor-promotive immune group.

In another example, MF profiles may be determined using set of gene groups that includes 30 gene groups where the gene groups associated with cancer malignancy consists of the proliferation rate group, the PI3 KJAKT/mTOR signaling group, the RAS/RAF/MEK signaling group, the receptor tyrosine kinases expression group, the growth factors group, the tumor suppressors group, the metastasis signature group, the anti-metastatic factors group, and the mutation status group, and the gene groups associated with cancer microenvironment consists of the MHCI group, the MHCII group, the coactivation molecules group, the effector cells group, the NK cells group, the T cell traffic group, the T cells group, the B cells group, theMI signatures group, the Th1 signature group, the antitumor cytokines group, the checkpoint inhibition group, the Treg group, the MDSC group, the granulocytes group, the M2 signature group, the Th2 signature group, the protumor cytokines group, the cancer associated fibroblasts group, the angiogenesis group, and the complement inhibition group, The MF profile may be determined using any number of gene groups (or functional modules) that relate to compositions and processes present within and/or surrounding the subject's tumor. Gene groups may comprise any number of genes and may be related to any composition and process. Further aspects relating to the gene groups are provided in section "MF Profile Modules". Gene group expression levels, in some embodiments, may be calculated as a gene set enrichment (GSEA) score for the gene group. Further aspects relating to determining MF profiles are provided in section "MF Profiles".

Next, process 3940 proceeds to act 3946, where information specifying MF profile clusters for the particular cancer type are accessed. Different MF profile clusters are accessed for different cancers. For example, MF profile clusters associated with lung cancer are accessed when process 3940 is performed for a patient having lung cancer and MF profile clusters associated with melanoma are accessed when process 3940 is performed for a patient having melanoma. Any number of MF profile clusters for the particular cancer may be accessed including at least two, at least 5, at least 10 or at least 20. The number of accessed MF profiles, in some embodiments, may be between 2--20, between 2-10, or between 15-20. The number of accessed MF profile clusters may vary depending on the particular cancer with which the MF profile clusters are associated. For example, 5 MF profile clusters may be accessed when the particular cancer type is lung cancer and 12 MF profile clusters may be accessed when the particular cancer is melanoma. Accessing information specifying MF profile clusters for the particular cancer may include accessing information from a variety of sources and/or a variety of databases.

Next, process 3940 proceeds to act 3948, where a MF profile cluster with which to associate the MF profile of the subject is identified. The MF profile of the subject may be associated with any of the types of MF profile clusters types described herein. A subject's MF profile may be associated with one or multiple of the MF profile clusters in any suitable way. For example, an MF profile may be associated with one of the MF profile clusters using a similarity metric (e.g., by associating the MF profile with the MF profile cluster whose centroid is closest to the MF profile according to the similarity metric). As another example, a statistical classifier (e.g., k-means classifier or any other suitable type of statistical classifier) may be trained to classify the MF profile as belonging to one or multiple of the M F clusters. Further aspects relating to determining MF profiles are provided in section "MF Profiles".

The MF profile of the subject may be output to a user, in some embodiments, by displaying the MF profile to the user in a graphical user interface (GUI), including the information about the MF profile in a report, sending an email to the user, and/or in any other suitable way. For example, the M F profile of the subject and other patient related information may be provided to a user in a GUI as shown in FIGS. 18-52.

In this way, a patient's M F profile can be identified and used for various clinical purposes including assessing the efficacy of a treatment for cancer and/or evaluating suitability of a patient for participating in a clinical trial.

Systems and methods described herein provide for generating MF profile clusters and for generating a MF profile for a patient and associating that MF profile to a generated MF cluster. For example, a computer-implemented process 3920 for generating MF profile clusters using RNA expression data obtained from subjects having a particular type of cancer is described with reference to FIG. 5413, As another example, a computer-implemented process 3960 for generating MF profile clusters using RNA expression data obtained from subjects having a particular type of cancer, and associating a subject with one of the generated MF clusters based on the subject's MF profile is described with reference to FIG. 54D.

FIG. 54B is a flowchart of an illustrative computer-implemented process 3920 for generating MF profile clusters using expression data obtained from subjects having a particular type of cancer, in accordance with some embodiments of the technology described herein, MF profile clusters may be generated for any cancer using expression data obtained from patients having that type of cancer. For example MF profile clusters associated with melanoma may be generated using expression data from melanoma patients. In another example MF profile clusters associated with lung cancer may be generated using expression data from lung cancer patients, Process 3920 begins at act 3922, where RNA expression data and/or whole exome sequencing (WES) data for a plurality of subjects having a particular cancer are obtained. The plurality of subjects for which expression data is obtained may comprise any number of patients having a particular cancer. For example, expression data may be obtained for a plurality of melanoma patients, for example, 100 melanoma patients, 1000 melanoma patients, or any number of melanoma patients as the technology is not so limited. RNA expression data may be acquired using any method known in the art, e.g., whole transcriptome sequencing, total RNA sequencing, and mRNA sequencing. Further aspects relating to obtaining expression data are provided in section "Obtaining Expression Data". Next, process 3920 proceeds to act 3924, where the MF profile for each subject in the plurality of subject is determined by determining a set of expression levels for a respective set of gene groups that includes gene groups associated with cancer malignancy and cancer microenvironment. MF profiles may be determined using any number of gene groups that relate to compositions and processes present within and/or surrounding the subject's tumor. Gene group expression levels, in some embodiments, may be calculated as a gene set enrichment (GSEA) score for the gene group, Further aspects relating to determining MF profiles are provided in section titled "MF Profiles".

Next, process 3920 proceeds to act 3926, where the plurality of MIF profiles are clustered to obtain MF profile clusters. MF profiles may be clustered using any of the techniques described herein including, for example, community detection clustering, dense clustering, k-means clustering, or hierarchical clustering. MF profiles may be clustered for any type of cancer using MF profiles generated for patients having that type of cancer. MF profile clusters, in some embodiments, comprises a $1^{st}$ MF profile cluster, a $2^{nd}$ MF profile cluster, a $3^{rd}$ MF profile, and a $4^{th}$ MF profile. The relative sizes of $1\text{-}^{th}$ MF clusters may vary among cancer types. For example, the size of the 3 MF profile cluster (shown as C) was larger for ACC (adrenocortical carcinoma) than that of BLCA (bladder urothelial carcinoma. MF profiles were clustered for different cancers as shown in Example 4. Further aspects relating to MF profile clusters are provided in section titled "MF profiles".

Next, process 3920 proceeds to act 3928, where the plurality of MF profiles in association with information identifying the particular cancer type are stored. MF profiles may be stored in a database in any suitable format and/or using any suitable data structure(s), as aspects of the technology described herein are not limited in this respect. The database may store data in any suitable way, for example, one or more databases and/or one or more files. The database may be a single database or multiple databases.

In this way, MF profile clusters can be stored and used as existing MF profile clusters with which a patient's MF profile can be associated. Existing MF profiles clusters, in some embodiments. may be associated with a patient's MF profile generated using five gene groups, 19 gene groups, or 30 gene groups as described with respect to FIG. 54C.

FIG. 54D is a flowchart of an illustrative computer-implemented process 3960 for generating MF profile clusters using expression data obtained from subjects having a particular type of cancer, and associating a subject with one of the generated MF clusters based on the subject's MF profile, in accordance with some embodiments of the technology described herein. Process 3960 may be performed by any suitable computing device(s). For example, may be performed by a laptop computer, a desktop computer, one or more servers, in a cloud computing environment, or in any other suitable way.

Process 3960 begins at act 3962, where RNA expression data and/or whole exome sequencing (WES) data for each subject in a plurality of subjects having a particular type of cancer is obtained. RNA expression data may be acquired using any method known in the art, e.g., whole transcriptome sequencing, total RNA sequencing, and mRNA sequencing. In some embodiments, obtaining RNA expression data and/or whole exome sequencing (WES) data comprises obtaining expression data from a biological sample from a patient and/or from a database storing such expression data, Further aspects relating to obtaining expression data are provided in section "Obtaining Expression Data".

Next, process 3960 proceeds to act 3964, where theMF profile for each subject in the plurality of subjects is determined by determining a set of expression levels for a respective set of gene groups that includes at least one gene group associated with cancer malignancy and at least four gene groups associated with cancer microenvironment. The MF profile may be determined using any number of gene groups (or functional modules) that relate to compositions and processes present within and/or surrounding the subject's tumor. Gene groups may comprise any number of genes and may be related to any composition and process. Further aspects relating to the gene groups are provided in section "MF Profile Modules". Gene group expression levels, in some embodiments, may be calculated as a gene set enrichment (GSEA) score for the gene group. Further aspects relating to determining MF profiles are provided in section MF Profiles. Next, process 3960 proceeds to act 3966, where the plurality of MF profiles are clustered to obtain MF profile clusters. MF profiles may be clustered using any of the techniques described herein including, for example, community detection clustering, dense clustering, k-means clustering, or hierarchical clustering. MF profiles may be clustered for any type of cancer using MF profiles generated for patients having that type of cancer. MF profile clusters, in some embodiments, comprises a $1^{st}$ MF profile cluster, a $2^{nd}$ d M F profile cluster, a $3^{rd}$ MF profile, and a $4^{th}$ MF profile. The relative sizes of $1^{st}\text{-}4^{th}$ MF clusters may vary among cancer types. For example, the size of the 3 MF profile cluster (shown as C) was larger for ACC (adrenocortical carcinoma) than that of BLCA (bladder urothelial carcinoma. MF profiles were clustered for different cancers as shown in Example 4. Further aspects relating to MF profile clusters are provided in section titled "M F profiles", Next, process 3960 proceeds to act 3968, where RNA expression data and/or whole exome sequencing (WES) data for an additional subject is obtained. Expression data for an additional subject may be obtained by any suitable means as described in further detail in section "Obtaining Expression Data", Expression data for the additional subject may be obtained in the same manner used for obtaining expression data of the plurality of subjects. Alternatively or in addition to, expression data for the additional subject may be obtained in a manner different from that used to obtain expression data of the plurality of subjects. Further aspects relating to obtaining expression data are provided in section "Obtaining Expression Data".

Next, process 3960 proceeds to act 3970, where MF profiles for the additional subject are determined using the additional subject's expression data. The MF profile for the additional subject is determined by determining a set of expression levels for a respective set of gene groups that includes at least one gene group associated with cancer malignancy and at least four gene groups associated with cancer microenvironment. The MF profile may be determined using any number of gene groups (or functional modules) that relate to compositions and processes present within and/or surrounding the subject's tumor. Gene groups may comprise any number of genes and may be related to any composition and process. Further aspects relating to the gene groups are provided in section "MF Profile Modules". Gene group expression levels, in some embodiments, may be calculated as a gene set enrichment (GSEA) score for the gene group. Further aspects relating to determining MF profiles are provided in section "MF Profiles".

Next, process 3960 proceeds to act 3972, where a MF profile cluster with which to associate the MF profile of the subject is identified. The MF profile of the subject may be associated with any of the types of MF profile clusters determined in act 3966. A subject's MF profile may be associated with one or multiple of the MF profile clusters in any suitable way. For example, an MF profile may be associated with one of the MF profile clusters using a similarity metric (e.g. by associating the MF profile with the MF profile cluster whose centroid is closest to the MF profile according to the similarity metric). As another example, a statistical classifier (e.g., k-means classifier or any other suitable type of statistical classifier) may be trained to classify the MF profile as belonging to one or multiple of the MF clusters. Further aspects relating to determining MF profiles are provided in section "MF Profiles".

Optionally, process 3960 proceeds to act 3974, where a therapy for the subject is identified based on the identified MF profile cluster. The identified therapy may be any type of anti-cancer therapy depending on the patient's cancer and their identified MF profile cluster. A single anti-cancer therapy or a combination of anti-cancer therapies may be identified in act 3974.

Identifying a therapy based on the MF profile cluster includes excluding those therapies that may be ineffective or harmful to the subject in order to identify a suitable therapy for the subject. Further aspects related to using a patient's identified MF profile cluster for clinical purposes are provided in section "Applications".

The MF profile of the subject may be output to a user, in some embodiments, by displaying the MF profile to the user in a graphical user interface (GUI), including the information about the MF profile in a report, sending an email to the user, and/or in any other suitable way. For example, the MF profile of the subject and other patient related information may be provided to a user in a GUI as shown in FIGS. 18-52.

In this way, a patient's M F profile can be identified and used for various clinical purposes including assessing the efficacy of a treatment for cancer and/or evaluating suitability of a patient for participating in a clinical trial.

Systems and methods described herein provide for generating a MF profile for a patient and generating a visualization of the generated MF profile as a MF portrait. For example, a computer-implemented process for generating a MF profile and an associated MF portrait is shown in FIG. 55A, and a computer-implemented process for generating a MF profile using five gene groups and an associated MF portrait is shown in FIG. 55B.

FIG. 55A is a flowchart of an illustrative computer-implemented process 4000 for generating a MF profile and an associated MF portrait, in accordance with some embodiments of the technology described herein. Process 4000 may be performed by any suitable computing device(s). For example, may be performed by a laptop computer, a desktop computer, one or more servers, in a cloud computing environment, or in any other suitable way.

Process 4000 begins at act 4002, where RNA expression data and/or whole exome sequencing (WES) data for a subject having a particular type of cancer is obtained. RNA expression data may be acquired using any method known in the art, e.g., whole transcriptome sequencing, total RNA sequencing, and mRNA sequencing. In some embodiments, obtaining RNA expression data and/or whole exome sequencing (WES) data comprises obtaining expression data from a biological sample from a patient and/or from a database storing such expression data. Further aspects relating to obtaining expression data are provided in section "Obtaining Expression Data", Next, process 4000 proceeds to act 4004, where the M F profile for the subject is determined by determining a set of expression levels for a respective set of gene groups that includes gene groups associated with cancer malignancy and gene groups associated with cancer microenvironment. The MF profile may be determined for a subject having any type of cancer, including any of the types described herein. The MF profile may be determined using any number of gene groups (or functional modules) that relate to compositions and processes present within and/or surrounding the subject's tumor. Gene group expression levels, in some embodiments, are calculated as a gene set enrichment (GSEA) score for the gene group. Further aspects relating to determining MF profiles are provided in section "MF Profiles".

Next, process 4000 proceeds to act 4006, where a first set of visual characteristics for a first plurality of GUI elements using the first gene group expression levels are determined. Examples of visual characteristics for a GU I element include color, shading or pattern, size, and/or shape.

A set of visual characteristics may contain any number of visual characteristics. GUI elements, for example, include genes, gene groups, biomarkers, and biomarker information. A plurality of GUI elements may contain any number of GUI elements.

Further aspects of visual characteristics and GUI elements are shown in and/or described with reference to FIGS. 18-52.

Next, process 4000 proceeds to act 4008, where a second set of visual characteristics for a second plurality of GU I elements using the second gene group expression levels are determined. Examples of visual characteristics for a GUI element include color, shading or pattern, size, and/or shape, A set of visual characteristics may contain any number of visual characteristics, GUI elements, for example, include genes, gene groups, biomarkers, and biomarker information. A plurality of GUI elements may contain any number of GUI elements, Further aspects of visual characteristics and GUI elements are shown in and/or described with reference to FIGS. 18-52. Next, process 4000 proceeds to act 4010, where a GUI containing a first portion including the first GUI element and a second portion including the second GUI element is generated. For example, the MF profile of the subject and other patient related information may be provided to a user in a GUI as shown in FIGS. 18-52. Further aspects relating to the GUI as shown in FIGS. 18-52 are provided in section "Visualization of MF Profiles".

Next, process 4000 proceeds to act 4012, where the generated personalized GUI is presented to a user. In some embodiments, the GUI may be presented to the user as part of a webpage displayed by a web browser, In some embodiments, the GUI may be presented to the user using an application program (different from a web-browser). For example, in some embodiments, the GUI may be presented to the user via an application program (e.g., "an app") executing on a mobile device.

FIG. 55B is a flowchart of an illustrative computer-implemented process 4020 for generating a MF profile using at least one gene group associated with cancer malignancy and at least four gene groups associated with cancer microenvironment, and an associated MF portrait, in accordance with some embodiments of the technology described herein, Process 4020 may be performed by any suitable computing device(s). For example, may be performed by a laptop computer, a desktop computer, one or more servers, in a cloud computing environment, or in any other suitable way.

Process 4020 begins at act 4022, where RNA expression data and/or whole exome sequencing (WES) data for a subject having a particular type of cancer is obtained. RNA expression data may be acquired using any method known in the art, e.g., whole transcriptome sequencing, total RNA sequencing, and nRNA sequencing. In some embodiments, obtaining RNA expression data and/or whole exome sequencing (WES) data comprises obtaining expression data from a biological sample from a patient and/or from a database storing such expression data. Further aspects relating to obtaining expression data are provided in section "Obtaining Expression Data", Next, process 4020 proceeds to act 4024, where the MF profile for the subject is determined by determining a set of expression levels for a respective set of gene groups that includes at least one gene group associated with cancer malignancy and at least four gene groups associated with cancer microenvironment. The at least one gene group associated with cancer malignancy, in some embodiments, consists of a tumor properties gene group. The at least four gene groups associated with cancer microenvironment, in some embodiments, consists of tumor-promoting immune microenvironment group, anti-tumor immune microenvironment group, angiogenesis group, and fibroblasts group.

It should be appreciated that act 4024 may be performed using any number of gene groups associated with cancer malignancy and cancer microenvironment. For example, MF profiles may be determined using set of gene groups that includes 19 gene groups where the gene groups associated with cancer malignancy consists of the proliferation rate group, the PI3K/AKT/mTOR signaling group, the RAS/RAF/MEK signaling group, the receptor tyrosine kinases expression group, the tumor suppressors group, the metastasis signature group, the anti--metastatic factors group, and the mutation status group, and the gene groups associated with cancer microenvironment consists of the antigen presentation group, the cytotoxic T and NK cells group, the B cells group, the anti-tumor microenvironment group, the checkpoint inhibition group, the Treg group, the MDSC group, the granulocytes group, the cancer associated fibroblasts group, the angiogenesis group, and the tumor-promotive immune group.

In another example, M F profiles may be determined using set of gene groups that includes 30 gene groups where the gene groups associated with cancer malignancy consists of the proliferation rate group, the PI3 K/AKT/mTOR signaling group, the RAS/RAF/M EK signaling group, the receptor tyrosine kinases expression group, the growth factors group, the tumor suppressors group, the metastasis signature group, the anti-metastatic factors group, and the mutation status group, and the gene groups associated with cancer microenvironment consists of the MHCI group, the MHCII group, the coactivation molecules group, the effector cells group, the NK cells group, the T cell traffic group, the T cells group, the B cells group, the MI signatures group, the Th1 signature group, the antitumor cytokines group, the checkpoint inhibition group, the Treg group, the MDSC group, the granulocytes group, the M2 signature group, the Th2 signature group, the protumor cytokines group, the cancer associated fibroblasts group, the angiogenesis group, and the complement inhibition group.

The MF profile may be determined using any number of gene groups (or functional modules) that relate to compositions and processes present within and/or surrounding the subject's tumor. Gene groups may comprise any number of genes and may be related to any composition and process. Further aspects relating to the gene groups are provided in section "MF Profile Modules". Gene group expression levels, in some embodiments, may be calculated as a gene set enrichment (GSEA) score for the gene group. Further aspects relating to determining MF profiles are provided in section "M F Profiles".

Next, process 4020 proceeds to act 4026, where a first set of visual characteristics for a first plurality of GUI elements using the first gene group expression levels are determined. Examples of visual characteristics for a GUI element include color, shading or pattern, size, and/or shape.

A set of visual characteristics may contain any number of visual characteristics. GU I elements, for example, include genes, gene groups, biomarkers, and biomarker information. A plurality of GUI elements may contain any number of GUI elements. Further aspects of visual characteristics and GUI elements are shown in and/or described with reference to FIGS. 18-52.

Figure 18:
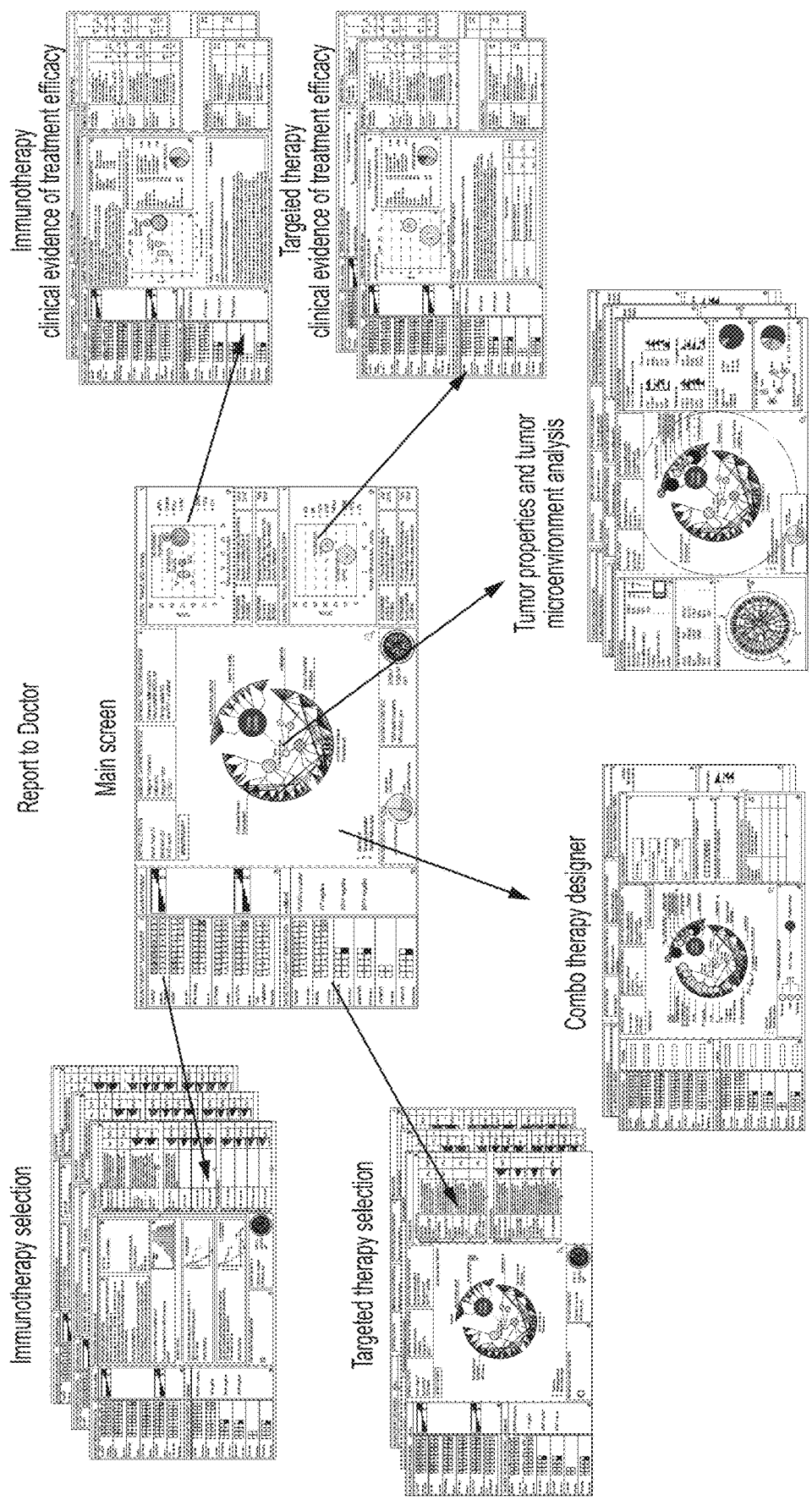
FIG. 18 is a graphic illustrating different types of screens that may be shown to a user of the software program.
Figure 19:
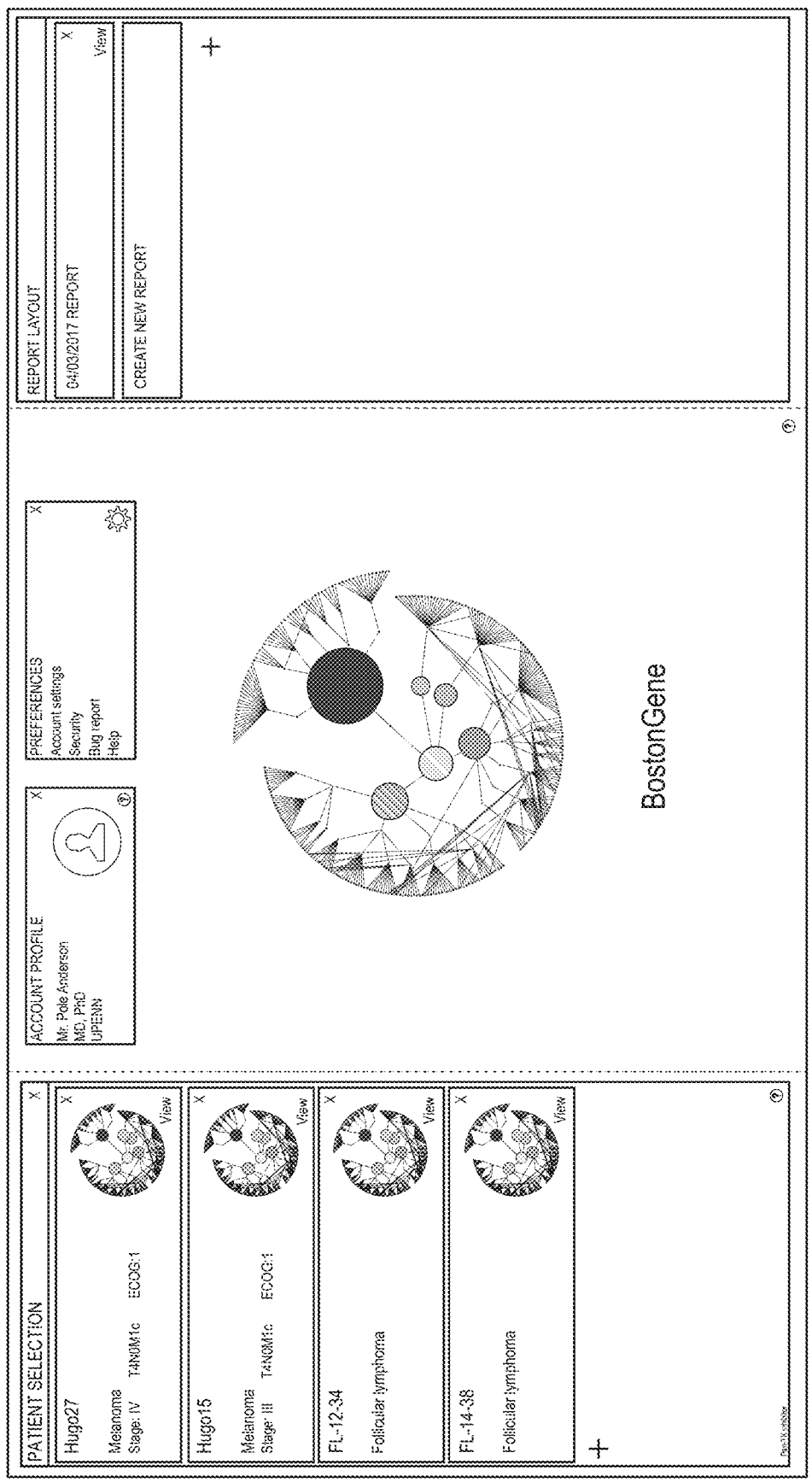
FIG. 19 is a screenshot of the user's account profile screen presented to the user in response to the user logging into the software program.
Figure 21:
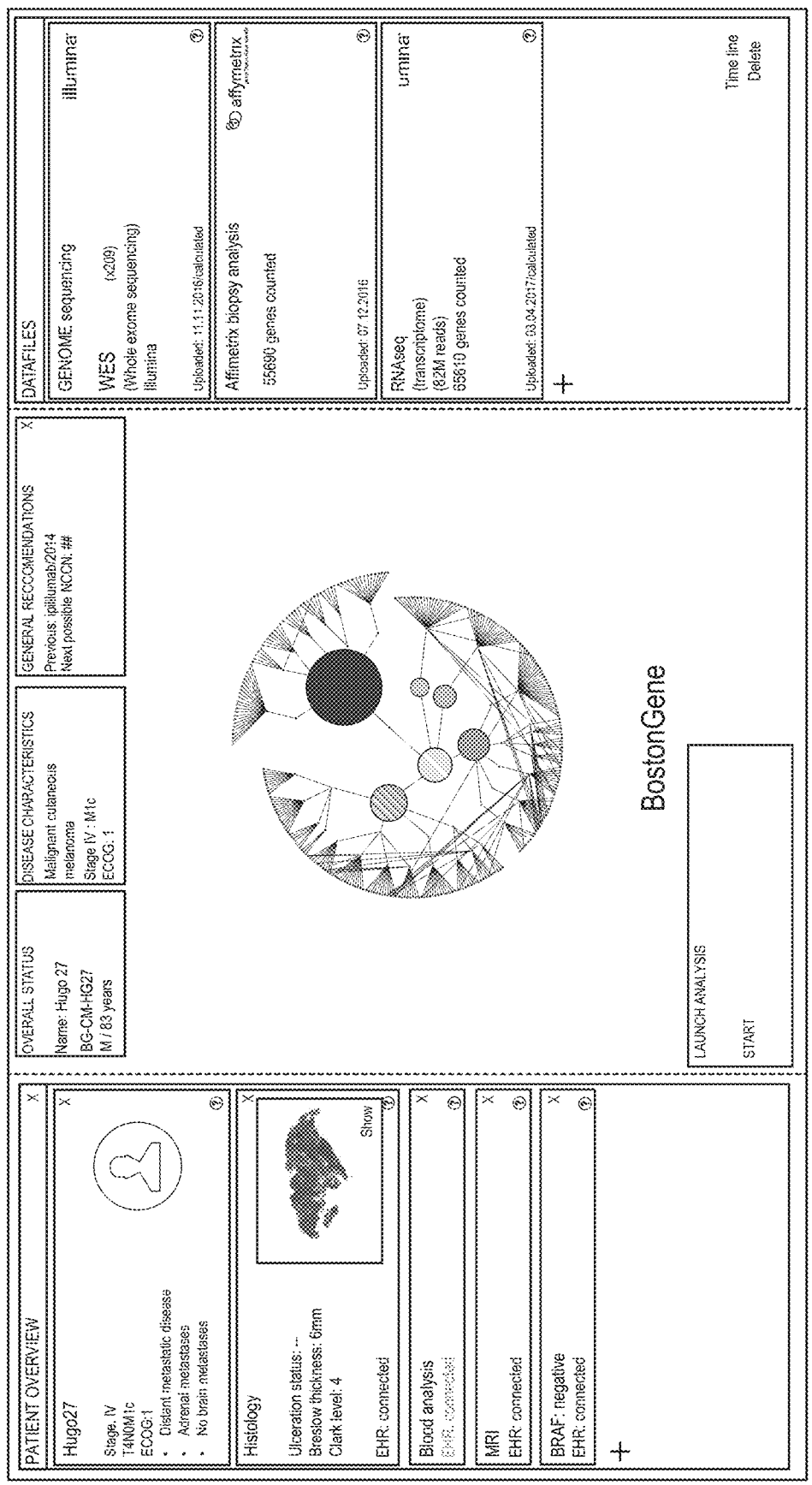
FIG. 21 is a screenshot presenting that the patient's tumor biopsy sequencing data was downloaded (as shown in the lower right panel).
Figure 22:
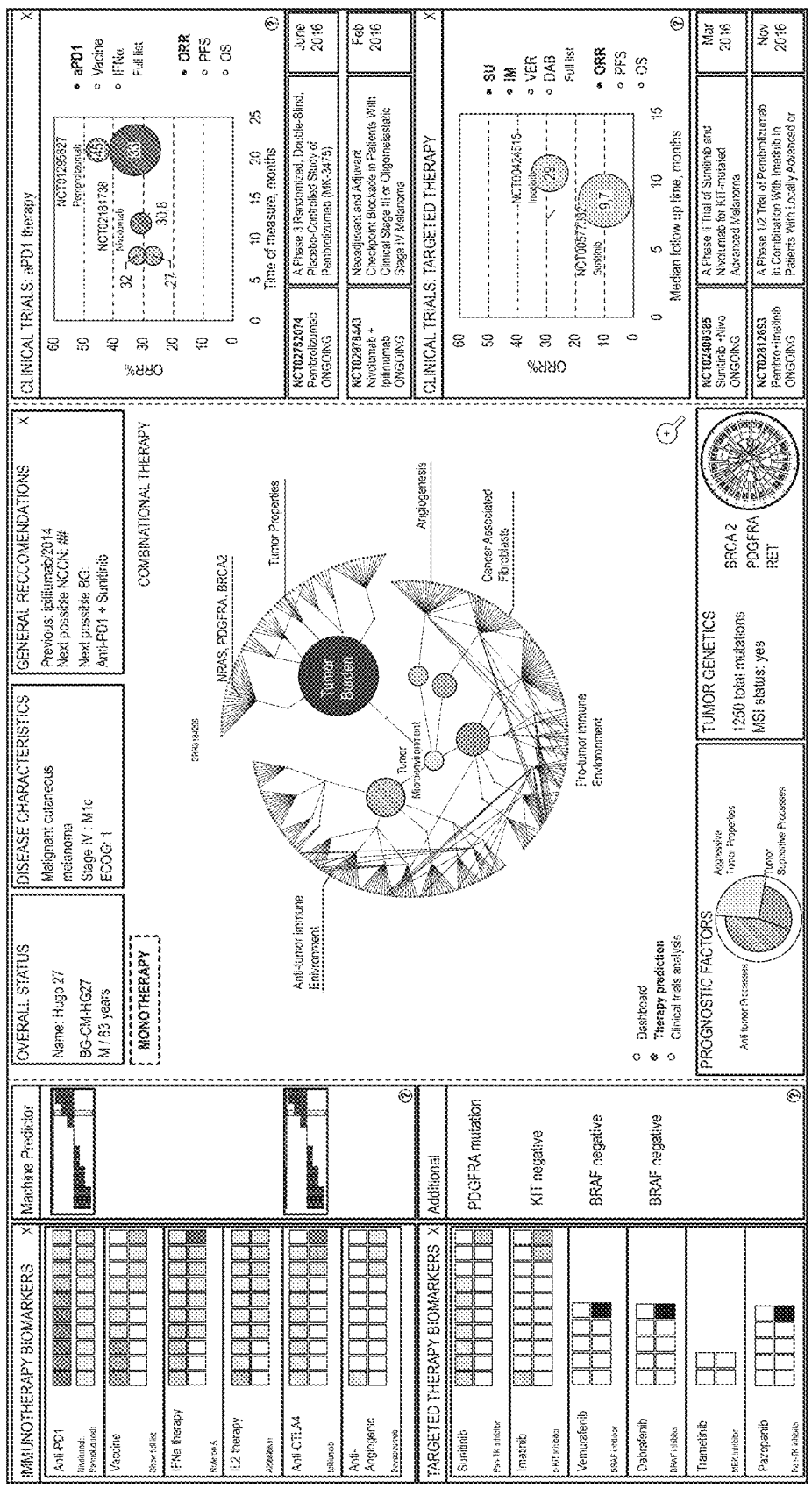
FIG. 22 is a screenshot presenting the selected patient's report including information related to the patient's sequencing data, the patient, and the patient's cancer.
Figure 23:
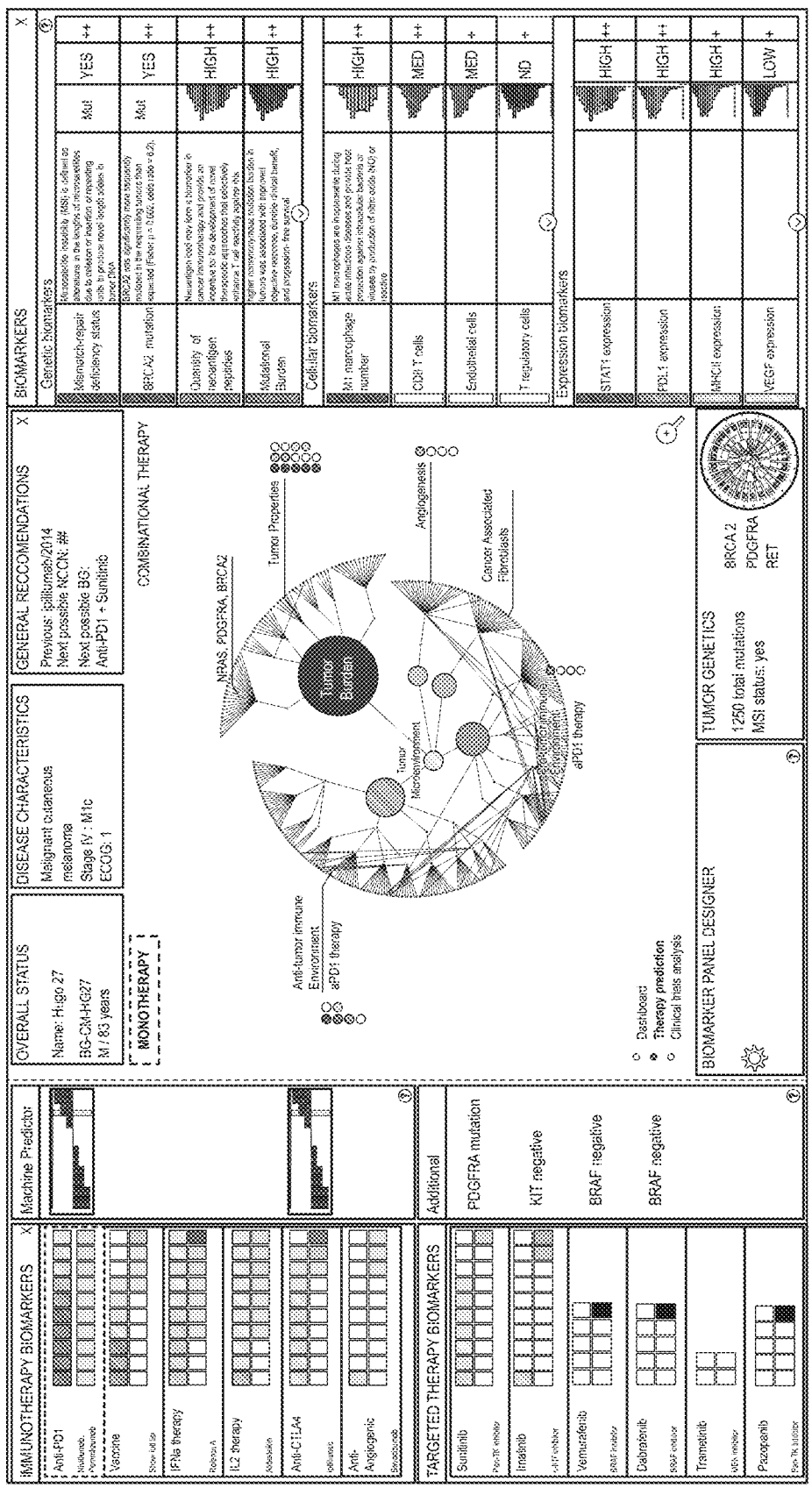
FIG. 23 is a screenshot presenting information related to anti-PD1 immunotherapy provided in response to selecting anti-PD1 immunotherapy (as shown by highlighting) in the immunotherapy biomarkers portion of the screen (as shown in the left panel).
Figure 24:
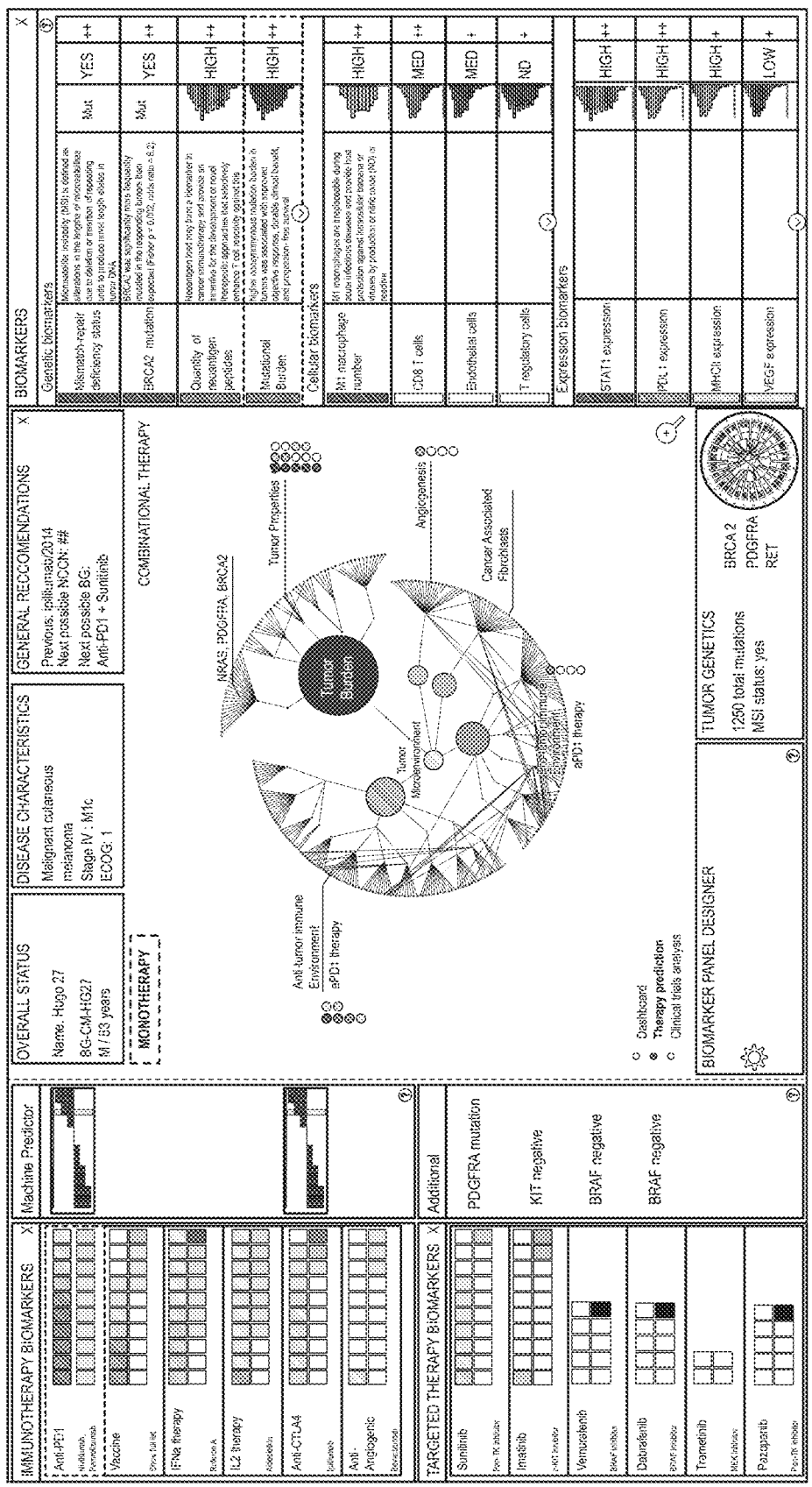
FIG. 24 is a screenshot presenting selection of mutational burden biomarker by a user.
Figure 26:
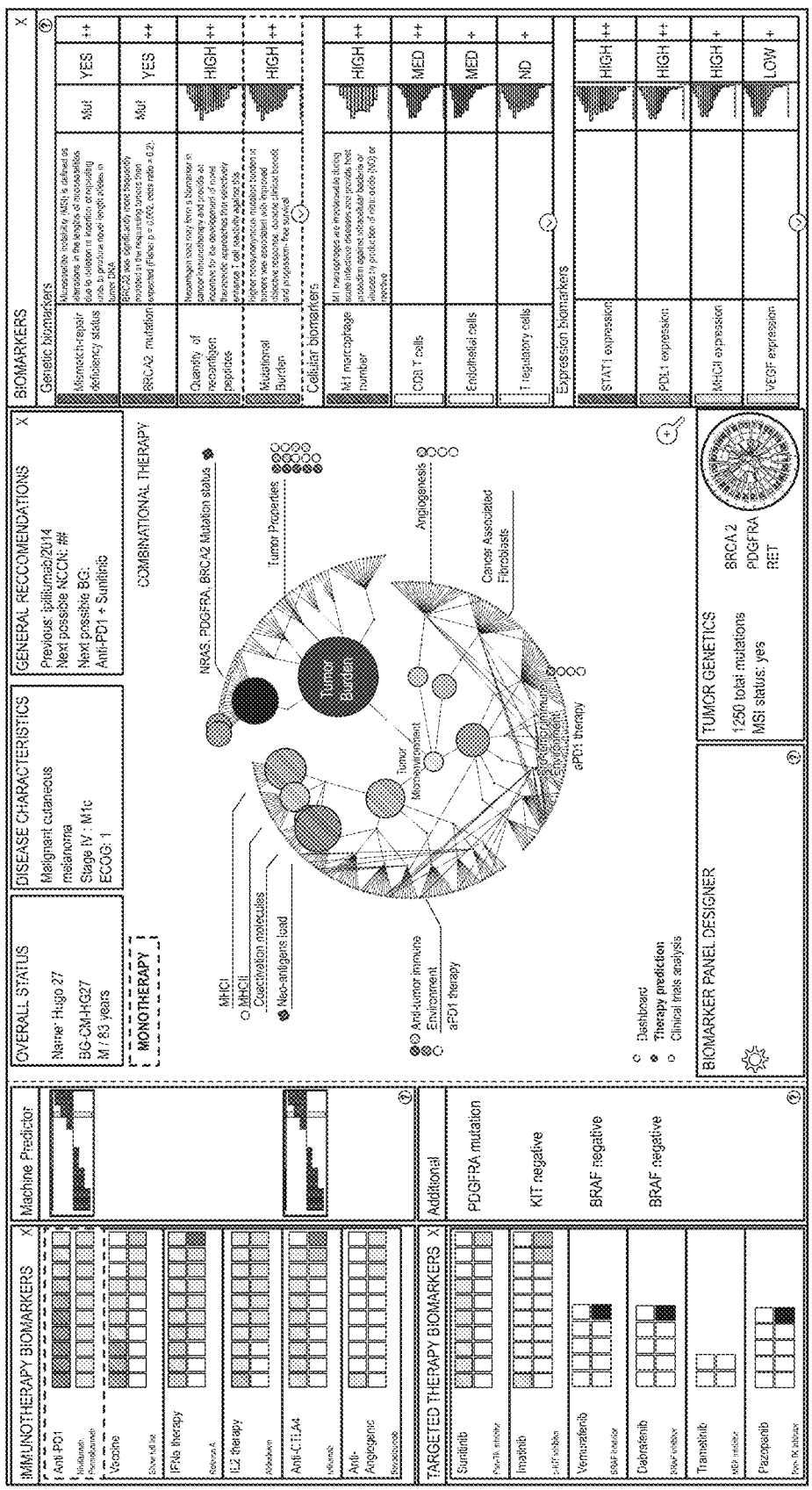
FIG. 26 is a screenshot presenting that the mutational status gene group and neo-antigens load gene group in the MF profile are highlighted in response to the user selecting the mutational burden biomarker (as shown in highlighting).
Figure 27:
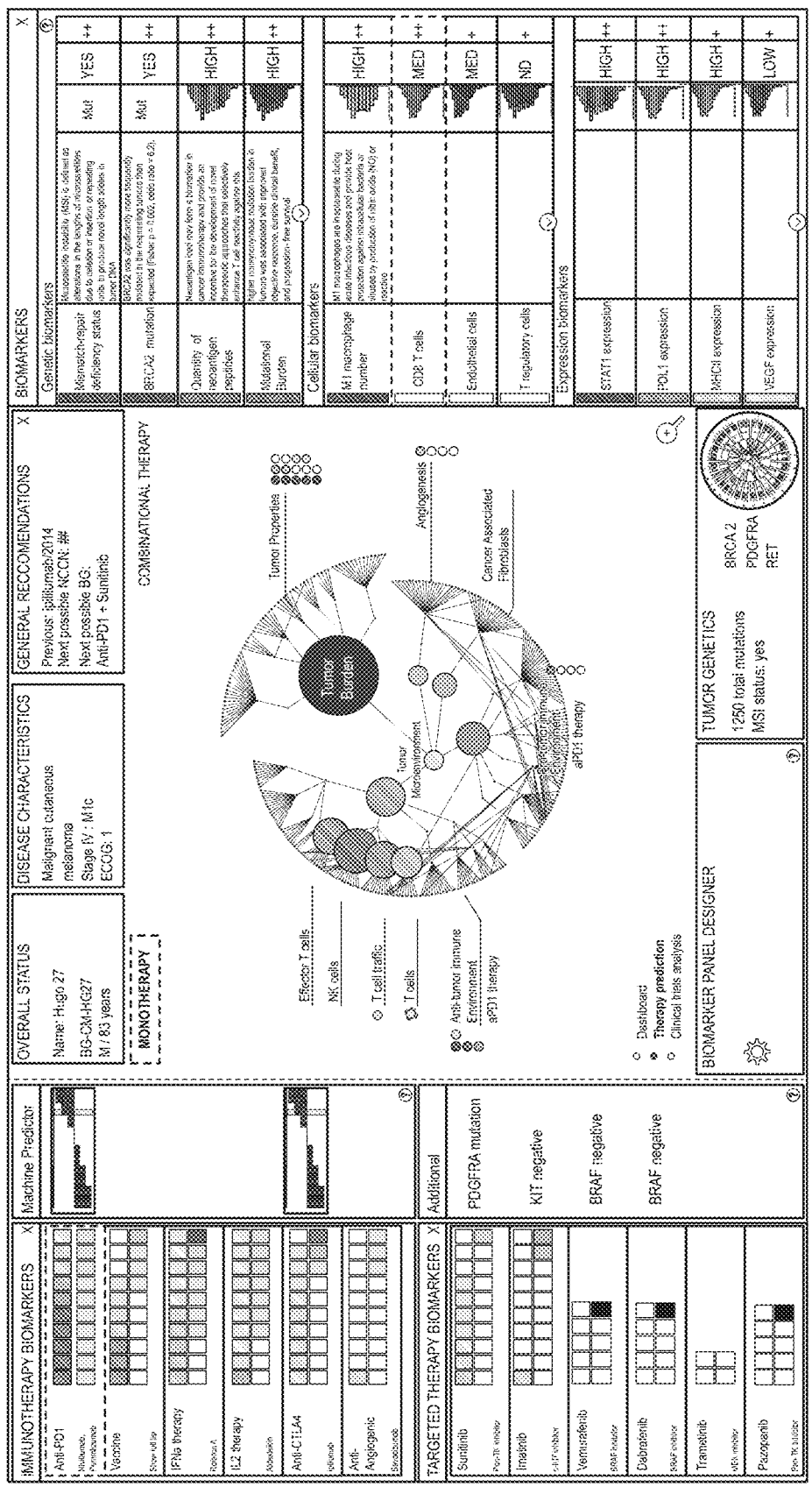
FIG. 27 is a screenshot presenting that the T cells gene group in the MF profile is highlighted in response to the user selecting the CD8 T cell biomarker (as shown in highlighting).
Figure 28:
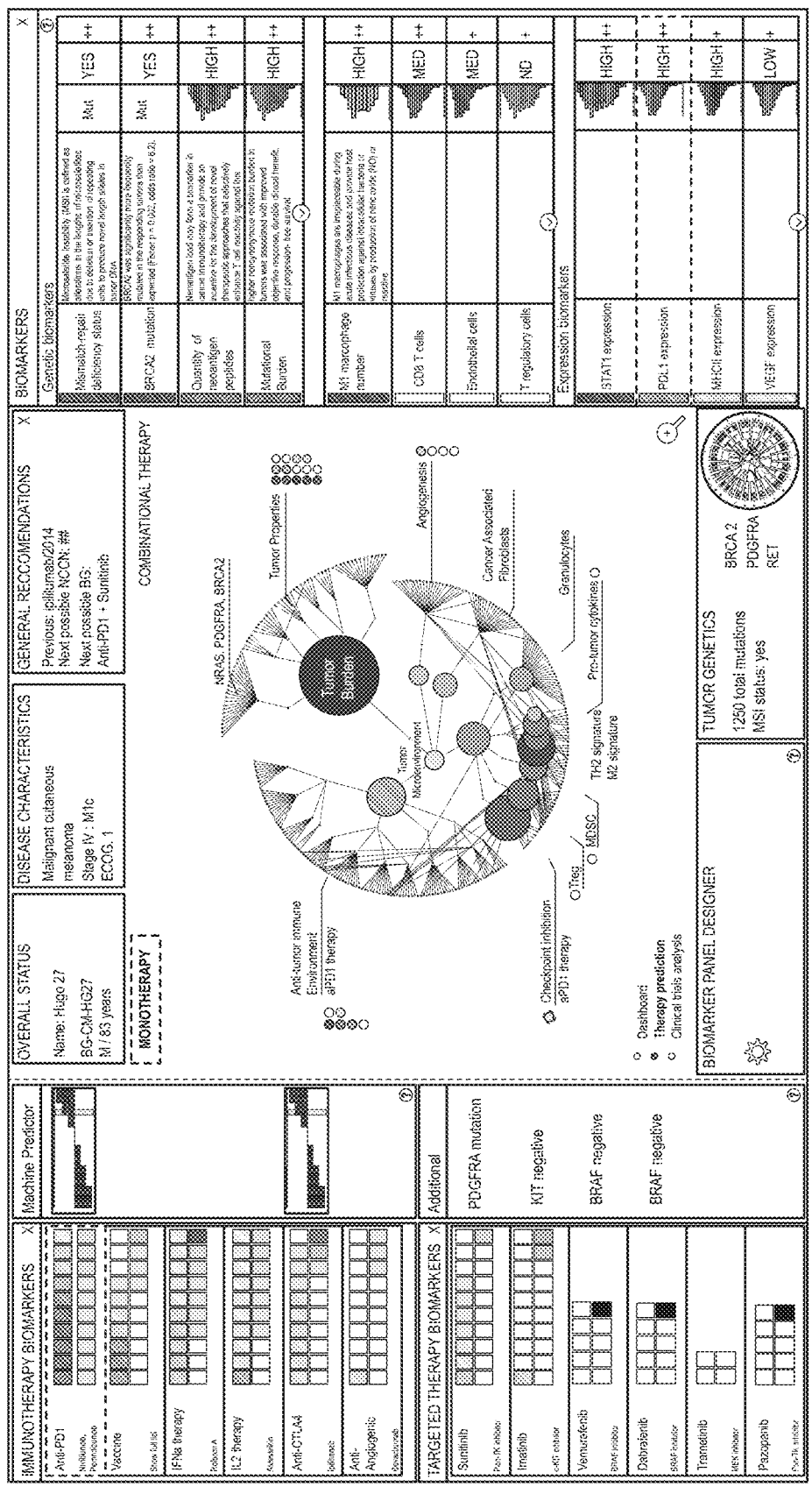
FIG. 28 is a screenshot presenting that the checkpoint inhibition gene group in the MF profile is highlighted in response to the user selecting the PDL1 expression biomarker.
Figure 29:
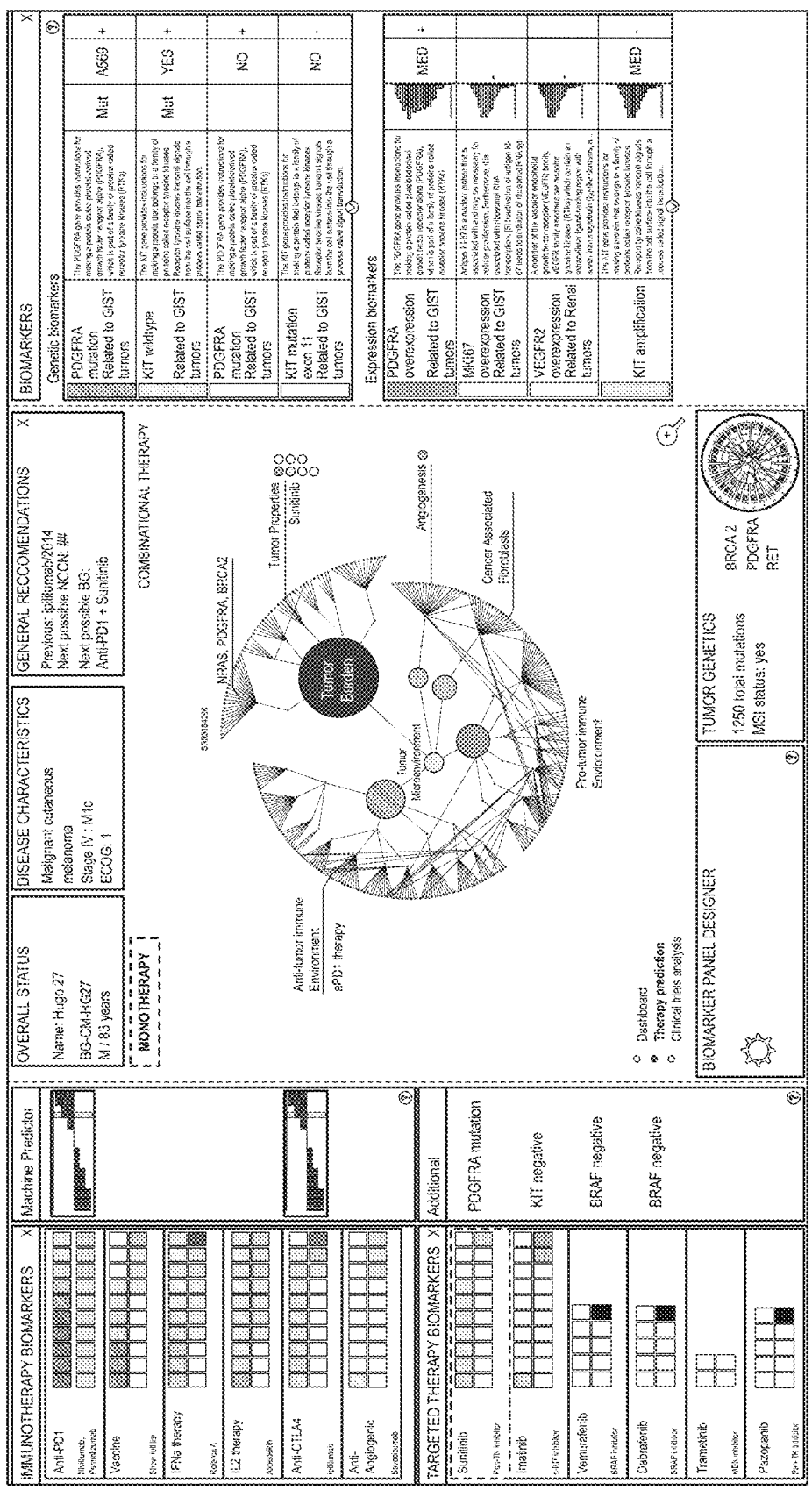
FIG. 29 is a screenshot presenting information related to sunitinib therapy provided in response to selecting sunitinib (as shown by highlighting) in the targeted therapy biomarkers portion of the screen (as shown in the left panel).
Figure 30:
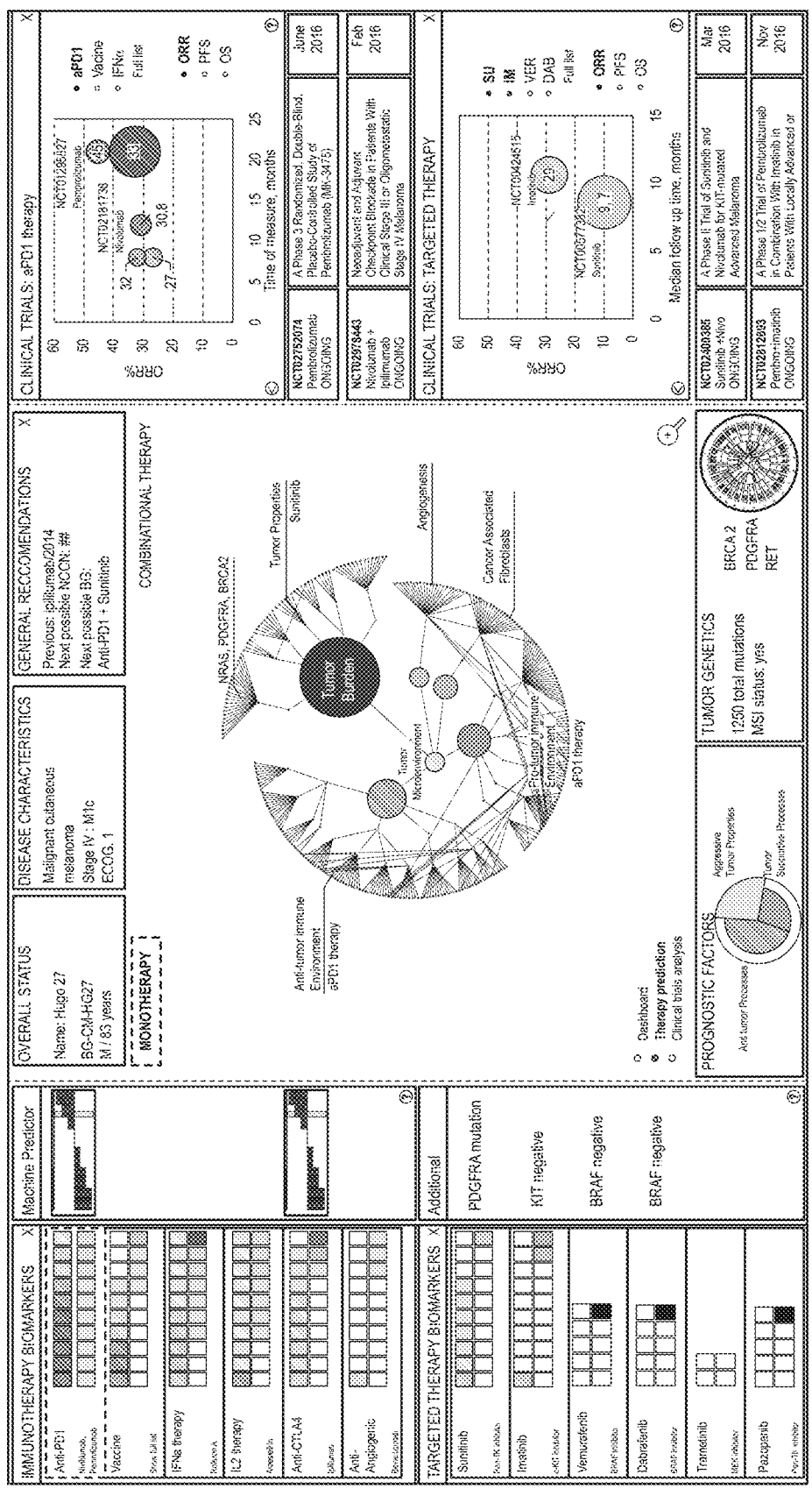
FIG. 30 is a screenshot presenting clinical trial data relating to anti-PD1 therapy effectivity in patients having stage IV metastatic melanoma (as shown in the right panel)

Next, process 4020 proceeds to act 4028, where a second set of visual characteristics for a second plurality of GUI elements using the second gene group expression levels are determined. Examples of visual characteristics for a GUI element include color, shading or pattern, size, and/or shape. A set of visual characteristics may contain any number of visual characteristics. GUI elements. for example, include genes, gene groups, biomarkers, and biomarker information. A plurality of GUI elements may contain any number of GU I elements. Further aspects of visual characteristics and GUI elements are shown in and/or described with reference to FIGS. 18-52. Next, process 4020 proceeds to act 4030, where a GUI containing a first portion including the first GUI element and a second portion including the second GUI element is generated. For example, the MF profile of the subject and other patient related information may be provided to a user in a GUI as shown in FIGS. 18-52. Further aspects relating to the GUI as shown in FIGS. 18--52 are provided in section "Visualization of MF Profiles".

Next, process 4020 proceeds to act 4032, where the generated personalized GUI is presented to a user. In some embodiments, the GUI may be presented to the user as part of a webpage displayed by a web browser. In some embodiments, the GUI may be presented to the user using an application program (different from a web-browser). For example, in some embodiments, the GUI may be presented to the user via an application program (e.g., "an app") executing on a mobile device.

Such MF portraits provided in the GUI can used for various clinical purposes described herein including assessing the efficacy of a treatment for cancer and/or evaluating suitability of a patient for participating in a clinical trial.

What is claimed is:

1. A method comprising:
obtaining nucleic acid data comprising:
sequence data indicating a nucleotide sequence for at least 5 kilobases (kb) of DNA and/or RNA from a previously obtained biological sample of a subject, wherein the subject has cancer; and,
asserted information comprising information indicative of the following features:
(i) an asserted MHC genotype of the subject;
(ii) as asserted tumor type of the biological sample; and
(iii) an asserted sequencing platform used to generate the sequence data;
processing the nucleic acid data to obtain validated nucleic acid data, the processing comprising:
(a) performing MHC allele analysis on the sequence data;
(b) performing tumor type classification on the sequence data;
(c) performing RNA-seq type classification on the sequence data; and
(d) identifying the nucleic acid data as validated nucleic acid data when information obtained from performing (a)-(d) matches the asserted information;
using the validated nucleic acid data as input in a method for determining a molecular functional (MF) profile for the subject by determining, using the validated nucleic acid data, a gene group expression level for a gene group associated with cancer malignancy and a different gene group associated with cancer microenvironment,
wherein the gene group associated with cancer malignancy includes the following genes: MKI67, ESCO2, CETN3, CDK2, CCND1, CCNE1, AURKA, AURKB, CDK4, CDK6, PRC1, E2F1, MYBL2, BUB1, PLK1, CCNB1, MCM2, MCM6, PIK3CA, PIK3CB, PIK3CG, PIK3CD, AKT1, MTOR, PTEN, PRKCA, AKT2, AKT3, BRAF, FNTA, FNTB, MAP2K1, MAP2K2, MKNK1, MKNK2, ALK, AXL, KIT, EGFR, ERBB2, FLT3, MET, NTRK1, FGFR1, FGFR2, FGFR3, ERBB4, ERBB3, BCR-ABL, PDGFRA, PDGFRB, NGF, CSF3, CSF2, FGF7, IGF1, IGF2, IL7, FGF2, TP53, SIK1, PTEN, DCN, MTAP, AIM2, RB1, ESRP1, CTSL, HOXA1, SMARCA4, SNAI2, TWIST1, NEDD9, PAPPA, HPSE, KISS1, ADGRG1, BRMS1, TCF21, CDH1, PCDH10, NCAM1, MITF, APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL
wherein the gene group associated with cancer microenvironment includes the following genes: LGALS1, COL1A1, COL1A2, COL4A1, COL5A1, TGFB1, TGFB2, TGFB3, ACTA2, FGF2, FAP, LRP1, CD248, COL6A1, COL6A2, COL6A3, VEGFA, VEGFB, VEGFC, PDGFC, CXCL8, CXCR2, FLT1, PlGF, CXCL5, KDR, ANGPT1, ANGPT2, TEK, VWF, CDH5, NOS3, KDR, VCAM1, MMRN1, LDHA, HIF1A, EPAS1, CA9, SPP1, LOX, SLC2A1, LAMP3, HLA-A, HLA-B, HLA-C, B2M, TAP1, TAP2, HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, HLA-DRB6, CD80, CD86, CD40, CD83, TNFRSF4, ICOSLG, CD28, IFNG, GZMA, GZMB, PRF1, LCK, GZMK, ZAP70, GNLY, FASLG, TBX21, EOMES, CD8A, CD8B, NKG7, CD160, CD244, NCR1, KLRC2, KLRK1, CD226, GZMH, GNLY, IFNG, KIR2DL4, KIR2DS1, KIR2DS2, KIR2DS3, KIR2DS4, KIR2DS5, CXCL9, CXCL10, CXCR3, CX3CL1, CCR7, CXCL11, CCL21, CCL2, CCL3, CCL4, CCL5, EOMES, TBX21, ITK, CD3D, CD3E, CD3G, TRAC, TRBC1, TRBC2, LCK, UBASH3A, TRAT1, CD19, MS4A1, TNFRSF13C, CD27, CD24, CR2, TNFRSF17, TNFRSF13B, CD22, CD79A, CD79B, BLK, NOS2, IL12A, IL12B, IL23A, TNF, IL1B, SOCS3, IFNG, IL2, CD40LG, IL15, CD27, TBX21, LTA, IL21, HMGB1, TNF, IFNB1, IFNA2, CCL3, TNFSF10, FASLG, PDCD1, CD274, CTLA4, LAG3, PDCD1LG2, BTLA, HAVCR2, VSIR, CXCL12, TGFB1, TGFB2, TGFB3, FOXP3, CTLA4, IL10, TNFRSF1B, CCL17, CXCR4, CCR4, CCL22, CCL1, CCL2, CCL5, CXCL13, CCL28, IDO1, ARG1, IL4R, IL10, TGFB1, TGFB2, TGFB3, NOS2, CYBB, CXCR4, CD33, CXCL1, CXCL5, CCL2, CCL4, CCL8, CCR2, CCL3, CCL5, CSF1, CXCL8, CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, CMA1, TPSAB1, MS4A2, CPA3, IL4, IL5, IL13, SIGLEC8, MPO, ELANE, PRTN3, CTSG, IL10, VEGFA, TGFB1, IDO1, PTGES, MRC1, CSF1, LRP1, ARG1, PTGS1, MSR1, CD163, CSF1R, IL4, IL5, IL13, IL10, IL25, GATA3, IL10, TGFB1, TGFB2, TGFB3, IL22, MIF, CFD, CFI, CD55, CD46, and CR1;
and identifying, from among multiple MF profile clusters, an MF profile cluster with which to associate the MF profile for the subject, the MF profile clusters comprising:
a first MF profile cluster associated with inflamed and vascularized biological samples and/or inflamed and fibroblast-enriched biological samples, a second MF profile cluster associated with inflamed and non-vascularized biological samples and/or inflamed and non-fibroblast-enriched biological samples, a third MF profile cluster associated with non-inflamed and vascularized biological samples and/or non-inflamed and fibroblast-enriched biological samples, and a fourth MF profile cluster associated with non-inflamed and non-vascularized biological samples and/or non-inflamed and non-fibroblast-enriched biological samples, wherein the MF profile clusters were generated by:
determining a plurality of MF profiles for a respective plurality of subjects using RNA expression data obtained from biological samples from the plurality of subjects, each of the plurality of MF profiles containing gene group expression levels for a gene group associated with cancer malignancy and a different gene group associated with cancer microenvironment, wherein the gene group associated with cancer malignancy includes the following genes: MKI67, ESCO2, CETN3, CDK2, CCND1, CCNE1, AURKA, AURKB, CDK4, CDK6, PRC1, E2F1, MYBL2, BUB1, PLK1, CCNB1, MCM2, MCM6, PIK3CA, PIK3CB, PIK3CG, PIK3CD, AKT1, MTOR, PTEN, PRKCA, AKT2, AKT3, BRAF, FNTA, FNTB, MAP2K1, MAP2K2, MKNK1, MKNK2, ALK, AXL, KIT, EGFR, ERBB2, FLT3, MET, NTRK1, FGFR1, FGFR2, FGFR3, ERBB4, ERBB3, BCR-ABL, PDGFRA, PDGFRB, NGF, CSF3, CSF2, FGF7, IGF1, IGF2, IL7, FGF2, TP53, SIK1, PTEN, DCN, MTAP, AIM2, RB1, ESRP1, CTSL, HOXA1, SMARCA4, SNAI2, TWIST1, NEDD9, PAPPA, HPSE, KISS1, ADGRG1, BRMS1, TCF21, CDH1, PCDH10, NCAM1, MITF, APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL wherein the gene group associated with cancer microenvironment includes the following genes: LGALS1, COL1A1, COL1A2, COL4A1, COL5A1, TGFB1, TGFB2, TGFB3, ACTA2, FGF2, FAP, LRP1, CD248, COL6A1, COL6A2, COL6A3, VEGFA, VEGFB, VEGFC, PDGFC, CXCL8, CXCR2, FLT1, PIGF, CXCL5, KDR, ANGPT1, ANGPT2, TEK, VWF, CDH5, NOS3, KDR, VCAM1, MMRN1, LDHA, HIF1A, EPAS1, CA9, SPP1, LOX, SLC2A1, LAMP3, HLA-A, HLA-B, HLA-C, B2M, TAP1, TAP2, HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, HLA-DRB6, CD80, CD86, CD40, CD83, TNFRSF4, ICOSLG, CD28, IFNG, GZMA, GZMB, PRF1, LCK, GZMK, ZAP70, GNLY, FASLG, TBX21, EOMES, CD8A, CD8B, NKG7, CD160, CD244, NCR1, KLRC2, KLRK1, CD226, GZMH, GNLY, IFNG, KIR2DL4, KIR2DS1, KIR2DS2, KIR2DS3, KIR2DS4, KIR2DS5, CXCL9, CXCL10, CXCR3, CX3CL1, CCR7, CXCL11, CCL21, CCL2, CCL3, CCL4, CCL5, EOMES, TBX21, ITK, CD3D, CD3E, CD3G, TRAC, TRBC1, TRBC2, LCK, UBASH3A, TRAT1, CD19, MS4A1, TNFRSFI3C, CD27, CD24, CR2, TNFRSFI7, TNFRSFI3B, CD22, CD79A, CD79B, BLK, NOS2, IL12A, IL12B, IL23A, TNF, IL1B, SOCS3, IFNG, IL2, CD40LG, IL15, CD27, TBX21, LTA, IL21, HMGB1, TNF, IFNB1, IFNA2, CCL3, TNFSF10, FASLG, PDCD1, CD274, CTLA4, LAG3, PDCD1LG2, BTLA, HAVCR2, VSIR, CXCL12, TGFB1, TGFB2, TGFB3, FOXP3, CTLA4, IL10, TNFRSF1B, CCL17, CXCR4, CCR4, CCL22, CCL1, CCL2, CCL5, CXCL13, CCL28, IDO1, ARG1, IL4R, IL10, TGFB1, TGFB2, TGFB3, NOS2, CYBB, CXCR4, CD33, CXCL1, CXCL5, CCL2, CCL4, CCL8, CCR2, CCL3, CCL5, CSF1, CXCL8, CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, CMA1, TPSAB1, MS4A2, CPA3, IL4, IL5, IL13, SIGLEC8, MPO, ELANE, PRTN3, CTSG, IL10, VEGFA, TGFB1, IDO1, PTGES, MRC1, CSF1, LRP1, ARG1, PTGS1, MSR1, CD163, CSFIR, IL4, IL5, IL13, IL10, IL25, GATA3, IL10, TGFB1, TGFB2, TGFB3, IL22, MIF, CFD, CFI, CD55, CD46, and CR1; and clustering the plurality of MF profiles to obtain the MF profile clusters;

clustering the MF profile of the subject with the plurality of MF profile clusters and determining that the subject has an inflamed/non-vascularized MF profile; and administering to the subject an immune checkpoint blockade therapy to the subject having the inflamed/non-vascularized MF profile.

* * * * *

UNITED STATES PATENT AND TRADEMARK OFFICE
CERTIFICATE OF CORRECTION

PATENT NO. : 12,205,675 B2  
APPLICATION NO. : 16/920641  
DATED : January 21, 2025  
INVENTOR(S) : Ekaterina Nuzhdina et al.

Page 1 of 1

It is certified that error appears in the above-identified patent and that said Letters Patent is hereby corrected as shown below:

In the Claims

At Column 184, Claim 1, Line 11 "TNFRSFI3C" should read --TNFRSF13C--.

At Column 184, Claim 1, Line 12 "TNFRSFI7, TNFRSFI3B" should read --TNFRSF17, TNFRSF13B--.

At Column 184, Claim 1, Line 31 "CSFIR" should read --CSF1R--.

Signed and Sealed this  
Fifteenth Day of April, 2025

Coke Morgan Stewart  
*Acting Director of the United States Patent and Trademark Office*